United States Patent
Duffy et al.

(10) Patent No.: US 11,098,047 B2
(45) Date of Patent: *Aug. 24, 2021

(54) ANTIMICROBIALS AND METHODS OF MAKING AND USING SAME

(71) Applicant: BIOVERSYS AG, Basel (CH)

(72) Inventors: Erin M. Duffy, Deep River, CT (US); Ashoke Bhattacharjee, Cheshire, CT (US); Zoltan F. Kanyo, North Haven, CT (US); Joseph A. Ippolito, Guilford, CT (US)

(73) Assignee: BIOVERSYS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/099,071

(22) PCT Filed: May 5, 2017

(86) PCT No.: PCT/US2017/031334
§ 371 (c)(1),
(2) Date: Nov. 5, 2018

(87) PCT Pub. No.: WO2017/193016
PCT Pub. Date: Nov. 9, 2017

(65) Prior Publication Data
US 2020/0017504 A1    Jan. 16, 2020

Related U.S. Application Data

(60) Provisional application No. 62/485,811, filed on Apr. 14, 2017, provisional application No. 62/444,276, filed on Jan. 9, 2017, provisional application No. 62/385,722, filed on Sep. 9, 2016, provisional application No. 62/333,012, filed on May 6, 2016.

(51) Int. Cl.
*C07D 487/04* (2006.01)

(52) U.S. Cl.
CPC .................. *C07D 487/04* (2013.01)

(58) Field of Classification Search
CPC .................................................. C07D 487/04
See application file for complete search history.

(56) References Cited

U.S. PATENT DOCUMENTS

| | | | | |
|---|---|---|---|---|
| 9,221,827 B2* | 12/2015 | Duffy | ........... | C07D 401/14 |
| 2012/0202792 A1* | 8/2012 | Duffy | ........... | C07D 487/04 |
| | | | | 514/217.06 |
| 2012/0220566 A1* | 8/2012 | Duffy | ........... | C07D 487/04 |
| | | | | 514/210.21 |
| 2013/0090326 A1* | 4/2013 | Duffy | ........... | C07D 487/04 |
| | | | | 514/210.18 |
| 2014/0163049 A1* | 6/2014 | Duffy | ........... | C07D 487/04 |
| | | | | 514/265.1 |
| 2016/0214988 A1* | 7/2016 | Kanyo | ........... | C07D 239/47 |
| 2018/0065966 A1* | 3/2018 | Bhattacharjee | ...... | C07D 471/04 |
| 2019/0194205 A1* | 6/2019 | Duffy | ........... | A61P 31/04 |
| 2019/0211018 A1* | 7/2019 | Duffy | ........... | A61P 31/04 |

FOREIGN PATENT DOCUMENTS

| | | | | |
|---|---|---|---|---|
| WO | WO-2012173689 A2 * | 12/2012 | ........... | C07D 401/14 |
| WO | WO-2015035426 A1 * | 3/2015 | ........... | C07D 519/00 |
| WO | WO-2016145417 A1 * | 9/2016 | ........... | C07D 487/04 |

OTHER PUBLICATIONS

CAS Abstract of Compound Registry No. RN 1801332-83-1 (Aug. 4, 2015) (Year: 2015).*
CAS Abstract of I. Morrissey et al., Int. J. Antimicrobial Agents (2015) (Year: 2015).*
I. Morrissey et al., 46 International Journal of Antimicrobial Agents, 352-354 (2015) (Year: 2015).*
Communication to CAS, Assistance Requested in locating RN 1801332-83-1 in Abstracted Document (2020) (Year: 2020).*
Communication From CAS, Assistance Requested in locating RN 1801332-83-1 in Abstracted Document (2020) (Year: 2020).*
CAS Abstract of WO 2016145417 (2016) (Year: 2016).*

* cited by examiner

*Primary Examiner* — Brenda L Coleman
(74) *Attorney, Agent, or Firm* — Brown Rudnick LLP; Thomas C. Meyers

(57) ABSTRACT

The present disclosure relates generally to the field of antimicrobial compounds and to methods of making and using them. These compounds are useful for treating, preventing, reducing the risk of, and delaying the onset of microbial infections in humans and animals. In some embodiments, the present disclosure provides a compound of Formula (I) or tautomer thereof or a pharmaceutically acceptable salt of the compound or tautomer.

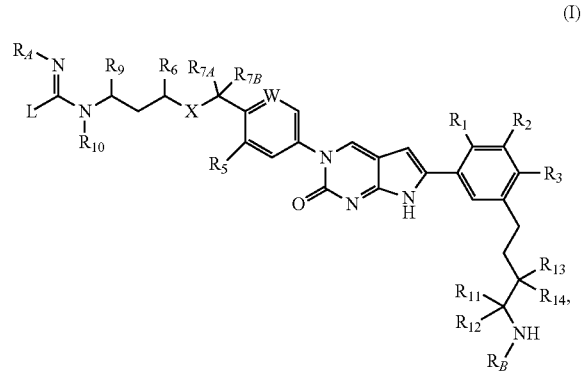

14 Claims, 5 Drawing Sheets

ANTIMICROBIALS AND METHODS OF MAKING AND USING SAME

CROSS-REFERENCE TO RELATED APPLICATIONS

This application is a National Stage application under 35 U.S.C. § 371 of International Application No. PCT/US2017/031334, filed May 5, 2017, which claims priority to U.S. Provisional Application Ser. No. 62/485,811, filed Apr. 14, 2017; 62/444,276, filed Jan. 9, 2017; 62/385,722, filed Sep. 9, 2016; and 62/333,012, filed May 6, 2016, all of which are herein incorporated by reference in their entireties.

TECHNICAL FIELD

This invention relates to antimicrobial compounds, and more particularly to pyrrolo[2,3-d]pyrimidin-2-ones useful for treating, preventing and reducing risk of microbial infections.

BACKGROUND

Since the discovery of penicillin in the 1920s and streptomycin in the 1940s, many new compounds have been discovered or specifically designed for use as antibiotic agents. It was once thought that infectious diseases could be completely controlled or eradicated with the use of such therapeutic agents. However, such views have been challenged because strains of cells or microorganisms resistant to currently effective therapeutic agents continue to evolve. Almost every antibiotic agent developed for clinical use has ultimately encountered problems with the emergence of resistant bacteria. For example, resistant strains of Gram-positive bacteria such as methicillin-resistant staphylococci, penicillin-resistant streptococci, and vancomycin-resistant enterococci have developed. Resistant bacteria can cause serious and even fatal results for infected patients. See, e.g., Lowry, F. D. "Antimicrobial Resistance: The Example of *Staphylococcus aureus*," *J. Clin. Invest.*, vol. 111, no. 9, pp. 1265-1273 (2003); and Gold, H. S. and Moellering, R. C., Jr., "Antimicrobial-Drug Resistance," *N. Engl. J. Med.*, vol. 335, pp. 1445-53 (1996).

The discovery and development of new antibacterial agents have been for decades a major focus of many pharmaceutical companies. Nonetheless, in more recent years there has been an exodus from this area of research and drug development resulting in very few new antibiotics entering the market. This lack of new antibiotics is particularly disturbing, especially at a time when bacterial resistance to current therapies is increasing both in the hospital and community settings.

One approach to developing new antimicrobial compounds is to design modulators, for example, inhibitors, of bacterial ribosome function. By modulating or inhibiting bacterial ribosome function, antimicrobial compounds could interfere with essential processes such as RNA translation and protein synthesis, thereby providing an antimicrobial effect. In fact, some antibiotic compounds such as erythromycin, clindamycin, and linezolid are known to bind to the ribosome.

SUMMARY

The present disclosure relates generally to the field of antimicrobial compounds and to methods of making and using them. These compounds and tautomers thereof are useful for treating, preventing, reducing the risk of, or delaying the onset of microbial infections in humans and animals. The present disclosure also provides pharmaceutically acceptable salts of these compounds and tautomers.

In some embodiments, provided herein is a compound of Formula (I):

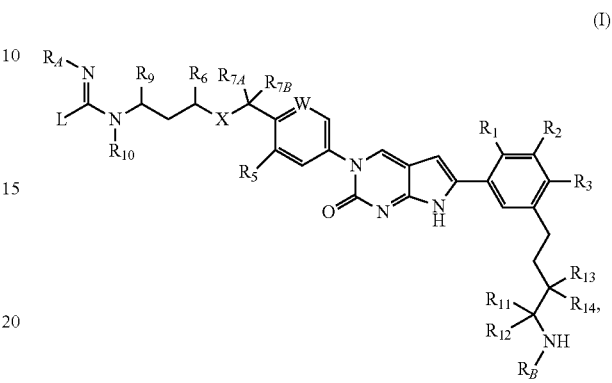

or a tautomer thereof or a pharmaceutically acceptable salt of the compound or tautomer, wherein:

$R_1$ is selected from H, halo, and $C_{1-4}$ alkoxy;

$R_2$ is selected from H, halo, $C_{1-6}$ alkyl, $C_{1-4}$ haloalkyl, and $OR^{a1}$;

$R_3$ is selected from H, $C_{1-6}$ alkyl, $C_{1-4}$ haloalkyl, and $C(O)OR^{a1}$;

W is selected from N and $CR_4$;

$R_4$ is selected from H, halo, $OR^{a2}$, $SR^{a2}$, 5-6 membered heterocycloalkyl, $S(O)_2R^{b2}$, $C_{1-6}$ alkyl, and $C_{2-6}$ alkenyl, wherein the $C_{1-6}$ alkyl is optionally substituted with a substituent selected from $OR^{a2}$;

$R_5$ is selected from H, halo, $C_{1-6}$ alkyl, and $C_{2-6}$ alkenyl, wherein the $C_{1-6}$ alkyl is optionally substituted with a substituent selected from $OR^{a2}$;

$R_6$ is selected from H, $C_{1-6}$ alkyl, $C_{3-5}$ cycloalkyl, and $C_{2-6}$ alkenyl, wherein the $C_{1-6}$ alkyl is optionally substituted with a substituent selected from $OR^{a3}$, $SR^{a3}$, and $NR^{c3}R^{d3}$;

$R_{7A}$ is selected from H, $C_{1-6}$ alkyl, $C_{1-4}$ haloalkyl, and $C_{2-6}$ alkenyl, wherein the $C_{1-6}$ alkyl is optionally substituted with a substituent selected from $OR^{a3}$ and $SR^{a3}$;

$R_{7B}$ is H; or $R_{7A}$ and $R_{7B}$ together with the carbon atom to which they are attached form a group selected from oxo, and $C_{3-6}$ cycloalkyl; or $R_6$ and $R_{7A}$ together with the carbon atoms to which they are attached and the X atom connecting the two carbon atoms form a 5- to 6-membered heterocycloalkyl containing 1-3 heteroatoms selected from N, O and S;

X is selected from O and $NR_8$;

$R_8$ is selected from H, $C_{1-6}$ alkyl, and $C_{1-4}$ haloalkyl, wherein the $C_{1-6}$ alkyl is optionally substituted with $R_{8A}$;

$R_{8A}$ is selected from $OR^{a3}$ and 5- to 6-membered heteroaryl, wherein the 5- to 6-membered heteroaryl is optionally substituted with one or two $C_{1-6}$ alkyl;

$R_9$ is selected from H, $C_{2-4}$ alkenyl, $C_{1-4}$ haloalkyl and $C_{1-4}$ alkyl optionally substituted with a substituent selected from amino, $C_{1-4}$ alkoxy, $C_{3-5}$ cycloalkyl, and 3-to 6-membered heterocycloalkyl;

$R_{10}$ is selected from H and $C_{2-6}$ alkenyl;

$R_A$ is selected from H and $C_{1-6}$ alkyl;

L is selected from $C_{1-6}$ alkyl and $C_{2-6}$ alkenyl, wherein the $C_{1-6}$ alkyl is optionally substituted with 1, 2, or 3 substituents independently selected from halo, $OR^{a4}$, $SR^{a4}$, and Z;

$R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with 1, 2, or 3 substituents independently selected from CN, $OR^{a5}$, $SR^{a5}$, $C(O)NR^{c5}R^{d5}$, $NR^{c5}R^{d5}$, and $S(O)_2R^{b5}$;

$R_{12}$ is selected from H and $C_{1-6}$ alkyl; or $R_{11}$ and $R_{12}$ together with the carbon atom to which they are attached form a $C_{3-5}$ cycloalkyl;

$R_{13}$ is selected from H, halo, and $C_{1-6}$ alkyl;

$R_{14}$ is selected from H, halo, and $C_{1-6}$ alkyl; and $R_B$ is selected from H and $C(=NR^{e5})R^{b5}$; or $R_{11}$ and $R_B$ together with the carbon atom to which $R_{11}$ is attached and the nitrogen atom to which $R_B$ is attached form a 5- to 6-membered heterocycloalkyl containing 1-3 heteroatoms selected from N, O and S, wherein the 5- to 6-membered heterocycloalkyl is optionally substituted with oxo;

each $R^{a1}$, $R^{a2}$, $R^{a3}$, $R^{a4}$, $R^{a5}$, $R^{b2}$, $R^{b5}$, $R^{c3}$, $R^{d3}$, $R^{c5}$, and $R^{d5}$ is independently selected from H, $C_{1-6}$ alkyl, $C_{1-4}$ haloalkyl, and 5-membered heteroaryl;

$R^{e5}$ is selected from H and $C_{1-4}$ alkyl; and Z is $-O(CH_2CH_2O)CH_3$.

In some embodiments, provided herein is a compound of Formula (II):

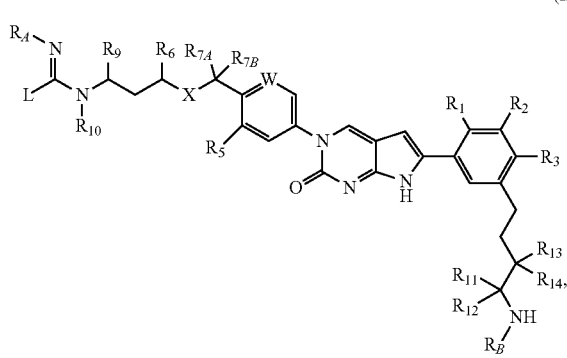

(II)

or a tautomer thereof or a pharmaceutically acceptable salt of the compound or tautomer, wherein:

$R_1$ is selected from H and halo;

$R_2$ is selected from H, halo, $C_{1-6}$ alkyl, $C_{1-4}$ haloalkyl, and $OR^{a1}$;

$R_3$ is selected from H, $C_{1-6}$ alkyl, $C_{1-4}$ haloalkyl, and $C(O)OR^{a1}$;

W is selected from N and $CR_4$;

$R_4$ is selected from H, halo, $OR^{a2}$, $SR^{a2}$, 5-6 membered heterocycloalkyl, $S(O)_2R^{b2}$, $C_{1-6}$ alkyl, and $C_{2-6}$ alkenyl, wherein the $C_{1-6}$ alkyl is optionally substituted with a substituent selected from $OR^{a2}$;

$R_5$ is selected from H, halo, $C_{1-6}$ alkyl, and $C_{2-6}$ alkenyl, wherein the $C_{1-6}$ alkyl is optionally substituted with a substituent selected from $OR^{a2}$;

$R_6$ is selected from H, $C_{1-6}$ alkyl, $C_{3-5}$ cycloalkyl, and $C_{2-6}$ alkenyl, wherein the $C_{1-6}$ alkyl is optionally substituted with a substituent selected from $OR^{a3}$, $SR^{a3}$, and $NR^{c3}R^{d3}$;

$R_{7A}$ is selected from H, $C_{1-6}$ alkyl, $C_{1-4}$ haloalkyl, and $C_{2-6}$ alkenyl, wherein the $C_{1-6}$ alkyl is optionally substituted with a substituent selected from $OR^{a3}$ and $SR^{a3}$;

$R_{7B}$ is H; or $R_{7A}$ and $R_{7B}$ together with the carbon atom to which they are attached form a group selected from oxo, and $C_{3-6}$ cycloalkyl; or $R_6$ and $R_{7A}$ together with the carbon atoms to which they are attached and the X atom connecting the two carbon atoms form a 5- to 6-membered heterocycloalkyl containing 1-3 heteroatoms selected from N, O and S;

X is selected from O and $NR_8$;

$R_8$ is selected from H, $C_{1-6}$ alkyl, and $C_{1-4}$ haloalkyl, wherein the $C_{1-6}$ alkyl is optionally substituted with $R_{8A}$;

$R_{8A}$ is selected from 5- to 6-membered heteroaryl, and $OR^{a3}$, wherein the 5- to 6-membered heteroaryl is optionally substituted with one or two $C_{1-6}$ alkyl;

$R_9$ is selected from H, $C_{2-4}$ alkenyl, $C_{1-4}$ haloalkyl and $C_{1-4}$ alkyl optionally substituted with a substituent selected from amino, $C_{1-4}$ alkoxy, $C_{3-5}$ cycloalkyl, and 3-to 6-membered heterocycloalkyl;

$R_{10}$ is selected from H and $C_{2-6}$ alkenyl;

$R_A$ is selected from H and $C_{1-6}$ alkyl;

L is selected from $C_{1-6}$ alkyl and $C_{2-6}$ alkenyl, wherein the $C_{1-6}$ alkyl is optionally substituted with 1, 2, or 3 substituents independently selected from halo, $OR^{a4}$, and $SR^{a4}$;

$R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with 1, 2, or 3 substituents independently selected from CN, $OR^{a5}$, $SR^{a5}$, $C(O)NR^{c5}R^{d5}$, $NR^{c5}R^{d5}$, and $S(O)_2R^{b5}$;

$R_{12}$ is selected from H and $C_{1-6}$ alkyl; or $R_{11}$ and $R_{12}$ together with the carbon atom to which they are attached form a $C_{3-5}$ cycloalkyl;

$R_{13}$ is selected from H, halo, and $C_{1-6}$ alkyl;

$R_{14}$ is selected from H, halo, and $C_{1-6}$ alkyl; and $R_B$ is selected from H and $C(=NR^{e5})R^{b5}$; or $R_{11}$ and $R_B$ together with the carbon atom to which $R_{11}$ is attached and the nitrogen atom to which $R_B$ is attached form a 5- to 6-membered heterocycloalkyl containing 1-3 heteroatoms selected from N, O and S, wherein the 5- to 6-membered heterocycloalkyl is optionally substituted with oxo;

each $R^{a1}$, $R^{a2}$, $R^{a3}$, $R^{a4}$, $R^{a5}$, $R^{b2}$, $R^{b5}$, $R^{c3}$, $R^{d3}$, $R^{c5}$, and $R^{d5}$ is independently selected from H, $C_{1-6}$ alkyl, $C_{1-4}$ haloalkyl, and 5-membered heteroaryl; and $R^{e5}$ is selected from H and $C_{1-4}$ alkyl.

In some embodiments provided herein is a pharmaceutical composition comprising a compound of Formula I, or a tautomer thereof or a pharmaceutically acceptable salt of the compound or tautomer, and a pharmaceutically acceptable carrier.

In some embodiments provided herein is a method of treating a microbial infection comprising administering to a subject in need thereof an effective amount of a compound of Formula (I) or Formula (II), or a tautomer thereof or a pharmaceutically acceptable salt of the compound or tautomer, or a pharmaceutically acceptable composition as provided herein.

In some embodiments provided herein is a method of preventing a microbial infection comprising administering to a subject in need thereof an effective amount of a compound of Formula (I) or Formula (II), or a tautomer thereof or a pharmaceutically acceptable salt of the compound or tautomer, or a pharmaceutically acceptable composition as provided herein.

In some embodiments provided herein is a method of reducing the risk of a microbial infection comprising administering to a subject in need thereof an effective amount of a compound of Formula (I) or Formula (II), or a tautomer thereof or a pharmaceutically acceptable salt of the compound or tautomer, or a pharmaceutically acceptable composition as provided herein.

In some embodiments provided herein is a method of delaying the onset of a microbial infection comprising administering to a subject in need thereof an effective amount of a compound of Formula (I) or Formula (II), or a tautomer thereof or a pharmaceutically acceptable salt of the compound or tautomer, or a pharmaceutically acceptable composition as provided herein.

In some embodiments provided herein is a method of treating a microbial infection comprising administering to a subject in need thereof an effective amount of a compound of Formula (I) or Formula (II), or a tautomer thereof or a pharmaceutically acceptable salt of the compound or tautomer, or a pharmaceutically acceptable composition as provided herein.

In some embodiments provided herein is a use of a compound of Formula (I) or Formula (II), or a tautomer thereof or a pharmaceutically acceptable salt of the compound or tautomer, in the manufacture of a medicament for treating, preventing, or reducing a microbial infection in a subject.

In some embodiments provided herein is a compound of Formula (I) or Formula (II), or a tautomer thereof or a pharmaceutically acceptable salt of the compound or tautomer, for use in treating, preventing, or reducing a microbial infection in a subject.

In addition, the disclosure provides methods of synthesizing the foregoing compounds and tautomers thereof, and pharmaceutically acceptable salts of said compounds and tautomers. Following synthesis, an effective amount of one or more of the compounds or tautomers thereof, or pharmaceutically acceptable salts of said compounds or tautomers can be formulated with a pharmaceutically acceptable carrier for administration to a human or animal for use as antimicrobial agents, particularly as antibacterial agents. In certain embodiments, the compounds of the present disclosure are useful for treating, preventing, reducing the risk of, or delaying the onset of microbial infections or for the manufacture of a medicament for treating, preventing, reducing the risk of, or delaying the onset of microbial infections.

Accordingly, the compounds or tautomers thereof, or pharmaceutically acceptable salts of said compounds or tautomers or their formulations can be administered, for example, via oral, parenteral, intravenous, otic, ophthalmic, nasal, or topical routes, to provide an effective amount of the compound or tautomer thereof, or pharmaceutically acceptable salt of said compound or tautomer to the human or animal.

The foregoing and other aspects and embodiments of the disclosure can be more fully understood by reference to the following detailed description and claims.

DETAILED DESCRIPTION

Figure 1:
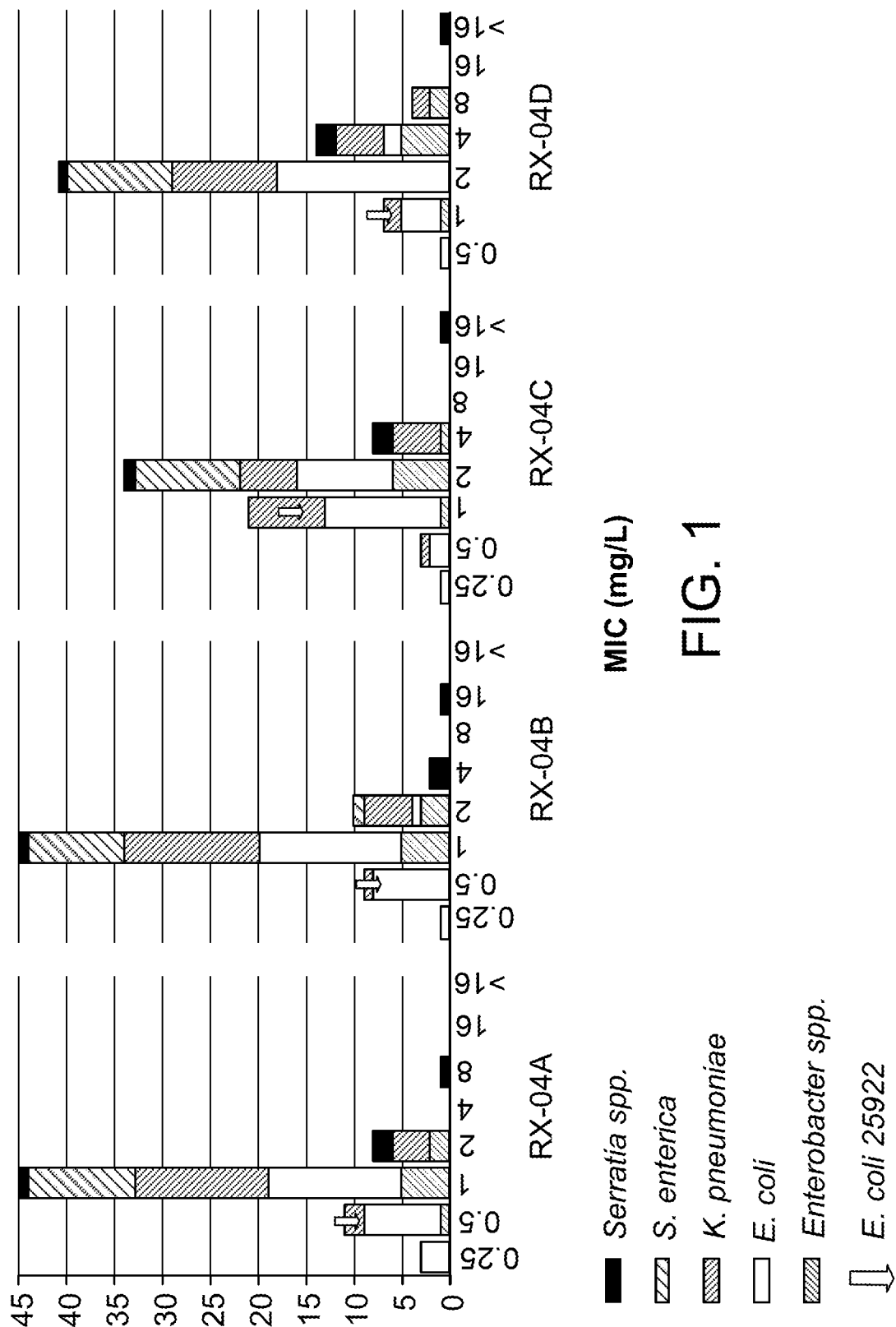
FIG. 1 provides bar graphs illustrating the MIC distribution of RX-04A-D for all Enterobacteriaceae tested by species (n=68).

The present disclosure utilizes a structure based drug design approach for discovering and developing new antimicrobial agents. This approach starts with a high resolution X-ray crystal of a ribosome to design new classes of antimicrobial compounds having specific chemical structures, ribosome binding characteristics, and antimicrobial activity. This structure based drug discovery approach is described in the following publication: Franceschi, F. and Duffy, E. M., "Structure-based drug design meets the ribosome", *Biochemical Pharmacology*, vol. 71, pp. 1016-1025 (2006).

Based on this structure based drug design approach, the present disclosure describes new chemical classes of antimicrobial compounds useful for treating bacterial infections in humans and animals. Without being limited by theories, these compounds are believed to inhibit bacterial ribosome function by binding to the ribosome. By taking advantage of these ribosome binding sites, the antimicrobial compounds of the present disclosure can provide better activity, especially against resistant strains of bacteria, than currently available antibiotic compounds.

The present disclosure therefore fills an important ongoing need for new antimicrobial agents, particularly for antimicrobial agents, having activity against resistant pathogenic bacterial organisms.

The present disclosure provides a family of compounds or tautomers thereof, that can be used as antimicrobial agents, more particularly as antibacterial agents.

The present disclosure also includes pharmaceutically acceptable salts of said compounds and tautomers.

The compounds or tautomers thereof, or pharmaceutically acceptable salts of said compounds or tautomers disclosed herein can have asymmetric centers.

Compounds or tautomers thereof, or pharmaceutically acceptable salts of said compounds or tautomers of the present disclosure containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds or tautomers thereof, or pharmaceutically acceptable salts of said compounds or tautomers disclosed herein, and all such stable isomers are contemplated in the present disclosure. Cis and trans geometric isomers of the compounds or tautomers thereof, or pharmaceutically acceptable salts of said compounds or tautomers of the present disclosure are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds or tautomers thereof, or pharmaceutically acceptable salts of said compounds or tautomers of the present disclosure and intermediates made herein are considered to be part of the present disclosure. All tautomers of shown or described compounds are also considered to be part of the present disclosure. Furthermore, the disclosure also includes metabolites of the compounds disclosed herein.

The disclosure also comprehends isotopically-labeled compounds or tautomers thereof, or pharmaceutically acceptable salts of said compounds or tautomers, which are identical to those recited in formulae of the disclosure, but for the replacement of one or more atoms by an atom having an atomic mass or mass number different from the atomic mass or mass number most commonly found in nature. Examples of isotopes that can be incorporated into compounds or tautomers thereof, or pharmaceutically acceptable salts of said compounds or tautomers of the disclosure include isotopes of hydrogen, carbon, nitrogen, and fluorine, such as $^3$H, $^{11}$C, $^{14}$C, and $^{18}$F.

The compounds of the present disclosure or tautomers thereof, or pharmaceutically acceptable salts of said compounds or tautomers that contain the aforementioned isotopes and/or isotopes of other atoms are within the scope of the present disclosure. Isotopically-labeled compounds or tautomers thereof, or pharmaceutically acceptable salts of said compounds or tautomers of the present disclosure, for example, those into which radioactive isotopes such as $^3$H and $^{14}$C are incorporated, are useful in drug and/or substrate tissue distribution assays. Tritium, i.e., $^3$H and carbon-14, i.e., $^{14}$C, isotopes are particularly preferred due to their ease of preparation and detectability. $^{11}$C and $^{18}$F isotopes are particularly useful in PET (positron emission tomography). PET is useful in brain imaging. Further, substitution with heavier isotopes such as deuterium, i.e., $^2$H, can afford certain therapeutic advantages resulting from greater metabolic stability, i.e., increased in vivo half-life or reduced dosage requirements and, hence, may be preferred in some circumstances. Isotopically labeled compounds or tautomers thereof, or pharmaceutically acceptable salts of said compounds or tautomers having a formula of the disclosed herein can generally be prepared as described in the procedures, Schemes and/or in the Examples disclosed herein, by substituting a non-isotopically labeled reagent with a readily available isotopically labeled reagent. In one embodiment, the compounds or tautomers thereof, or pharmaceutically acceptable salts of said compounds or tautomers disclosed herein are not isotopically labeled.

When any variable (e.g., R) occurs more than one time in any constituent or formulae of the disclosed herein, its definition at each occurrence is independent of its definition at every other occurrence. Thus, for example, if a group is shown to be substituted with one or more R moieties, then R at each occurrence is selected independently from the definition of R. Also, combinations of substituents and/or variables are permissible, but only if such combinations result in stable compounds within a designated atom's normal valence.

A chemical structure showing a dotted line representation for a chemical bond indicates that the bond is optionally present. For example, a dotted line drawn next to a solid single bond indicates that the bond can be either a single bond or a double bond.

When a bond to a substituent is shown to cross a bond connecting two atoms in a ring, then such substituent can be bonded to any atom on the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

In cases wherein compounds of the present disclosure, or tautomers thereof, or pharmaceutically acceptable salts of said compounds or tautomers thereof, contain nitrogen atoms, these, where appropriate, can be converted to N-oxides by treatment with an oxidizing agent (e.g., meta-chloroperoxybenzoic acid (mCPBA) and/or hydrogen peroxides). Thus, shown and claimed nitrogen atoms are considered to cover both the shown nitrogen and its N-oxide (N→O) derivative, as appropriate. In some embodiments, the present disclosure relates to N-oxides of the compounds or tautomers thereof, or pharmaceutically acceptable salts of said compounds or tautomers disclosed herein.

One approach to developing improved anti-proliferative and anti-infective agents is to provide modulators (for example, inhibitors) of ribosome function.

Ribosomes are ribonucleoproteins, which are present in both prokaryotes and eukaryotes. Ribosomes are the cellular organelles responsible for protein synthesis. During gene expression, ribosomes translate the genetic information encoded in a messenger RNA into protein (Garrett et al. (2000) "*The Ribosome: Structure, Function, Antibiotics and Cellular Interactions*," American Society for Microbiology, Washington, D.C.).

Ribosomes comprise two nonequivalent ribonucleoprotein subunits. The larger subunit (also known as the "large ribosomal subunit") is about twice the size of the smaller subunit (also known as the "small ribosomal subunit"). The small ribosomal subunit binds messenger RNA (mRNA) and mediates the interactions between mRNA and transfer RNA (tRNA) anticodons on which the fidelity of translation depends. The large ribosomal subunit catalyzes peptide bond formation, i.e., the peptidyl-transferase reaction of protein synthesis, and includes, at least, three different tRNA binding sites known as the aminoacyl, peptidyl, and exit sites. The aminoacyl site or A-site accommodates the incoming aminoacyl-tRNA that is to contribute its amino acid to the growing peptide chain. Also, the A space of the A-site is important. The peptidyl site or P-site accommodates the peptidyl-tRNA complex, i.e., the tRNA with its amino acid that is part of the growing peptide chain. The exit or E-site accommodates the deacylated tRNA after it has donated its amino acid to the growing polypeptide chain.

1. Definitions

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. A compound with one chiral center has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J., *Chem. Educ.* 1964, 41, 116).

"Geometric Isomers" means the diastereomers that owe their existence to hindered rotation about double bonds.

These configurations are differentiated in their names by the prefixes cis and trans, or Z and E, which indicate that the groups are on the same or opposite side of the double bond in the molecule according to the Cahn-Ingold-Prelog rules.

Further, the compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however, as a result of recent advances in chromatography techniques, it has been possible to separate mixtures of two atropic isomers in select cases.

Some compounds of the present disclosure can exist in a tautomeric form which is also intended to be encompassed within the scope of the present disclosure. "Tautomers" refers to compounds whose structures differ markedly in the arrangement of atoms, but which exist in easy and rapid equilibrium. It is to be understood that compounds of present disclosure may be depicted as different tautomers. It should also be understood that when compounds have tautomeric forms, all tautomeric forms are intended to be within the scope of the disclosure, and the naming of the compounds does not exclude any tautomeric form.

The compounds and pharmaceutically acceptable salts of the present disclosure can exist in one or more tautomeric forms, including the enol and imine form and the keto and enamine form, and geometric isomers and mixtures thereof. All such tautomeric forms are included within the scope of the present disclosure. Tautomers exist as mixtures of a tautomeric set in solution. In solid form, usually one tautomer predominates. Even though one tautomer may be described, the present disclosure includes all tautomers of the compounds disclosed herein.

A tautomer is one of two or more structural isomers that exist in equilibrium and are readily converted from one isomeric form to another. This reaction results in the formal migration of a hydrogen atom accompanied by a shift of adjacent conjugated double bonds. In solutions where tautomerization is possible, a chemical equilibrium of the tautomers can be reached. The exact ratio of the tautomers depends on several factors, including temperature, solvent, and pH. The concept of tautomers that are interconvertible by tautomerizations is called tautomerism.

Of the various types of tautomerism that are possible, two are commonly observed. In keto-enol tautomerism, a simultaneous shift of electrons and a hydrogen atom occurs. Ring-chain tautomerism, exhibited by glucose and other sugars, arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs include: ketone-enol, amide-nitrile, lactam-lactim, amide-imidic acid tautomerism in heterocyclic rings (e.g., in the nucleobases guanine, thymine, and cytosine), amine-enamine and enamine-enamine. Examples below are included for illustrative purposes, and the present disclosure is not limited to the examples:

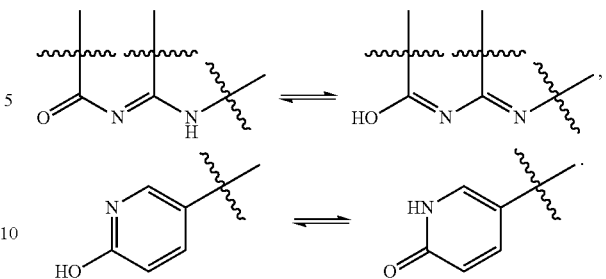

The term "substituted," as used herein, means that any one or more hydrogens on the designated atom, usually a carbon, oxygen, or nitrogen atom, is replaced with a selection from the indicated group, provided that the designated atom's normal valency is not exceeded, and that the substitution results in a stable compound. When a substituent is keto or oxo (i.e., =O), then 2 hydrogens on the atom are replaced. Ring double bonds, as used herein, are double bonds that are formed between two adjacent ring atoms (e.g., C=C, C=N, N=N, etc.).

As used herein, "alkyl" is intended to include both branched and straight-chain saturated aliphatic hydrocarbon groups having the specified number of carbon atoms. For example $C_{1-4}$ is intended to include $C_1$, $C_2$, $C_3$, and $C_4$. $C_{1-6}$ alkyl is intended to include $C_1$, $C_2$, $C_3$, $C_4$, $C_5$, and $C_6$ alkyl groups and $C_{1-8}$ is intended to include $C_1$, $C_2$, $C_3$, $C_4$, $C_5$, $C_6$, $C_7$, and $C_8$. Some examples of alkyl include, but are not limited to, methyl, ethyl, n-propyl, i-propyl, n-butyl, s-butyl, t-butyl, n-pentyl, s-pentyl, n-hexyl, n-heptyl, and n-octyl.

As used herein, "alkenyl" is intended to include hydrocarbon chains of either straight or branched configuration and one or more unsaturated carbon-carbon bonds that can occur in any stable point along the chain, such as ethenyl and propenyl. For example $C_{2-6}$ alkenyl is intended to include $C_2$, $C_3$, $C_4$, $C_5$, and $C_6$ alkenyl groups and $C_{2-8}$ alkenyl is intended to include $C_2$, $C_3$, $C_4$, $C_5$, $C_6$, $C_7$, and $C_8$.

As used herein, "alkylene" is intended to include moieties which are diradicals, i.e., having two points of attachment. A non-limiting example of such alkylene moiety that is a diradical is —CH$_2$CH$_2$—, i.e., a $C_2$ alkyl group that is covalently bonded via each terminal carbon atom to the remainder of the molecule. The alkylene diradicals are also known as "alkylenyl" radicals. Alkylene groups can be saturated or unsaturated (e.g., containing —CH=CH— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms). Some examples of alkylene groups include, but not limited to, methylene, ethylene, n-propylene, iso-propylene, n-butylene, iso-butylene, sec-butylene, tert-butylene, n-pentylene, iso-pentylene, sec-pentylene and neo-pentylene.

As used herein, "cycloalkyl" is intended to include saturated or unsaturated nonaromatic ring groups, such as cyclopropyl, cyclobutyl, or cyclopentyl. $C_{3-8}$ cycloalkyl is intended to include $C_3$, $C_4$, $C_5$, $C_6$, $C_7$, and $C_8$ cycloalkyl groups. Cycloalkyls may include multiple spiro- or fused rings.

As used herein, the term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

As used herein, "amine" or "amino" refers to unsubstituted —$NH_2$ unless otherwise specified.

As used herein, "halo" or "halogen" refers to fluoro, chloro, bromo, and iodo substituents.

As used herein, "haloalkyl" is intended to include both branched and straight-chain saturated aliphatic hydrocarbon groups having the specified number of carbon atoms, substituted with one or more halogen (for example —$C_vF_wH_{2V-w+1}$ wherein v=1 to 3 and w=1 to (2v+1)). Examples of haloalkyl include, but are not limited to, trifluoromethyl, trichloromethyl, pentafluoroethyl, and pentachloroethyl.

The term "haloalkoxy" as used herein refers to an alkoxy group, as defined herein, which is substituted one or more halogen. Examples of haloalkoxy groups include, but are not limited to, trifluoromethoxy, difluoromethoxy, pentafluoroethoxy, trichloromethoxy, etc.

As used herein, "alkoxyl" or "alkoxy" refers to an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "Aryl" includes groups with aromaticity, including "conjugated," or multicyclic systems with at least one aromatic ring and do not contain any heteroatom in the ring structure. Aryl may be monocyclic or polycyclic (e.g., having 2, 3 or 4 fused rings). The term "$C_{n-m}$ aryl" refers to an aryl group having from n to m ring carbon atoms. In some embodiments, aryl groups have from 6 to 10 carbon atoms. In some embodiments, the aryl group is phenyl or naphtyl.

As used herein, the term "aromatic heterocycle", "aromatic heterocyclic" or "heteroaryl" ring is intended to mean a stable 5, 6, 7, 8, 9, 10, 11, or 12-membered monocyclic or bicyclic aromatic ring which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic aromatic heterocyclic or heterocycle or heteroaryl rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and S(O)$_p$, wherein p=1 or 2). In certain compounds, the total number of S and O atoms in the aromatic heterocycle is not more than 1.

Examples of aromatic heterocycles, aromatic heterocyclics or heteroaryls include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, benzooxadiazoly, carbazolyl, 4aH-carbazolyl, carbolinyl, cinnolinyl, furazanyl, imidazolyl, imidazolonyl, 1H-indazolyl, indolizinyl, indolyl, 3H-indolyl, isobenzofuranyl, isochromanyl, isoindazolyl, isoindolyl, isoquinolinyl, isothiazolyl, isoxazolyl, methylbenztriazolyl, methylfuranyl, methylimidazolyl, methylthiazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, phenanthridinyl, phenanthrolinyl, phenazinyl, phenothiazinyl, phenoxathinyl, phenoxazinyl, phthalazinyl, pteridinyl, purinyl, pyrazinyl, pyrazolyl, pyridazinyl, pyridooxazolyl, pyridoimidazolyl, pyridothiazolyl, pyridinyl, pyridinonyl, pyridyl, pyrimidinyl, 2H-pyrrolyl, pyrrolyl, quinazolinyl, quinolinyl, 4H-quinolizinyl, quinoxalinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, triazolopyrimidinyl, 1,2,3-triazolyl, 1,2,4-triazolyl, 1,2,5-triazolyl, and 1,3,4-triazolyl.

The term "hydroxyalkyl" means an alkyl group as defined above, where the alkyl group is substituted with one or more OH groups. Examples of hydroxyalkyl groups include HO—$CH_2$—, HO—$CH_2$—$CH_2$— and $CH_3$—CH(OH)—.

The term "cyano" as used herein means a substituent having a carbon atom joined to a nitrogen atom by a triple bond, i.e., C≡N.

As used herein, "oxo" is means a "=O" group.

As used herein, the phrase "pharmaceutically acceptable" refers to those compounds or tautomers thereof, or salts thereof, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds or tautomers thereof, wherein the parent compound or a tautomer thereof, is modified by making of the acid or base salts thereof of the parent compound or a tautomer thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound, or a tautomer thereof, formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present disclosure can be synthesized from the parent compound or a tautomer thereof that contains a basic or acidic moiety by conventional chemical methods. Generally, such pharmaceutically acceptable salts can be prepared by reacting the free acid or base forms of these compounds or tautomers thereof with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., USA, p. 1445 (1990).

As used herein, "stable compound" and "stable structure" are meant to indicate a compound that is sufficiently robust to survive isolation to a useful degree of purity from a reaction mixture, and formulation into an efficacious therapeutic agent.

As used herein, the term "treating" means to provide a therapeutic intervention to cure or ameliorate an infection. In some embodiments, "treating" refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

As used herein, the term "preventing", as used herein means, to completely or almost completely stop an infection from occurring, for example when the patient or subject is predisposed to an infection or at risk of contracting an infection. Preventing can also include inhibiting, i.e., arresting the development, of an infection.

As used herein, the term "reducing the risk of", as used herein, means to lower the likelihood or probability of an infection occurring, for example when the patient or subject is predisposed to an infection or at risk of contracting an infection.

As used herein, "unsaturated" refers to compounds having at least one degree of unsaturation (e.g., at least one multiple bond) and includes partially and fully unsaturated compounds.

As used herein, the term "effective amount" refers to an amount of a compound or a tautomer thereof, or a pharmaceutically acceptable salt of said compound or tautomer (including combinations of compounds and/or tautomers thereof, and/or pharmaceutically acceptable salts of said compound or tautomer) of the present disclosure that is effective when administered alone or in combination as an antimicrobial agent. For example, an effective amount refers to an amount of the compound or tautomer thereof, or a pharmaceutically acceptable salt said compound or tautomer that is present in a composition, a formulation or on a medical device given to a recipient patient or subject sufficient to elicit biological activity, for example, anti-infective activity, such as e.g., anti-microbial activity, anti-bacterial activity, anti-fungal activity, anti-viral activity, or anti-parasitic activity.

The term "prophylactically effective amount" means an amount of a compound or a tautomer of said compound or tautomer, or a pharmaceutically acceptable salt of said compound or tautomer (including combinations of compounds and/or tautomers thereof, and/or pharmaceutically acceptable salts thereof), of the present disclosure that is effective prophylactically when administered alone or in combination as an antimicrobial agent. For example, a prophylactically effective amount refers to an amount of the compound or tautomer thereof, or a pharmaceutically acceptable salt of said compound or tautomer that is present in a composition, a formulation, or on a medical device given to a recipient patient or subject sufficient to prevent or reduce the risk of an infection due to a surgical procedure or an invasive medical procedure.

In the specification, the singular forms also include the plural, unless the context clearly dictates otherwise. Unless defined otherwise, all technical and scientific terms used herein have the same meaning as commonly understood by one of ordinary skill in the art to which this disclosure belongs. In the case of conflict, the present specification will control. As used herein, "mammal" refers to human and non-human patients.

As used herein, the term ESBL is extended spectrum beta-lactamase. The term KPC is *Klebsiella pneumoniae* carbapenemase.

As used herein, the term acute bacterial skin and skin structure infection (ABSSSI) encompasses complicated skin and skin structure infections (cSSSI) and complication skin and soft tissue infections (cSSTI), which have been used interchangeably. The terms uncomplicated skin and skin structure infections (uCSSSI) and uncomplicated skin and soft tissue infections (uCSSTI) have been used interchangeably.

As used herein, the term "spp." is the abbreviation for species.

As used herein, the term "formulae of the disclosure" or "formulae disclosed herein" includes one or more of the Formulae: (I), (Ia), (Ia-1), (Ia-2), (Ib-a), (Ib), (Ia-3), (Ic), (Ic-1), (Id), (Ie), (If), (Ig). (Ie-1), (Ih), (Ii), (Ij), and (Ik).

As used herein, the term "compound of the disclosure" or "compound disclosed herein" includes one or more compounds of the formulae of the disclosure or a compound explicitly disclosed herein.

All percentages and ratios used herein, unless otherwise indicated, are by weight.

Throughout the description, where compositions are described as having, including, or comprising specific components, or where processes are described as having, including, or comprising specific process steps, it is contemplated that compositions of the present disclosure also consist essentially of, or consist of, the recited components, and that the processes of the present disclosure also consist essentially of, or consist of, the recited processing steps. Further, it should be understood that the order of steps or order for performing certain actions are immaterial so long as the invention remains operable. Moreover, two or more steps or actions can be conducted simultaneously.

2. Compounds of the Disclosure

In some embodiments, provided herein is a compound of Formula (I):

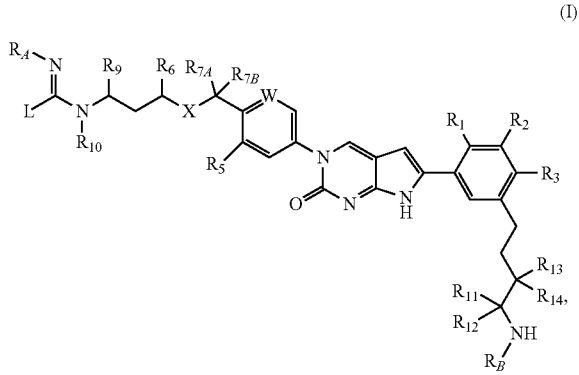

(I)

or a tautomer thereof or a pharmaceutically acceptable salt of the compound or tautomer, wherein:

$R_1$ is selected from H, halo, and $C_{1-4}$ alkoxy;

$R_2$ is selected from H, halo, $C_{1-6}$ alkyl, $C_{1-4}$ haloalkyl, and $OR^{a1}$;

$R_3$ is selected from H, $C_{1-6}$ alkyl, $C_{1-4}$ haloalkyl, and $C(O)OR^{a1}$;

W is selected from N and $CR_4$;

$R_4$ is selected from H, halo, $OR^{a2}$, $SR^{a2}$, 5-6 membered heterocycloalkyl, $S(O)_2R^{b2}$, $C_{1-6}$ alkyl, and $C_{2-6}$ alkenyl, wherein the $C_{1-6}$ alkyl is optionally substituted with a substituent selected from $OR^{a2}$;

$R_5$ is selected from H, halo, $C_{1-6}$ alkyl, and $C_{2-6}$ alkenyl, wherein the $C_{1-6}$ alkyl is optionally substituted with a substituent selected from $OR^{a2}$;

$R_6$ is selected from H, $C_{1-6}$ alkyl, $C_{3-5}$ cycloalkyl, and $C_{2-6}$ alkenyl, wherein the $C_{1-6}$ alkyl is optionally substituted with a substituent selected from $OR^{a3}$, $SR^{a3}$, and $NR^{c3}R^{d3}$;

$R_{7A}$ is selected from H, $C_{1-6}$ alkyl, $C_{1-4}$ haloalkyl, and $C_{2-6}$ alkenyl, wherein the $C_{1-6}$ alkyl is optionally substituted with a substituent selected from $OR^{a3}$ and $SR^{a3}$;

$R_{7B}$ is H; or $R_{7A}$ and $R_{7B}$ together with the carbon atom to which they are attached form a group selected from oxo, and $C_{3-6}$ cycloalkyl; or $R_6$ and $R_{7A}$ together with the carbon atoms to which they are attached and the X atom connecting the two carbon atoms form a 5- to 6-membered heterocycloalkyl containing 1-3 heteroatoms selected from N, O and S;

X is selected from O and $NR_8$;

$R_8$ is selected from H, $C_{1-6}$ alkyl, and $C_{1-4}$ haloalkyl, wherein the $C_{1-6}$ alkyl is optionally substituted with $R_{8A}$;

$R_{8A}$ is selected from $OR^{a3}$ and 5- to 6-membered heteroaryl, wherein the 5- to 6-membered heteroaryl is optionally substituted with one or two $C_{1-6}$ alkyl;

$R_9$ is selected from H, $C_{2-4}$ alkenyl, $C_{1-4}$ haloalkyl and $C_{1-4}$ alkyl optionally substituted with a substituent selected from amino, $C_{1-4}$ alkoxy, $C_{3-5}$ cycloalkyl, and 3-to 6-membered heterocycloalkyl;

$R_{10}$ is selected from H and $C_{2-6}$ alkenyl;

$R_A$ is selected from H and $C_{1-6}$ alkyl;

L is selected from $C_{1-6}$ alkyl and $C_{2-6}$ alkenyl, wherein the $C_{1-6}$ alkyl is optionally substituted with 1, 2, or 3 substituents independently selected from halo, $OR^{a4}$, $SR^{a4}$, and Z;

$R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with 1, 2, or 3 substituents independently selected from CN, $OR^{a5}$, $SR^{a5}$, $C(O)NR^{c5}R^{d5}$, $NR^{c5}R^{d5}$, and $S(O)_2R^{b5}$;

$R_{12}$ is selected from H and $C_{1-6}$ alkyl; or $R_{11}$ and $R_{12}$ together with the carbon atom to which they are attached form a $C_{3-5}$ cycloalkyl;

$R_{13}$ is selected from H, halo, and $C_{1-6}$ alkyl;

$R_{14}$ is selected from H, halo, and $C_{1-6}$ alkyl; and $R_B$ is selected from H and $C(=NR^{e5})R^{b5}$; or $R_{11}$ and $R_B$ together with the carbon atom to which $R_{11}$ is attached and the nitrogen atom to which $R_B$ is attached form a 5- to 6-membered heterocycloalkyl containing 1-3 heteroatoms selected from N, O and S, wherein the 5- to 6-membered heterocycloalkyl is optionally substituted with oxo;

each $R^{a1}$, $R^{a2}$, $R^{a3}$, $R^{a4}$, $R^{a5}$, $R^{b2}$, $R^{b5}$, $R^{c3}$, $R^{d3}$, $R^{c5}$, and $R^{d5}$ is independently selected from H, $C_{1-6}$ alkyl, $C_{1-4}$ haloalkyl, and 5-membered heteroaryl;

$R^{e5}$ is selected from H and $C_{1-4}$ alkyl; and Z is $-O(CH_2CH_2O)CH_3$.

In some embodiments, the present application provides a compound of Formula (II):

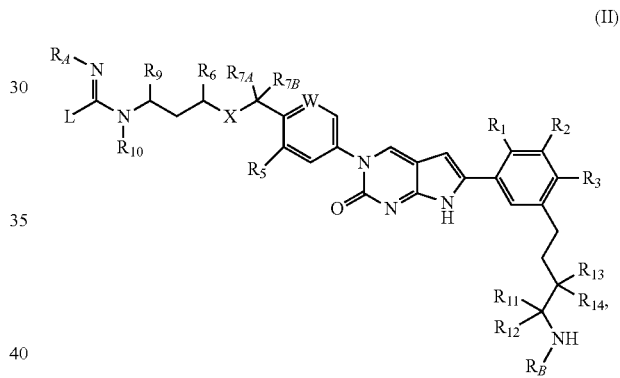

(II)

or tautomer thereof or a pharmaceutically acceptable salt of the compound or tautomer, wherein:

$R_1$ is selected from H and halo;

$R_2$ is selected from H, halo, $C_{1-6}$ alkyl, $C_{1-4}$ haloalkyl, and $OR^{a1}$;

$R_3$ is selected from H, $C_{1-6}$ alkyl, $C_{1-4}$ haloalkyl, and $C(O)OR^{a1}$;

W is selected from N and $CR_4$;

$R_4$ is selected from H, halo, $C_{1-6}$ alkyl, $OR^{a2}$, $SR^{a2}$, 5-6 membered heterocycloalkyl, and $S(O)_2R^{b2}$;

$R_5$ is selected from H and halo;

$R_6$ is selected from H, $C_{1-6}$ alkyl, $C_{3-5}$ cycloalkyl, and $C_{2-6}$ alkenyl, wherein the $C_{1-6}$ alkyl is optionally substituted with a substituent selected from $OR^{a3}$, $SR^{a3}$, and $NR^{c3}R^{d3}$;

$R_{7A}$ is selected from H, $C_{1-6}$ alkyl, $C_{1-4}$ haloalkyl, and $C_{2-6}$ alkenyl, wherein the $C_{1-6}$ alkyl is optionally substituted with a substituent selected from $OR^{a3}$, and $SR^{a3}$;

$R_{7B}$ is H; or $R_{7A}$ and $R_{7B}$ together with the carbon atom to which they are attached form a group selected from oxo and $C_{3-6}$ cyclopropyl; or $R_6$ and $R_{7A}$ together with the carbon atoms to which they are attached and the X atom connecting the two carbon atoms form a 5- to 6-membered heterocycloalkyl containing 1-3 heteroatoms independently selected from N, O and S, wherein the 5- to 6-membered heterocycloalkyl is optionally substituted with a substituent selected from $C(=NR^{e3})R^{b3}$, and $NR^{c3}R^{d3}$;

X is selected from O and $NR_8$;

$R_8$ is selected from H, $C_{1-6}$ alkyl, and $C_{1-4}$ haloalkyl, wherein the $C_{1-6}$ alkyl is optionally substituted with $R_{8A}$;

$R_{8A}$ is selected from 5- to 6-membered heteroaryl, and $OR^{a3}$, wherein the 5- to 6-membered heteroaryl is optionally substituted with 1, or 2 $C_{1-6}$ alkyl;

$R_9$ is selected from H, $C_{2-4}$ alkenyl, $C_{1-4}$ haloalkyl and $C_{1-4}$ alkyl optionally substituted with a substituent selected from amino, $C_{1-4}$ alkoxy, $C_{3-5}$ cycloalkyl, and 3-to 6-membered heterocycloalkyl;

$R_{10}$ is selected from H and $C_{2-6}$ alkenyl;

$R_4$ is selected from H and $C_{1-6}$ alkyl;

L is selected from $C_{1-6}$ alkyl and $C_{2-6}$ alkenyl, wherein the $C_{1-6}$ alkyl is optionally substituted with 1, 2, or 3 substituents independently selected from halo, $OR^{a4}$, and $SR^{a4}$;

$R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with 1, 2, or 3 substituents independently selected from CN, $OR^{a5}$, $SR^{a5}$, $C(O)NR^{c5}R^{d5}$, $NR^{c5}R^{d5}$, and $S(O)_2R^{b5}$;

$R_{12}$ is selected from H and $C_{1-6}$ alkyl; or $R_{11}$ and $R_{12}$ together with the carbon atom to which they are attached form a $C_{3-5}$ cycloalkyl;

$R_{13}$ is selected from H, halo, and $C_{1-6}$ alkyl;

$R_{14}$ is selected from H, halo, and $C_{1-6}$ alkyl; and $R_B$ is selected from H and $C(=NR^{e5})R^{b5}$; or $R_{11}$ and $R_B$ together with the carbon atom to which $R_{11}$ is attached and the nitrogen atom to which $R_B$ is attached form a 5- to 6-membered heterocycloalkyl containing 1-3 heteroatoms selected from N, O and S, wherein the 5- to 6-membered heterocycloalkyl is optionally substituted with oxo;

each $R^{a1}$, $R^{a2}$, $R^{a3}$, $R^{a4}$, $R^{a5}$, $R^{b2}$, $R^{b3}$, $R^{b5}$, $R^{c3}$, $R^{d3}$, $R^{c5}$, and $R^{d5}$ is independently selected from H, $C_{1-6}$ alkyl, $C_{1-4}$ haloalkyl, and 5-membered heteroaryl; and each $R^{e3}$ and $R^{e5}$ is independently selected from H and $C_{1-4}$ alkyl.

In some embodiments of Formula (I) or Formula (II), $R_1$ is halo. In some embodiments, $R_1$ is selected from H and fluoro. In some embodiments, $R_1$ is fluoro. In some embodiments, $R_1$ is H.

In some embodiments of Formula (I), $R_1$ is $C_{1-4}$ alkoxy. For example, $R_1$ can be methoxy.

In some embodiments of Formula (I) or Formula (II), $R_2$ is selected from H, halo, $C_{1-4}$ haloalkyl, and $C_{1-4}$ haloalkoxy. In some embodiments, $R_2$ is halo. In some embodiments, $R_2$ is $C_{1-4}$ haloalkyl. In some embodiments, $R_2$ is $C_{1-4}$ haloalkoxy. In some embodiments, $R_2$ is selected from halo, $C_{1-4}$ haloalkyl, and $C_{1-4}$ haloalkoxy. In some embodiments, $R_2$ is selected from H, trifluoromethoxy, trifluoromethyl and chloro. In some embodiments, $R_2$ is selected from trifluoromethoxy, trifluoromethyl and chloro. In some embodiments, $R_2$ is trifluoromethoxy. In some embodiments, $R_2$ is trifluoromethyl. In some embodiments, $R_2$ is chloro. In some embodiments, $R_2$ is H. In some embodiments of Formula (I) or Formula (II), $R_1$ is halo and $R_2$ is halo. In some embodiments, $R_1$ is fluoro and $R_2$ is chloro. In some embodiments, $R_1$ is fluoro and $R_2$ is trifluoromethoxy. In some embodiments, $R_1$ is fluoro and $R_2$ is trifluoromethyl. In some embodiments, $R_1$ is H and $R_2$ is trifluoromethyl.

In some embodiments of Formula (I) or Formula (II), $R_1$ is H, $R_2$ is H, and $R_3$ is not H.

In some embodiments of Formula (I) or Formula (II), $R_3$ is selected from H, $C_{1-4}$ haloalkyl, and $C(O)OR^{a1}$. In some embodiments, $R_3$ is selected from H, $C_{1-4}$ haloalkyl, and $C(O)C_{1-4}$ alkoxy. In some embodiments, $R_3$ is selected from H, trifluoromethyl, and $C(=O)$(methoxy). In some embodiments, $R_3$ is trifluoromethyl. In some embodiments, $R_3$ is $C(=O)$(methoxy). In some embodiments, $R_3$ is H.

In some embodiments of Formula (I) or Formula (II), $R_1$ is H, $R_2$ is H, and $R_3$ is trifluoromethyl. In some embodiments, $R_1$ is H, $R_2$ is H, and $R_3$ is $C(=O)$(methoxy).

In some embodiments of Formula (I) or Formula (II), W is N.

In some embodiments of Formula (I) or Formula (II), W is $CR_4$.

In some embodiments of Formula (I) or Formula (II), $R_4$ is selected from H, halo, $C_{1-6}$ alkyl, $C_{1-4}$ alkoxy, $C_{1-4}$ haloalkoxy, $S(C_{1-4}$ alkyl), 6-membered heterocycloalkyl, and $S(O)_2$ $C_{1-4}$ alkyl. In some embodiments, $R_4$ is selected from halo, $C_{1-6}$ alkyl, $C_{1-4}$ alkoxy, $C_{1-4}$ haloalkoxy, $S(C_{1-4}$ alkyl), 6-membered heterocycloalkyl, and $S(O)_2$ $C_{1-4}$ alkyl. In some embodiments, $R_4$ is halo. In some embodiments, $R_4$ is $C_{1-4}$ alkoxy. In some embodiments, $R_4$ is $C_{1-4}$ haloalkoxy. In some embodiments, $R_4$ is $S(C_{1-4}$ alkyl). In some embodiments, $R_4$ is 6-membered heterocycloalkyl. In some embodiments, $R_4$ is $S(O)_2$ $C_{1-4}$ alkyl. In some embodiments, $R_4$ is selected from H, fluoro, chloro, methylthio, methoxy, methyl, $S(=O)_2$(methyl), trifluoromethoxy, and N-morpholino. In some embodiments, $R_4$ is selected from fluoro, chloro, methylthio, methoxy, methyl, $S(=O)_2$(methyl), trifluoromethoxy, and N-morpholino. In some embodiments, $R_4$ is fluoro. In some embodiments, $R_4$ is chloro. In some embodiments, $R_4$ is methylthio. In some embodiments, $R_4$ is methoxy. In some embodiments, $R_4$ is methyl. In some embodiments, $R_4$ is $S(=O)_2$(methyl). In some embodiments, $R_4$ is trifluoromethoxy. In some embodiments, $R_4$ is N-morpholino. In some embodiments, $R_4$ is H. In some embodiments, $R_4$ is not H.

In some embodiments of Formula (I) or Formula (II), $R_5$ is halo. In some embodiments, $R_5$ is selected from H and F. In some embodiments, $R_5$ is F. In some embodiments, $R_5$ is H.

In some embodiments of Formula (I) or Formula (II), $R_5$ is halo and $R_4$ is selected from halo, $S(C_{1-4}$ alkyl), and 6-membered heterocycloalkyl. In some embodiments, $R_5$ is halo, and $R_4$ is $S(C_{1-4}$ alkyl). In some embodiments, $R_5$ is fluoro and $R_4$ is selected from fluoro, methylthio, and N-morpholino. In some embodiments, $R_5$ is fluoro and $R_4$ is methylthio. In some embodiments, $R_5$ is fluoro and $R_4$ is fluoro. In some embodiments, $R_5$ is fluoro and $R_4$ is 6-membered heterocycloalkyl. In some embodiments, $R_5$ is halo and $R_4$ is N-morpholino. In some embodiments, $R_5$ is fluoro and $R_4$ is N-morpholino. In some embodiments of Formula (I) or Formula (II), $R_6$ is selected from H, $C_{3-5}$ cycloalkyl, $C_{2-6}$ alkenyl, and $C_{1-6}$ alkyl optionally substituted with a substituent selected from hydroxyl, $C_{1-4}$ alkoxy, $S(C_{1-4}$ alkyl), amino, and NH(5-membered heteroaryl). In some embodiments, $R_6$ is selected from $C_{3-5}$ cycloalkyl, $C_{2-6}$ alkenyl, and $C_{1-6}$ alkyl optionally substituted with a substituent selected from hydroxyl, $C_{1-4}$ alkoxy, $S(C_{1-4}$ alkyl), amino, and NH(5-membered heteroaryl). In some embodiments, $R_6$ is $C_{3-5}$ cycloalkyl. In some embodiments, $R_6$ is $C_{2-6}$ alkenyl. In some embodiments, $R_6$ is $C_{1-6}$ alkyl optionally substituted with a substituent selected from hydroxyl, $C_{1-4}$ alkoxy, $S(C_{1-4}$ alkyl), amino, and NH(5-membered heteroaryl). In some embodiments, $R_6$ is selected from H, cyclopropyl, ethenyl, aminomethyl, hydroxymethyl, $CH_2NH$-imidazolyl, methylthiomethyl, and methoxymethyl. In some embodiments, $R_6$ is cyclopropyl. In some embodiments, $R_6$ is ethenyl. In some embodiments, $R_6$ is aminomethyl. In some embodiments, $R_6$ is hydroxymethyl. In some embodiments, $R_6$ is CH$_2$NH-imidazole. In some embodiments, $R_6$ is methylthiomethyl. In some embodiments, $R_6$ is methoxymethyl. In some embodiments, $R_6$ is selected from cyclopropyl, ethenyl, aminomethyl, hydroxymethyl, CH$_2$NH-imidazolyl, methylthiomethyl, and methoxymethyl. In some embodiments, $R_6$ is H.

In some embodiments of Formula (I) or Formula (II), $R_{7A}$ is selected from H, $C_{1-6}$ alkyl, $C_{1-4}$ haloalkyl, $C_{1-4}$ hydroxyalkyl, and $C_{2-6}$ alkenyl. In some embodiments, $R_{7A}$ is selected from $C_{1-6}$ alkyl, $C_{1-4}$ haloalkyl, $C_{1-4}$ hydroxyalkyl, and $C_{2-6}$ alkenyl. In some embodiments, $R_{7A}$ is $C_{1-6}$ alkyl. In some embodiments, $R_{7A}$ is $C_{1-4}$ haloalkyl. In some embodiments, $R_{7A}$ is $C_{1-4}$ hydroxyalkyl. In some embodiments, $R_{7A}$ is $C_{2-6}$ alkenyl. In some embodiments, $R_{7A}$ is selected from H, methyl, trifluoromethyl, hydroxymethyl, difluoromethyl, and ethenyl. In some embodiments, $R_{7A}$ is selected from methyl, trifluoromethyl, hydroxymethyl, difluoromethyl, and ethenyl. In some embodiments, $R_{7A}$ is methyl. In some embodiments, $R_{7A}$ is trifluoromethyl. In some embodiments, $R_{7A}$ is hydroxymethyl. In some embodiments, $R_{7A}$ difluoromethyl. In some embodiments, $R_{7A}$ is ethenyl. In some embodiments, $R_{7A}$ is H.

In some embodiments of Formula (I) or Formula (II), $R_{7A}$ and $R_{7B}$ together with the carbon atom to which they are attached form oxo. In some embodiments, $R_{7A}$ and $R_{7B}$ together with the carbon atom to which they are attached form $C_{3-6}$ cyclopropyl.

In some embodiments of Formula (I) or Formula (II), $R_6$ is selected from $C_{2-6}$ alkenyl, $C_{1-6}$ hydroxyalkyl, and $C_{1-6}$ alkylene-NH(5-membered heteroaryl), and $R_{7A}$ is $C_{1-6}$ alkyl. In some embodiments, $R_6$ is selected from ethenyl, hydroxymethyl, and CH$_2$NH-imidazole, and $R_{7A}$ is $C_{1-6}$ alkyl. In some embodiments, $R_6$ is ethenyl and $R_{7A}$ is methyl. In some embodiments, $R_6$ is hydroxymethyl, and $R_{7A}$ is methyl. In some embodiments, $R_6$ is CH$_2$NH-imidazole, and $R_{7A}$ is methyl. In some embodiments, $R_6$ is H and $R_{7A}$ is $C_{1-6}$ alkyl. In some embodiments, $R_6$ is H and $R_{7A}$ is methyl.

In some embodiments of Formula (I) or Formula (II), the carbon atom to which $R_6$ is attached is in (S) configuration according to Cahn-Ingold-Prelog nomenclature. In some embodiments, the carbon atom to which $R_6$ is attached is in (R) configuration according to Cahn-Ingold-Prelog nomenclature. In some embodiments, the stereochemistry at the carbon atom bound to $R_6$ is as shown below:

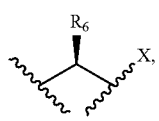

wherein x indicates a point of attachment to the X atom.
In some embodiments, the stereochemistry at the carbon atom bound to $R_6$ is as shown below:

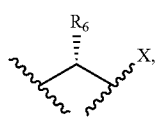

wherein x indicates a point of attachment to the X atom.
In some embodiments of Formula (I) or Formula (II), the carbon atom to which $R_{7A}$ is attached is in (S) configuration according to Cahn-Ingold-Prelog nomenclature. In some embodiments, the carbon atom to which $R_{7A}$ is attached is in (R) configuration according to Cahn-Ingold-Prelog nomenclature.

In some embodiments, the stereochemistry at the carbon atom bound to $R_{7A}$ is as shown below:

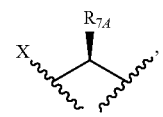

wherein x indicates a point of attachment to the X atom.
In some embodiments, the stereochemistry at the carbon atom bound to $R_{7A}$ is as shown below:

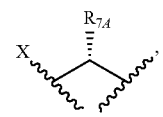

wherein x indicates a point of attachment to the X atom.
In some embodiments of Formula (I) or Formula (II), $R_6$ and $R_{7A}$ together with the carbon atoms to which they are attached and the X atom connecting the two carbon atoms form a 6-membered heterocycloalkyl containing 1-3 heteroatoms selected from N, O and S, wherein the 6-membered heterocycloalkyl is optionally substituted with a substituent selected from C(=NH)C$_{1-6}$ alkyl, and di(C$_{1-6}$ alkyl) amino.

In some embodiments of Formula (I) or Formula (II), $R_6$ and $R_{7A}$ together with the carbon atoms to which they are attached and the X atom connecting the two carbon atoms form a ring of any one of the following formulae:

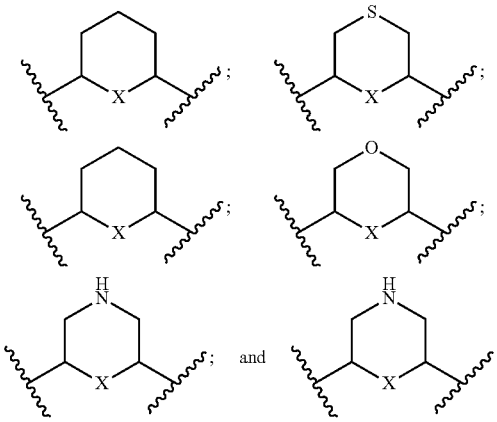

wherein any one of the formulae is optionally substituted with C(=NH)C$_{1-6}$ alkyl, or di(C$_{1-6}$ alkyl)amino.

In some embodiments of Formula (I) or Formula (II), $R_6$ and $R_{7A}$ together with the carbon atoms to which they are attached and the X atom connecting the two carbon atoms form a ring of the following formulae:

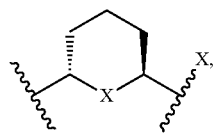

wherein x indicates a point of attachment to the ring containing the W atom and substituted with $R_5$.

In some embodiments of Formula (I) or Formula (II), $R_6$ and $R_{7A}$ together with the carbon atoms to which they are attached and the X atom connecting the two carbon atoms form a ring of any one of the following formulae:

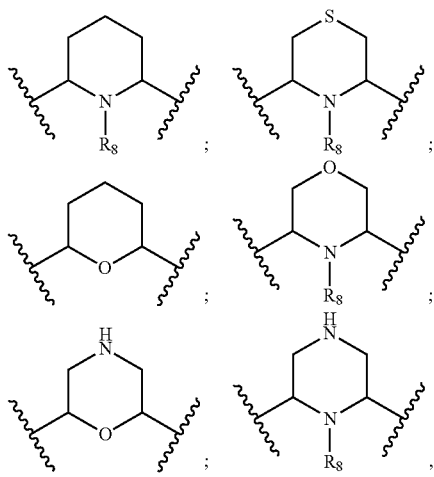

wherein any one of the formulae is optionally substituted with C(=NH)methyl, or dimethylamino.

In some embodiments of Formula (I) or Formula (II), $R_6$ and $R_{7A}$ together with the carbon atoms to which they are attached and the X atom connecting the two carbon atoms form a ring of any one of the following formulae:

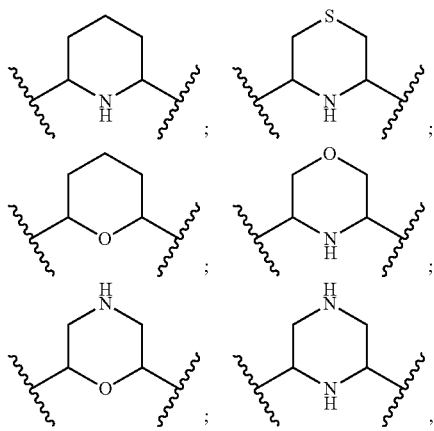

wherein any one of the formulae is optionally substituted with C(=NH)methyl, or dimethylamino.

In some embodiments of Formula (I) or Formula (II), $R_6$ and $R_{7A}$ together with the carbon atoms to which they are attached and the X atom connecting the two carbon atoms form a ring of formula:

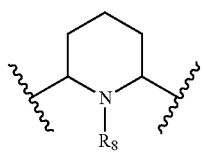

In some embodiments of Formula (I) or Formula (II), $R_6$ and $R_{7A}$ together with the carbon atoms to which they are attached and the X atom connecting the two carbon atoms form a ring of formula:

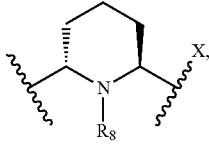

wherein x indicates a point of attachment to the ring containing the W atom and substituted with $R_5$.

In some embodiments of Formula (I) or Formula (II), $R_6$ and $R_{7A}$ together with the carbon atoms to which they are attached and the X atom connecting the two carbon atoms form a ring of formula:

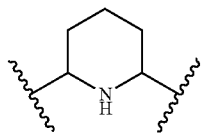

In some embodiments of Formula (I) or Formula (II), $R_6$ and $R_{7A}$ together with the carbon atoms to which they are attached and the X atom connecting the two carbon atoms form a ring of formula:

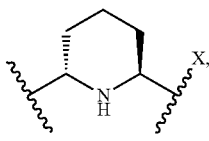

wherein x indicates a point of attachment to the ring containing the W atom and substituted with $R_5$.

In some embodiments of Formula (I) or Formula (II), $R_6$ and $R_{7A}$ together with the carbon atoms to which they are attached and the X atom connecting the two carbon atoms form a ring of any one of the following formulae:

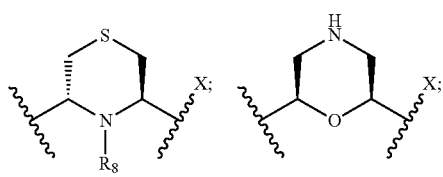

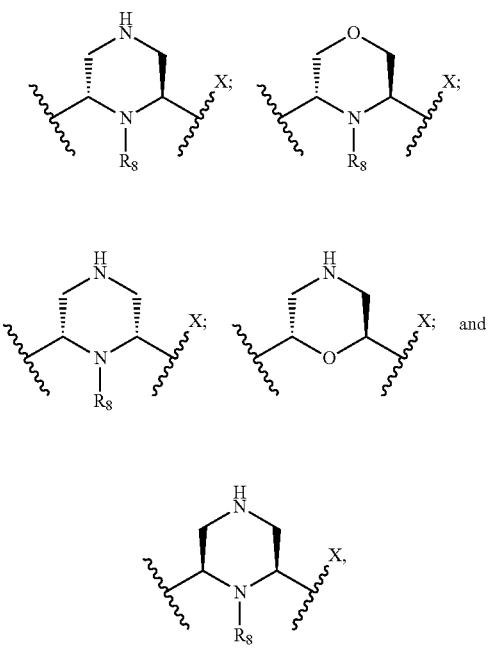

wherein x indicates a point of attachment to the ring containing the W atom and substituted with $R_5$.

In some embodiments of Formula (I) or Formula (II), $R_6$ and $R_{7A}$ together with the carbon atoms to which they are attached and the X atom connecting the two carbon atoms form a ring of any one of the following formulae:

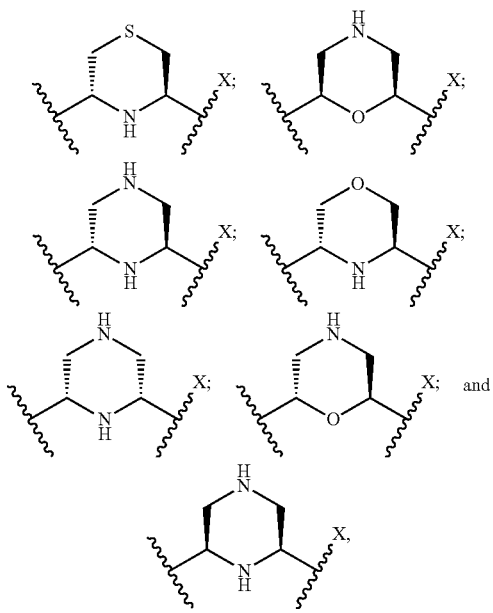

wherein x indicates a point of attachment to the ring containing the W atom and substituted with $R_5$.

In some embodiments of Formula (I) or Formula (II), $R_6$ and $R_{7A}$ together with the carbon atoms to which they are attached and the X atom connecting the two carbon atoms form a ring of any one of the following formulae:

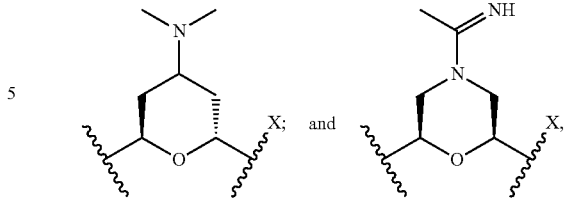

wherein x indicates a point of attachment to the ring containing the W atom and substituted with $R_5$.

In some embodiments of Formula (I) or Formula (II), X is O. In some embodiments of Formula (I) or Formula (II), X is $NR_8$.

In some embodiments of Formula (I) or Formula (II), $R_8$ is selected from H, $C_{1-6}$ alkyl, $C_{1-4}$ haloalkyl, $C_{1-4}$ hydroxyalkyl, $C_{1-6}$ alkyl substituted with $C_{1-6}$ alkoxy, and $C_{1-6}$ alkyl substituted with 5- to 6-membered heteroaryl, wherein the 5- to 6-membered heteroaryl is optionally substituted with one or two $C_{1-6}$ alkyl. In some embodiments, $R_8$ is $C_{1-6}$ alkyl. In some embodiments, $R_8$ is $C_{1-4}$ haloalkyl. In some embodiments, $R_8$ is $C_{1-4}$ hydroxyalkyl. In some embodiments, $R_8$ is $C_{1-6}$ alkyl substituted with $C_{1-6}$ alkoxy. In some embodiments, $R_8$ is $C_{1-6}$ alkyl substituted with 5- to 6-membered heteroaryl, wherein the 5- to 6-membered heteroaryl is optionally substituted with 1, or 2 $C_{1-6}$ alkyl.

In some embodiments of Formula (I), $R_8$ is selected from H, methyl, tert-butyl, 2-fluoroethenyl, 3-fluoropropyl, 2-methoxyethyl, 3-hydroxypropyl, 2-methyl-3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl.

In some embodiments of Formula (I) or Formula (II), $R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl.

In some embodiments of Formula (I) or Formula (II), $R_8$ is selected from any one of the following formulae:

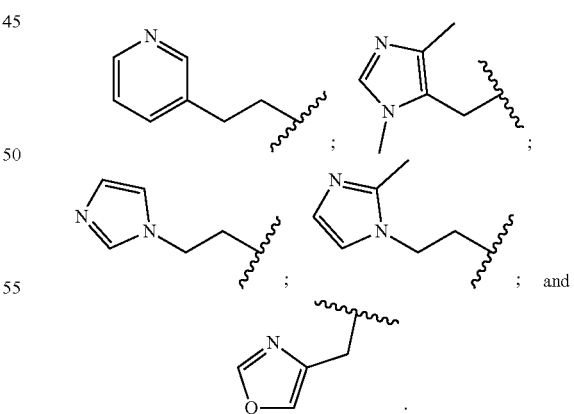

In some embodiments of Formula (I) or Formula (II), $R_8$ is selected from methyl, 3-fluoropropyl, 2-methoxyethyl, and 3-hydroxypropyl. In some embodiments, $R_8$ is methyl. In some embodiments, $R_8$ is 3-fluoropropyl. In some embodiments, $R_8$ is 2-methoxyethyl. In some embodiments, $R_8$ is 3-hydroxypropyl. In some embodiments, $R_8$ is H.

In some embodiments of Formula (I) or Formula (II), $R_9$ is selected from H and $C_{1-6}$ alkyl. In some embodiments, $R_9$ is H. In some embodiments, $R_9$ is $C_{1-6}$ alkyl. In some embodiments, $R_9$ is methyl. In some embodiments, $R_9$ is ethyl. In some embodiments, $R_9$ is n-propyl. In some embodiments, $R_9$ is i-propyl.

In some embodiments of Formula (I) or Formula (II), the carbon atom to which $R_9$ is attached is in (S) configuration according to Cahn-Ingold-Prelog nomenclature. In some embodiments, the carbon atom to which $R_9$ is attached is in (R) configuration according to Cahn-Ingold-Prelog nomenclature.

In some embodiments, the stereochemistry at the carbon atom bound to $R_9$ is as shown below:

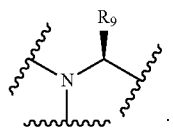

In some embodiments, the stereochemistry at the carbon atom bound to $R_9$ is as shown below:

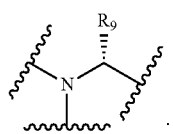

In some embodiments of Formula (I) or Formula (II), $R_{10}$ is H. In some embodiments, $R_{10}$ is $C_{2-6}$ alkenyl. In some embodiments, $R_{10}$ is allyl.

In some embodiments of Formula (I) or Formula (II), $R_4$ is selected from H and methyl. In some embodiments, $R_4$ is H.

In some embodiments of Formula (I), L is selected from $C_{1-6}$ alkyl, $C_{1-6}$ haloalkyl, $C_{1-6}$ hydroxyalkyl, $C_{2-6}$ alkenyl, and —O(CH$_2$CH$_2$O)CH$_3$, wherein the $C_{1-6}$ alkyl is optionally substituted with a substituent selected from $C_{1-6}$ alkoxy, and S($C_{1-6}$ alkyl).

In some embodiments of Formula (I) or Formula (II), L is selected from $C_{1-6}$ alkyl, $C_{1-6}$ haloalkyl, $C_{1-6}$ hydroxyalkyl, and $C_{2-6}$ alkenyl, wherein the $C_{1-6}$ alkyl is optionally substituted with a substituent selected from $C_{1-6}$ alkoxy, and S($C_{1-6}$ alkyl). In some embodiments, L is $C_{1-6}$ alkyl. In some embodiments, L is not $C_{1-6}$ alkyl. In some embodiments, L is $C_{1-6}$ haloalkyl. In some embodiments, L is not $C_{1-6}$ haloalkyl. In some embodiments, L is $C_{1-6}$ hydroxyalkyl. In some embodiments, L is $C_{2-6}$ alkenyl. In some embodiments, L is $C_{1-6}$ alkyl substituted with $C_{1-6}$ alkoxy. In some embodiments, L is $C_{1-6}$ alkyl substituted with S($C_{1-6}$ alkyl). In some embodiments, L is selected from $C_{1-6}$ hydroxyalkyl, and $C_{1-6}$ alkyl substituted with a substituent selected from $C_{1-6}$ alkoxy, and S($C_{1-6}$ alkyl). In some embodiments, L is selected from methyl, fluoromethyl, 2,2,2-trifluoroethyl, trichloromethyl, methylthiomethyl, methoxymethyl, hydroxyethyl, ethoxyethyl, and allyl. In some embodiments, L is fluoromethyl. In some embodiments, L is 2,2,2-trifluoroethyl. In some embodiments, L is trichloromethyl. In some embodiments, L is methylthiomethyl. In some embodiments, L is methoxymethyl. In some embodiments, L is hydroxyethyl. In some embodiments, L is ethoxyethyl. In some embodiments, L is allyl. In some embodiments, L is selected from 2,2,2-trifluoroethyl, trichloromethyl, methylthiomethyl, methoxymethyl, hydroxyethyl, and ethoxyethyl. In some embodiments, L is selected from methylthiomethyl, methoxymethyl, hydroxyethyl, and ethoxyethyl. In some embodiments, L is methyl. In some embodiments, L is not methyl. In some embodiments, L is not 3-chloropropyl, ethyl, isopropyl, fluoromethyl, or chloromethyl. In some embodiments, L is not 3-chloropropyl, fluoromethyl, or chloromethyl. In some embodiments, L is not ethyl or isopropyl.

In some embodiments of Formula (I) or Formula (II), $R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from CN, OH, $C_{1-6}$ alkoxy, S($C_{1-6}$ alkyl), amino, C(O)NH$_2$, and S(O)$_2$C$_{1-6}$ alkyl. In some embodiments, $R_{11}$ is selected from $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from OH, $C_{1-6}$ alkoxy, S(O)$_2$C$_{1-6}$ alkyl, and S($C_{1-6}$ alkyl). In some embodiments, $R_{11}$ is $C_{1-6}$ alkyl. In some embodiments, $R_{11}$ is not $C_{1-6}$ alkyl. In some embodiments, $R_{11}$ is $C_{3-5}$ cycloalkyl. In some embodiments, $R_{11}$ is $C_{1-4}$ haloalkyl. In some embodiments, $R_{11}$ is $C_{2-6}$ alkenyl. In some embodiments, $R_{11}$ is $C_{1-6}$ alkyl substituted with a substituent selected from OH, $C_{1-6}$ alkoxy, S(O)$_2$C$_{1-6}$ alkyl, and S($C_{1-6}$ alkyl). In some embodiments, $R_{11}$ is $C_{1-6}$ alkyl substituted with $C_{1-6}$ alkoxy. In some embodiments, $R_{11}$ is selected from $C_{1-6}$ alkyl, $C_{3-5}$ cycloalkyl, $C_{2-6}$ alkenyl, and $C_{1-6}$ alkyl substituted with $C_{1-6}$ alkoxy. In some embodiments, $R_{11}$ is selected from H, methyl, ethenyl, fluoromethyl, difluoromethyl, trifluoromethyl, hydroxymethyl, methoxymethyl, methylthiomethyl, cyanomethyl, aminomethyl, cyclopropyl, CH$_2$S(O)$_2$CH$_3$, and CH$_2$C(O)NH$_2$. In some embodiments, $R_{11}$ is methyl. In some embodiments, $R_{11}$ is not methyl. In some embodiments, $R_{11}$ is ethenyl. In some embodiments, $R_{11}$ is fluoromethyl. In some embodiments, $R_{11}$ is difluoromethyl. In some embodiments, $R_{11}$ is trifluoromethyl. In some embodiments, $R_{11}$ is hydroxymethyl. In some embodiments, $R_{11}$ is methoxymethyl. In some embodiments, $R_{11}$ is methylthiomethyl. In some embodiments, $R_{11}$ is cyanomethyl. In some embodiments, $R_{11}$ is aminomethyl. In some embodiments, $R_{11}$ is cyclopropyl. In some embodiments, $R_{11}$ is CH$_2$S(O)$_2$CH$_3$. In some embodiments, $R_{11}$ is CH$_2$C(O)NH$_2$. In some embodiments, $R_{11}$ is selected from methyl, ethenyl, CH$_2$S(O)$_2$CH$_3$, methylthiomethyl, fluoromethyl, methoxymethyl, hydroxymethyl, and cyclopropyl. In some embodiments, $R_{11}$ is selected from methyl, cyclopropyl, ethenyl, and methoxymethyl.

In some embodiments of Formula (I) or Formula (II), the carbon atom to which $R_{11}$ is attached is in (S) configuration according to Cahn-Ingold-Prelog nomenclature. In some embodiments, the carbon atom to which $R_{11}$ is attached is in (R) configuration according to Cahn-Ingold-Prelog nomenclature.

In some embodiments, the stereochemistry at the carbon atom bound to $R_{11}$ is as shown below:

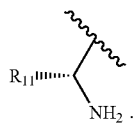

In some embodiments, the stereochemistry at the carbon atom bound to $R_{11}$ is as shown below:

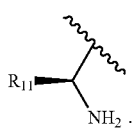

In some embodiments of Formula (I) or Formula (II), $R_{12}$ is selected from H and methyl. In some embodiments, $R_{12}$ is methyl. In some embodiments, $R_{12}$ is H.

In some embodiments of Formula (I) or Formula (II), $R_{11}$ and $R_{12}$ together with the carbon atom to which they are attached form a cyclopropyl ring. In some embodiments, $R_{11}$ is methyl and $R_{12}$ is methyl. In some embodiments of Formula (I) or Formula (II), $R_{13}$ is selected from H, fluoro, and methyl. In some embodiments, $R_{13}$ is fluoro. In some embodiments, $R_{13}$ is methyl. In some embodiments, $R_{13}$ is H.

In some embodiments of Formula (I) or Formula (II), $R_{14}$ is selected from H, fluoro, and methyl. In some embodiments, $R_{14}$ is fluoro. In some embodiments, $R_{14}$ is methyl. In some embodiments, $R_{14}$ is H.

In some embodiments of Formula (I) or Formula (II), $R_{13}$ is fluoro and $R_{14}$ is fluoro. In some embodiments, $R_{13}$ is methyl and $R_{14}$ is methyl.

In some embodiments of Formula (I) or Formula (II), $R_B$ is selected from H and C(=NH)CH$_3$. In some embodiments, $R_B$ is C(=NH)CH$_3$. In some embodiments, $R_B$ is H.

In some embodiments of Formula (I) or Formula (II), $R_{11}$ and $R_B$ together with the carbon atom to which $R_{11}$ is attached and the nitrogen atom to which $R_B$ is attached form a 6-membered heterocycloalkyl containing 1-3 heteroatoms selected from N and O, wherein the 6-membered heterocycloalkyl is optionally substituted with oxo.

In some embodiments of Formula (I) or Formula (II), $R_{11}$ and $R_B$ together with the carbon atom to which $R_{11}$ is attached and the nitrogen atom to which $R_B$ is attached form a ring of any one of the following formulae:

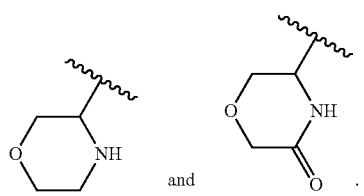 [SMILES: *C1COCCN1 ; *C1COCC(=O)N1]

In some embodiments of Formula (I) or Formula (II), $R_{11}$ and $R_B$ together with the carbon atom to which $R_{11}$ is attached and the nitrogen atom to which $R_B$ is attached form a ring of formula:

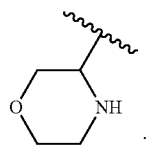

In Some Embodiments of Formula (I) or Formula (II)

$R_2$ is selected from H, halo, $C_{1-4}$ haloalkyl, and $C_{1-4}$ haloalkoxy;
$R_3$ is selected from H, $C_{1-4}$ haloalkyl, and C(O)$C_{1-4}$ alkoxy;
$R_4$ is selected from H, halo, $C_{1-6}$ alkyl, $C_{1-4}$ alkoxy, $C_{1-4}$ haloalkoxy, S($C_{1-4}$ alkyl), 6-membered heterocycloalkyl, and S(O)$_2$ $C_{1-4}$ alkyl;
$R_5$ is selected from H and fluoro;
$R_6$ is selected from H, $C_{3-5}$ cycloalkyl, $C_{2-6}$ alkenyl, and $C_{1-6}$ alkyl optionally substituted with a substituent selected from hydroxyl, $C_{1-4}$ alkoxy, S($C_{1-6}$ alkyl), amino, and NH(5-membered heteroaryl);
$R_{7A}$ is selected from H, $C_{1-6}$ alkyl, $C_{1-4}$ haloalkyl, $C_{1-4}$ hydroxyalkyl, and $C_{2-6}$ alkenyl;
$R_8$ is selected from H, $C_{1-6}$ alkyl, $C_{1-4}$ haloalkyl, $C_{1-4}$ hydroxyalkyl, $C_{1-6}$ alkyl substituted with $C_{1-6}$ alkoxy, and $C_{1-6}$ alkyl substituted with 5- to 6-membered heteroaryl, wherein the 5- to 6-membered heteroaryl is optionally substituted with 1, or 2 $C_{1-6}$ alkyl;
$R_9$ is selected from H, methyl, ethyl, n-propyl and i-propyl;
$R_{10}$ is selected from H and allyl;
$R_A$ is selected from H and methyl;
L is selected from $C_{1-6}$ alkyl, $C_{1-6}$ haloalkyl, $C_{1-6}$ hydroxyalkyl, and $C_{2-6}$ alkenyl, wherein the $C_{1-6}$ alkyl is optionally substituted with a substituent selected from $C_{1-6}$ alkoxy, and S($C_{1-6}$ alkyl);
$R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from CN, OH, $C_{1-6}$ alkoxy, S($C_{1-6}$ alkyl), amino, C(O)NH$_2$, and S(O)$_2C_{1-6}$ alkyl;
$R_{12}$ is selected from H and methyl;
$R_{13}$ is selected from H, fluoro, and methyl;
$R_{14}$ is selected from H, fluoro, and methyl; and
$R_B$ is selected from H and C(=NH)CH$_3$.

In Some Embodiments of Formula (I) or Formula (II)

$R_2$ is selected from H, halo, $C_{1-4}$ haloalkyl, and $C_{1-4}$ haloalkoxy;
$R_3$ is selected from H, $C_{1-4}$ haloalkyl, and C(O)$C_{1-4}$ alkoxy;
$R_4$ is selected from halo, $C_{1-6}$ alkyl, $C_{1-4}$ alkoxy, $C_{1-4}$ haloalkoxy, S($C_{1-4}$ alkyl), 6-membered heterocycloalkyl, and S(O)$_2$ $C_{1-4}$ alkyl;
$R_8$ is selected from H and fluoro;
$R_6$ is selected from H, $C_{3-5}$ cycloalkyl, $C_{2-6}$ alkenyl, and $C_{1-6}$ alkyl optionally substituted with a substituent selected from hydroxyl, $C_{1-4}$ alkoxy, S($C_{1-4}$ alkyl), amino, and NH(5-membered heteroaryl);
$R_{7A}$ is selected from H, $C_{1-6}$ alkyl, $C_{1-4}$ haloalkyl, $C_{1-4}$ hydroxyalkyl, and $C_{2-6}$ alkenyl;
$R_8$ is selected from H, $C_{1-6}$ alkyl, $C_{1-4}$ haloalkyl, $C_{1-4}$ hydroxyalkyl, $C_{1-6}$ alkyl substituted with $C_{1-6}$ alkoxy, and $C_{1-6}$ alkyl substituted with 5- to 6-membered heteroaryl, wherein the 5- to 6-membered heteroaryl is optionally substituted with 1, or 2 $C_{1-6}$ alkyl;
$R_9$ is selected from H, methyl, ethyl, n-propyl and i-propyl;
$R_{10}$ is selected from H and allyl;
$R_A$ is selected from H and methyl;
L is selected from $C_{1-6}$ alkyl, $C_{1-6}$ haloalkyl, $C_{1-6}$ hydroxyalkyl, and $C_{2-6}$ alkenyl, wherein the $C_{1-6}$ alkyl is optionally substituted with a substituent selected from $C_{1-6}$ alkoxy, and S($C_{1-6}$ alkyl);
$R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from CN, OH, C$_{1-6}$ alkoxy, S(C$_{1-6}$ alkyl), amino, C(O)NH$_2$, and S(O)$_2$C$_{1-6}$ alkyl;
R$_{12}$ is selected from H and methyl;
R$_{13}$ is selected from H, fluoro, and methyl;
R$_{14}$ is selected from H, fluoro, and methyl; and
R$_B$ is selected from H and C(=NH)CH$_3$.

In Some Embodiments of Formula (I) or Formula (II)

R$_2$ is selected from H, halo, C$_{1-4}$ haloalkyl, and C$_{1-4}$ haloalkoxy;
R$_3$ is selected from H, C$_{1-4}$ haloalkyl, and C(O)C$_{1-4}$ alkoxy;
R$_4$ is selected from H, halo, C$_{1-6}$ alkyl, C$_{1-4}$ alkoxy, C$_{1-4}$ haloalkoxy, S(C$_{1-4}$ alkyl), 6-membered heterocycloalkyl, and S(O)$_2$ C$_{1-4}$ alkyl;
R$_8$ is selected from H and fluoro;
R$_6$ and R$_{7A}$ together with the carbon atoms to which they are attached and the X atom connecting the two carbon atoms form a ring of any one of the following formulae:

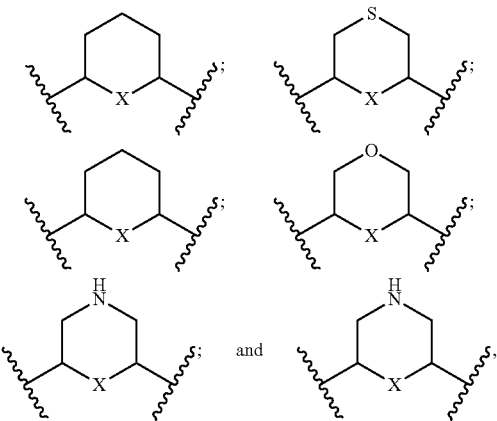

R$_8$ is selected from H, C$_{1-6}$ alkyl, C$_{1-4}$ haloalkyl, C$_{1-4}$ hydroxyalkyl, C$_{1-6}$ alkyl substituted with C$_{1-6}$ alkoxy, and C$_{1-6}$ alkyl substituted with 5- to 6-membered heteroaryl, wherein the 5- to 6-membered heteroaryl is optionally substituted with 1, or 2 C$_{1-6}$ alkyl;
R$_9$ is selected from H, methyl, ethyl, n-propyl and i-propyl;
R$_{10}$ is selected from H and allyl;
R$_A$ is selected from H and methyl;
L is selected from C$_{1-6}$ alkyl, C$_{1-6}$ haloalkyl, C$_{1-6}$ hydroxyalkyl, and C$_{2-6}$ alkenyl, wherein the C$_{1-6}$ alkyl is optionally substituted with a substituent selected from C$_{1-6}$ alkoxy, and S(C$_{1-6}$ alkyl);
R$_{11}$ is selected from H, C$_{1-6}$ alkyl, C$_{3-5}$ cycloalkyl, C$_{1-4}$ haloalkyl, and C$_{2-6}$ alkenyl, wherein the C$_{1-6}$ alkyl is optionally substituted with a substituent selected from CN, OH, C$_{1-6}$ alkoxy, S(C$_{1-6}$ alkyl), amino, C(O)NH$_2$, and S(O)$_2$C$_{1-6}$ alkyl;
R$_{12}$ is selected from H and methyl;
R$_{13}$ is selected from H, fluoro, and methyl;
R$_{14}$ is selected from H, fluoro, and methyl; and
R$_B$ is selected from H and C(=NH)CH$_3$.

In Some Embodiments of Formula (I) or Formula (II)

R$_2$ is selected from H, halo, C$_{1-4}$ haloalkyl, and C$_{1-4}$ haloalkoxy;
R$_3$ is selected from H, C$_{1-4}$ haloalkyl, and C(O)C$_{1-4}$ alkoxy;
R$_4$ is selected from halo, C$_{1-6}$ alkyl, C$_{1-4}$ alkoxy, C$_{1-4}$ haloalkoxy, S(C$_{1-4}$ alkyl), 6-membered heterocycloalkyl, and S(O)$_2$ C$_{1-4}$ alkyl;
R$_5$ is selected from H and fluoro;
R$_6$ and R$_{7A}$ together with the carbon atoms to which they are attached and the X atom connecting the two carbon atoms form a ring of any one of the following formulae:

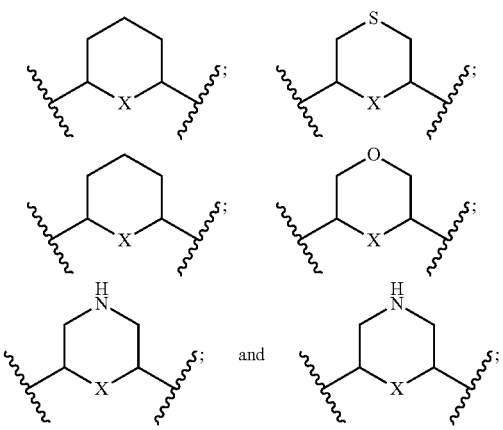

R$_8$ is selected from H, C$_{1-6}$ alkyl, C$_{1-4}$ haloalkyl, C$_{1-4}$ hydroxyalkyl, C$_{1-6}$ alkyl substituted with C$_{1-6}$ alkoxy, and C$_{1-6}$ alkyl substituted with 5- to 6-membered heteroaryl, wherein the 5- to 6-membered heteroaryl is optionally substituted with 1, or 2 C$_{1-6}$ alkyl;
R$_9$ is selected from H, methyl, ethyl, n-propyl and i-propyl;
R$_{10}$ is selected from H and allyl;
R$_A$ is selected from H and methyl;
L is selected from C$_{1-6}$ alkyl, C$_{1-6}$ haloalkyl, C$_{1-6}$ hydroxyalkyl, and C$_{2-6}$ alkenyl, wherein the C$_{1-6}$ alkyl is optionally substituted with a substituent selected from C$_{1-6}$ alkoxy and S(C$_{1-6}$ alkyl);
R$_{11}$ is selected from H, C$_{1-6}$ alkyl, C$_{3-5}$ cycloalkyl, C$_{1-4}$ haloalkyl, and C$_{2-6}$ alkenyl, wherein the C$_{1-6}$ alkyl is optionally substituted with a substituent selected from CN, OH, C$_{1-6}$ alkoxy, S(C$_{1-6}$ alkyl), amino, C(O)NH$_2$, and S(O)$_2$C$_{1-6}$ alkyl;
R$_{12}$ is selected from H and methyl;
R$_{13}$ is selected from H, fluoro, and methyl;
R$_{14}$ is selected from H, fluoro, and methyl; and
R$_B$ is selected from H and C(=NH)CH$_3$.

In Some Embodiments of Formula (I) or Formula (II)

R$_1$ is selected from H and fluoro;
R$_2$ is selected from H, trifluoromethoxy, trifluoromethyl, and chloro;
R$_3$ is selected from H, trifluoromethyl, and C(=O)(methoxy);
W is CR$_4$;
R$_4$ is selected from H, fluoro, chloro, methylthio, methoxy, methyl, S(=O)$_2$(methyl), trifluoromethoxy, and N-morpholino;
R$_5$ is selected from H and fluoro;
R$_6$ is selected from H, cyclopropyl, ethenyl, aminomethyl, hydroxymethyl, CH$_2$NH-imidazole, methylthiomethyl, and methoxymethyl;

$R_{7A}$ is selected from H, methyl, trifluoromethyl, hydroxymethyl, difluoromethyl, and ethenyl;
$R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl;
$R_9$ is selected from H and methyl;
$R_{10}$ is selected from H and allyl;
$R_A$ is selected from H and methyl;
L is selected from methyl, fluoromethyl, 2,2,2-trifluoroethyl, trichloromethyl, methylthiomethyl, methoxymethyl, hydroxyethyl, ethoxyethyl, and allyl;
$R_{11}$ is selected from H, methyl, ethenyl, fluoromethyl, difluoromethyl, trifluoromethyl, hydroxymethyl, methoxymethyl, methylthiomethyl, cyanomethyl, aminomethyl, cyclopropyl, $CH_2S(O)_2CH_3$, and $CH_2C(O)NH_2$;
$R_{12}$ is selected from H and methyl;
$R_{13}$ is selected from H, fluoro, and methyl;
$R_{14}$ is selected from H, fluoro, and methyl; and
$R_B$ is selected from H and C(=NH)CH$_3$.

In Some Embodiments of Formula (I) or Formula (II)

$R_1$ is selected from H and fluoro;
$R_2$ is selected from H, trifluoromethoxy, trifluoromethyl and chloro;
$R_3$ is selected from H, trifluoromethyl, and C(=O)(methoxy);
W is $CR_4$;
$R_4$ is selected from fluoro, chloro, methylthio, methoxy, methyl, S(=O)$_2$(methyl), trifluoromethoxy, and N-morpholino;
$R_5$ is selected from H and fluoro;
$R_6$ is selected from H, cyclopropyl, ethenyl, aminomethyl, hydroxymethyl, CH$_2$NH-imidazole, methylthiomethyl, and methoxymethyl;
$R_{7A}$ is selected from H, methyl, trifluoromethyl, hydroxymethyl, difluoromethyl, and ethenyl;
$R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl;
$R_9$ is selected from H and methyl;
$R_{10}$ is selected from H and allyl;
$R_A$ is selected from H and methyl;
L is selected from methyl, fluoromethyl, 2,2,2-trifluoroethyl, trichloromethyl, methylthiomethyl, methoxymethyl, hydroxyethyl, ethoxyethyl, and allyl;
$R_{11}$ is selected from H, methyl, ethenyl, fluoromethyl, difluoromethyl, trifluoromethyl, hydroxymethyl, methoxymethyl, methylthiomethyl, cyanomethyl, aminomethyl, cyclopropyl, $CH_2S(O)_2CH_3$, and $CH_2C(O)NH_2$;
$R_{12}$ is selected from H and methyl;
$R_{13}$ is selected from H, fluoro, and methyl;
$R_{14}$ is selected from H, fluoro, and methyl; and
$R_B$ is selected from H and C(=NH)CH$_3$.

In Some Embodiments of Formula (I) or Formula (II)

$R_1$ is selected from H and fluoro;
$R_2$ is selected from H, trifluoromethoxy, trifluoromethyl and chloro;
$R_3$ is selected from H, trifluoromethyl, and C(=O)(methoxy);
W is $CR_4$;
$R_4$ is selected from H, fluoro, chloro, methylthio, methoxy, methyl, S(=O)$_2$(methyl), trifluoromethoxy, and N-morpholino;
$R_5$ is selected from H and fluoro;
$R_6$ and $R_{7A}$ together with the carbon atoms to which they are attached and the X atom connecting the two carbon atoms form a ring of any one of the following formulae:

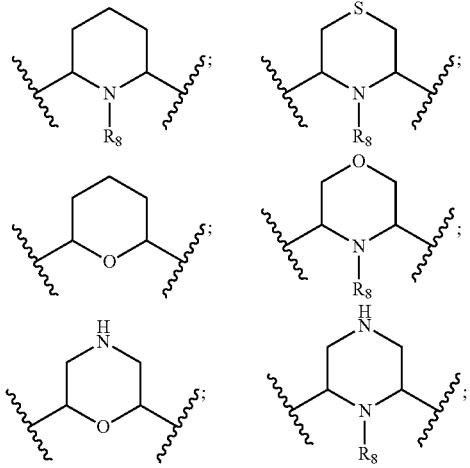

$R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl;
$R_9$ is selected from H, methyl, ethyl, n-propyl and i-propyl;
$R_{10}$ is selected from H and allyl;
$R_A$ is selected from H and methyl;
L is selected from methyl, fluoromethyl, 2,2,2-trifluoroethyl, trichloromethyl, methylthiomethyl, methoxymethyl, hydroxyethyl, ethoxyethyl, and allyl;
$R_{11}$ is selected from H, methyl, ethenyl, fluoromethyl, difluoromethyl, trifluoromethyl, hydroxymethyl, methoxymethyl, methylthiomethyl, cyanomethyl, aminomethyl, cyclopropyl, $CH_2S(O)_2CH_3$, and $CH_2C(O)NH_2$;
$R_{12}$ is selected from H and methyl;
$R_{13}$ is selected from H, fluoro, and methyl;
$R_{14}$ is selected from H, fluoro, and methyl; and
$R_B$ is selected from H and C(=NH)CH$_3$.

In Some Embodiments of Formula (I) or Formula (II)

$R_1$ is selected from H and fluoro;
$R_2$ is selected from H, trifluoromethoxy, trifluoromethyl and chloro;
$R_3$ is selected from H, trifluoromethyl, and C(=O)(methoxy);
W is $CR_4$;
$R_4$ is selected from fluoro, chloro, methylthio, methoxy, methyl, S(=O)$_2$(methyl), trifluoromethoxy, and N-morpholino;

$R_5$ is selected from H and fluoro;
$R_6$ and $R_{7A}$ together with the carbon atoms to which they are attached and the X atom connecting the two carbon atoms form a ring of any one of the following formulae:

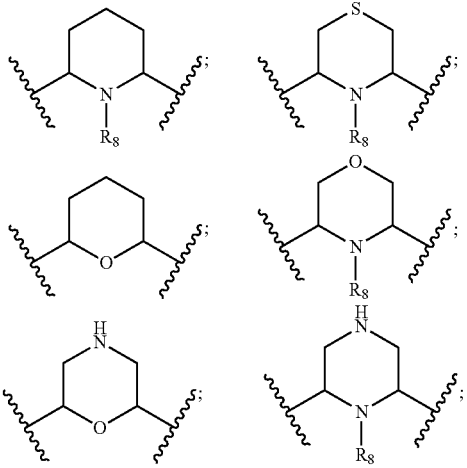

$R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl;
$R_9$ is selected from H and methyl;
$R_{10}$ is selected from H and allyl;
$R_A$ is selected from H and methyl;
L is selected from methyl, fluoromethyl, 2,2,2-trifluoroethyl, trichloromethyl, methylthiomethyl, methoxymethyl, hydroxyethyl, ethoxyethyl, and allyl;
$R_{11}$ is selected from H, methyl, ethenyl, fluoromethyl, difluoromethyl, trifluoromethyl, hydroxymethyl, methoxymethyl, methylthiomethyl, cyanomethyl, aminomethyl, cyclopropyl, $CH_2S(O)_2CH_3$, and $CH_2C(O)NH_2$;
$R_{12}$ is selected from H and methyl;
$R_{13}$ is selected from H, fluoro, and methyl;
$R_{14}$ is selected from H, fluoro, and methyl; and
$R_B$ is selected from H and $C(=NH)CH_3$.

In Some Embodiments of Formula (I) or Formula (II)

$R_1$ is fluoro;
$R_2$ is selected from $OCF_3$, $CF_3$ and $C_1$;
$R_3$ is H;
$R_4$ is selected from H, fluoro, chloro, methylthio, methoxy, and methyl;
$R_5$ is selected from H and fluoro;
$R_6$ is selected from H, cyclopropyl, ethenyl, aminomethyl, hydroxymethyl, $CH_2NH$-imidazolyl, methylthiomethyl, and methoxymethyl;
$R_{7A}$ is selected from H, methyl, trifluoromethyl, hydroxymethyl, difluoromethyl, and ethenyl;
$R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl;
$R_9$ is selected from H and methyl;
$R_{10}$ is H;
$R_A$ is H;
L is selected from methyl, fluoromethyl, 2,2,2-trifluoroethyl, trichloromethyl, methylthiomethyl, methoxymethyl, hydroxyethyl, and ethoxyethyl;
$R_{12}$ is selected from H and methyl;
$R_{11}$ is selected from methyl, cyclopropyl, ethenyl, and methoxymethyl;
$R_{13}$ is selected from H, fluoro, and methyl;
$R_{14}$ is selected from H, fluoro, and methyl; and
$R_B$ is H.

In Some Embodiments of Formula (I) or Formula (II)

$R_1$ is fluoro;
$R_2$ is selected from $OCF_3$, $CF_3$ and $C_1$;
$R_3$ is H;
$R_4$ is selected from fluoro, chloro, methylthio, methoxy, and methyl;
$R_5$ is selected from H and fluoro;
$R_6$ is selected from H, cyclopropyl, ethenyl, aminomethyl, hydroxymethyl, $CH_2NH$-imidazole, methylthiomethyl, and methoxymethyl;
$R_{7A}$ is selected from H, methyl, trifluoromethyl, hydroxymethyl, difluoromethyl, and ethenyl;
$R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl;
$R_9$ is selected from H, methyl, ethyl, n-propyl and i-propyl;
$R_{10}$ is H;
$R_A$ is H;
L is selected from methyl, fluoromethyl, 2,2,2-trifluoroethyl, trichloromethyl, methylthiomethyl, methoxymethyl, hydroxyethyl, and ethoxyethyl;
$R_{12}$ is selected from H and methyl;
$R_{11}$ is selected from methyl, cyclopropyl, ethenyl, and methoxymethyl;
$R_{13}$ is selected from H, fluoro, and methyl;
$R_{14}$ is selected from H, fluoro, and methyl; and
$R_B$ is H.

In Some Embodiments of Formula (I) or Formula (II)

$R_1$ is selected from H and halo;
$R_2$ is selected from H, $OR^{a1}$, $C_{1-4}$ haloalkyl and halo;
$R_3$ is selected from H and $C_{1-4}$ haloalkyl;
$R_4$ is selected from H, halo, $S(C_{1-4}$ alkyl), $C_{1-6}$ alkoxy, and $C_{1-6}$ alkyl;
$R_5$ is selected from H and halo;
$R_6$ and $R_{7A}$ together with the carbon atoms to which they are attached and the X atom connecting the two carbon atoms form a ring of any one of the following formulae:

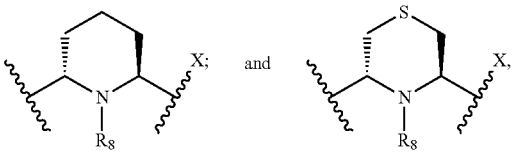

wherein x indicates a point of attachment to the ring containing the W atom and substituted with $R_5$;

$R_8$ is selected from H, $C_{1-6}$ alkyl, and $C_{1-4}$ haloalkyl, wherein the $C_{1-6}$ alkyl is optionally substituted with $OR^{a3}$;

$R_9$ is selected from H, methyl, ethyl, n-propyl and i-propyl;

$R_{10}$ is H;

$R_A$ is H;

L is $C_{1-6}$ alkyl;

$R_{11}$ is selected from selected from $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from OH, $C_{1-6}$ alkoxy, $S(O)_2C_{1-6}$ alkyl, and $S(C_{1-6}$ alkyl);

$R_{12}$ is H;

$R_{13}$ is H;

$R_{14}$ is H;

$R_B$ is H; or $R_{11}$ and $R_B$ together with the carbon atom to which $R_{11}$ is attached and the nitrogen atom to which $R_B$ is attached form a ring of formula:

[structure: morpholine ring with O and NH]

In Some Embodiments of Formula (I) or Formula (II)

$R_1$ is selected from H and fluoro;

$R_2$ is selected from H, $OCF_3$, $CF_3$ and $C_1$;

$R_3$ is selected from H and trifluoromethyl;

$R_4$ is selected from H, fluoro, chloro, methylthio, methoxy, and methyl;

$R_5$ is selected from H and fluoro;

$R_6$ and $R_{7A}$ together with the carbon atoms to which they are attached and the X atom connecting the two carbon atoms form a ring of any one of the following formulae:

[two ring structures with X and N-$R_8$]

and wherein x indicates a point of attachment to the ring containing the W atom and substituted with $R_5$;

$R_8$ is selected from H, methyl, 3-fluoropropyl, 2-methoxyethyl, and 3-hydroxypropyl;

$R_9$ is selected from H and methyl;

$R_{10}$ is H;

$R_A$ is H;

L is methyl;

$R_{11}$ is selected from methyl, ethenyl, $CH_2S(O)_2CH_3$, methylthiomethyl, fluoromethyl, methoxymethyl, hydroxymethyl, and cyclopropyl;

$R_{12}$ is H;

$R_{13}$ is H; and $R_{14}$ is H.

In some embodiments, the compounds of Formula (I) or Formula (II) are compounds of Formula (Iaa):

(Iaa)

[chemical structure]

or a tautomer thereof or a pharmaceutically acceptable salt of the compound or tautomer, wherein:

$R_2$ is selected from H, halo, $C_{1-4}$ haloalkyl, and $C_{1-4}$ haloalkoxy;

$R_4$ is selected from H, fluoro, methyl, ethyl, n-propyl, isopropyl, methylthio, and methoxy; and $R_{11}$ is selected from H, methyl, ethyl, isopropyl, cyclopropyl, cyclobutyl, cyclopentyl, fluoromethyl, and cyanomethyl.

In some embodiments of Formula (Iaa), $R_2$ is selected from H, $OCF_3$, $CF_3$ and $C_1$. In some embodiments of Formula (Iaa), $R_2$ is $C_1$.

In some embodiments of Formula (Iaa), $R_4$ is selected from H, methyl, methylthio, and methoxy.

In some embodiments of Formula (Iaa), $R_{11}$ is selected from H, methyl, isopropyl, cyclopropyl, and fluoromethyl.

In some embodiments of Formula (Iaa), $R_2$ is selected from $OCF_3$, $CF_3$ and $C_1$; $R_4$ is selected from methylthio and methoxy; and $R_{11}$ is selected from methyl, cyclopropyl and fluoromethyl. In some embodiments of Formula (Iaa), $R_2$ is $C_1$; $R_4$ is selected from methylthio and methoxy; and Rn is selected from cyclopropyl and methyl. In some embodiments of Formula (Iaa), $R_2$ is $C_1$; $R_4$ is methylthio; and $R_{11}$ is methyl. In some embodiments of Formula (Iaa), $R_2$ is $C_1$; $R_4$ is methoxy; and $R_{11}$ is methyl. In some embodiments of Formula (Iaa), $R_2$ is $C_1$; $R_4$ is methylthio; and $R_{11}$ is cyclopropyl. In some embodiments of Formula (Iaa), $R_2$ is $C_1$; $R_4$ is methoxy; and $R_{11}$ is cyclopropyl.

In some embodiments, the compounds of Formula (I) or Formula (II) are compounds of Formula (Iab):

(Iab)

[chemical structure]

or a tautomer thereof or a pharmaceutically acceptable salt of the compound or tautomer, wherein:

$R_2$ is selected from H, halo, $C_{1-4}$ haloalkyl, and $C_{1-4}$ haloalkoxy;

$R_8$ is selected from H, methyl, n-propyl, n-butyl, 2-chloroethyl, 3,3,3-trifluoropropyl, 3-fluoropropyl, 2-methoxyethyl, 2-hydroxypropyl, and 3-hydroxypropyl.

$R_{11}$ is selected from H, methyl, ethyl, isopropyl, cyclopropyl, cyclobutyl, cyclopentyl, fluoromethyl, and cyanomethyl.

In some embodiments of Formula (Iab), $R_2$ is selected from H, $OCF_3$, $CF_3$ and $C_1$. In some embodiments of Formula (Iab), $R_2$ is $C_1$.

In some embodiments of Formula (Iab), $R_8$ is selected from H, methyl, n-propyl, 3,3,3-trifluoropropyl, 3-fluoropropyl, 2-methoxyethyl, and 3-hydroxypropyl. In some embodiments of Formula (Iab), $R_8$ is selected from n-propyl, 3,3,3-trifluoropropyl, 3-fluoropropyl, and 3-hydroxypropyl.

In some embodiments of Formula (Iab), $R_2$ is selected from $OCF_3$, $CF_3$ and $C_1$; $R_8$ is selected from 3-fluoropropyl and 3-hydroxypropyl; and $R_{11}$ is selected from methyl, cyclopropyl and fluoromethyl. In some embodiments of Formula (Iab), $R_2$ is $C_1$; $R_8$ is selected from 3-fluoropropyl and 3-hydroxypropyl; and $R_{11}$ is selected from cyclopropyl and methyl. In some embodiments of Formula (Iab), $R_2$ is $C_1$; $R_8$ is 3-fluoropropyl; and $R_{11}$ is methyl. In some embodiments of Formula (Iab), $R_2$ is $C_1$; $R_8$ is 3-hydroxypropyl; and $R_{11}$ is methyl. In some embodiments of Formula (Iab), $R_2$ is $C_1$; $R_8$ is 3-fluoropropyl; and $R_{11}$ is cyclopropyl. In some embodiments of Formula (Iab), $R_2$ is $C_1$; $R_8$ is 3-hydroxypropyl; and $R_{11}$ is cyclopropyl.

In Some Embodiments of Formula (II)

$R_1$ is selected from H and halo;
$R_2$ is selected from H, $OR^{a1}$, $C_{1-4}$ haloalkyl and halo;
$R_3$ is selected from H and $C_{1-4}$ haloalkyl;
$R_4$ is selected from halo, $S(C_{1-4}$ alkyl), $C_{1-6}$ alkoxy, and $C_{1-6}$ alkyl;
$R_5$ is selected from H and halo;
$R_6$ and $R_{7A}$ together with the carbon atoms to which they are attached and the
X atom connecting the two carbon atoms form a ring of any one of the following formulae:

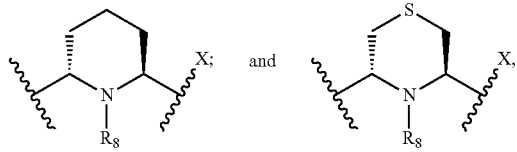

wherein x indicates a point of attachment to the ring containing the W atom and substituted with $R_5$;
$R_8$ is selected from H, $C_{1-6}$ alkyl, and $C_{1-4}$ haloalkyl, wherein the $C_{1-6}$ alkyl is optionally substituted with $OR^{a3}$;
$R_9$ is selected from H, methyl, ethyl, n-propyl and i-propyl;
$R_{10}$ is H;
$R_A$ is H;
L is $C_{1-6}$ alkyl;
$R_{11}$ is selected from selected from $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from OH, $C_{1-6}$ alkoxy, $S(O)_2C_{1-6}$ alkyl, and $S(C_{1-6}$ alkyl);
$R_{12}$ is H;
$R_{13}$ is H;
$R_{14}$ is H;
$R_B$ is H; or
$R_{11}$ and $R_B$ together with the carbon atom to which $R_{11}$ is attached and the nitrogen atom to which $R_B$ is attached form a ring of formula:

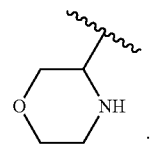 [SMILES: *C1COCCN1]

In Some Embodiments of Formula (II)

$R_1$ is selected from H and fluoro;
$R_2$ is selected from H, $OCF_3$, $CF_3$ and $C_1$;
$R_3$ is selected from H and trifluoromethyl;
$R_4$ is selected from fluoro, chloro, methylthio, methoxy, and methyl;
$R_5$ is selected from H and fluoro;
$R_6$ and $R_{7A}$ together with the carbon atoms to which they are attached and the X atom connecting the two carbon atoms form a ring of any one of the following formulae:

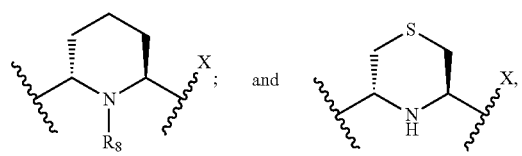

wherein x indicates a point of attachment to the ring containing the W atom and substituted with $R_5$;
$R_8$ is selected from H, methyl, 3-fluoropropyl, 2-methoxyethyl, and 3-hydroxypropyl;
$R_9$ is selected from H and methyl;
$R_{10}$ is H;
$R_A$ is H;
L is methyl;
$R_{11}$ is selected from methyl, ethenyl, $CH_2S(O)_2CH_3$, methylthiomethyl, fluoromethyl, methoxymethyl, hydroxymethyl, and cyclopropyl;
$R_{12}$ is H;
$R_{13}$ is H;
$R_{14}$ is H;
$R_B$ is H; or
$R_{11}$ and $R_B$ together with the carbon atom to which $R_{11}$ is attached and the nitrogen atom to which $R_B$ is attached form a ring of formula:

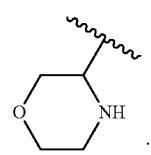 [SMILES: *C1COCCN1]

In Some Embodiments of Formula (II)

$R_1$ is selected from H and halo;
$R_2$ is selected from H, halo, $C_{1-4}$ haloalkyl, and $C_{1-4}$ haloalkoxy;
$R_3$ is selected from H and $C_{1-4}$ haloalkyl;
$R_4$ is selected from halo, $S(C_{1-4}$ alkyl), $C_{1-4}$ alkoxy, and $C_{1-6}$ alkyl;
$R_5$ is selected from H and halo;
$R_6$ and $R_{7A}$ together with the carbon atoms to which they are attached and the X atom connecting the two carbon atoms form a ring of formula:

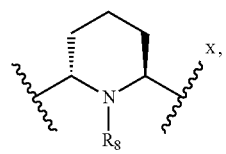

wherein x indicates a point of attachment to the ring containing the W atom and substituted with $R_5$;
$R_8$ is selected from H, $C_{1-6}$ alkyl, $C_{1-4}$ haloalkyl, $C_{1-4}$ hydroxyalkyl, $C_{1-6}$ alkyl substituted with $C_{1-6}$ alkoxy;
$R_9$ is selected from H, methyl, ethyl, n-propyl and i-propyl;
$R_{10}$ is H;
$R_A$ is H;
L is $C_{1-6}$ alkyl;
$R_{11}$ is selected from $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from OH, $C_{1-6}$ alkoxy, $S(O)_2C_{1-6}$ alkyl, and $S(C_{1-6}$ alkyl)
$R_{12}$ is H;
$R_{13}$ is H;
$R_{14}$ is H; and
$R_B$ is H; or
$R_{11}$ and $R_B$ together with the carbon atom to which $R_{11}$ is attached and the nitrogen atom to which $R_B$ is attached form a ring of formula:

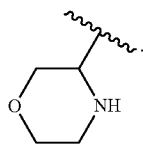 [SMILES: *C1COCCN1]

In Some Embodiments of Formula (II)

$R_1$ is selected from H and fluoro;
$R_2$ is selected from H, $OCF_3$, $CF_3$ and $Cl$;
$R_3$ is selected from H and trifluoromethyl;
$R_4$ is selected from fluoro, chloro, methylthio, methoxy, and methyl;
$R_5$ is selected from H and fluoro;
$R_6$ and $R_{7A}$ together with the carbon atoms to which they are attached and the X atom connecting the two carbon atoms form a ring of formula:

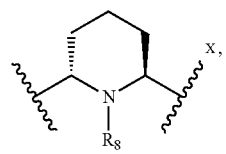

wherein x indicates a point of attachment to the ring containing the W atom and substituted with $R_5$;
$R_8$ is selected from H, methyl, 3-fluoropropyl, 2-methoxyethyl, and 3-hydroxypropyl;
$R_9$ is selected from H and methyl;
$R_{10}$ is H;
$R_A$ is H;
L is methyl;
$R_{11}$ is selected from methyl, ethenyl, $CH_2S(O)_2CH_3$, methylthiomethyl, fluoromethyl, methoxymethyl, hydroxymethyl, and cyclopropyl;
$R_{12}$ is H;
$R_{13}$ is H;
$R_{14}$ is H; and
$R_B$ is H; or
$R_{11}$ and $R_B$ together with the carbon atom to which $R_{11}$ is attached and the nitrogen atom to which $R_B$ is attached form a ring of formula:

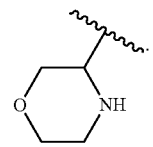

In Some Embodiments of Formula (II)

$R_1$ is selected from H and halo;
$R_2$ is selected from H, halo, $C_{1-4}$ haloalkyl, and $C_{1-4}$ haloalkoxy;
$R_3$ is selected from H and $C_{1-4}$ haloalkyl;
$R_4$ is selected from H, halo, $S(C_{1-4}$ alkyl), $C_{1-4}$ alkoxy, and $C_{1-6}$ alkyl;
$R_5$ is selected from H and halo;
$R_6$ and $R_{7A}$ together with the carbon atoms to which they are attached and the X atom connecting the two carbon atoms form a ring of formula:

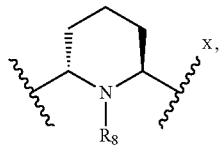

wherein x indicates a point of attachment to the ring containing the W atom and substituted with $R_5$;
$R_8$ is selected from H, $C_{1-6}$ alkyl, $C_{1-4}$ haloalkyl, $C_{1-4}$ hydroxyalkyl, $C_{1-6}$ alkyl substituted with $C_{1-6}$ alkoxy;
$R_9$ is selected from H, methyl, ethyl, n-propyl and i-propyl;
$R_{10}$ is H;
$R_A$ is H;
L is $C_{1-6}$ alkyl;
$R_{11}$ is selected from $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from OH, $C_{1-6}$ alkoxy, $S(O)_2C_{1-6}$ alkyl, and $S(C_{1-6}$ alkyl)
$R_{12}$ is H;
$R_{13}$ is H;

$R_{14}$ is H; and
$R_B$ is H; or
$R_{11}$ and $R_B$ together with the carbon atom to which $R_{11}$ is attached and the nitrogen atom to which $R_B$ is attached form a ring of formula:

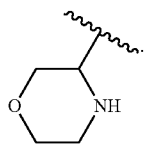

In Some Embodiments of Formula (II)

$R_1$ is selected from H and fluoro;
$R_2$ is selected from H, $OCF_3$, $CF_3$ and $C_1$;
$R_3$ is selected from H and trifluoromethyl;
$R_4$ is selected from H, fluoro, chloro, methylthio, methoxy, and methyl;
$R_5$ is selected from H and fluoro;
$R_6$ and $R_{7A}$ together with the carbon atoms to which they are attached and the X atom connecting the two carbon atoms form a ring of formula:

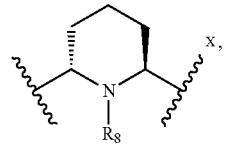

wherein x indicates a point of attachment to the ring containing the W atom and substituted with $R_5$;
$R_8$ is selected from H, methyl, 3-fluoropropyl, 2-methoxyethyl, and 3-hydroxypropyl;
$R_9$ is selected from H and methyl;
$R_{10}$ is H;
$R_A$ is H;
L is methyl;
$R_{11}$ is selected from methyl, ethenyl, $CH_2S(O)_2CH_3$, methylthiomethyl, fluoromethyl, methoxymethyl, hydroxymethyl, and cyclopropyl;
$R_{12}$ is selected from H;
$R_{13}$ is H;
$R_{14}$ is H; and
$R_B$ is H; or
$R_{11}$ and $R_B$ together with the carbon atom to which $R_{11}$ is attached and the nitrogen atom to which $R_B$ is attached form a ring of formula:

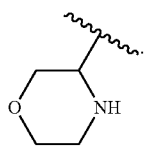

In some embodiments, the compounds of Formula (I) or Formula (II) are compound of Formula (Ia):

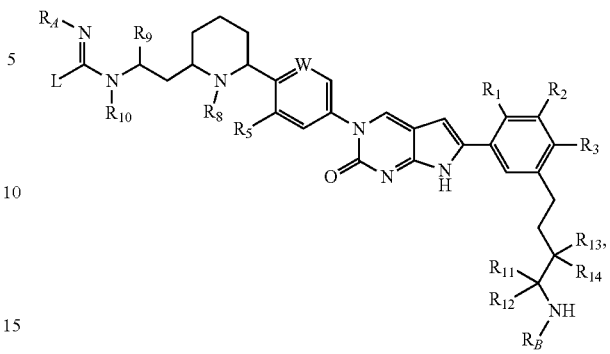

or a tautomer thereof or a pharmaceutically acceptable salt of the compound or tautomer,
wherein $R_1$, $R_2$, $R_3$, $R_4$, $R_5$, $R_8$, $R_9$, $R_{10}$, $R_{11}$, $R_{12}$, $R_{13}$, $R_{14}$, $R_A$, $R_B$, L and W are as described herein.

In some embodiments, the compounds of Formula (I) or Formula (II) are compound of Formula (Ia-1):

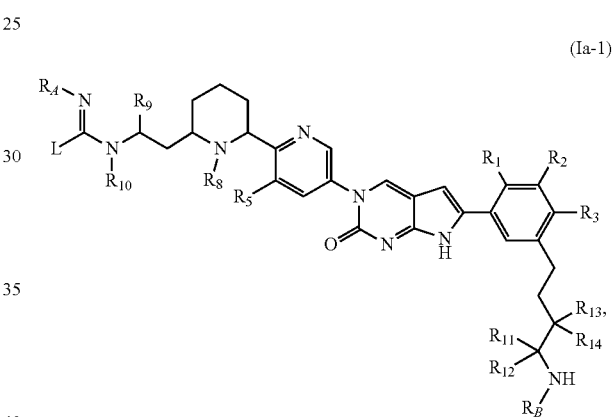

or a tautomer thereof or a pharmaceutically acceptable salt of the compound or tautomer, wherein $R_1$, $R_2$, $R_3$, $R_5$, $R_8$, $R_9$, $R_{10}$, $R_{11}$, $R_{12}$, $R_{13}$, $R_{14}$, $R_A$, $R_B$, and L are as described herein.

In some embodiments, the compounds of Formula (I) or Formula (II) are compounds of Formula (Ia-2):

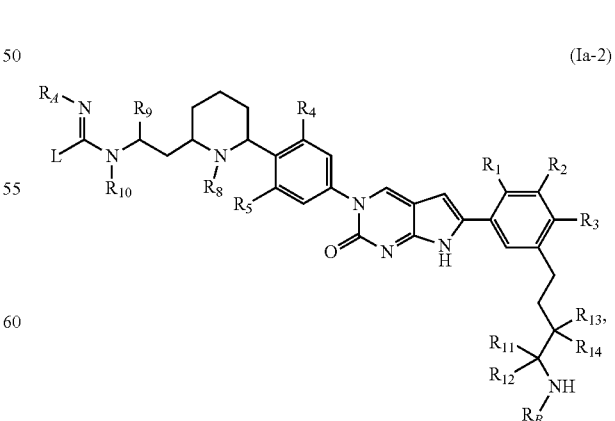

or a tautomer thereof or a pharmaceutically acceptable salt of the compound or tautomer, wherein $R_1$, $R_2$, $R_3$, $R_4$, $R_5$, $R_8$, $R_9$, $R_{10}$, $R_{11}$, $R_{12}$, $R_{13}$, $R_{14}$, $R_A$, $R_B$, and L are as described herein.

In some embodiments, the compounds of Formula (I) or Formula (II) are compounds of Formula (Ib-a):

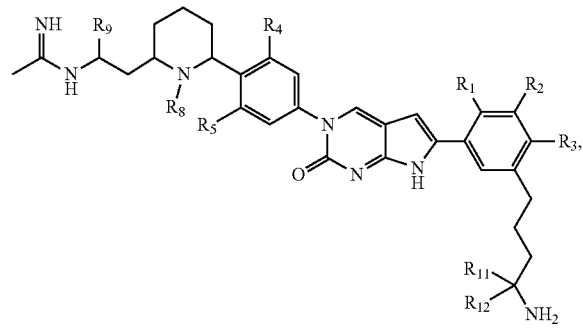

(Ib-a)

or a tautomer thereof or a pharmaceutically acceptable salt of the compound or tautomer
wherein $R_1$, $R_2$, $R_3$, $R_4$, $R_5$, $R_8$, $R_9$, $R_{11}$, and $R_{12}$ are as described herein.

In some embodiments, the compounds of Formula (I) or Formula (II) are compounds of Formula (Ib):

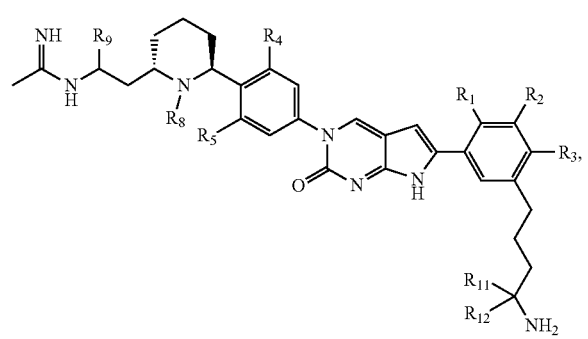

(Ib)

or a tautomer thereof or a pharmaceutically acceptable salt of the compound or tautomer,
wherein $R_1$, $R_2$, $R_3$, $R_4$, $R_5$, $R_8$, $R_9$, $R_{11}$, and $R_{12}$ are as described herein.

In some embodiments, the compound of Formula (I) or Formula (II) has Formula (Ia-3):

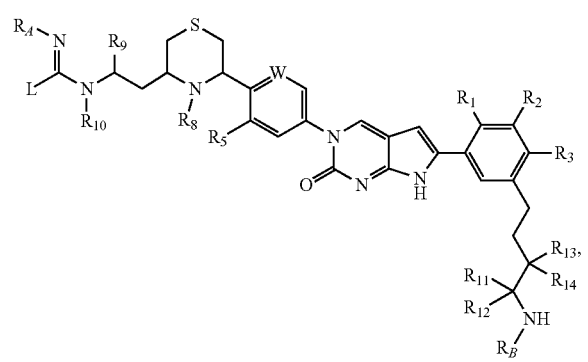

(Ia-3)

or a tautomer thereof or a pharmaceutically acceptable salt of the compound or tautomer,
wherein $R_1$, $R_2$, $R_3$, $R_5$, $R_8$, $R_9$, $R_{10}$, $R_{11}$, $R_{12}$, $R_{13}$, $R_{14}$, $R_A$, $R_B$, L and W are as described herein.

In some embodiments, the compounds of Formula (I) or Formula (II) are compounds of Formula (Ic):

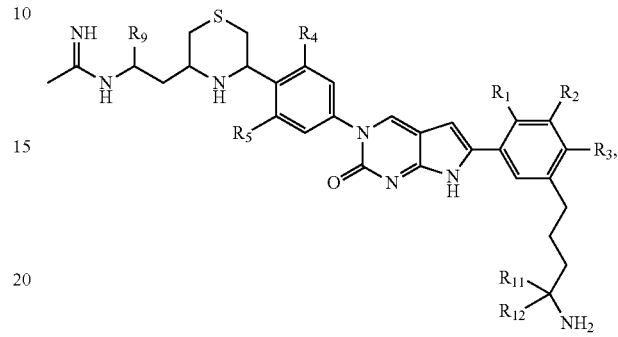

(Ic)

or a tautomer thereof or a pharmaceutically acceptable salt of the compound or tautomer, wherein $R_1$, $R_2$, $R_3$, $R_4$, $R_5$, $R_9$, $R_{11}$, and $R_{12}$ are as described herein.

In some embodiments, the compounds of Formula (I) or Formula (II) are compounds of Formula (Ic-1):

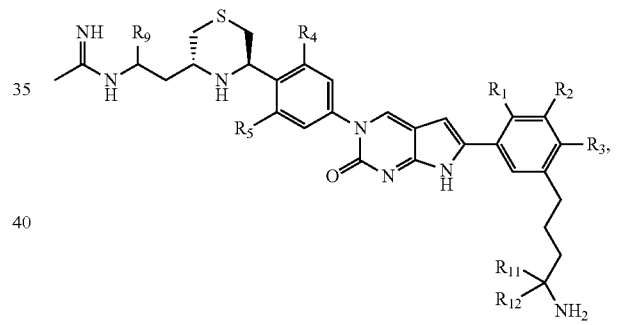

(Ic-1)

or a tautomer thereof or a pharmaceutically acceptable salt of the compound or tautomer, wherein $R_1$, $R_2$, $R_3$, $R_4$, $R_5$, $R_9$, $R_{11}$, and $R_{12}$ are as described herein.

In some embodiments, the compounds of Formula (I) or Formula (II) are compounds of any one of Formulae (Id)-(Ig):

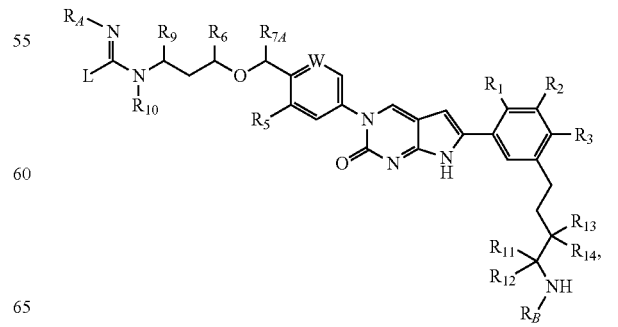

(Id)

or a tautomer thereof or a pharmaceutically acceptable salt of the compound or tautomer;

(Ie)
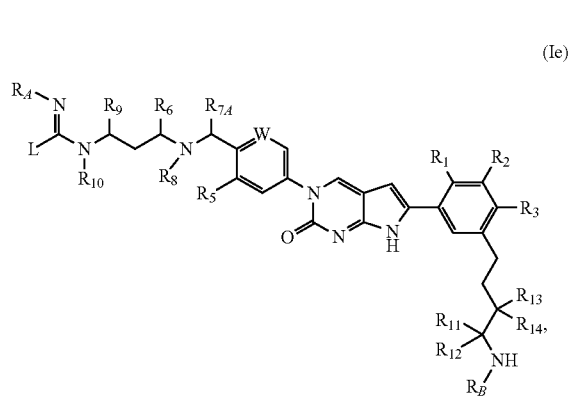

or a tautomer thereof or a pharmaceutically acceptable salt of the compound or tautomer;

(If)
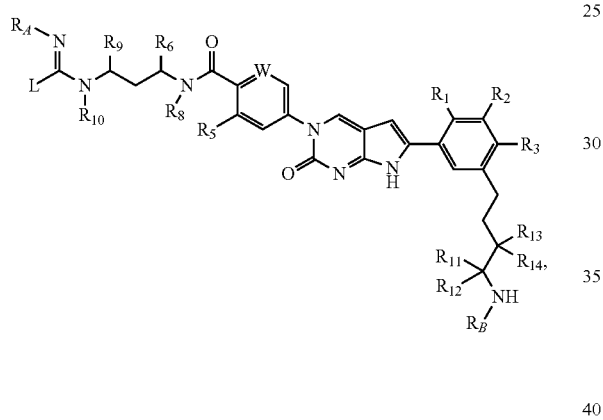

or a tautomer thereof or a pharmaceutically acceptable salt of the compound or tautomer; and (Ig)
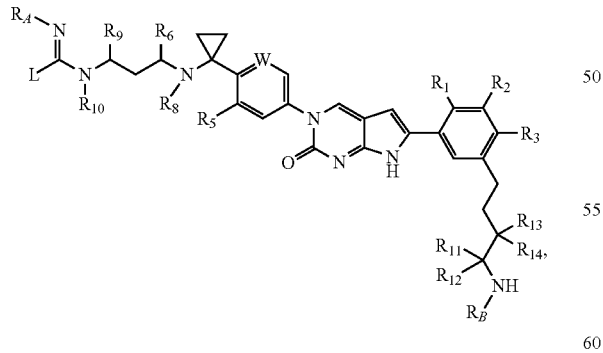

or a tautomer thereof or a pharmaceutically acceptable salt of the compound or tautomer, wherein $R_1$, $R_2$, $R_3$, $R_4$, $R_5$, $R_8$, $R_9$, $R_{10}$, $R_{11}$, $R_{12}$, $R_{13}$, $R_{14}$, $R_A$, $R_B$, L and W are as described herein.

In some embodiments, the compounds of Formula (I) or Formula (II) are compounds of Formula (Ie-1):

(Ie-1)
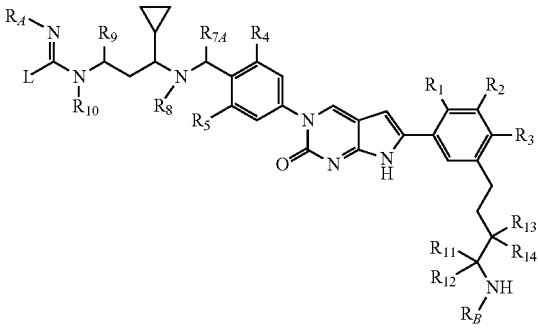

or a tautomer thereof or a pharmaceutically acceptable salt of the compound or tautomer, wherein $R_1$, $R_2$, $R_3$, $R_4$, $R_5$, $R_{7A}$, $R_8$, $R_9$, $R_{10}$, $R_{11}$, $R_{12}$, $R_{13}$, $R_{14}$, $R_A$, $R_B$, L and W are as described herein.

In some embodiments, the compounds of Formula (I) or Formula (II) are compounds of any one of Formulae (Ih)-(Ik):

(Ih)
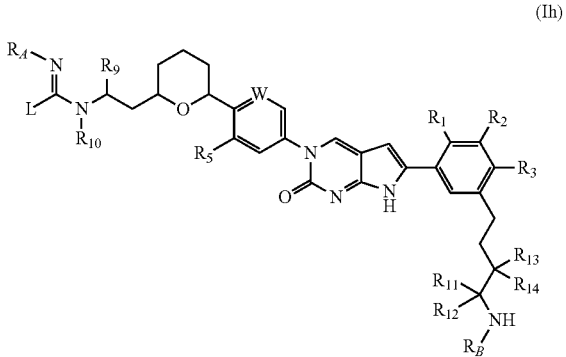

or a tautomer thereof or a pharmaceutically acceptable salt of the compound or tautomer;

(Ii)
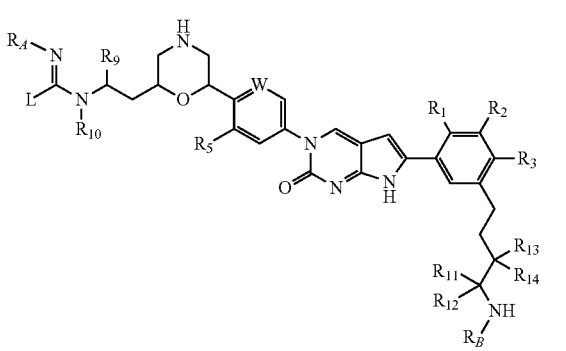

or a tautomer thereof or a pharmaceutically acceptable salt of the compound or tautomer;

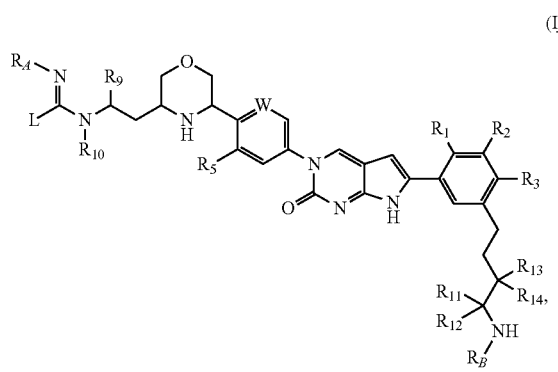

(Ij)

or a tautomer thereof or a pharmaceutically acceptable salt of the compound or tautomer; and

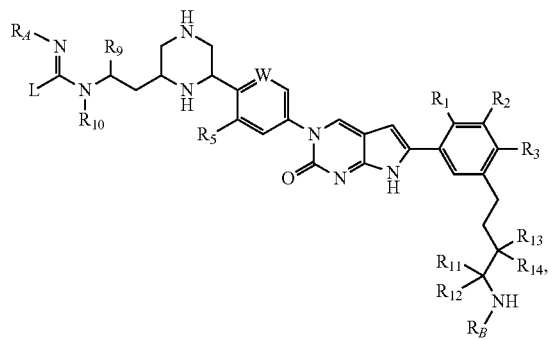

(Ik)

or a tautomer thereof or a pharmaceutically acceptable salt of the compound or tautomer, wherein $R_1$, $R_2$, $R_3$, $R_4$, $R_5$, $R_8$, $R_9$, $R_{10}$, $R_{11}$, $R_{12}$, $R_{13}$, $R_{14}$, $R_A$, $R_B$, L and W are as described herein.

In some embodiments of any one of Formulae disclosed herein, the fragment:

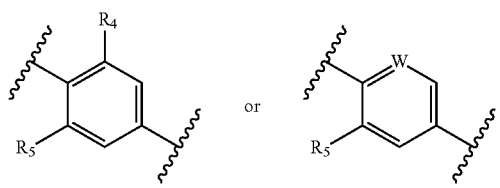

In some embodiments of any one of Formulae disclosed herein, the fragment

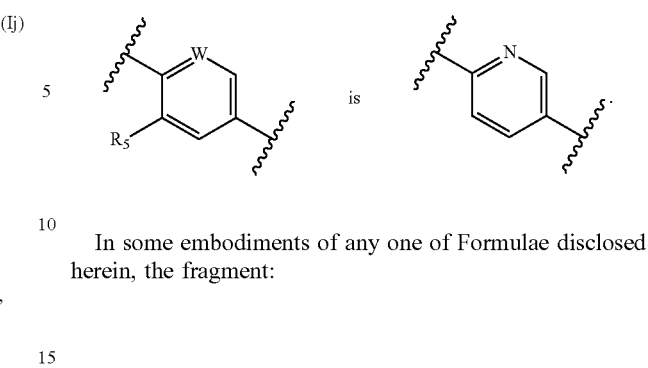

is

In some embodiments of any one of Formulae disclosed herein, the fragment:

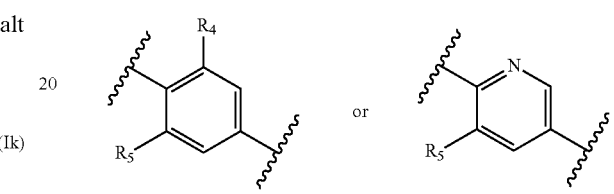

is selected from any one the following fragments:

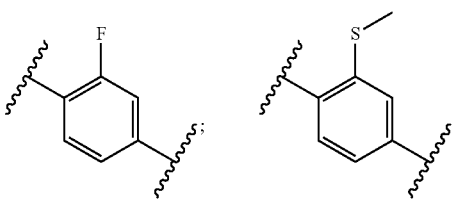

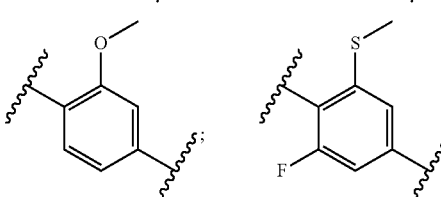

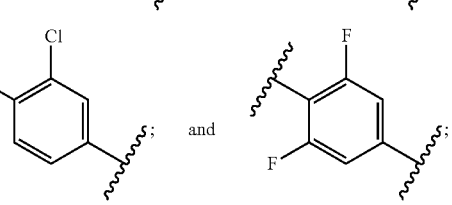

and

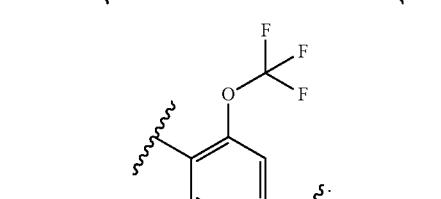

In some embodiments of any one of Formulae described herein, the fragment:

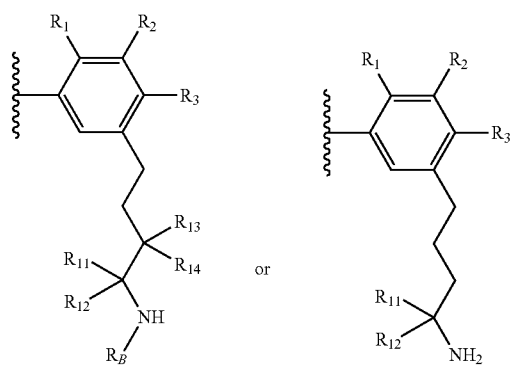
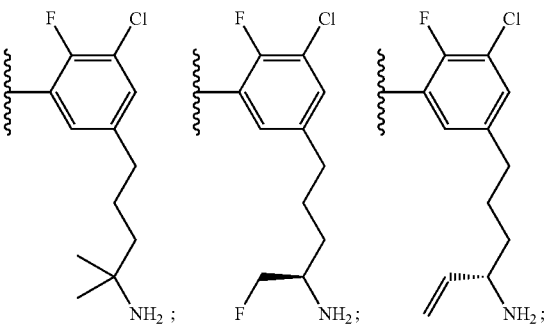
is selected from any one the following fragments:
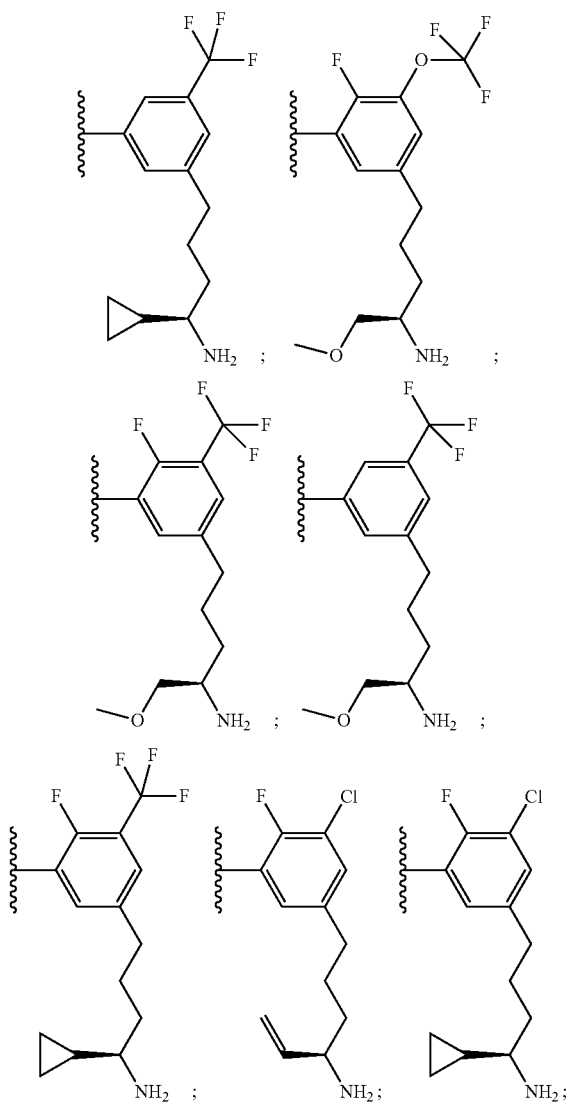
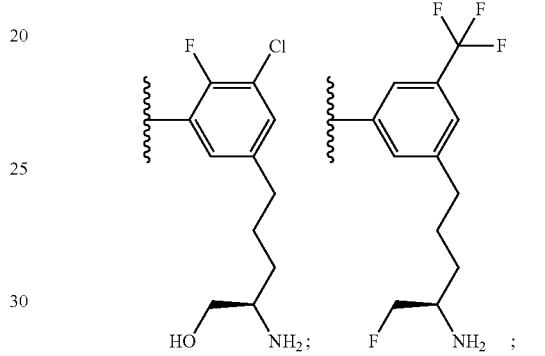
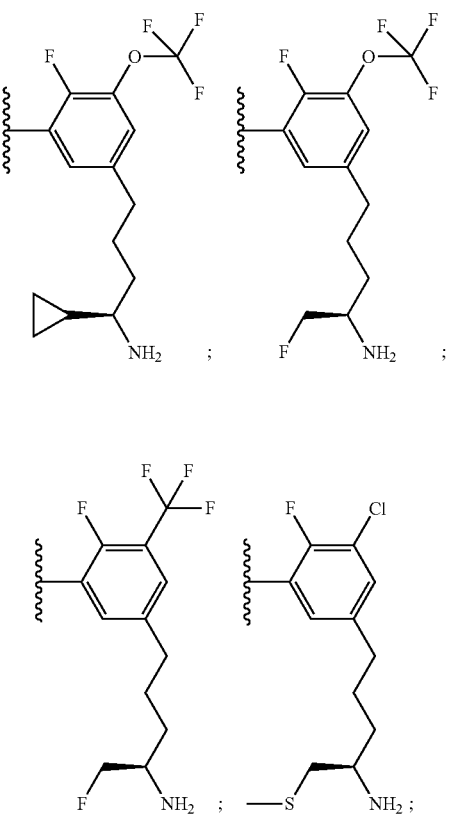

-continued
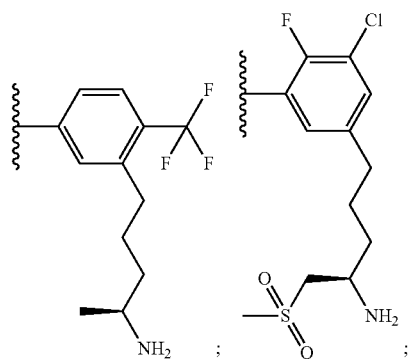
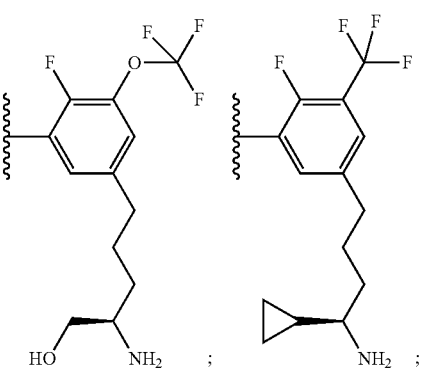
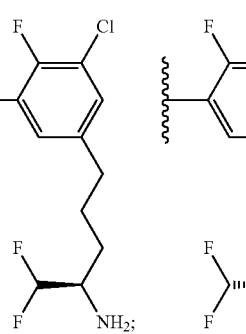
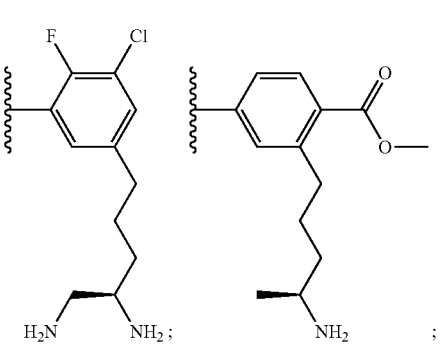
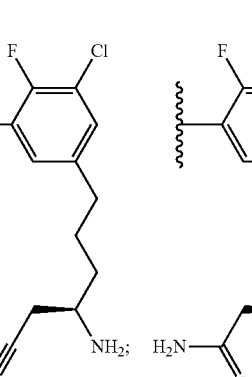
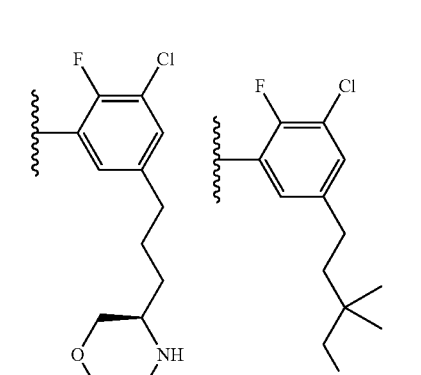
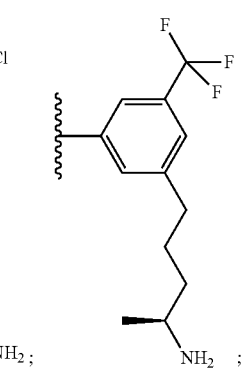
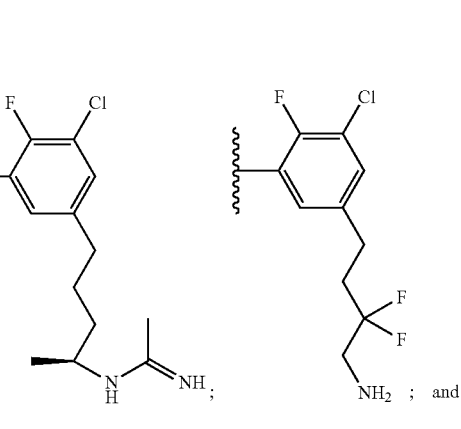

-continued

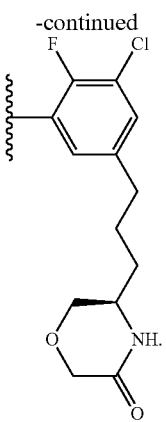

In some embodiments of any one of Formulae described herein, the fragment

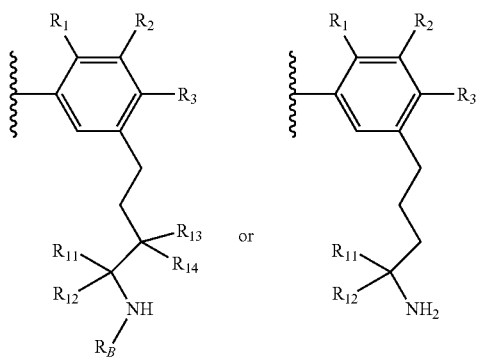

is selected from any one the following fragments:

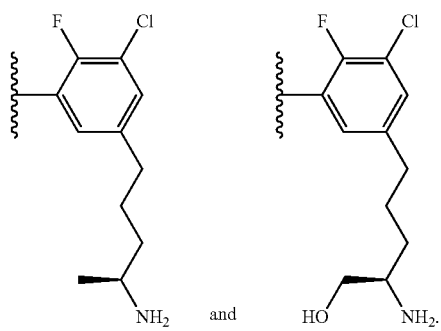 [SMILES: *c1cc(CCC[C@H](C)N)cc(Cl)c1F ; *c1cc(CCC[C@@H](N)CO)cc(Cl)c1F]

and

In some embodiments of any one of Formulae described herein, the fragment:

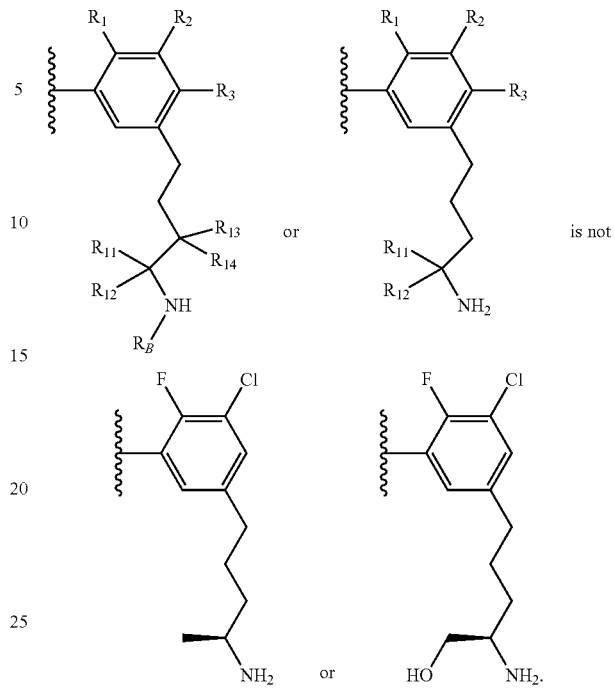

or is not

In some embodiments of any one of Formulae described herein, the fragment:

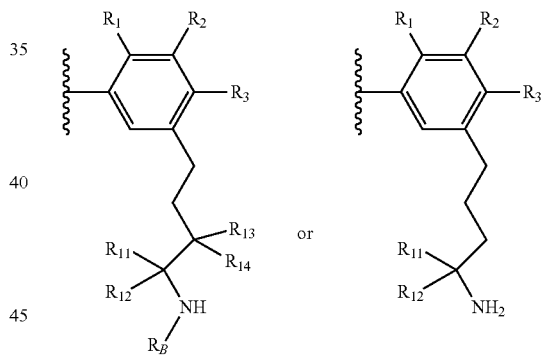

or is

In some embodiments of any one of the Formulae disclosed herein, the fragment

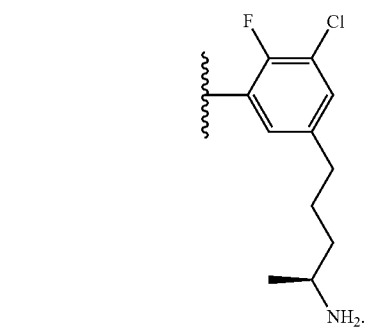

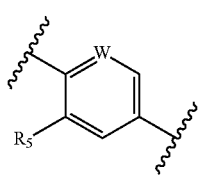
is selected from any one the following fragments:
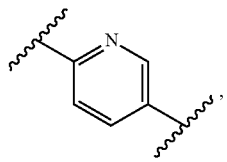 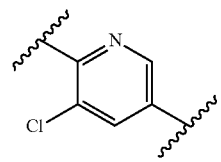 and
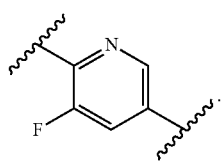
In some embodiments, the compound of Formula (I) or Formula (II) is not any one of the following compounds:
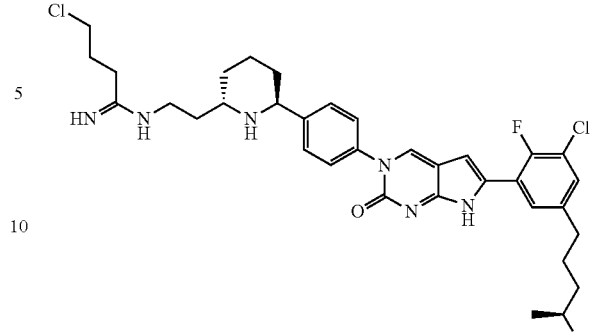
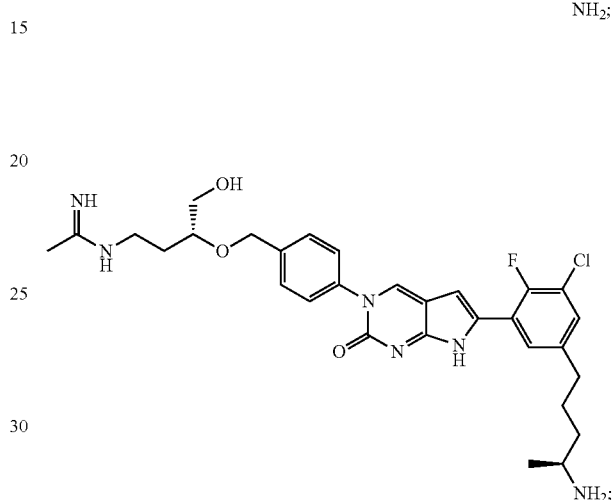
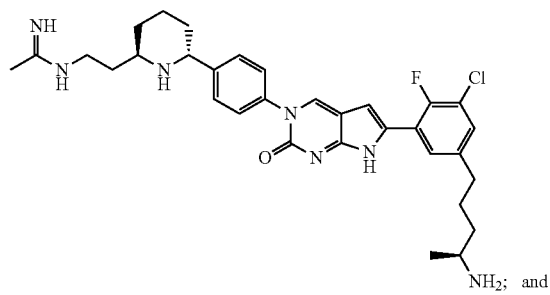
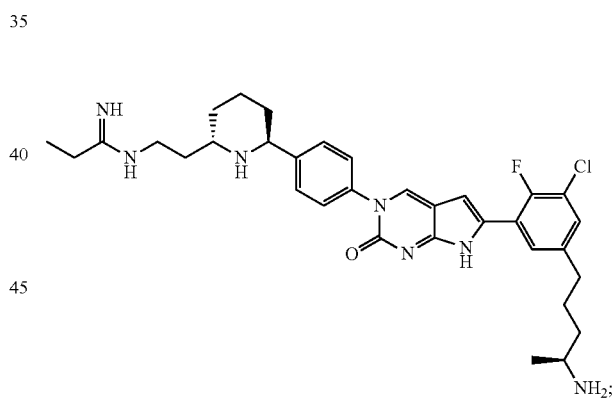
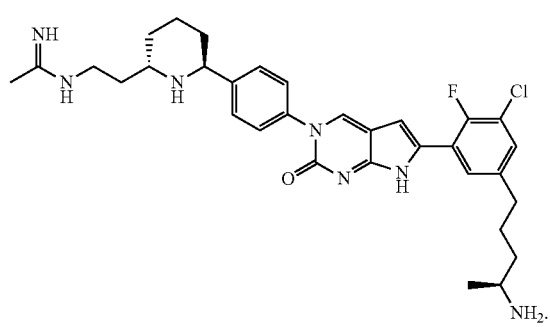
In some embodiments, the compound of Formula (I) or Formula (II) is not any one of the following compounds:

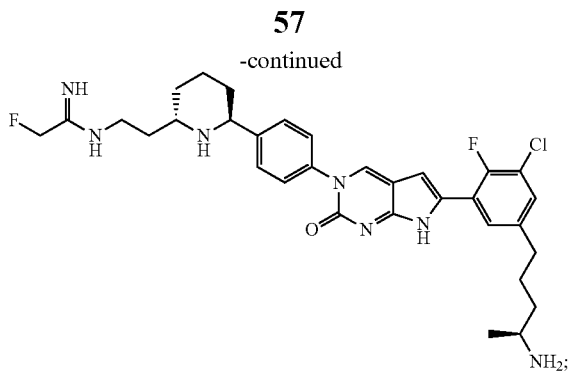

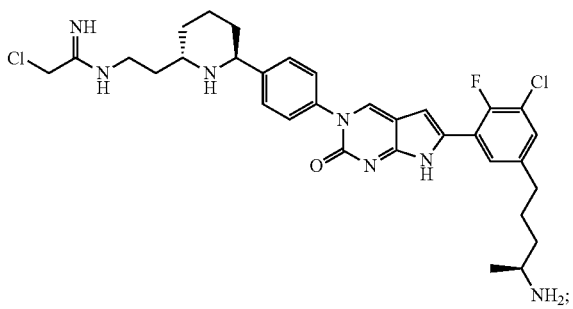

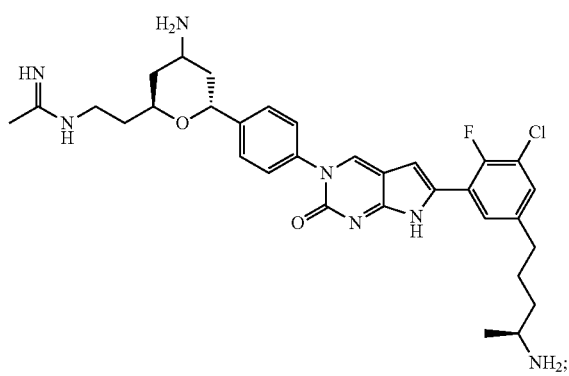

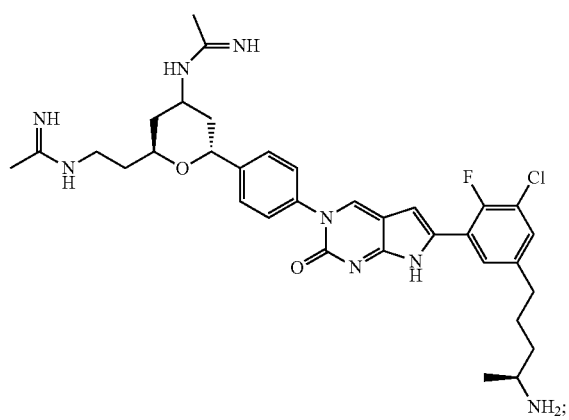

or tautomer or a pharmaceutically acceptable salt of the compound or tautomer.

In some embodiments, the compounds of Formula (I) or Formula (II) are not any of the compounds explicitly disclosed in PCT application No. PCT/US2010/052922 (published as WO 2011/047319), PCT application No. PCT/US2012/032994 (published as WO 2012/173689), PCT application No. PCT/US2014/054869 (published as WO 2015/035426), PCT application No. PCT/US2014/054860 (published as WO 2015/035421); or PCT application No. PCT/US2016/022216.

In some embodiments, a compound of Formula (I) or Formula (II) is not compound 516 disclosed in Table 1 of PCT application No. PCT/US2014/054869 (published as WO 2015/035426). In some embodiments, the compounds of Formula (I) or Formula (II) are not compound 1, 28, 72, 81, 82, 85, 86, 97, 120, 137, 150, or 151 disclosed in Table 1 of PCT application No. PCT/US2016/022216.

In some embodiments, the compound of Formula (I) or Formula (II) is any one of the compounds listed in Table 1, or a tautomer thereof or a pharmaceutically acceptable salt of the compound or tautomer.

TABLE 1

| # | Structure | ESI, m/z [M + H]+ |
|---|-----------|-------------------|
| 2 | 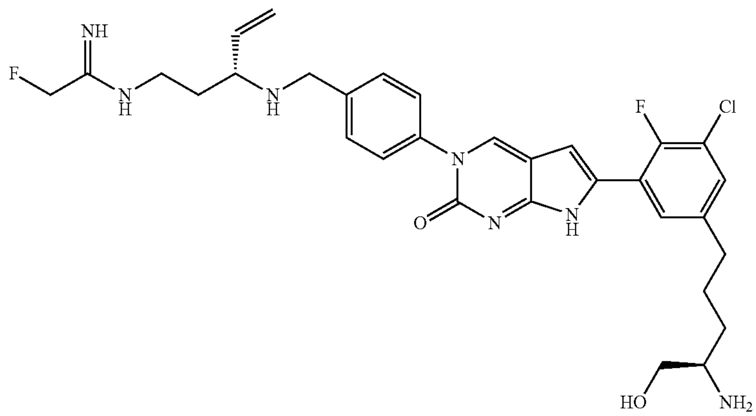 [SMILES: C=C[C@@H](CCNC(=N)CF)NCc1ccc(-n2cc3cc(-c4cc(CCC[C@@H](N)CO)cc(Cl)c4F)[nH]c3nc2=O)cc1] | 612.6 |
| 3 | 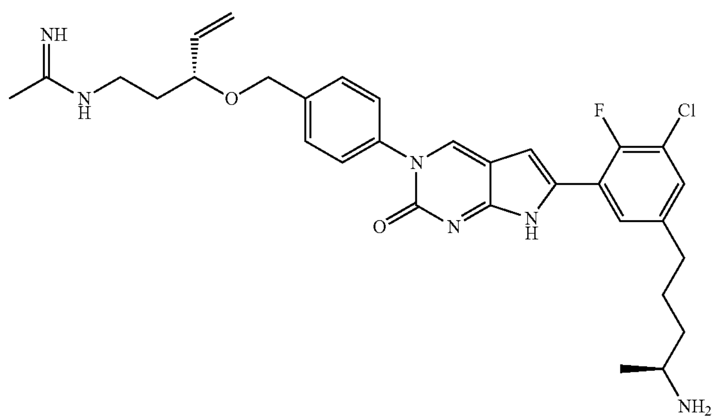 [SMILES: C=C[C@@H](CCNC(C)=N)OCc1ccc(-n2cc3cc(-c4cc(CCC[C@H](C)N)cc(Cl)c4F)[nH]c3nc2=O)cc1] | 579 |
| 4 | 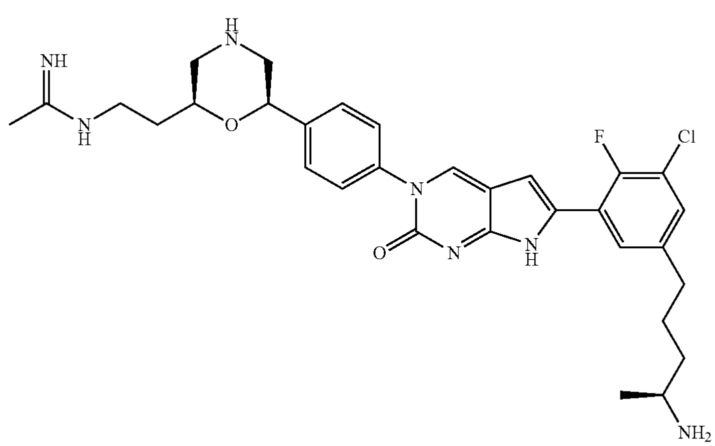 [SMILES: CC(=N)NCC[C@H]1CNC[C@@H](c2ccc(-n3cc4cc(-c5cc(CCC[C@H](C)N)cc(Cl)c5F)[nH]c4nc3=O)cc2)O1] | 594.7 |

TABLE 1-continued

| # | Structure | ESI, m/z [M + H]+ |
|---|-----------|-------------------|
| 6 | 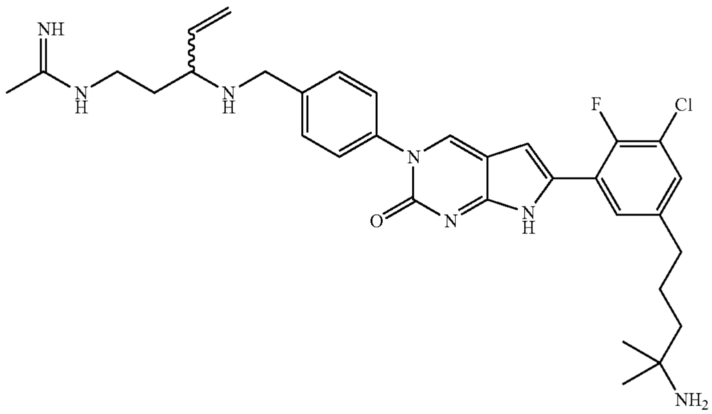 [SMILES: C=CC(CCNC(C)=N)NCc1ccc(-n2cc3cc(-c4cc(CCCC(C)(C)N)cc(Cl)c4F)[nH]c3nc2=O)cc1] | 592.7 |
| 7 | 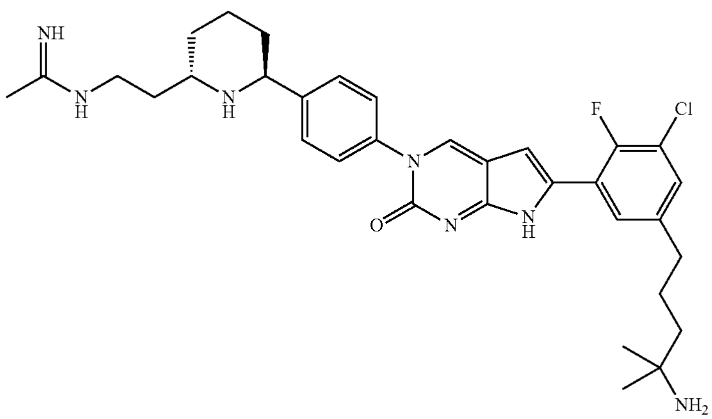 [SMILES: CC(=N)NCC[C@@H]1CCC[C@@H](c2ccc(-n3cc4cc(-c5cc(CCCC(C)(C)N)cc(Cl)c5F)[nH]c4nc3=O)cc2)N1] | 606.7 |
| 8 | 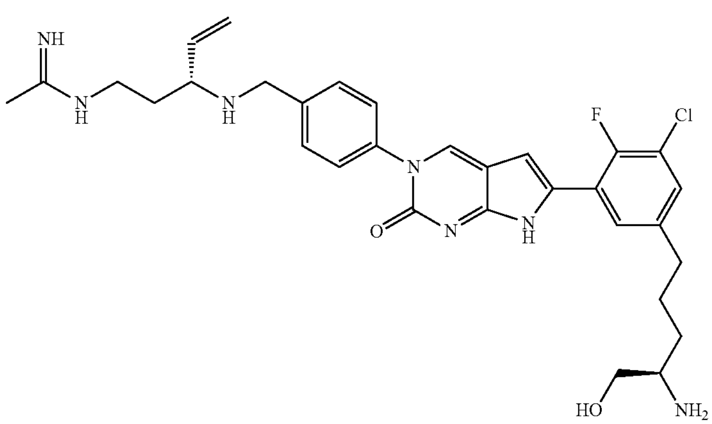 [SMILES: C=C[C@@H](CCNC(C)=N)NCc1ccc(-n2cc3cc(-c4cc(CCC[C@@H](N)CO)cc(Cl)c4F)[nH]c3nc2=O)cc1] | 594.7 |

TABLE 1-continued
| # | Structure | ESI, m/z [M + H]+ |
|---|---|---|
| 9 | 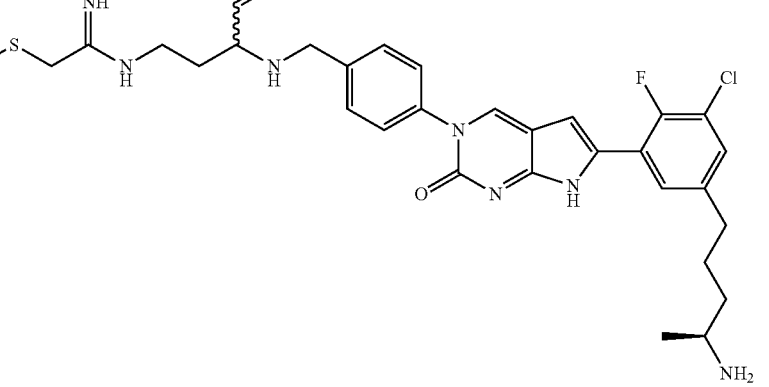 | 624.27 |
| 10 | 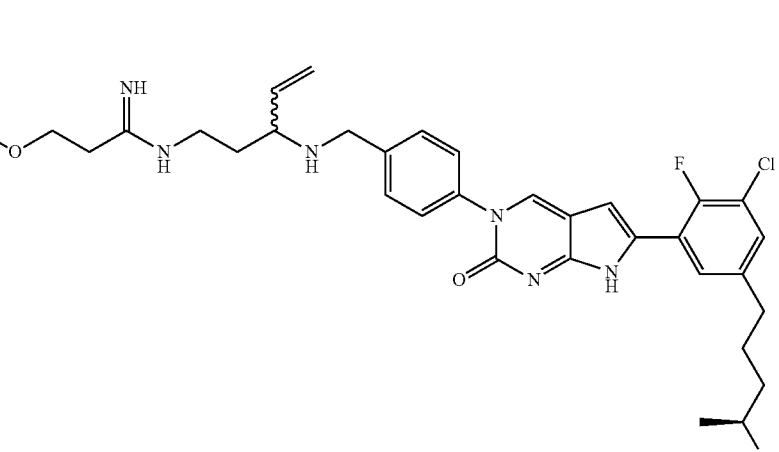 | 636.32 |
| 11 | 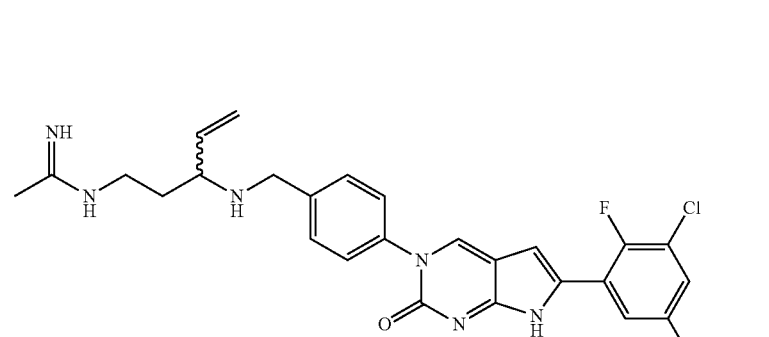 | 632.6 |

TABLE 1-continued
| # | Structure | ESI, m/z [M + H]+ |
|---|---|---|
| 12 | 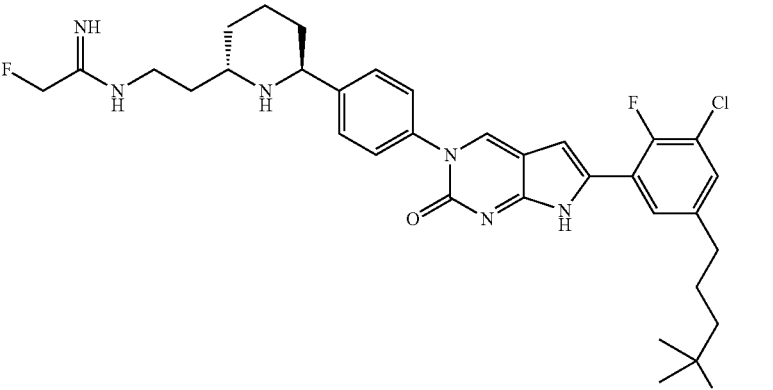 | 624.7 |
| 13 | 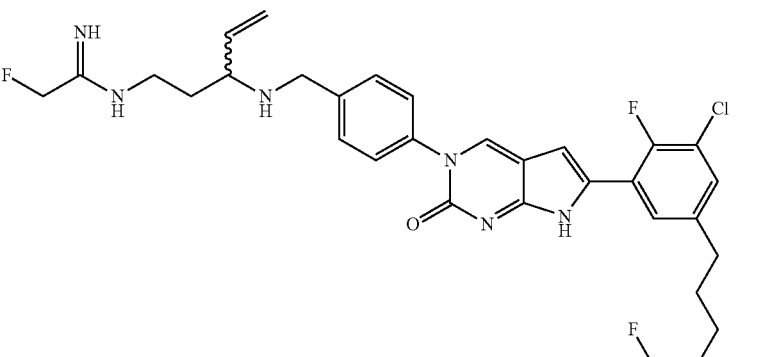 | 650.6 |
| 14 | 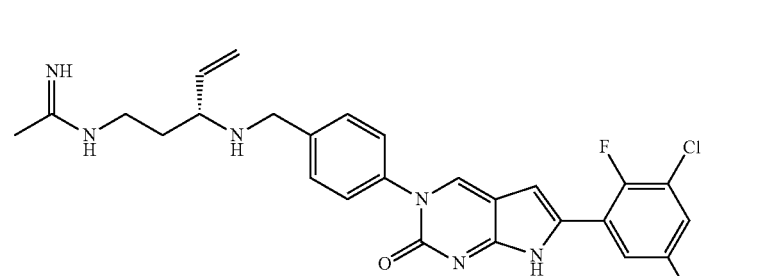 | 578 |

TABLE 1-continued

| # | Structure | ESI, m/z [M + H]+ |
|---|---|---|
| 15 | 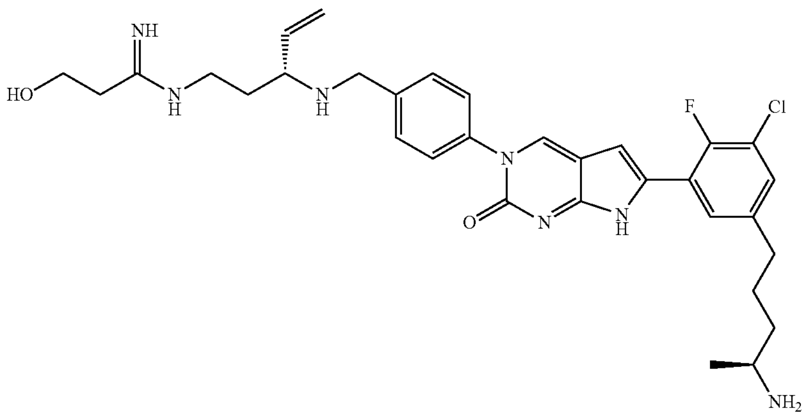 [SMILES: C=C[C@@H](CCNC(=N)CCO)NCc1ccc(-n2cc3cc(-c4cc(CCC[C@H](C)N)cc(Cl)c4F)[nH]c3nc2=O)cc1] | 608.7 |
| 16 | 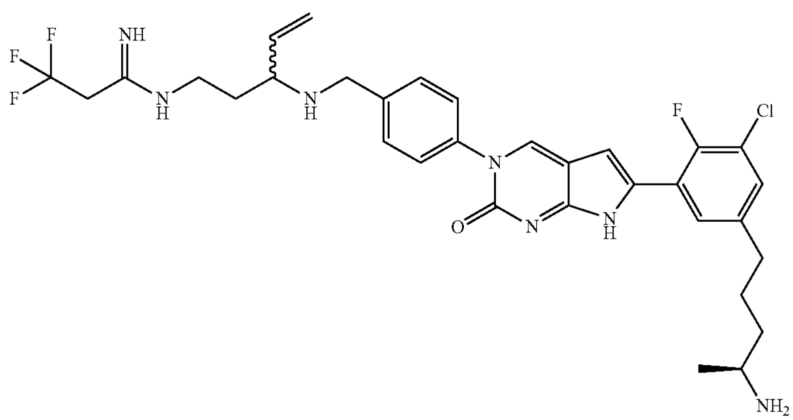 [SMILES: C=CC(CCNC(=N)CC(F)(F)F)NCc1ccc(-n2cc3cc(-c4cc(CCC[C@H](C)N)cc(Cl)c4F)[nH]c3nc2=O)cc1] | 647.13 |
| 17 | 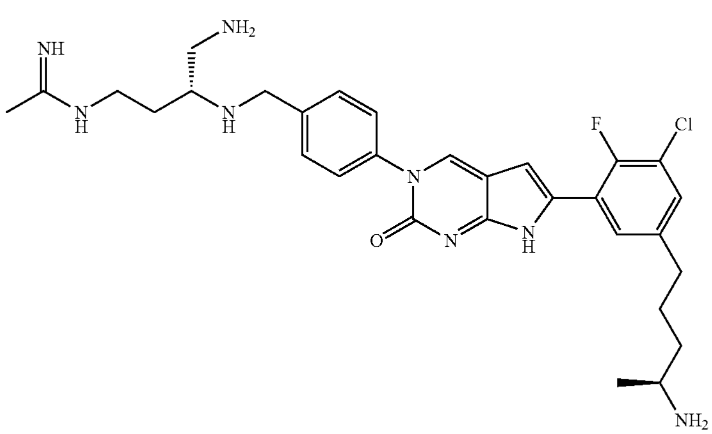 [SMILES: CC(=N)NCC[C@H](CN)NCc1ccc(-n2cc3cc(-c4cc(CCC[C@H](C)N)cc(Cl)c4F)[nH]c3nc2=O)cc1] | 581 |

TABLE 1-continued

| # | Structure | ESI, m/z [M + H]+ |
|---|---|---|
| 18 | 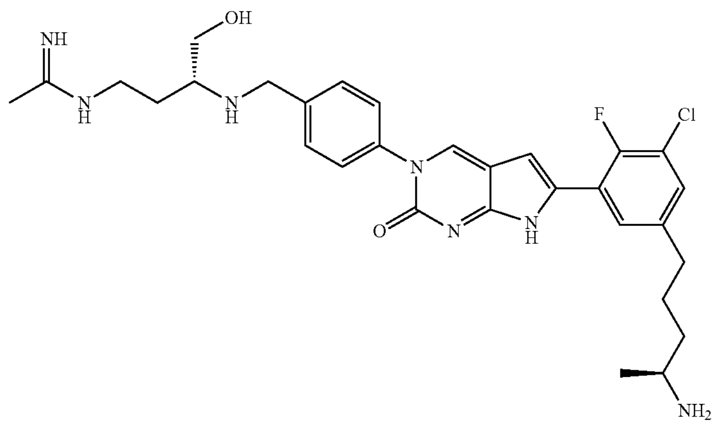 [SMILES: CC(=N)NCC[C@H](CO)NCc1ccc(-n2cc3cc(-c4cc(CCC[C@H](C)N)cc(Cl)c4F)[nH]c3nc2=O)cc1] | 582 |
| 19 | 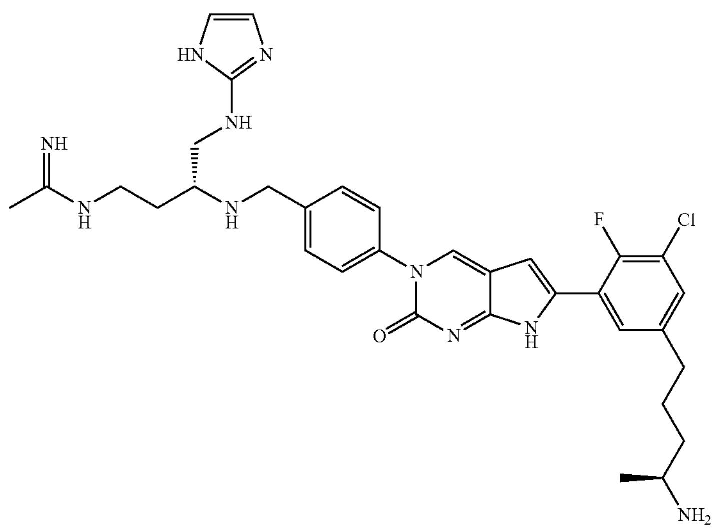 [SMILES: CC(=N)NCC[C@H](CNc1ncc[nH]1)NCc1ccc(-n2cc3cc(-c4cc(CCC[C@H](C)N)cc(Cl)c4F)[nH]c3nc2=O)cc1] | 647 |
| 20 | 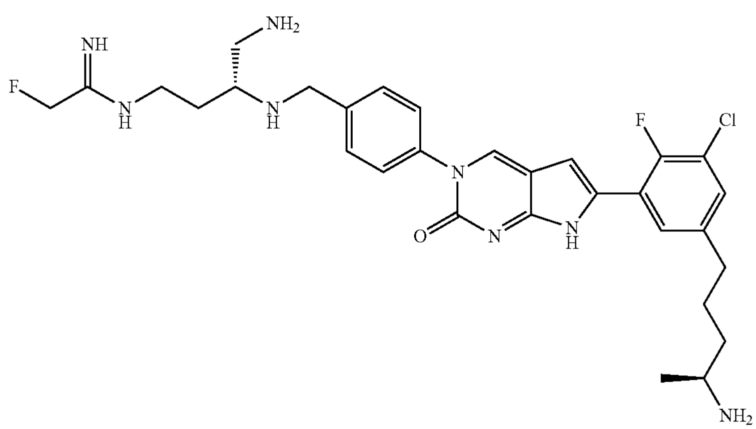 | 599 |

TABLE 1-continued

| # | Structure | ESI, m/z [M + H]+ |
|---|---|---|
| 21 | 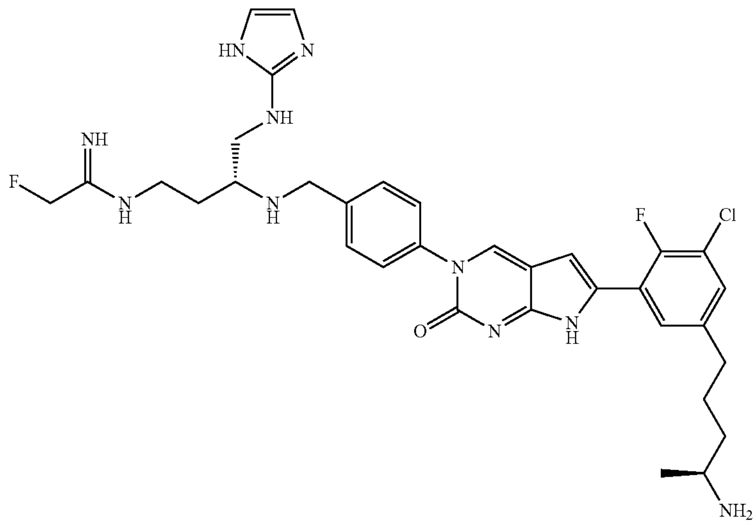 [SMILES: C[C@H](N)CCCc1cc(Cl)c(F)c(-c2cc3cn(-c4ccc(CN[C@H](CCNC(=N)CF)CNc5ncc[nH]5)cc4)c(=O)nc3[nH]2)c1] | 665 |
| 22 | 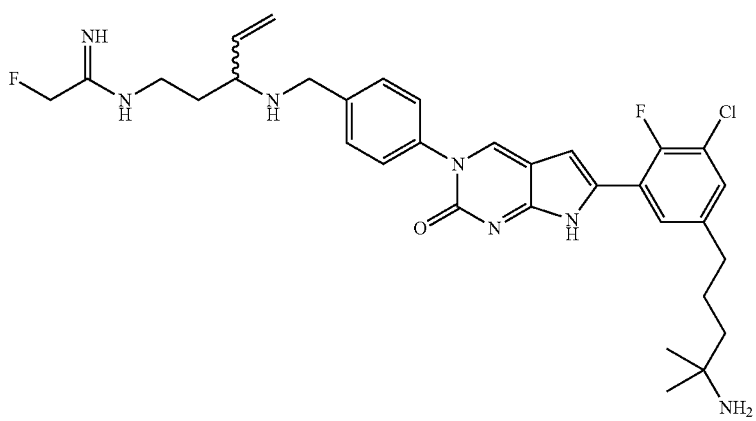 [SMILES: C=CC(CCNC(=N)CF)NCc1ccc(-n2cc3cc(-c4cc(CCCC(C)(C)N)cc(Cl)c4F)[nH]c3nc2=O)cc1] | 610.6 |
| 23 | 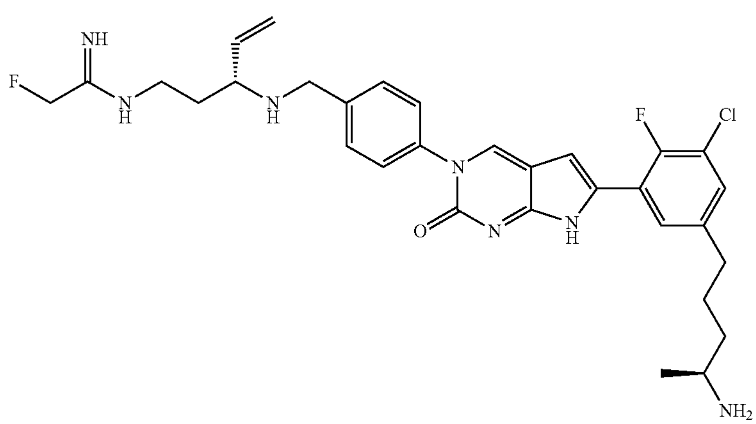 [SMILES: C=C[C@@H](CCNC(=N)CF)NCc1ccc(-n2cc3cc(-c4cc(CCC[C@H](C)N)cc(Cl)c4F)[nH]c3nc2=O)cc1] | 596 |

TABLE 1-continued

| # | Structure | ESI, m/z [M + H]+ |
|---|---|---|
| 24 | 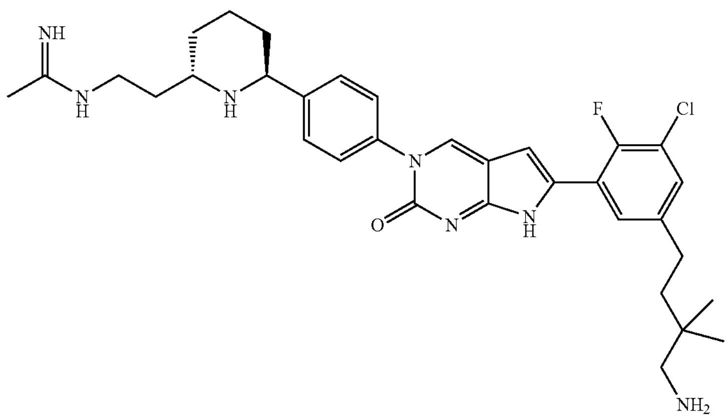 [SMILES: CC(=N)NCC[C@@H]1CCC[C@@H](c2ccc(-n3cc4cc(-c5cc(CCC(C)(C)CN)cc(Cl)c5F)[nH]c4nc3=O)cc2)N1] | 606.6 |
| 25 | 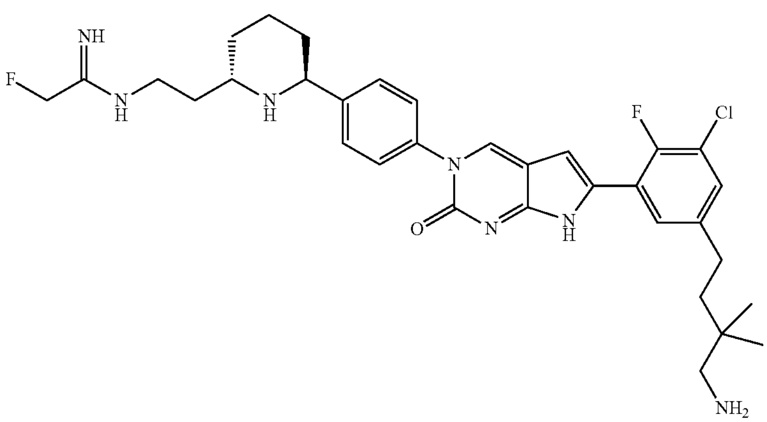 [SMILES: CC(C)(CN)CCc1cc(Cl)c(F)c(-c2cc3cn(-c4ccc([C@@H]5CCC[C@@H](CCNC(=N)CF)N5)cc4)c(=O)nc3[nH]2)c1] | 624.6 |
| 26 | 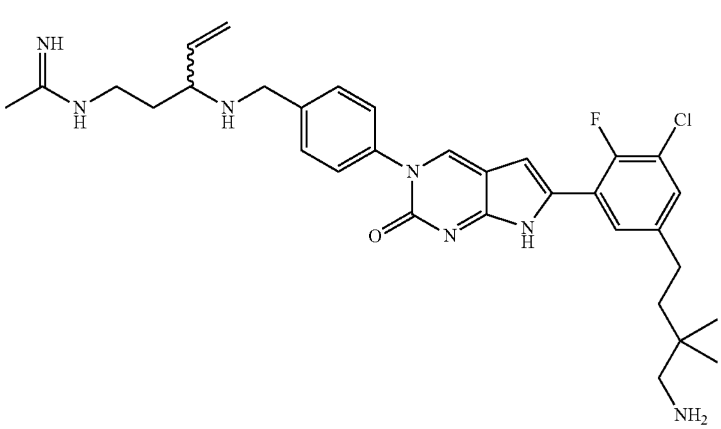 [SMILES: C=CC(CCNC(C)=N)NCc1ccc(-n2cc3cc(-c4cc(CCC(C)(C)CN)cc(Cl)c4F)[nH]c3nc2=O)cc1] | 592.6 |

TABLE 1-continued
| # | Structure | ESI, m/z [M + H]+ |
|---|---|---|
| 27 | 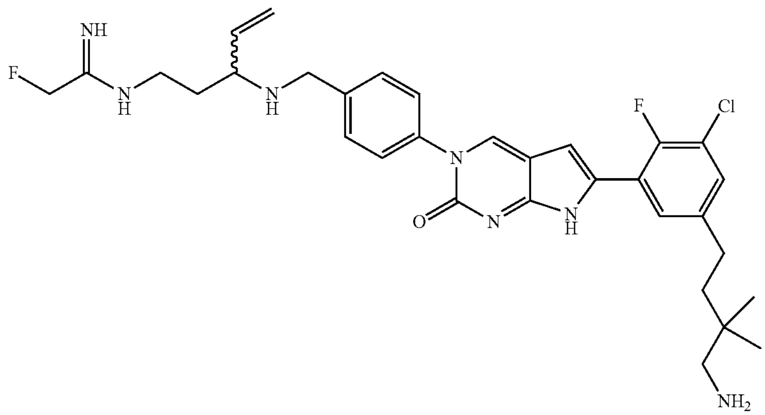 [SMILES: C=CC(CCNC(=N)CF)NCc1ccc(-n2cc3cc(-c4cc(CCC(C)(C)CN)cc(Cl)c4F)[nH]c3nc2=O)cc1] | 610.6 |
| 28 | 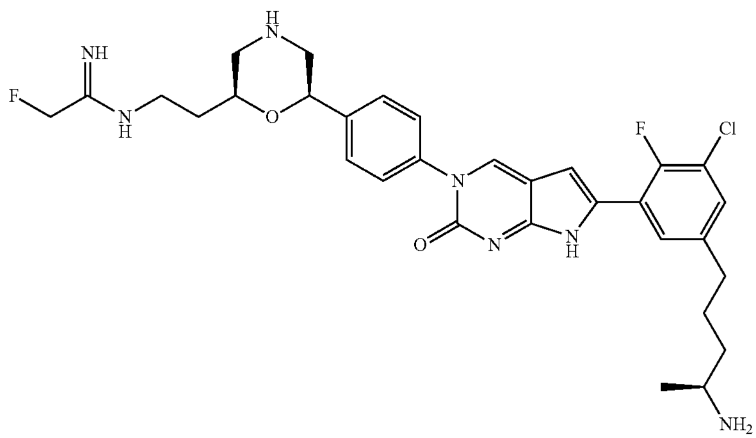 [SMILES: C[C@H](N)CCCc1cc(Cl)c(F)c(-c2cc3cn(-c4ccc([C@@H]5CNC[C@H](CCNC(=N)CF)O5)cc4)c(=O)nc3[nH]2)c1] | 612.6 |
| 29 | 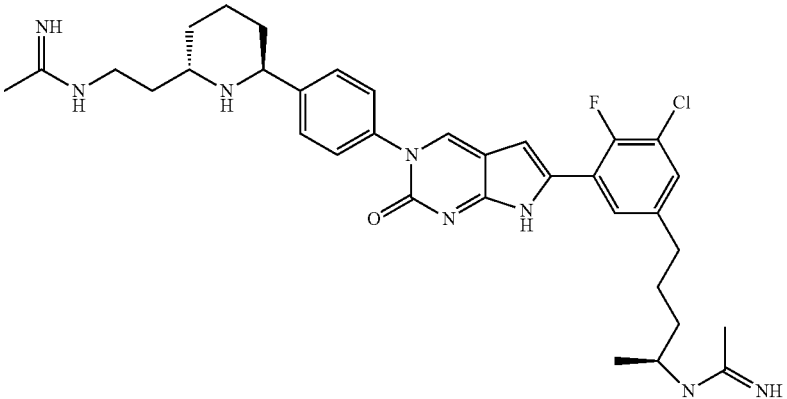 | 633.7 |

TABLE 1-continued
| # | Structure | ESI, m/z [M + H]+ |
|---|-----------|-------------------|
| 30 | 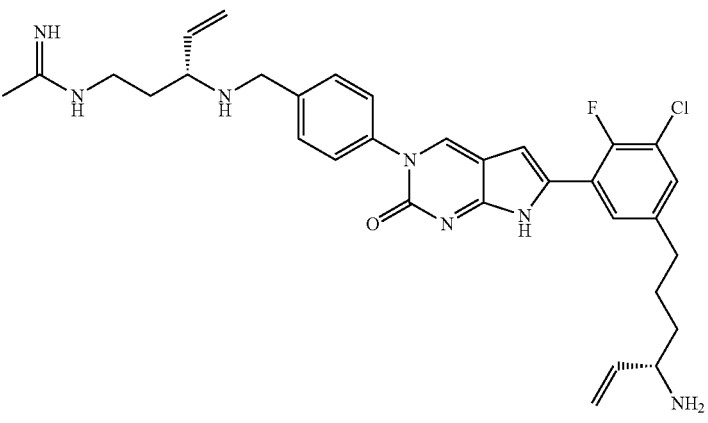 [SMILES: C=C[C@@H](N)CCCc1cc(Cl)c(F)c(-c2cc3cn(-c4ccc(CN[C@@H](C=C)CCNC(C)=N)cc4)c(=O)nc3[nH]2)c1] | 590.6 |
| 31 | 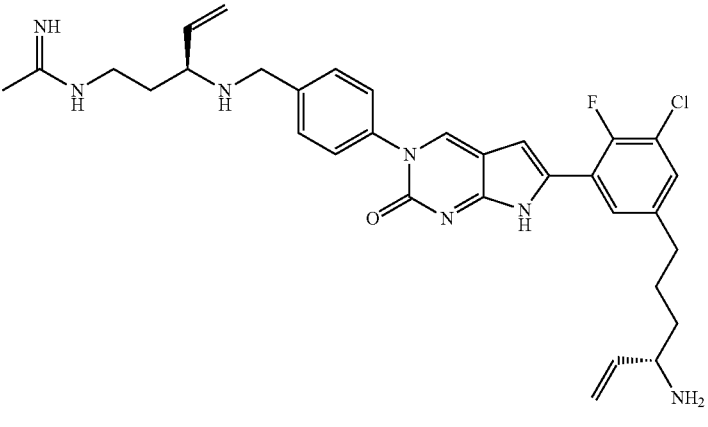 [SMILES: C=C[C@@H](N)CCCc1cc(Cl)c(F)c(-c2cc3cn(-c4ccc(CN[C@H](C=C)CCNC(C)=N)cc4)c(=O)nc3[nH]2)c1] | 590.6 |
| 32 | 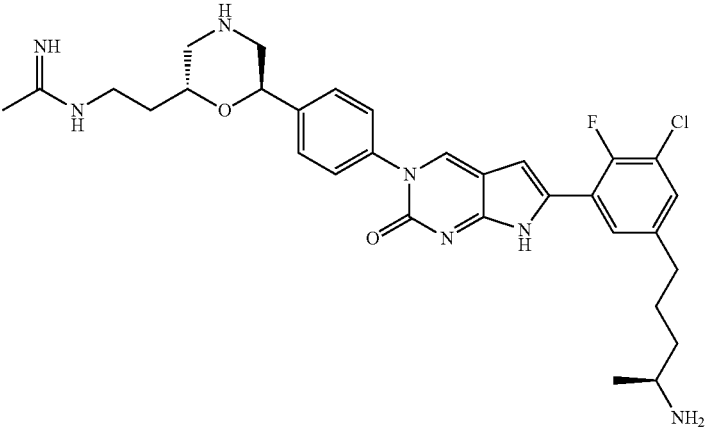 [SMILES: CC(=N)NCC[C@@H]1CNC[C@@H](c2ccc(-n3cc4cc(-c5cc(CCC[C@H](C)N)cc(Cl)c5F)[nH]c4nc3=O)cc2)O1] | 594.6 |

TABLE 1-continued
| # | Structure | ESI, m/z [M + H]+ |
|---|---|---|
| 33 | 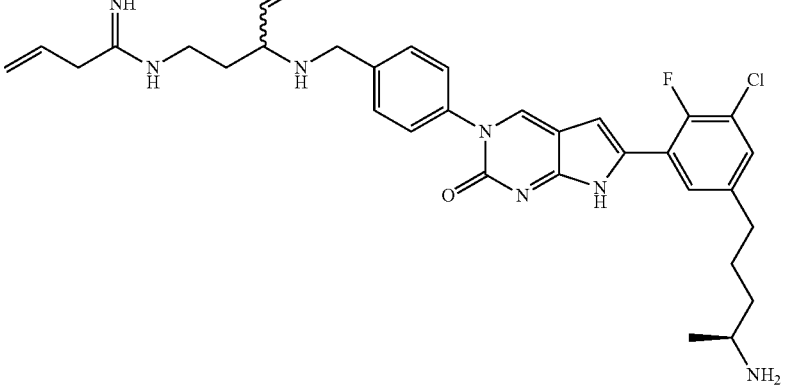 | 605.17 |
| 34 | 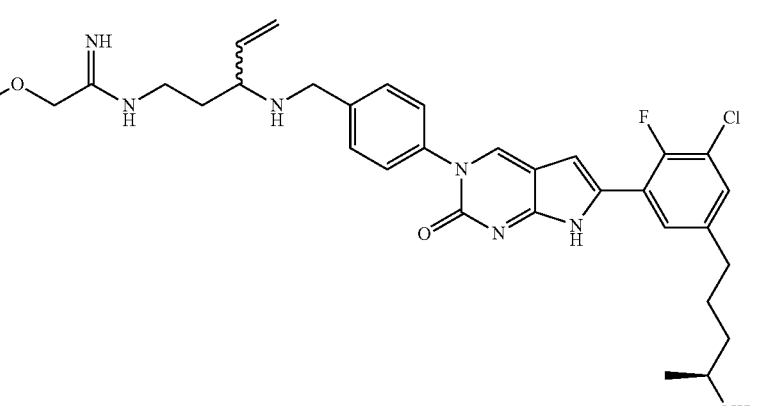 | 609.16 |
| 35 | 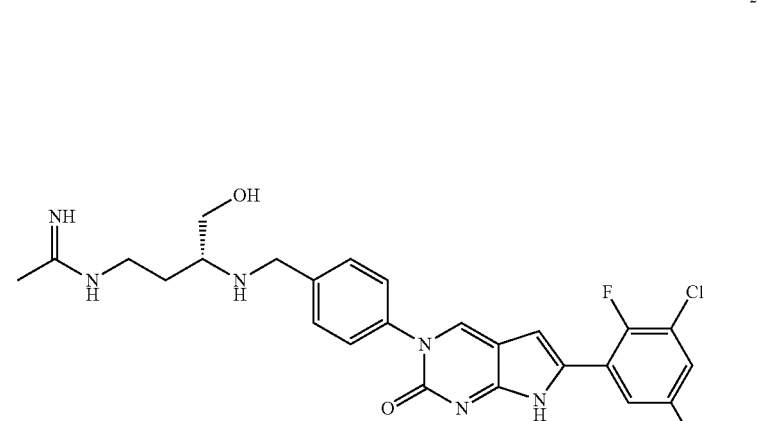 | 598.6 |

TABLE 1-continued

| # | Structure | ESI, m/z [M + H]+ |
|---|---|---|
| 36 | 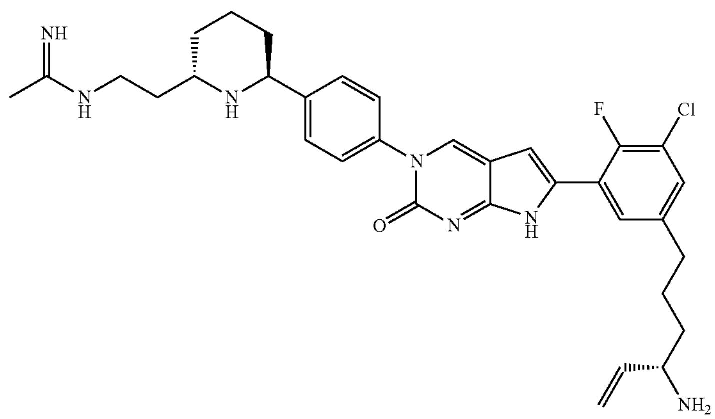 [SMILES: C=C[C@@H](N)CCCc1cc(Cl)c(F)c(-c2cc3cn(-c4ccc([C@@H]5CCC[C@@H](CCNC(C)=N)N5)cc4)c(=O)nc3[nH]2)c1] | 604.6 |
| 37 | 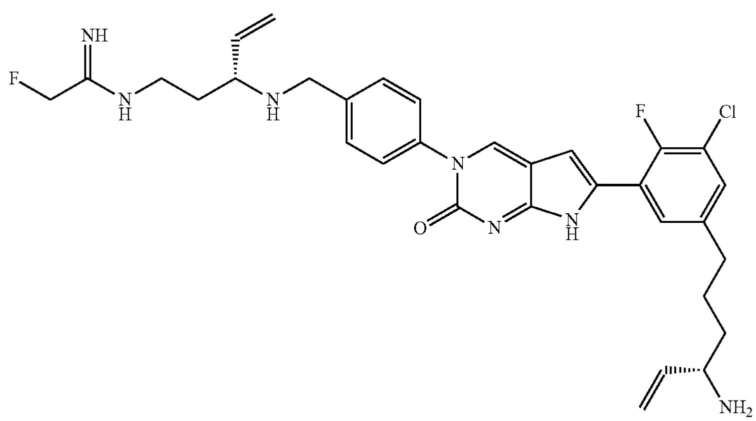 [SMILES: C=C[C@@H](N)CCCc1cc(Cl)c(F)c(-c2cc3cn(-c4ccc(CN[C@@H](C=C)CCNC(=N)CF)cc4)c(=O)nc3[nH]2)c1] | 608.6 |
| 38 | 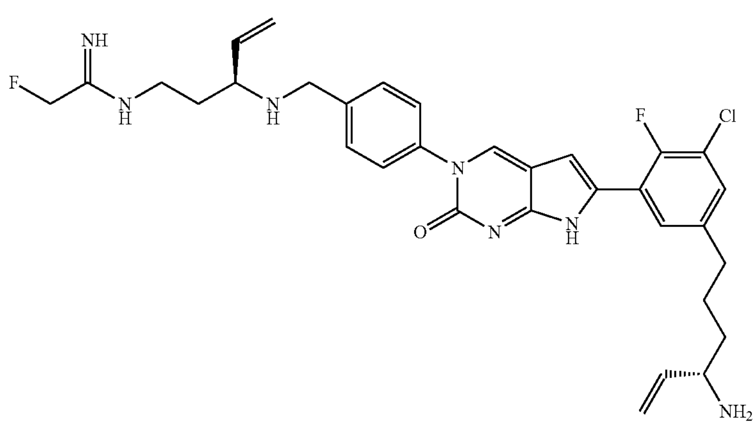 [SMILES: C=C[C@@H](N)CCCc1cc(Cl)c(F)c(-c2cc3cn(-c4ccc(CN[C@H](C=C)CCNC(=N)CF)cc4)c(=O)nc3[nH]2)c1] | 608.6 |

TABLE 1-continued
| # | Structure | ESI, m/z [M + H]+ |
|---|---|---|
| 39 | 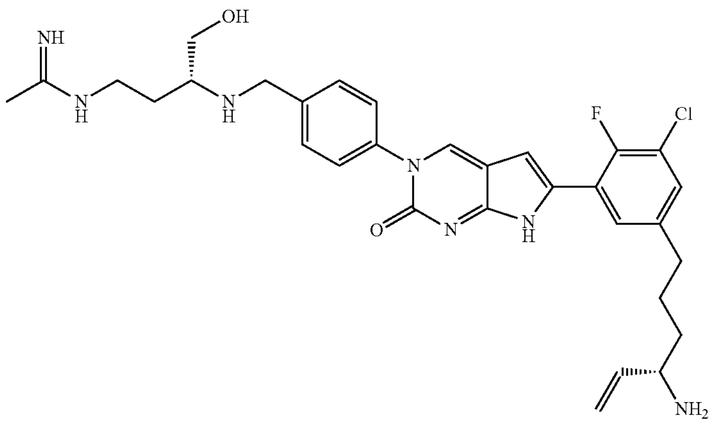 [SMILES: C=C[C@@H](N)CCCc1cc(Cl)c(F)c(-c2cc3cn(-c4ccc(CN[C@@H](CO)CCNC(C)=N)cc4)c(=O)nc3[nH]2)c1] | 594.6 |
| 40 | 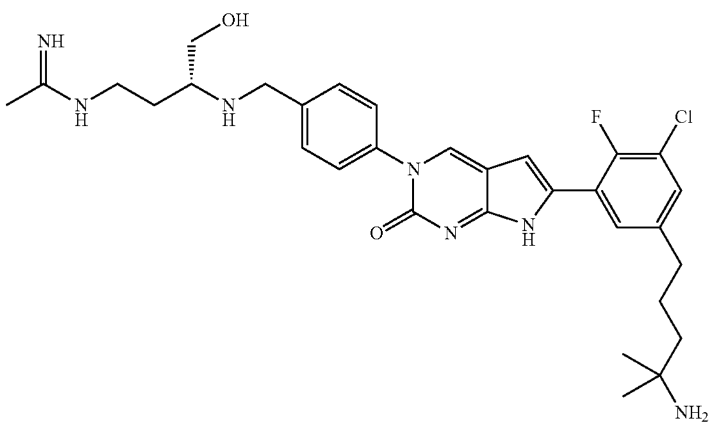 [SMILES: CC(=N)NCC[C@H](CO)NCc1ccc(-n2cc3cc(-c4cc(CCCC(C)(C)N)cc(Cl)c4F)[nH]c3nc2=O)cc1] | 596.6 |
| 41 | 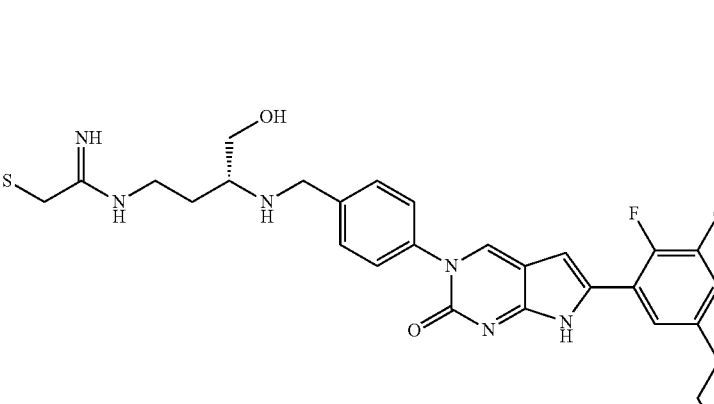 | 629.21 |

TABLE 1-continued
| # | Structure | ESI, m/z [M + H]+ |
|---|-----------|-------------------|
| 42 | 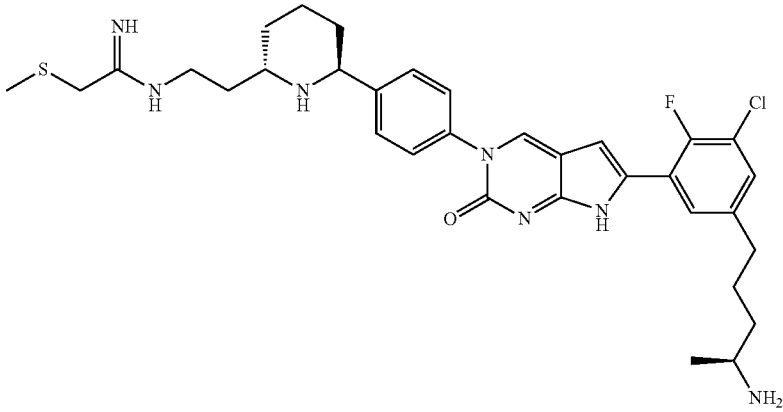 [SMILES: CSCC(=N)NCC[C@@H]1CCC[C@@H](c2ccc(-n3cc4cc(-c5cc(CCC[C@H](C)N)cc(Cl)c5F)[nH]c4nc3=O)cc2)N1] | 639.3 |
| 43 | 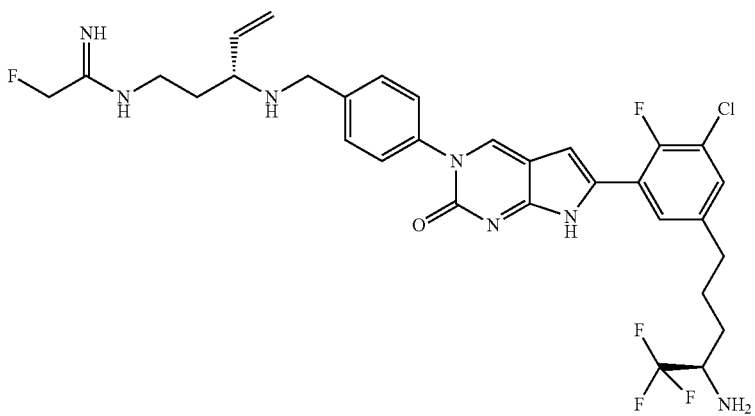 [SMILES: C=C[C@@H](CCNC(=N)CF)NCc1ccc(-n2cc3cc(-c4cc(CCC[C@@H](N)C(F)(F)F)cc(Cl)c4F)[nH]c3nc2=O)cc1] | 650.6 |
| 44 | 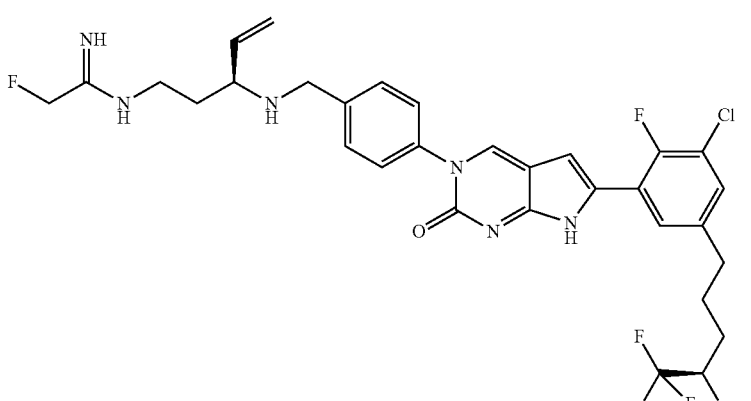 | 650.6 |

TABLE 1-continued
| # | Structure | ESI, m/z [M + H]+ |
|---|---|---|
| 45 | 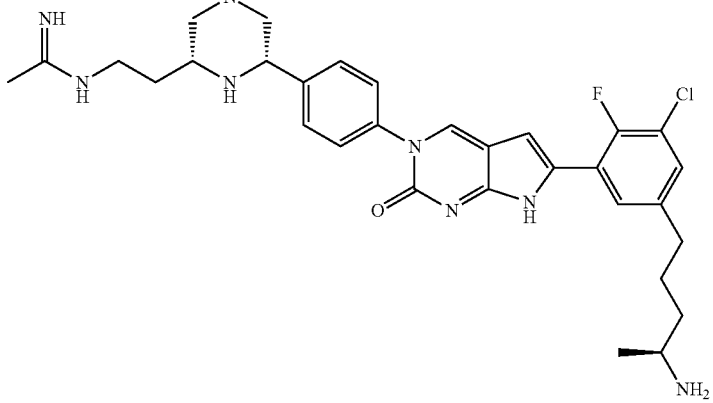 | 593.6 |
| 46 | 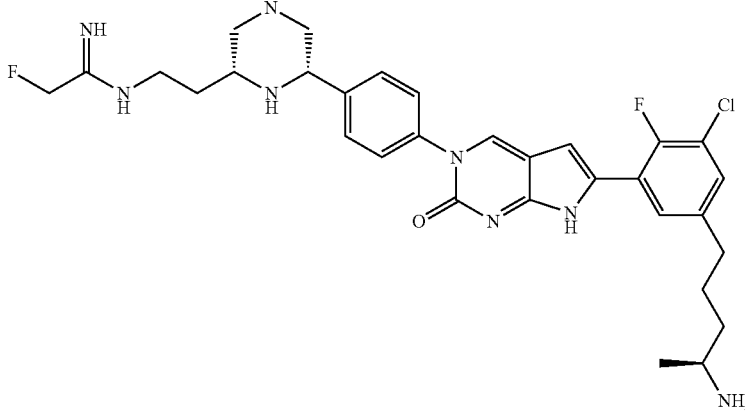 | 611.6 |
| 47 | 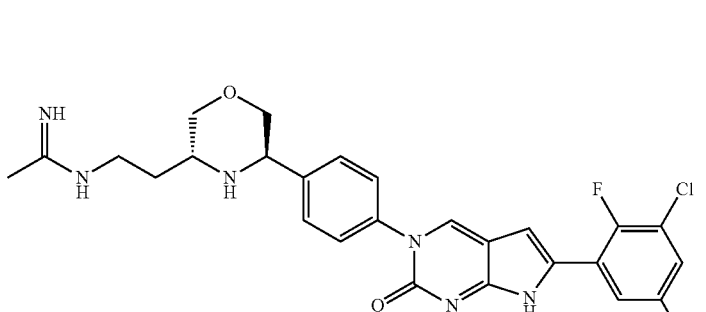 | 594.5 |

TABLE 1-continued

| # | Structure | ESI, m/z [M + H]+ |
|---|-----------|-------------------|
| 48 | 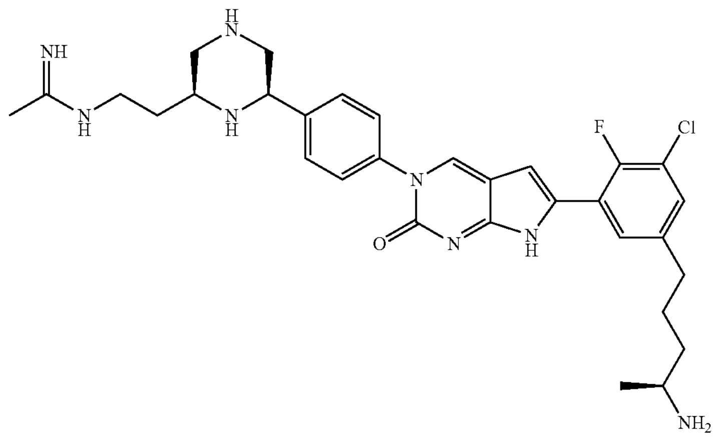 [SMILES: CC(=N)NCC[C@H]1CNC[C@@H](c2ccc(-n3cc4cc(-c5cc(CCC[C@H](C)N)cc(Cl)c5F)[nH]c4nc3=O)cc2)N1] | 593.5 |
| 49 | 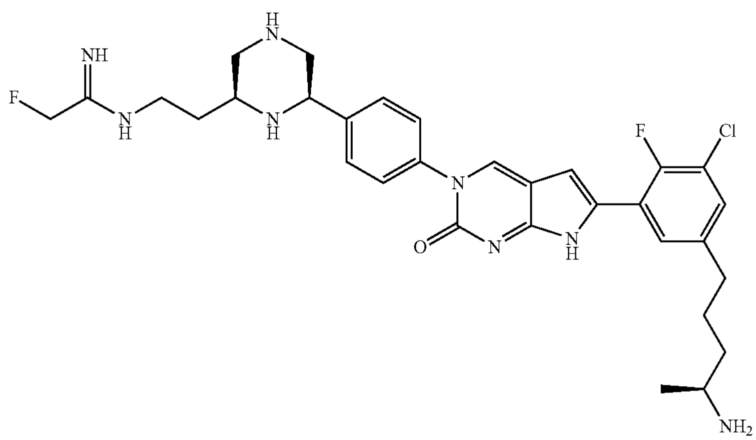 | 611.4 |
| 50 | 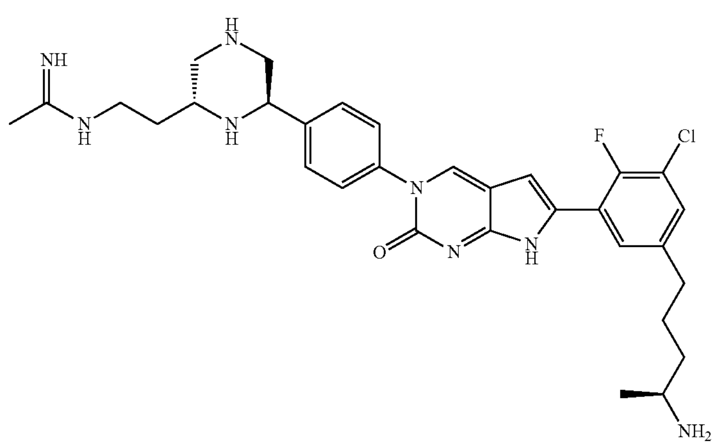 [SMILES: CC(=N)NCC[C@@H]1CNC[C@@H](c2ccc(-n3cc4cc(-c5cc(CCC[C@H](C)N)cc(Cl)c5F)[nH]c4nc3=O)cc2)N1] | 593.5 |

TABLE 1-continued

| # | Structure | ESI, m/z [M + H]+ |
|---|---|---|
| 51 | 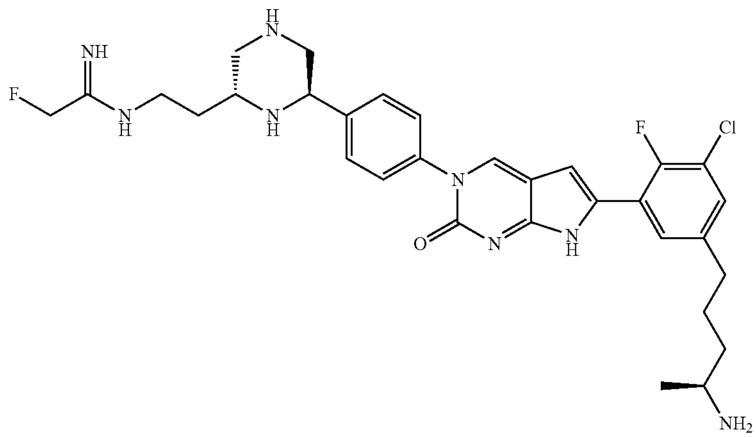 [SMILES: C[C@H](N)CCCc1cc(Cl)c(F)c(-c2cc3cn(-c4ccc([C@@H]5CNC[C@@H](CCNC(=N)CF)N5)cc4)c(=O)nc3[nH]2)c1] | 611.5 |
| 52 | 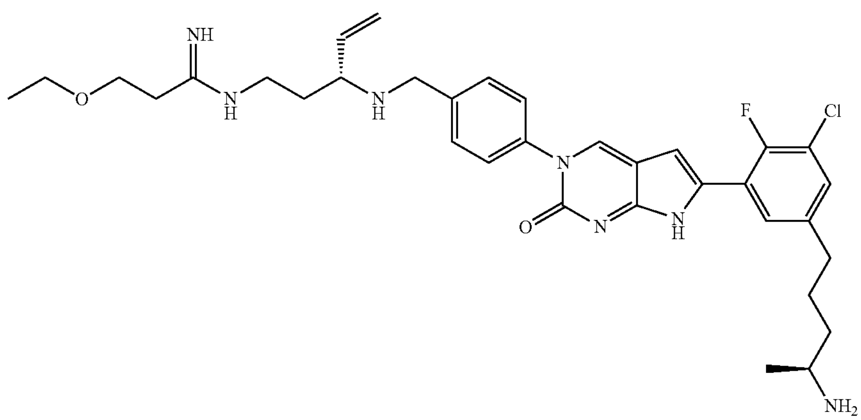 [SMILES: C=C[C@@H](CCNC(=N)CCOCC)NCc1ccc(-n2cc3cc(-c4cc(CCC[C@H](C)N)cc(Cl)c4F)[nH]c3nc2=O)cc1] | 637.2 |
| 53 | 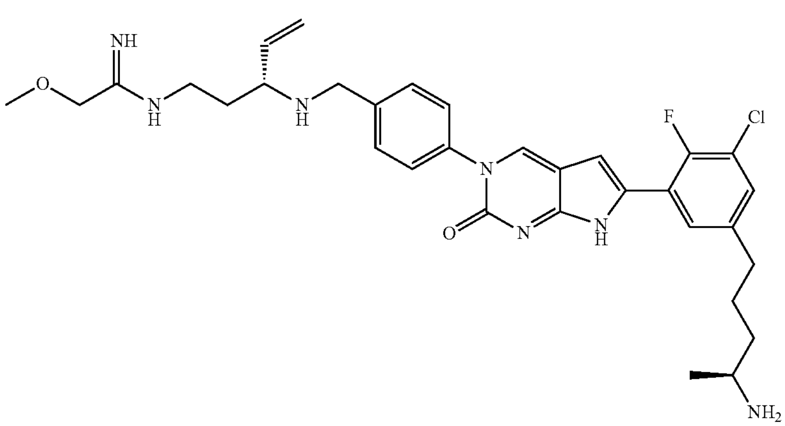 [SMILES: C=C[C@@H](CCNC(=N)COC)NCc1ccc(-n2cc3cc(-c4cc(CCC[C@H](C)N)cc(Cl)c4F)[nH]c3nc2=O)cc1] | 609.2 |

TABLE 1-continued
| # | Structure | ESI, m/z [M + H]+ |
|---|---|---|
| 54 | 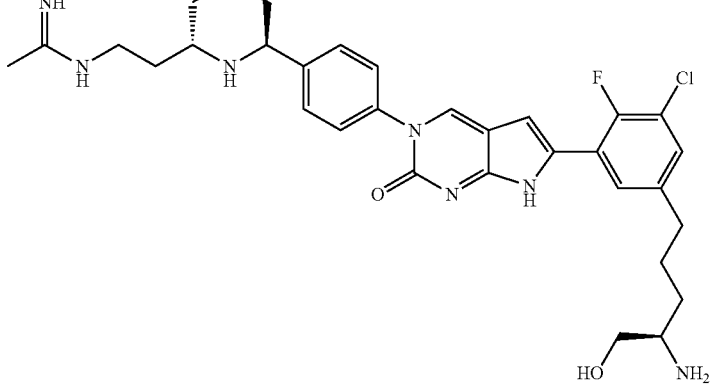 | 610.6 |
| 55 | 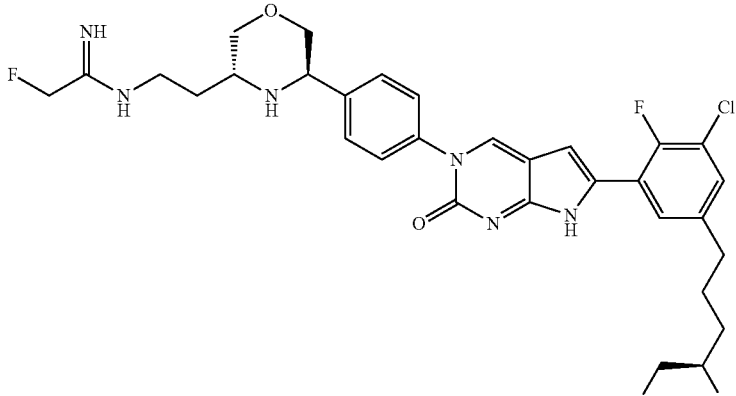 | 628.6 |
| 56 | 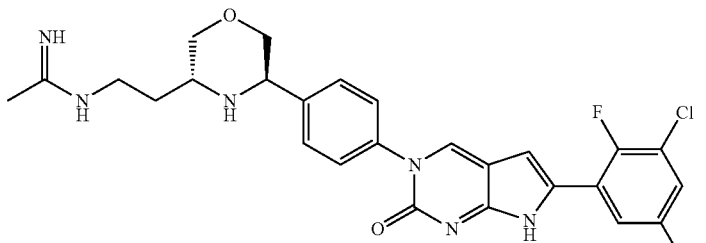 | 606.6 |

TABLE 1-continued
| # | Structure | ESI, m/z [M + H]+ |
|---|---|---|
| 57 | 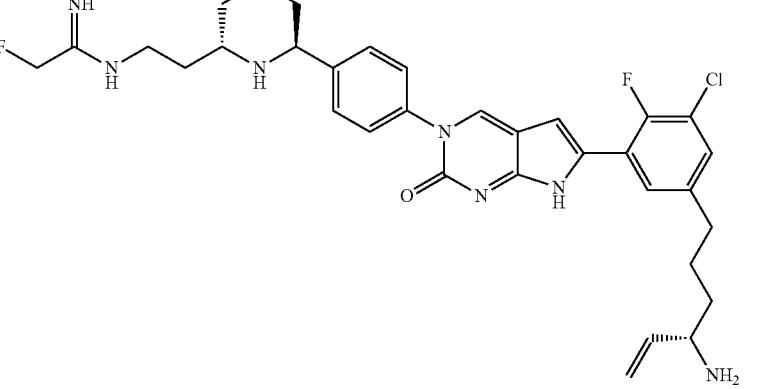 | 624.6 |
| 58 | 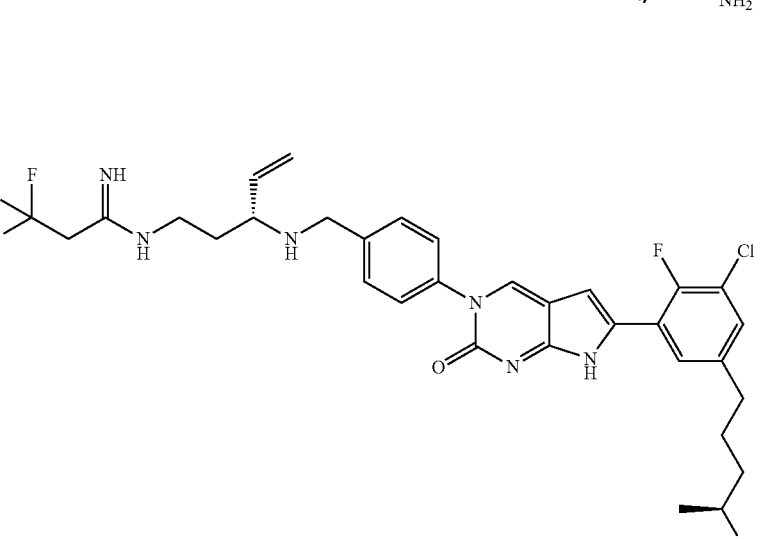 | 647.2 |
| 59 | 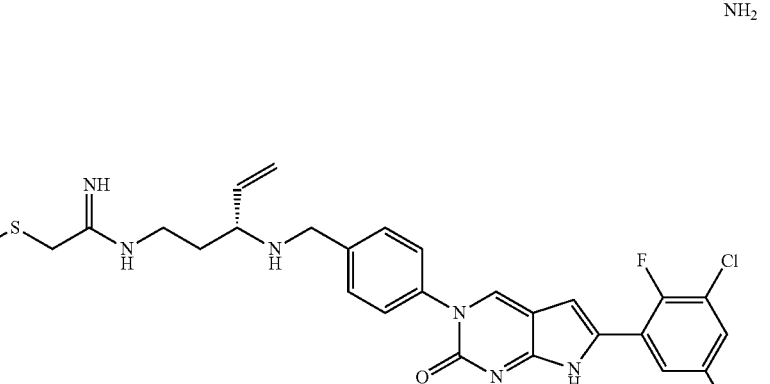 | 625.2 |

TABLE 1-continued
| # | Structure | ESI, m/z [M + H]+ |
|---|---|---|
| 60 | 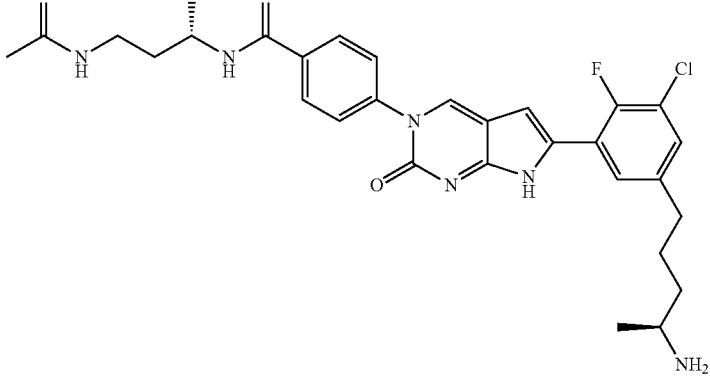 | 592 |
| 61 | 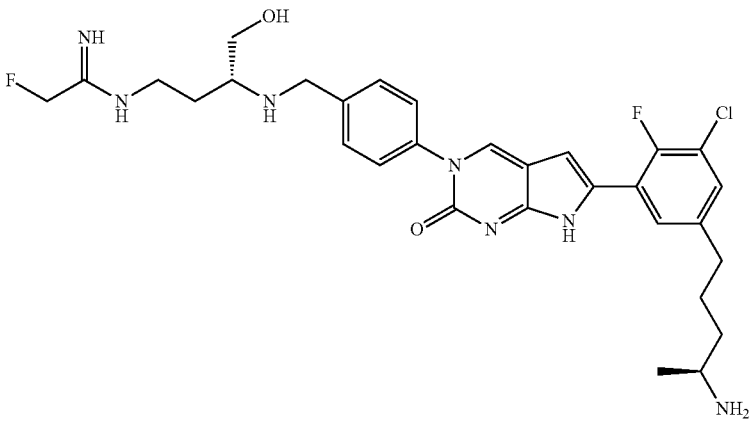 [SMILES: C[C@H](N)CCCc1cc(Cl)c(F)c(-c2cc3cn(-c4ccc(CN[C@@H](CO)CCNC(=N)CF)cc4)c(=O)nc3[nH]2)c1] | 600 |
| 62 | 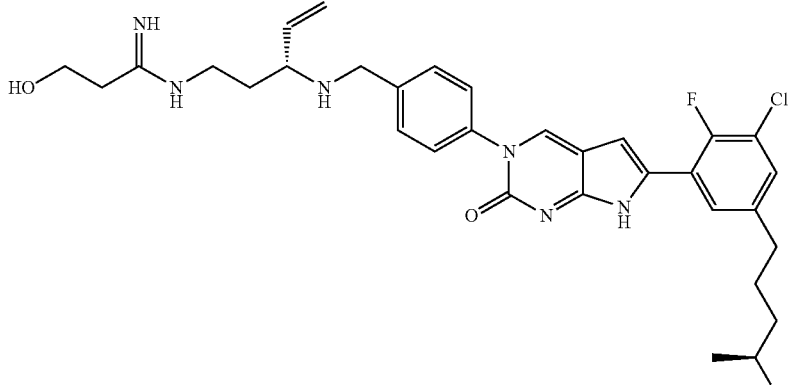 | 608. |

TABLE 1-continued

| # | Structure | ESI, m/z [M + H]+ |
|---|---|---|
| 63 | 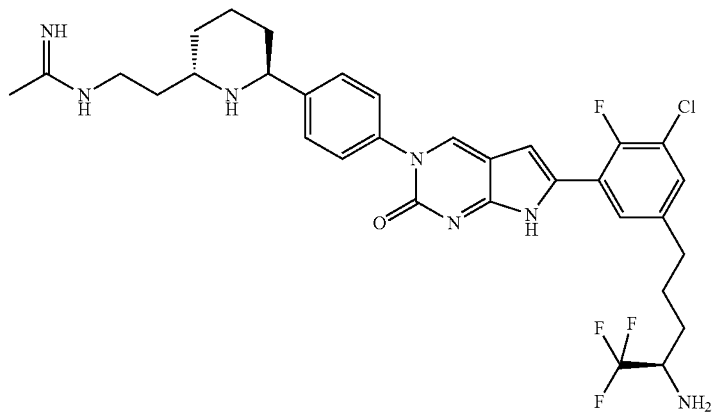 [SMILES: CC(=N)NCC[C@@H]1CCC[C@@H](c2ccc(-n3cc4cc(-c5cc(CCC[C@@H](N)C(F)(F)F)cc(Cl)c5F)[nH]c4nc3=O)cc2)N1] | 647.1 |
| 64 | 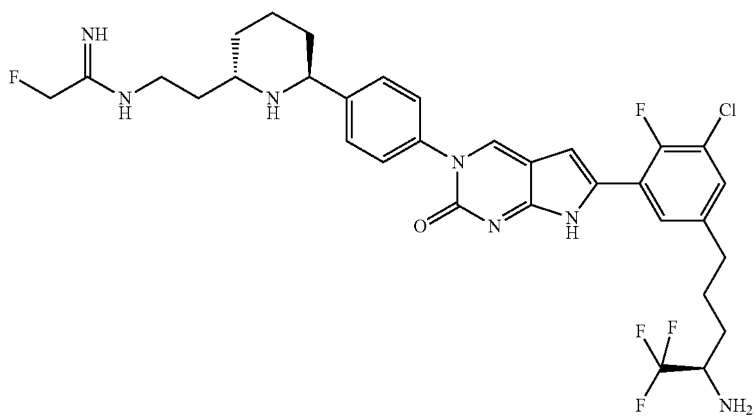 [SMILES: N=C(CF)NCC[C@@H]1CCC[C@@H](c2ccc(-n3cc4cc(-c5cc(CCC[C@@H](N)C(F)(F)F)cc(Cl)c5F)[nH]c4nc3=O)cc2)N1] | 665.1 |
| 65 | 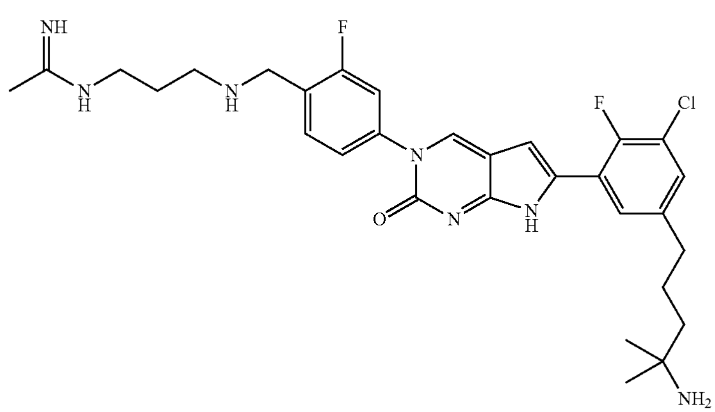 [SMILES: CC(=N)NCCCNCc1ccc(-n2cc3cc(-c4cc(CCCC(C)(C)N)cc(Cl)c4F)[nH]c3nc2=O)cc1F] | 586.6 |

TABLE 1-continued
| # | Structure | ESI, m/z [M + H]+ |
|---|-----------|-------------------|
| 66 | 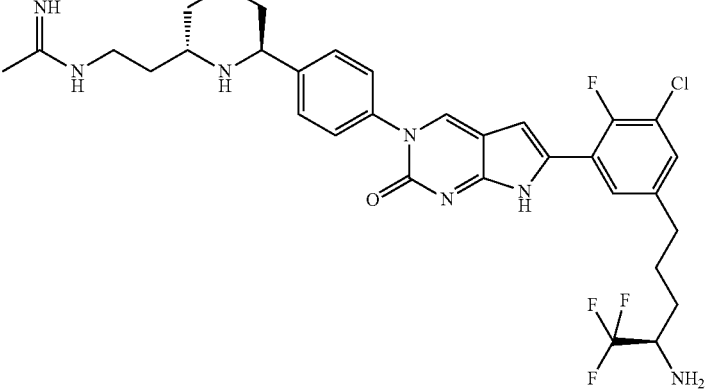 | 648.6 |
| 67 | 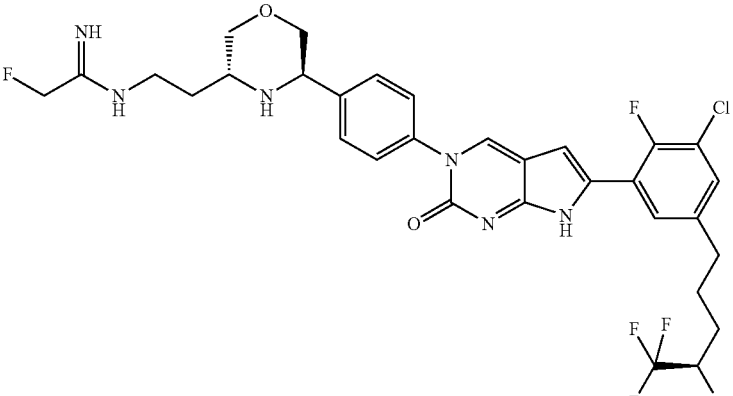 | 666.6 |
| 68 | 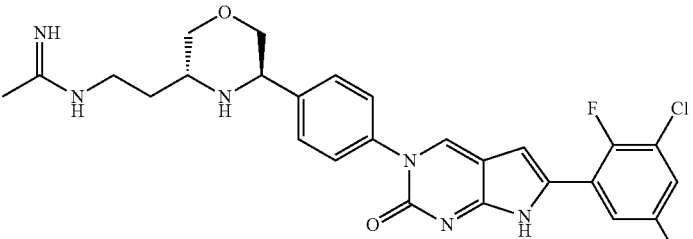 | 608.6 |

TABLE 1-continued
| # | Structure | ESI, m/z [M + H]+ |
|---|---|---|
| 69 | 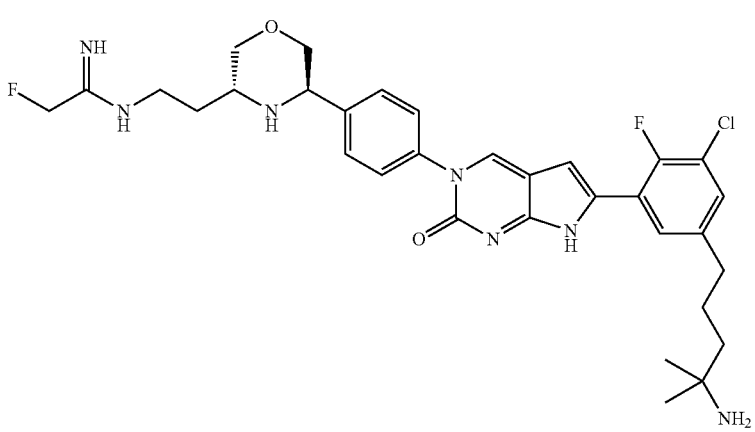 [SMILES: CC(C)(N)CCCc1cc(Cl)c(F)c(-c2cc3cn(-c4ccc([C@@H]5COC[C@@H](CCNC(=N)CF)N5)cc4)c(=O)nc3[nH]2)c1] | 626.6 |
| 70 | 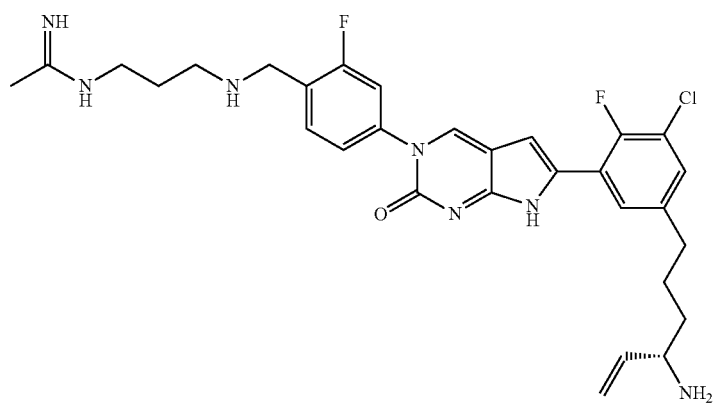 [SMILES: C=C[C@@H](N)CCCc1cc(Cl)c(F)c(-c2cc3cn(-c4ccc(CNCCCNC(C)=N)c(F)c4)c(=O)nc3[nH]2)c1] | 582.6 |
| 71 | 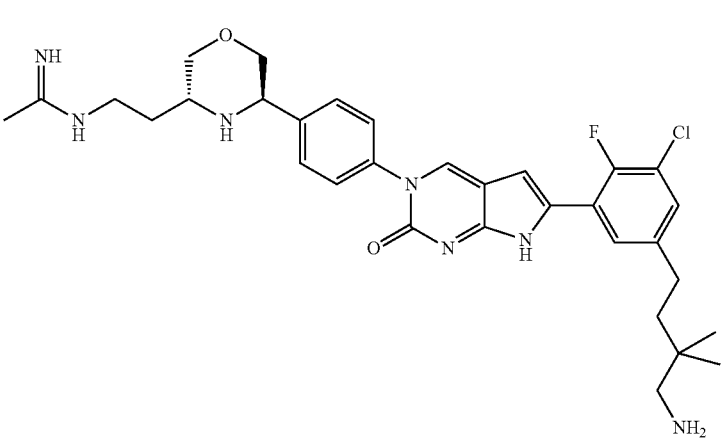 [SMILES: CC(=N)NCC[C@@H]1COC[C@@H](c2ccc(-n3cc4cc(-c5cc(CCC(C)(C)CN)cc(Cl)c5F)[nH]c4nc3=O)cc2)N1] | 608.6 |

TABLE 1-continued
| # | Structure | ESI, m/z [M + H]+ |
|---|-----------|-------------------|
| 72 | 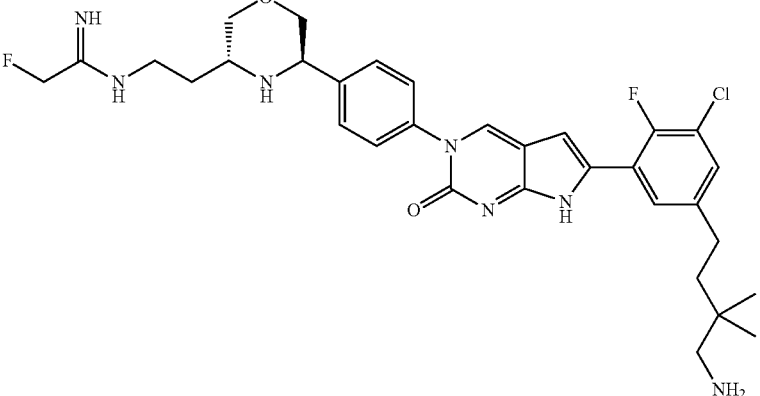 | 626.6 |
| 73 | 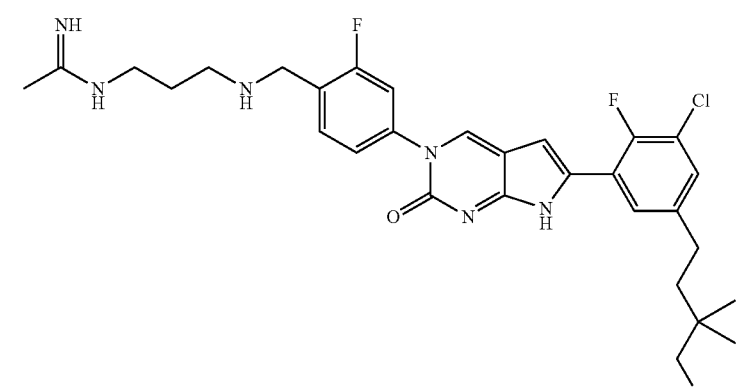 | 584.6 |
| 74 | 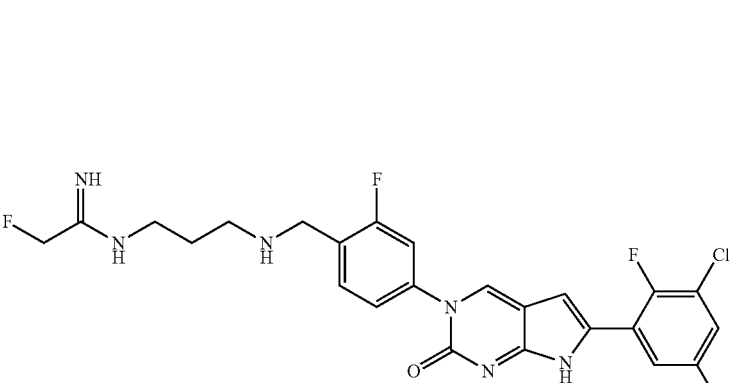 | 602.6 |

TABLE 1-continued
| # | Structure | ESI, m/z [M + H]+ |
|---|---|---|
| 75 | 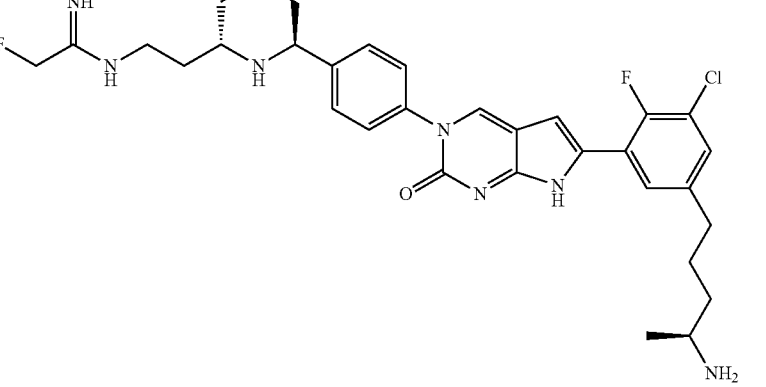 | 612.6 |
| 76 | 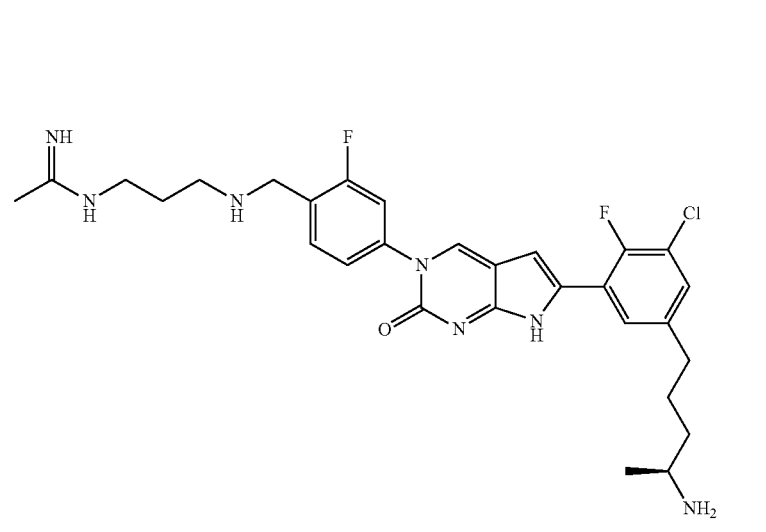 [SMILES: CC(=N)NCCCNCc1ccc(-n2cc3cc(-c4cc(CCC[C@H](C)N)cc(Cl)c4F)[nH]c3nc2=O)cc1F] | 570 |
| 77 | 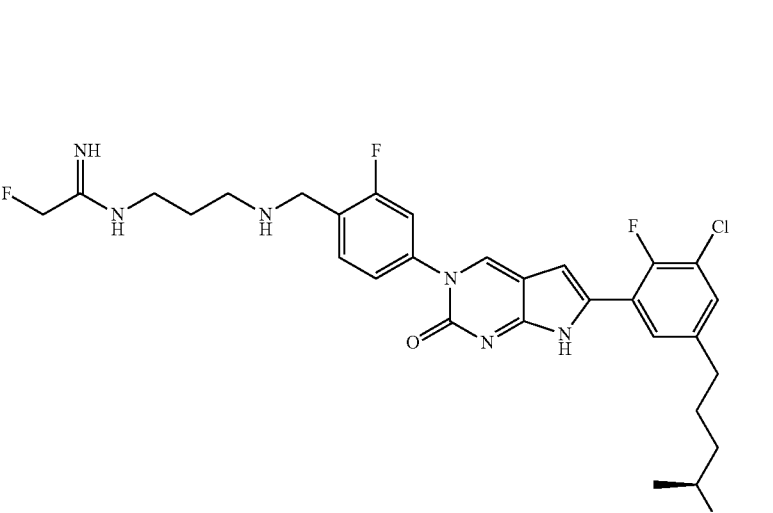 | 588 |

TABLE 1-continued
| # | Structure | ESI, m/z [M + H]+ |
|---|---|---|
| 78 | 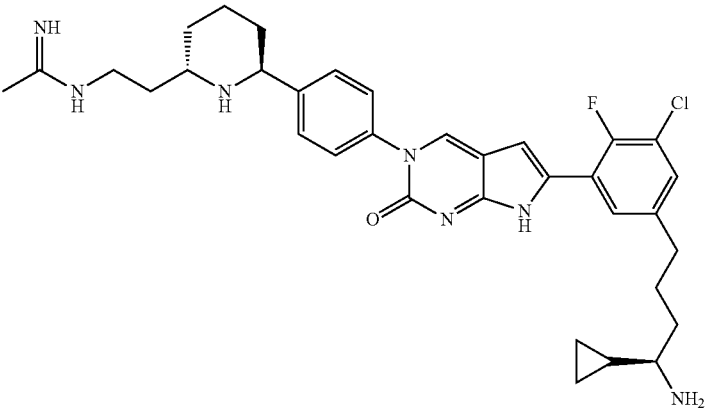 [SMILES: CC(=N)NCC[C@@H]1CCC[C@@H](c2ccc(-n3cc4cc(-c5cc(CCC[C@@H](N)C6CC6)cc(Cl)c5F)[nH]c4nc3=O)cc2)N1] | 620.6 |
| 79 | 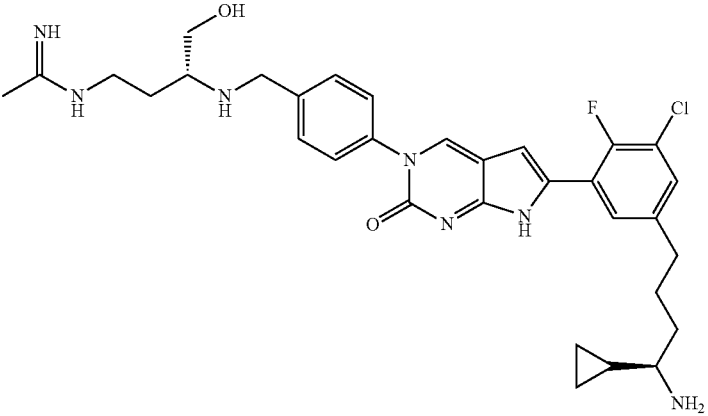 [SMILES: CC(=N)NCC[C@H](CO)NCc1ccc(-n2cc3cc(-c4cc(CCC[C@@H](N)C5CC5)cc(Cl)c4F)[nH]c3nc2=O)cc1] | 608.5 |
| 80 | 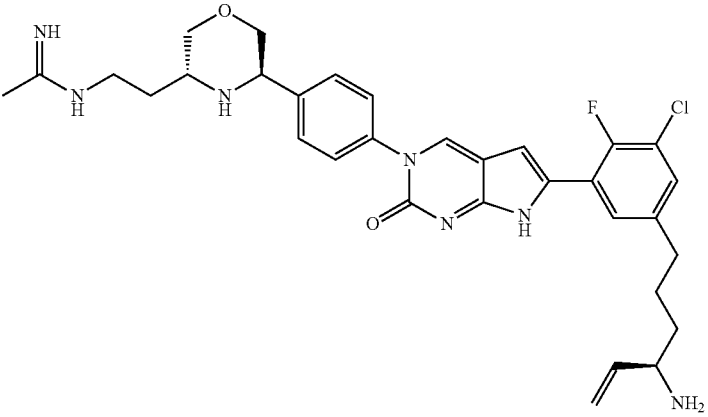 [SMILES: C=C[C@H](N)CCCc1cc(Cl)c(F)c(-c2cc3cn(-c4ccc([C@@H]5COC[C@@H](CCNC(C)=N)N5)cc4)c(=O)nc3[nH]2)c1] | 606.4 |

TABLE 1-continued

| # | Structure | ESI, m/z [M + H]+ |
|---|-----------|-------------------|
| 81 | 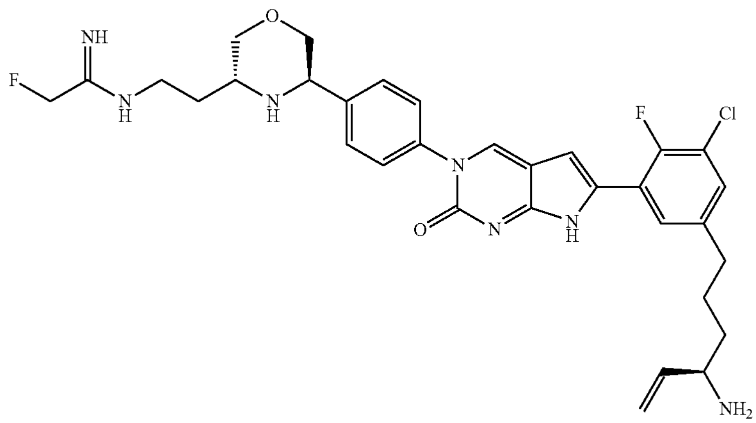 [SMILES: C=C[C@H](N)CCCc1cc(Cl)c(F)c(-c2cc3cn(-c4ccc([C@@H]5COC[C@@H](CCNC(=N)CF)N5)cc4)c(=O)nc3[nH]2)c1] | 624.4 |
| 82 | 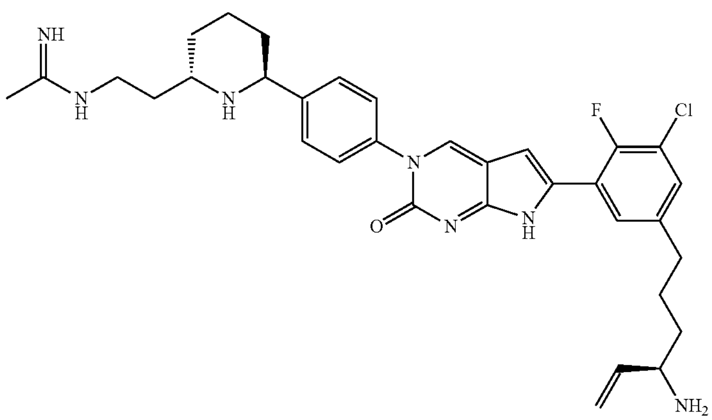 [SMILES: C=C[C@H](N)CCCc1cc(Cl)c(F)c(-c2cc3cn(-c4ccc([C@@H]5CCC[C@@H](CCNC(C)=N)N5)cc4)c(=O)nc3[nH]2)c1] | 606.2 |
| 83 | 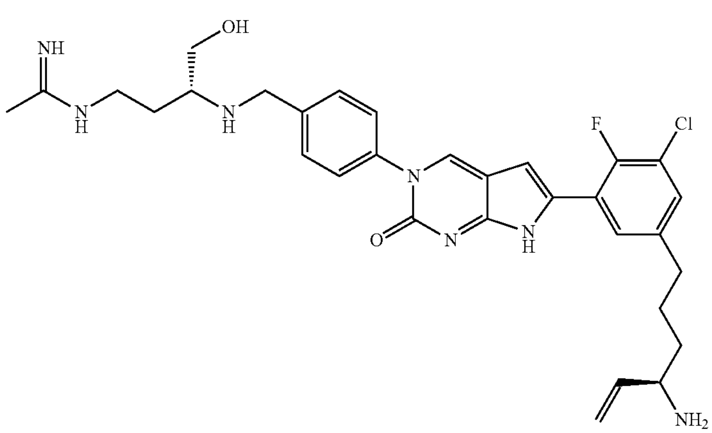 [SMILES: C=C[C@H](N)CCCc1cc(Cl)c(F)c(-c2cc3cn(-c4ccc(CN[C@@H](CO)CCNC(C)=N)cc4)c(=O)nc3[nH]2)c1] | 594.5 |

TABLE 1-continued

| # | Structure | ESI, m/z [M + H]+ |
|---|---|---|
| 84 | 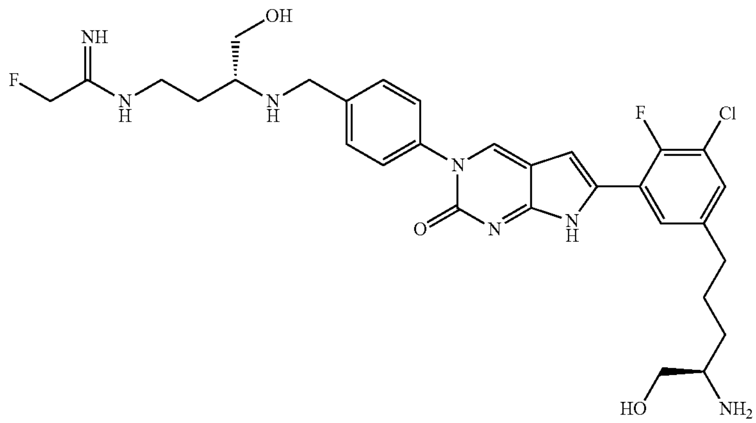 [SMILES: N=C(CF)NCC[C@H](CO)NCc1ccc(-n2cc3cc(-c4cc(CCC[C@@H](N)CO)cc(Cl)c4F)[nH]c3nc2=O)cc1] | 616.4 |
| 85 | 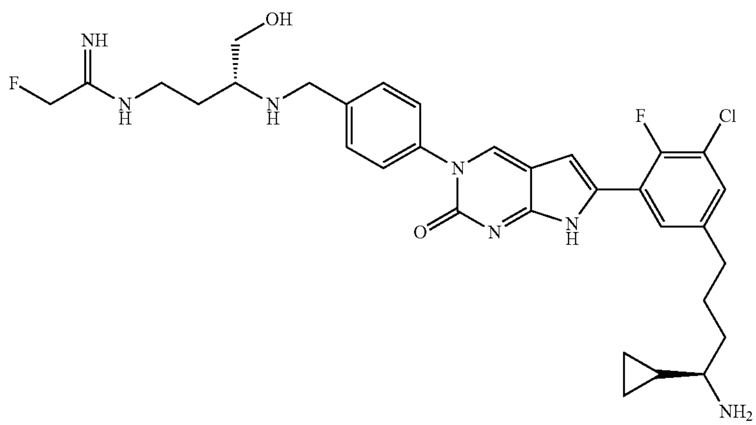 [SMILES: N=C(CF)NCC[C@H](CO)NCc1ccc(-n2cc3cc(-c4cc(CCC[C@@H](N)C5CC5)cc(Cl)c4F)[nH]c3nc2=O)cc1] | 627.7 |
| 86 | 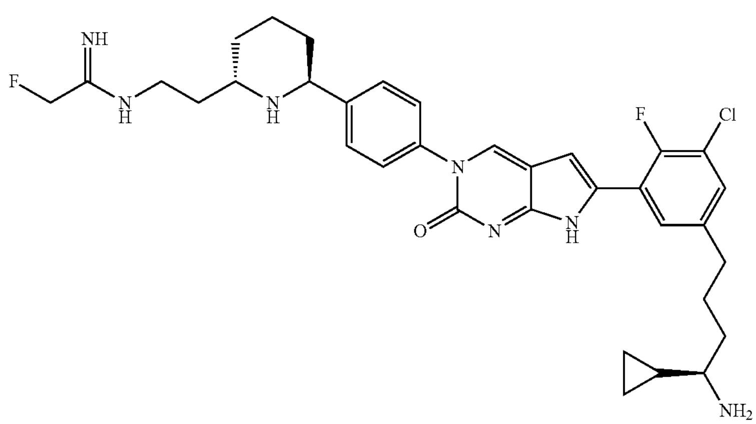 [SMILES: N=C(CF)NCC[C@@H]1CCC[C@@H](c2ccc(-n3cc4cc(-c5cc(CCC[C@@H](N)C6CC6)cc(Cl)c5F)[nH]c4nc3=O)cc2)N1] | 636.5 |

TABLE 1-continued
| # | Structure | ESI, m/z [M + H]+ |
|---|---|---|
| 87 | 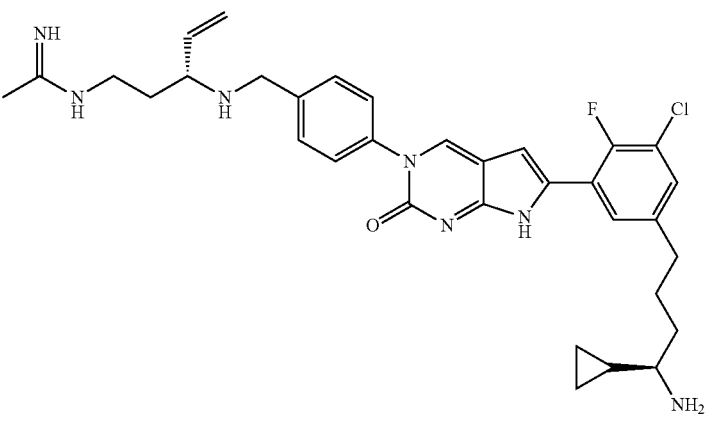 [SMILES: C=C[C@@H](CCNC(C)=N)NCc1ccc(-n2cc3cc(-c4cc(CCC[C@@H](N)C5CC5)cc(Cl)c4F)[nH]c3nc2=O)cc1] | 604.4 |
| 88 | 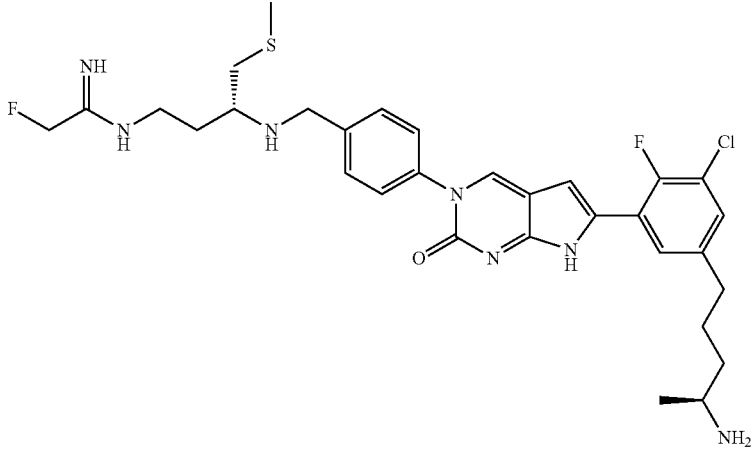 [SMILES: CSC[C@@H](CCNC(=N)CF)NCc1ccc(-n2cc3cc(-c4cc(CCC[C@H](C)N)cc(Cl)c4F)[nH]c3nc2=O)cc1] | 630 |
| 89 | 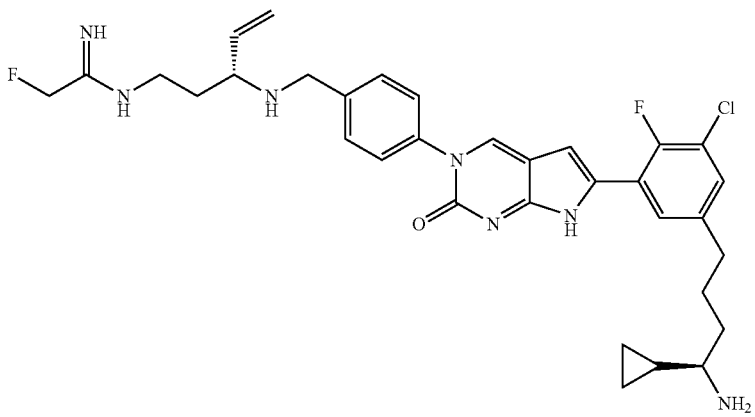 [SMILES: C=C[C@@H](CCNC(=N)CF)NCc1ccc(-n2cc3cc(-c4cc(CCC[C@@H](N)C5CC5)cc(Cl)c4F)[nH]c3nc2=O)cc1] | 622.4 |

TABLE 1-continued

| # | Structure | ESI, m/z [M + H]+ |
|---|---|---|
| 90 | 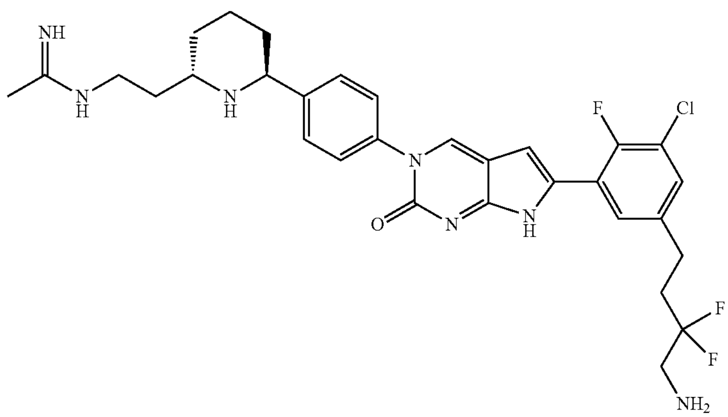 [SMILES: CC(=N)NCC[C@@H]1CCC[C@@H](c2ccc(-n3cc4cc(-c5cc(CCC(F)(F)CN)cc(Cl)c5F)[nH]c4nc3=O)cc2)N1] | 614.4 |
| 91 | 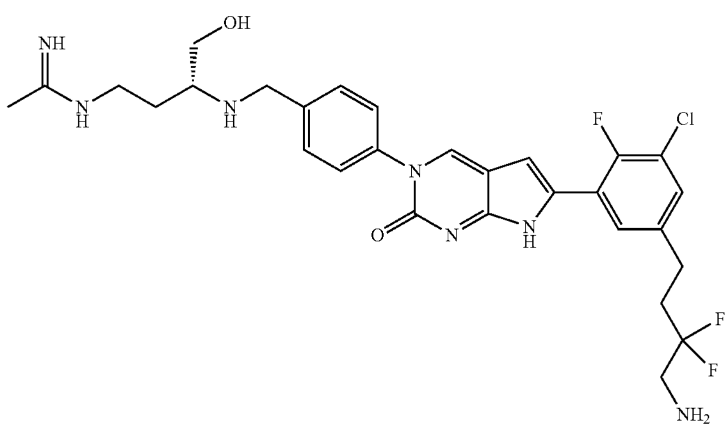 [SMILES: CC(=N)NCC[C@H](CO)NCc1ccc(-n2cc3cc(-c4cc(CCC(F)(F)CN)cc(Cl)c4F)[nH]c3nc2=O)cc1] | 604.4 |
| 92 | 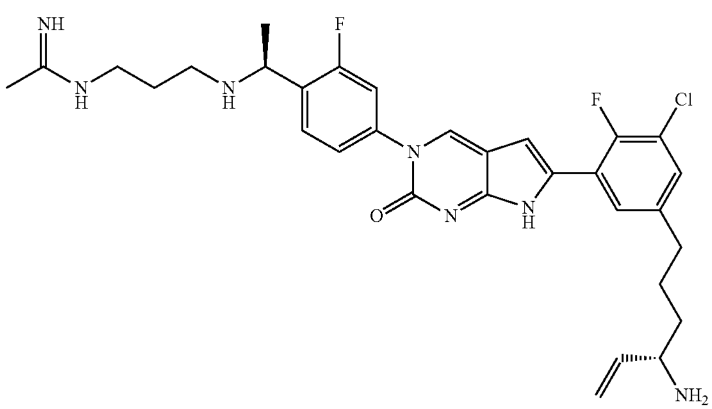 [SMILES: C=C[C@@H](N)CCCc1cc(Cl)c(F)c(-c2cc3cn(-c4ccc([C@H](C)NCCCNC(C)=N)c(F)c4)c(=O)nc3[nH]2)c1] | 596.5 |

TABLE 1-continued

| # | Structure | ESI, m/z [M + H]+ |
|---|---|---|
| 93 | 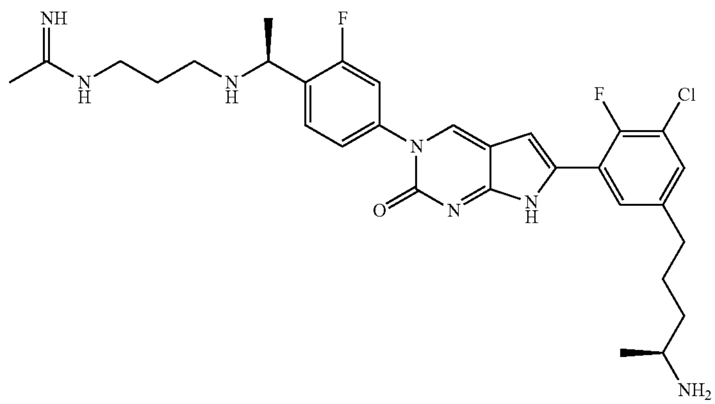 [SMILES: CC(=N)NCCCN[C@@H](C)c1ccc(-n2cc3cc(-c4cc(CCC[C@H](C)N)cc(Cl)c4F)[nH]c3nc2=O)cc1F] | 584 |
| 94 | 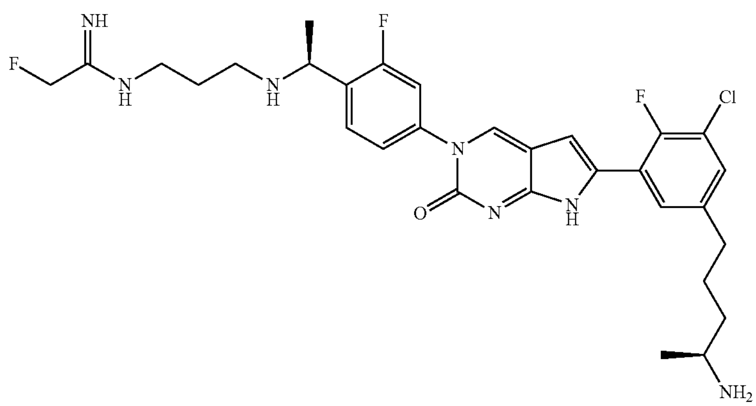 [SMILES: C[C@H](N)CCCc1cc(Cl)c(F)c(-c2cc3cn(-c4ccc([C@H](C)NCCCNC(=N)CF)c(F)c4)c(=O)nc3[nH]2)c1] | 602 |
| 95 | 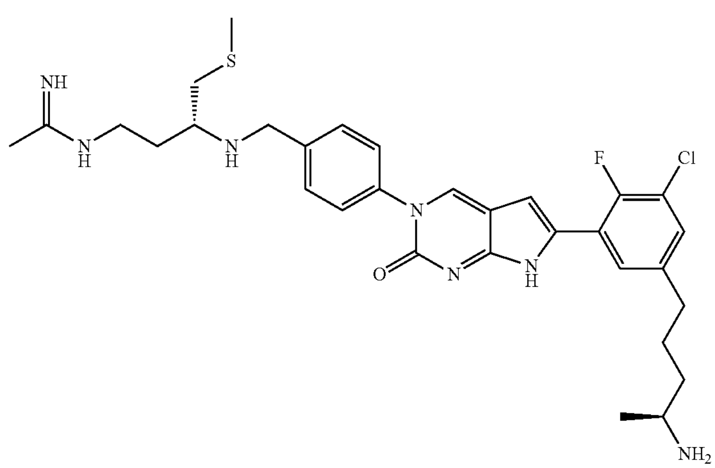 [SMILES: CSC[C@@H](CCNC(C)=N)NCc1ccc(-n2cc3cc(-c4cc(CCC[C@H](C)N)cc(Cl)c4F)[nH]c3nc2=O)cc1] | 612 |

TABLE 1-continued

| # | Structure | ESI, m/z [M + H]+ |
|---|---|---|
| 96 | 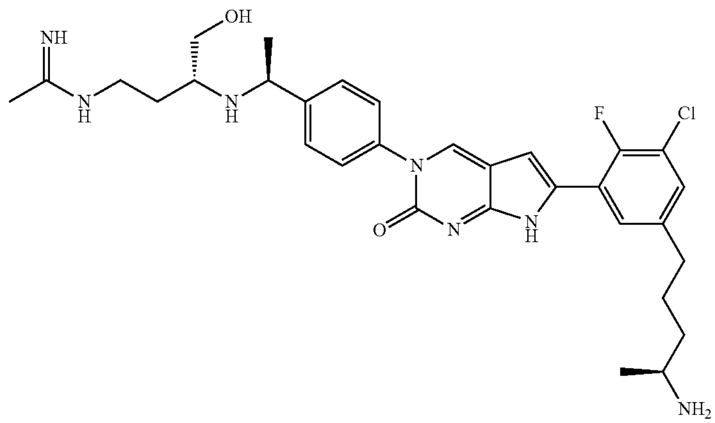 [SMILES: CC(=N)NCC[C@H](CO)N[C@@H](C)c1ccc(-n2cc3cc(-c4cc(CCC[C@H](C)N)cc(Cl)c4F)[nH]c3nc2=O)cc1] | 596.5 |
| 97 | 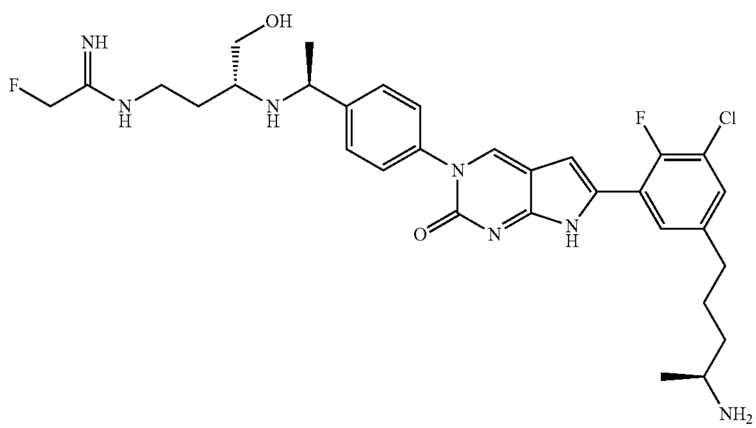 [SMILES: C[C@H](N)CCCc1cc(Cl)c(F)c(-c2cc3cn(-c4ccc([C@H](C)N[C@@H](CO)CCNC(=N)CF)cc4)c(=O)nc3[nH]2)c1] | 614.5 |
| 98 | 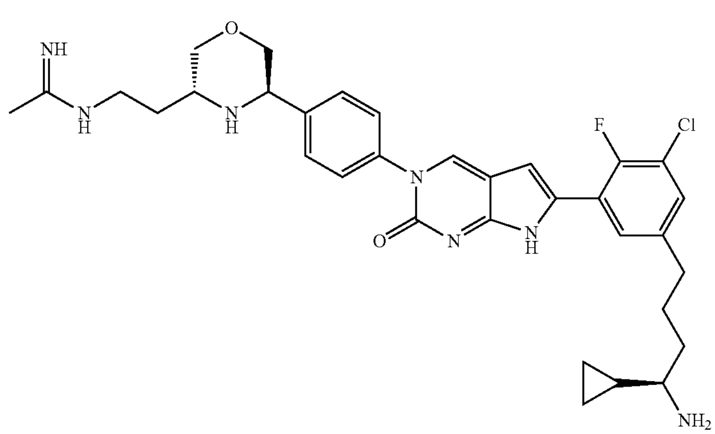 [SMILES: CC(=N)NCC[C@@H]1COC[C@@H](c2ccc(-n3cc4cc(-c5cc(CCC[C@@H](N)C6CC6)cc(Cl)c5F)[nH]c4nc3=O)cc2)N1] | 620.4 |

TABLE 1-continued
| # | Structure | ESI, m/z [M + H]+ |
|---|---|---|
| 99 | 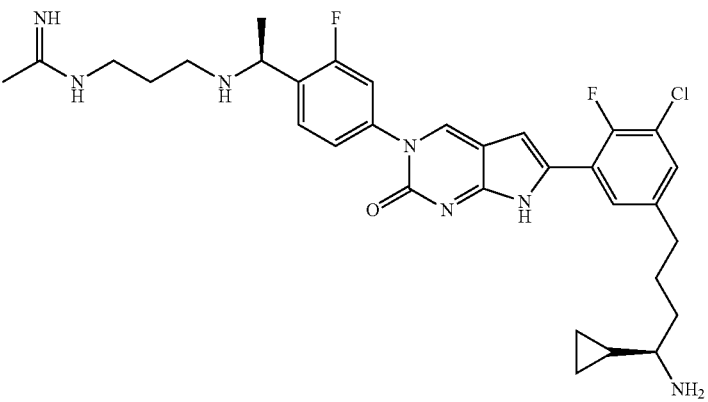 [SMILES: CC(=N)NCCCN[C@@H](C)c1ccc(-n2cc3cc(-c4cc(CCC[C@@H](N)C5CC5)cc(Cl)c4F)[nH]c3nc2=O)cc1F] | 610.5 |
| 100 | 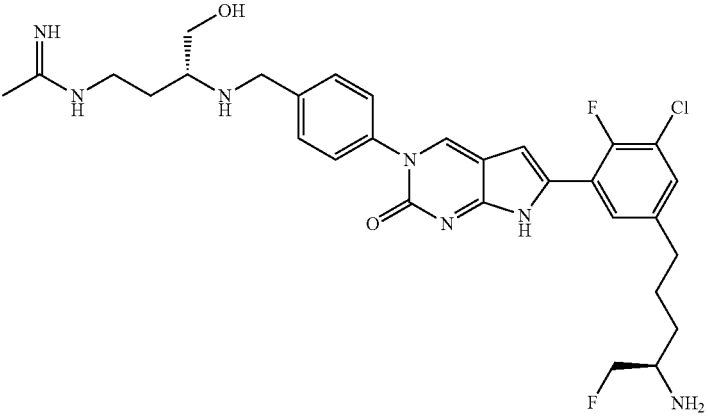 [SMILES: CC(=N)NCC[C@H](CO)NCc1ccc(-n2cc3cc(-c4cc(CCC[C@@H](N)CF)cc(Cl)c4F)[nH]c3nc2=O)cc1] | 600.4 |
| 101 | 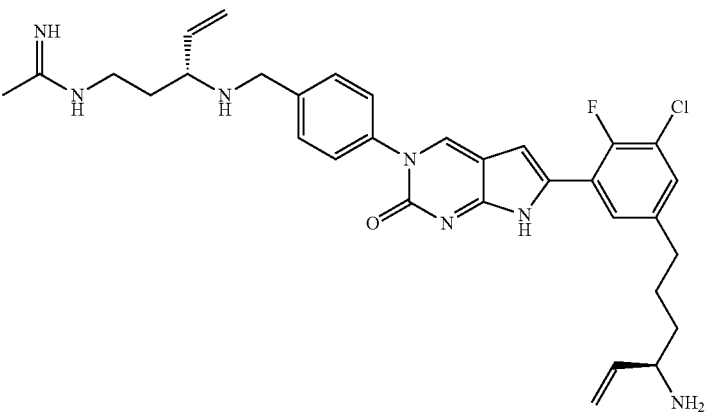 [SMILES: C=C[C@H](N)CCCc1cc(Cl)c(F)c(-c2cc3cn(-c4ccc(CN[C@@H](C=C)CCNC(C)=N)cc4)c(=O)nc3[nH]2)c1] | 590.5 |

TABLE 1-continued
| # | Structure | ESI, m/z [M + H]+ |
|---|---|---|
| 102 | 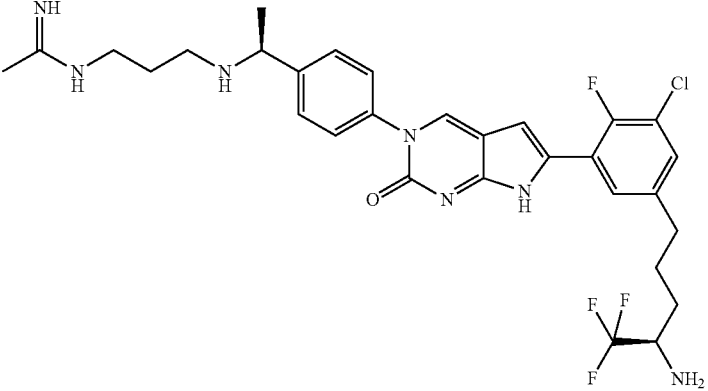 [SMILES: CC(=N)NCCCN[C@@H](C)c1ccc(-n2cc3cc(-c4cc(CCC[C@@H](N)C(F)(F)F)cc(Cl)c4F)[nH]c3nc2=O)cc1] | 620.4 |
| 103 | 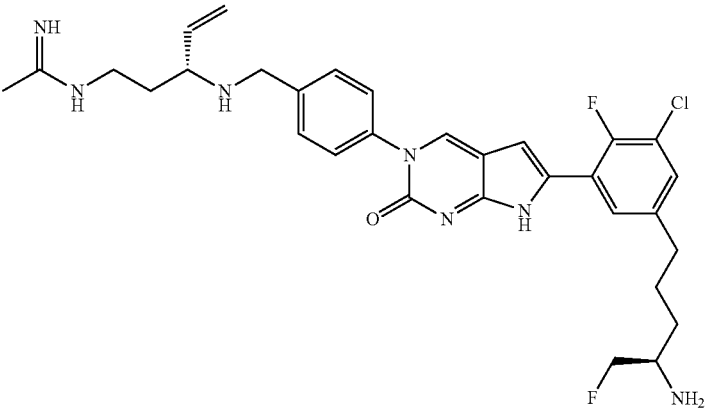 [SMILES: C=C[C@@H](CCNC(C)=N)NCc1ccc(-n2cc3cc(-c4cc(CCC[C@@H](N)CF)cc(Cl)c4F)[nH]c3nc2=O)cc1] | 596.5 |
| 104 | 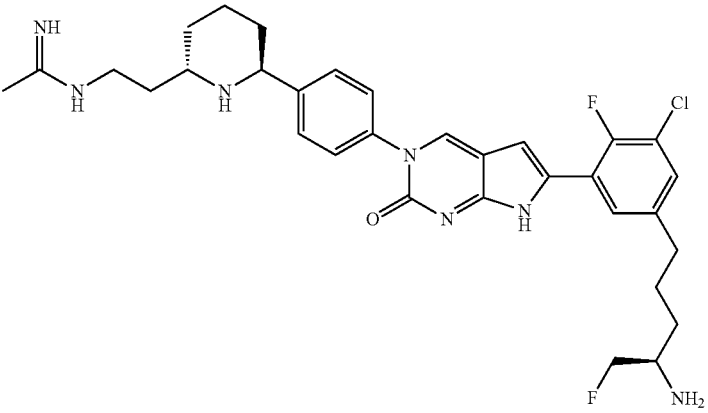 [SMILES: CC(=N)NCC[C@@H]1CCC[C@@H](c2ccc(-n3cc4cc(-c5cc(CCC[C@@H](N)CF)cc(Cl)c5F)[nH]c4nc3=O)cc2)N1] | 610.5 |

TABLE 1-continued
| # | Structure | ESI, m/z [M + H]+ |
|---|-----------|-------------------|
| 105 | 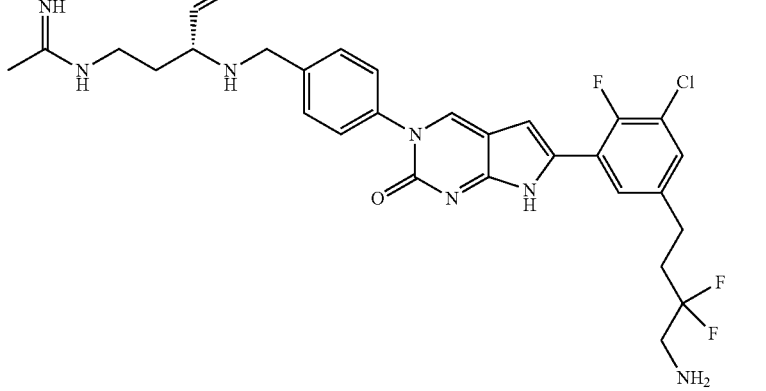 | 600.4 |
| 106 | 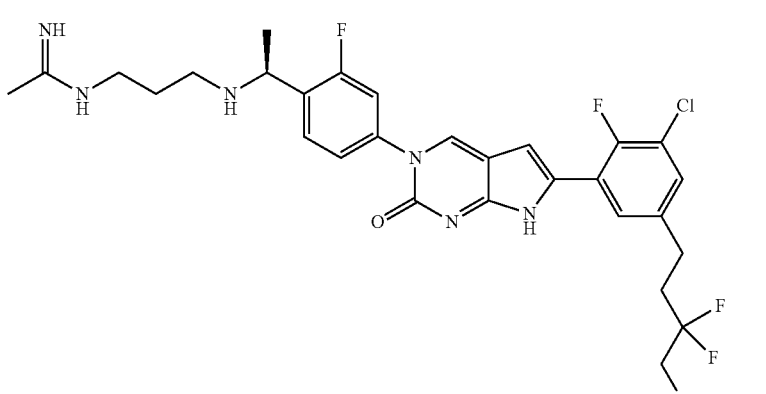 | 606.4 |
| 107 | 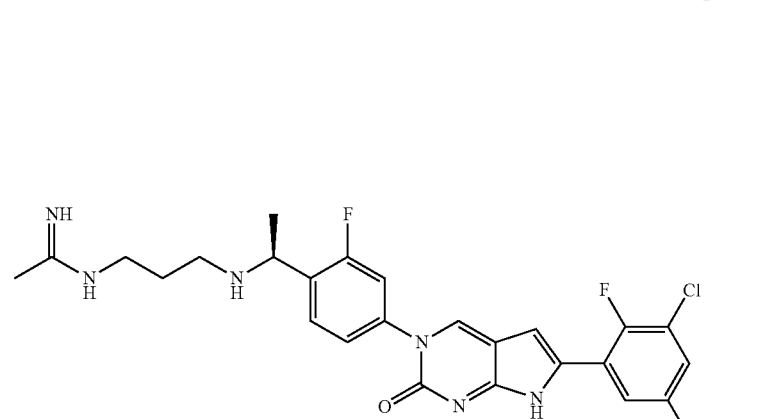 | 602.4 |

TABLE 1-continued
| # | Structure | ESI, m/z [M + H]+ |
|---|---|---|
| 108 | 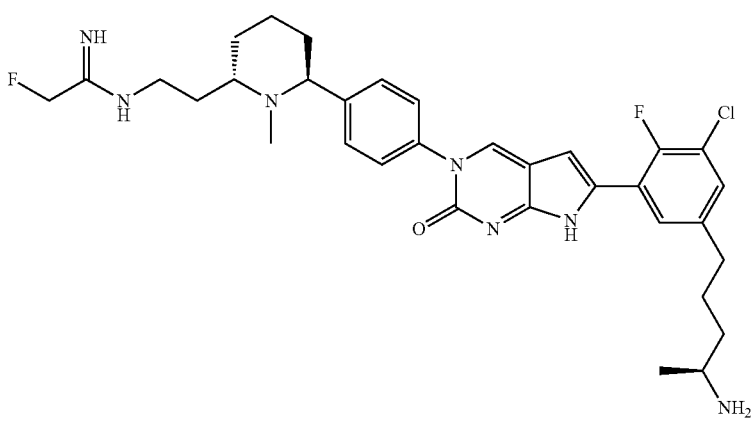 [SMILES: C[C@H](N)CCCc1cc(Cl)c(F)c(-c2cc3cn(-c4ccc([C@@H]5CCC[C@@H](CCNC(=N)CF)N5C)cc4)c(=O)nc3[nH]2)c1] | 624.5 |
| 109 | 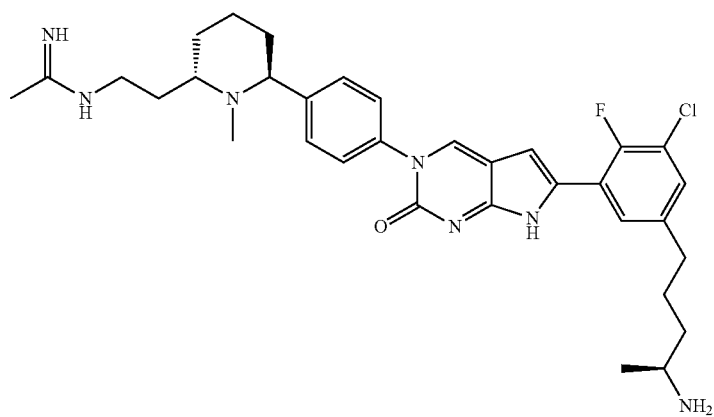 | 606.5 |
| 110 | 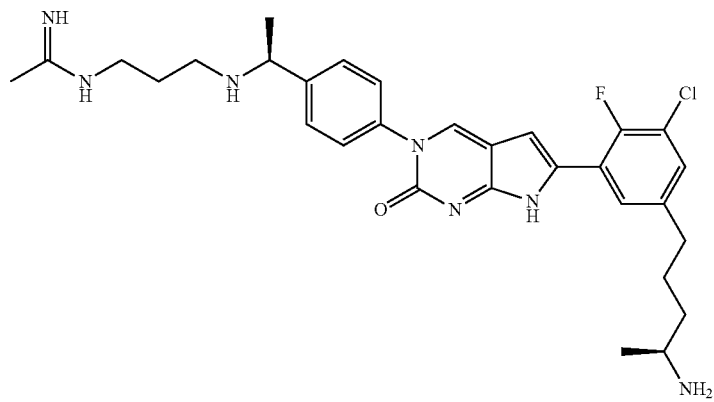 | 566.4 |

TABLE 1-continued
| # | Structure | ESI, m/z [M + H]+ |
|---|-----------|-------------------|
| 111 | 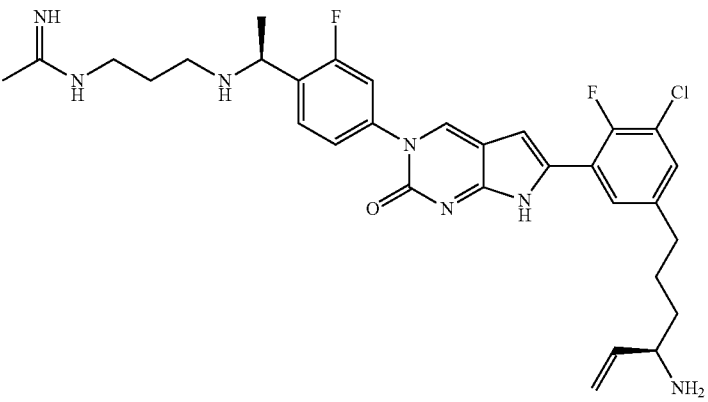 [SMILES: C=C[C@H](N)CCCc1cc(Cl)c(F)c(-c2cc3cn(-c4ccc([C@H](C)NCCCNC(C)=N)c(F)c4)c(=O)nc3[nH]2)c1] | 596.5 |
| 112 | 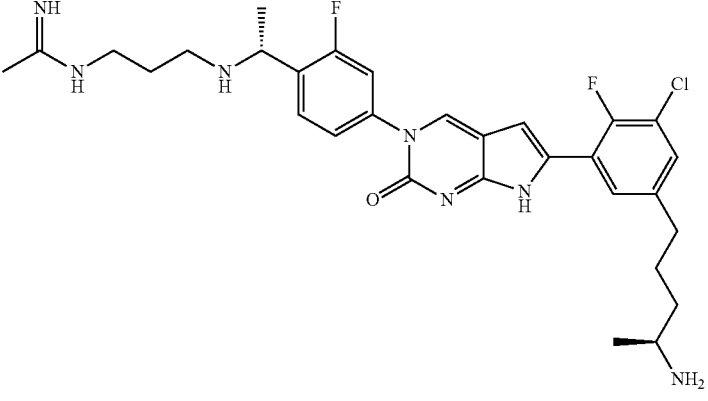 [SMILES: CC(=N)NCCCN[C@H](C)c1ccc(-n2cc3cc(-c4cc(CCC[C@H](C)N)cc(Cl)c4F)[nH]c3nc2=O)cc1F] | 584 |
| 113 | 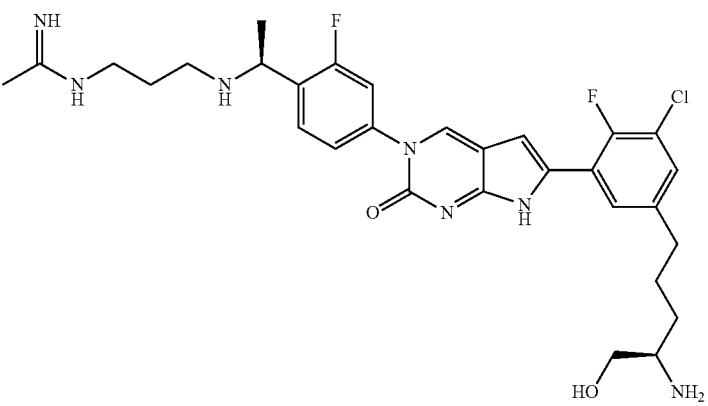 [SMILES: CC(=N)NCCCN[C@@H](C)c1ccc(-n2cc3cc(-c4cc(CCC[C@@H](N)CO)cc(Cl)c4F)[nH]c3nc2=O)cc1F] | 600 |

TABLE 1-continued
| # | Structure | ESI, m/z [M + H]+ |
|---|---|---|
| 114 | 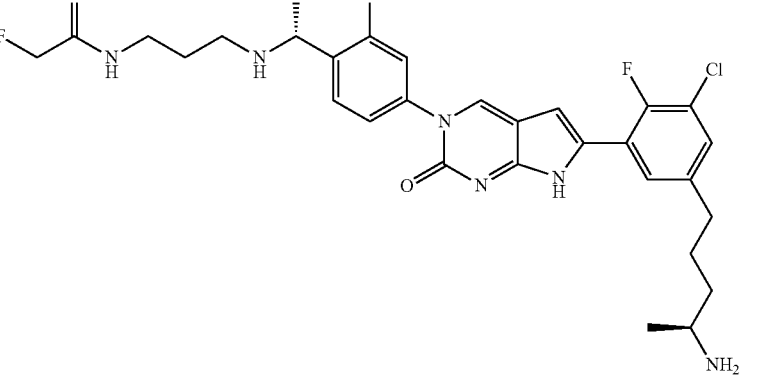 | 602 |
| 115 | 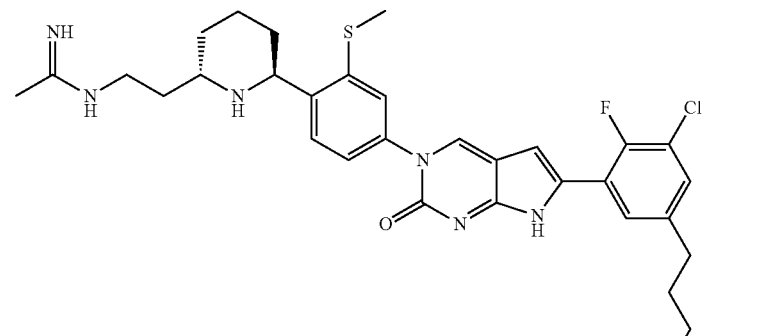 | 638.5 |
| 116 | 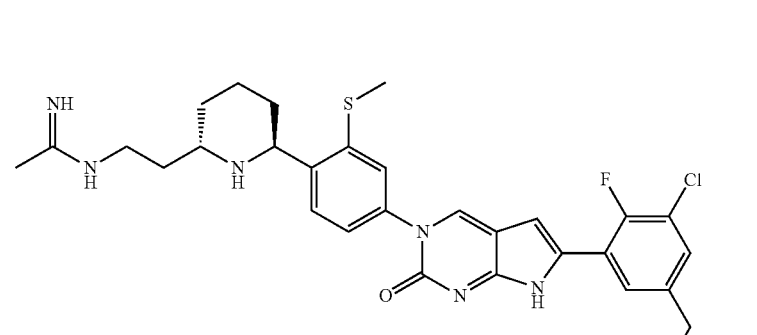 | 654.5 |

TABLE 1-continued

| # | Structure | ESI, m/z [M + H]+ |
|---|---|---|
| 117 | 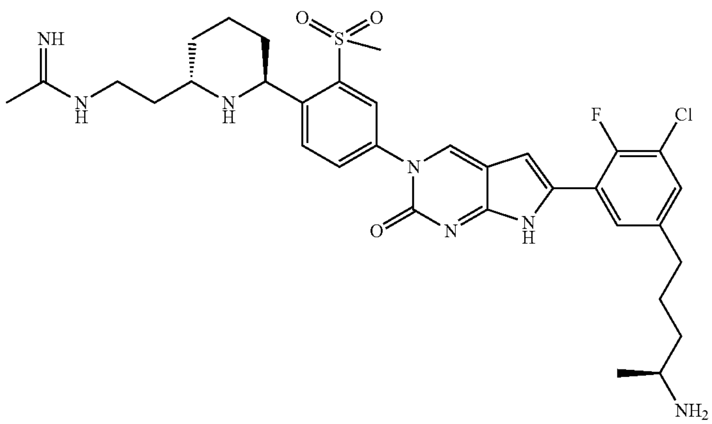 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2S(C)(=O)=O)N1] | 670.5 |
| 118 | 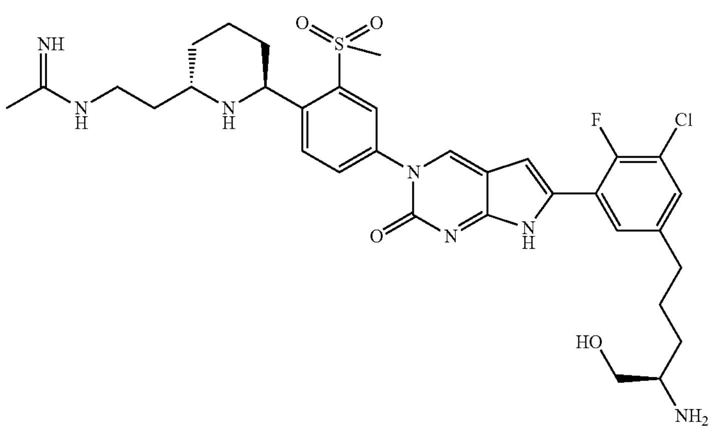 [SMILES: CC(=N)NCC[C@@H]1CCC[C@@H](c2ccc(-n3cc4cc(-c5cc(CCC[C@@H](N)CO)cc(Cl)c5F)[nH]c4nc3=O)cc2S(C)(=O)=O)N1] | 686.1 |
| 119 | 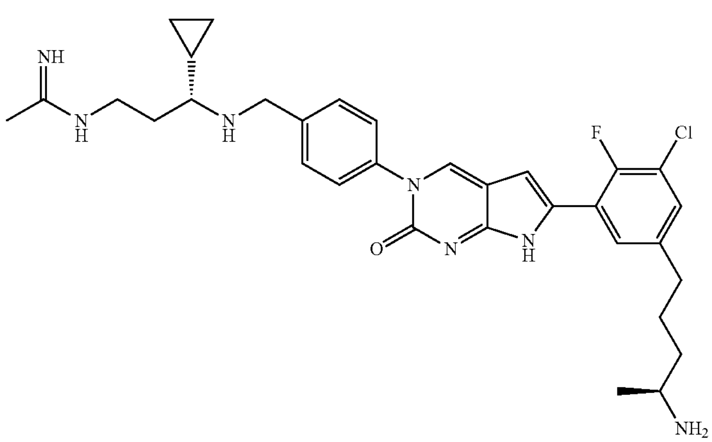 [SMILES: CC(=N)NCC[C@@H](NCc1ccc(-n2cc3cc(-c4cc(CCC[C@H](C)N)cc(Cl)c4F)[nH]c3nc2=O)cc1)C1CC1] | 592.5 |

TABLE 1-continued
| # | Structure | ESI, m/z [M + H]+ |
|---|---|---|
| 120 | 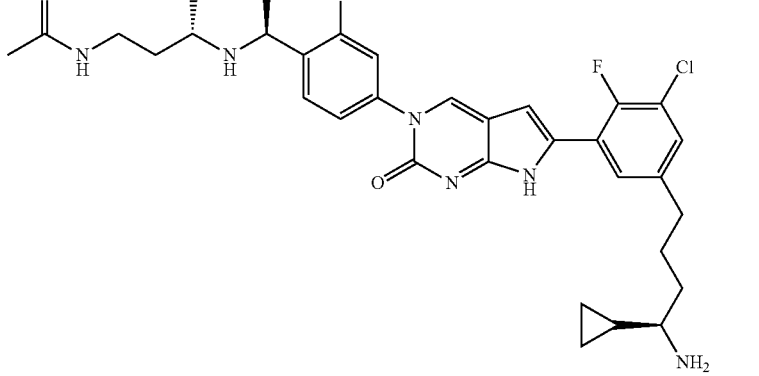 | 664.5 |
| 121 | 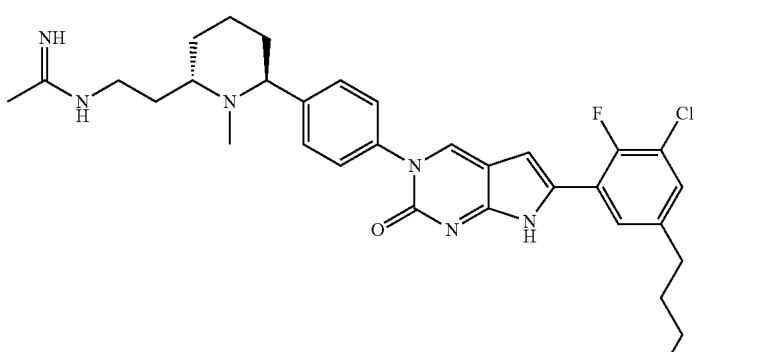 | 622.5 |
| 122 | 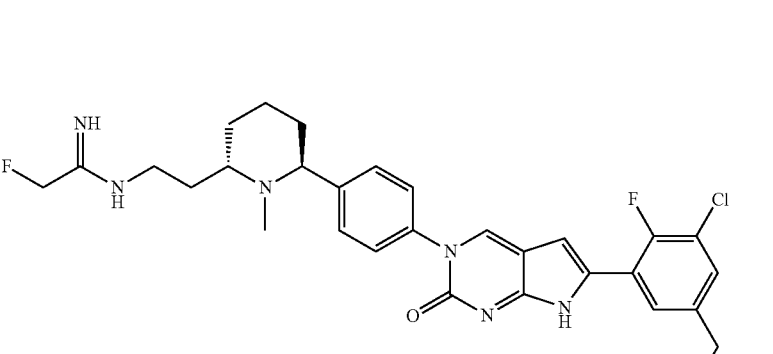 | 640.5 |

TABLE 1-continued
| # | Structure | ESI, m/z [M + H]+ |
|---|---|---|
| 123 | 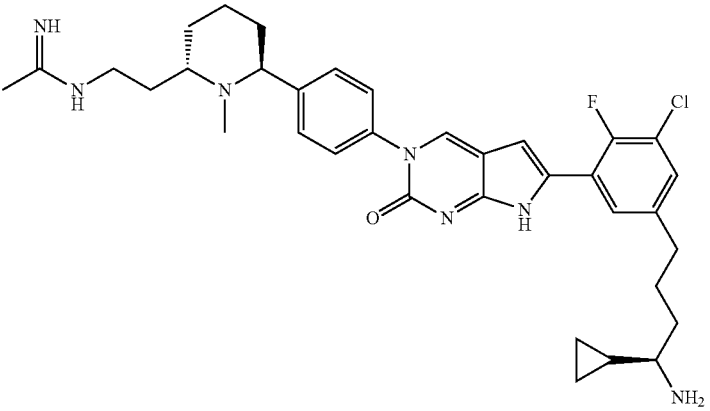 [SMILES: CC(=N)NCC[C@@H]1CCC[C@@H](c2ccc(-n3cc4cc(-c5cc(CCC[C@@H](N)C6CC6)cc(Cl)c5F)[nH]c4nc3=O)cc2)N1C] | 632.5 |
| 124 | 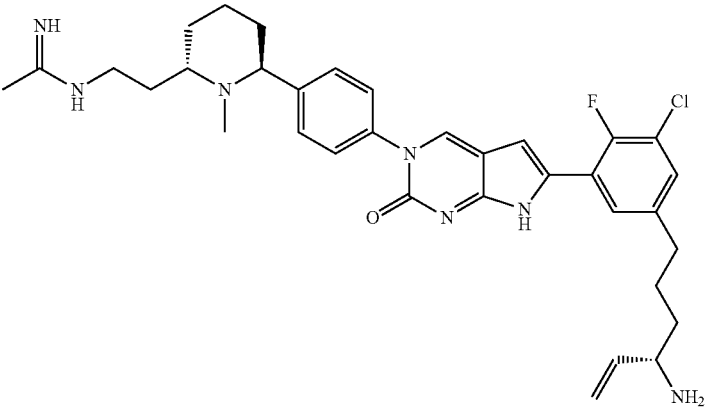 | 618.5 |
| 125 | 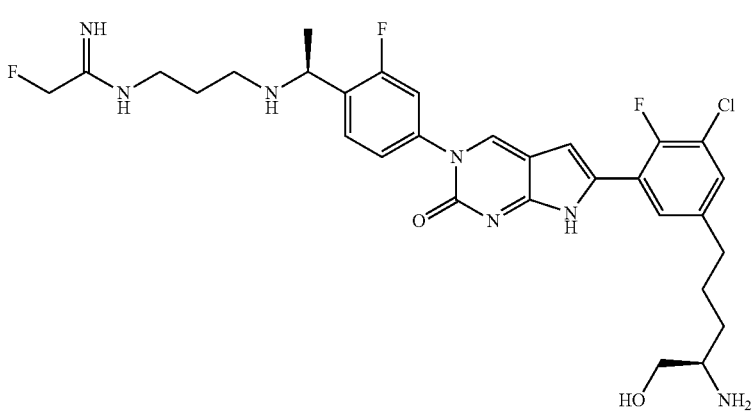 [SMILES: C[C@H](NCCCNC(=N)CF)c1ccc(-n2cc3cc(-c4cc(CCC[C@@H](N)CO)cc(Cl)c4F)[nH]c3nc2=O)cc1F] | 618 |

TABLE 1-continued
| # | Structure | ESI, m/z [M + H]+ |
|---|---|---|
| 126 | 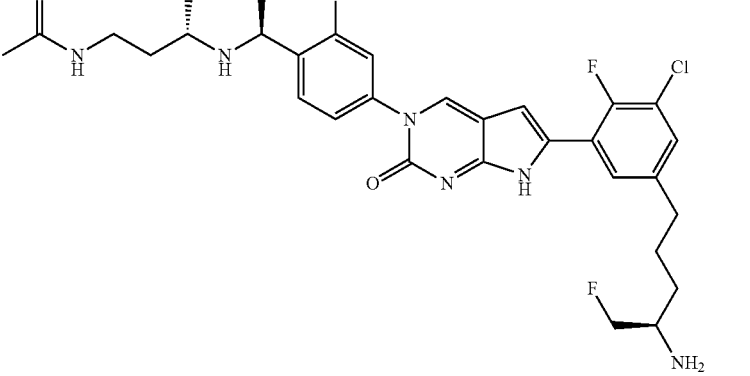 | 656.5 |
| 127 | 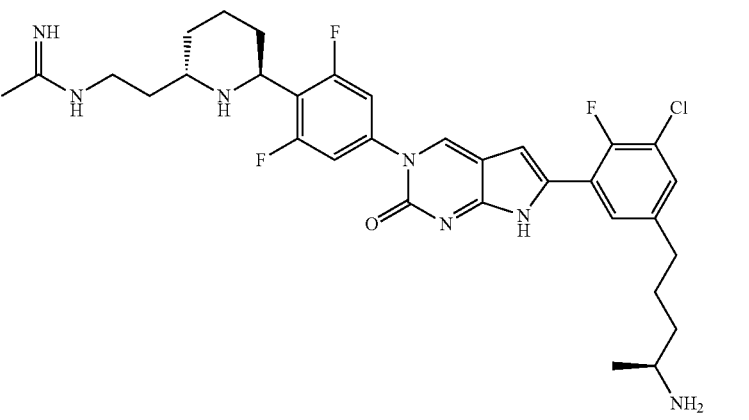 [SMILES: CC(=N)NCC[C@@H]1CCC[C@@H](c2c(F)cc(-n3cc4cc(-c5cc(CCC[C@H](C)N)cc(Cl)c5F)[nH]c4nc3=O)cc2F)N1] | 628.5 |
| 128 | 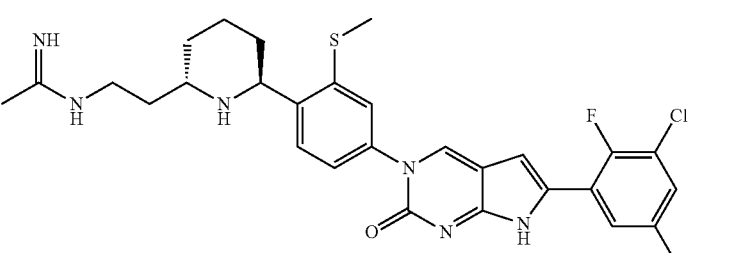 | 650.5 |

TABLE 1-continued

| # | Structure | ESI, m/z [M + H]+ |
|---|---|---|
| 129 | 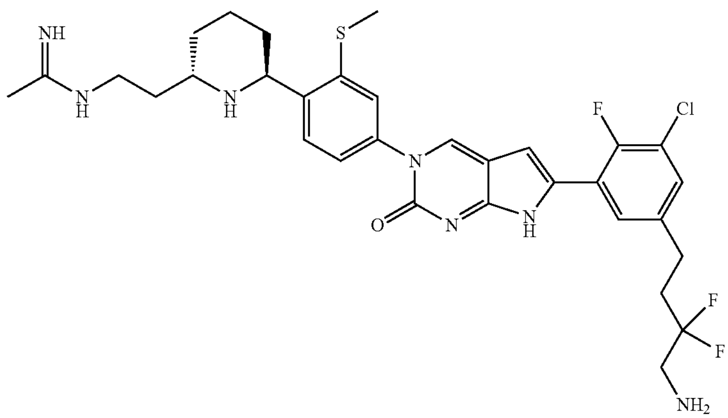 [SMILES: CSc1cc(-n2cc3cc(-c4cc(CCC(F)(F)CN)cc(Cl)c4F)[nH]c3nc2=O)ccc1[C@@H]1CCC[C@@H](CCNC(C)=N)N1] | 660.5 |
| 130 | 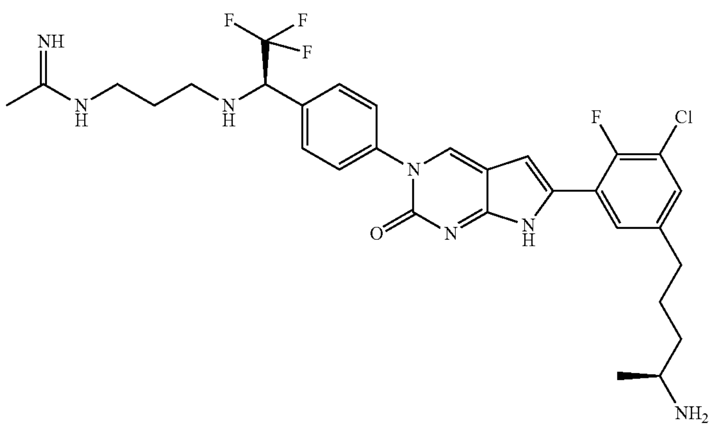 [SMILES: CC(=N)NCCCN[C@H](c1ccc(-n2cc3cc(-c4cc(CCC[C@H](C)N)cc(Cl)c4F)[nH]c3nc2=O)cc1)C(F)(F)F] | 620.4 |
| 131 | 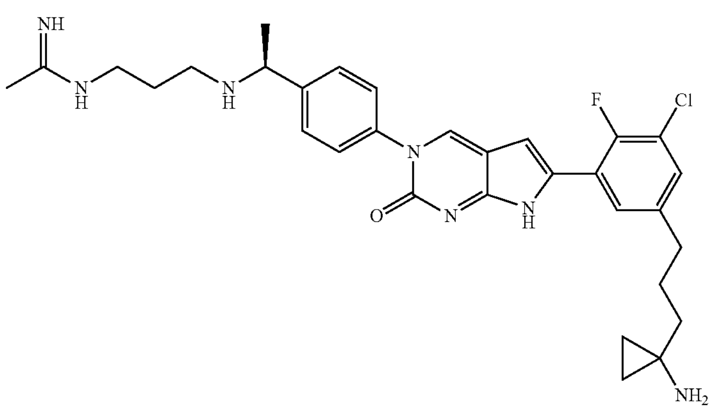 [SMILES: CC(=N)NCCCN[C@@H](C)c1ccc(-n2cc3cc(-c4cc(CCCC5(N)CC5)cc(Cl)c4F)[nH]c3nc2=O)cc1] | 578.5 |

TABLE 1-continued

| # | Structure | ESI, m/z [M + H]+ |
|---|---|---|
| 132 | 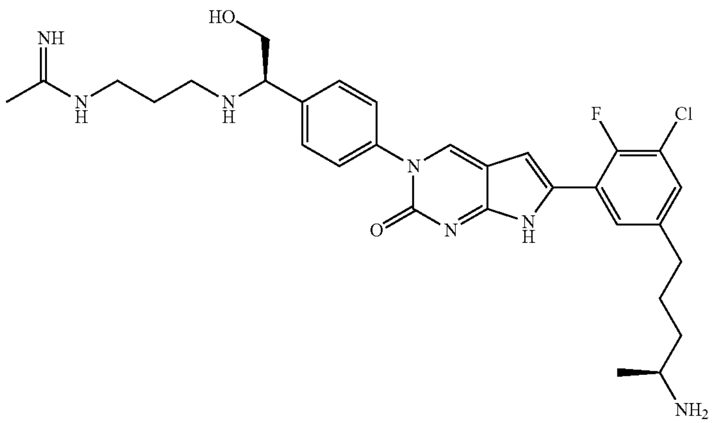 [SMILES: CC(=N)NCCCN[C@@H](CO)c1ccc(-n2cc3cc(-c4cc(CCC[C@H](C)N)cc(Cl)c4F)[nH]c3nc2=O)cc1] | 582.5 |
| 133 | 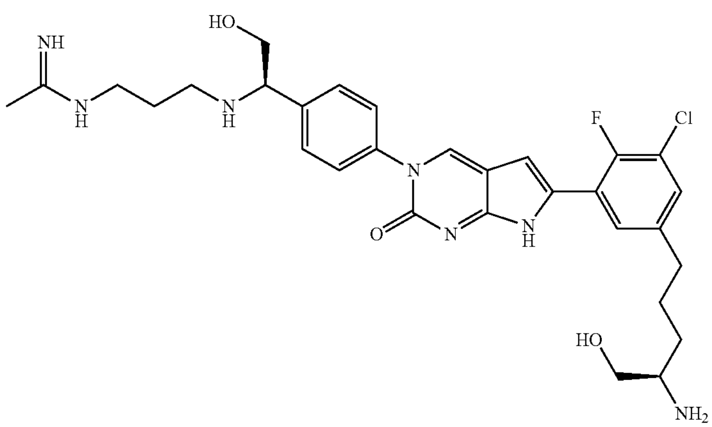 [SMILES: CC(=N)NCCCN[C@@H](CO)c1ccc(-n2cc3cc(-c4cc(CCC[C@@H](N)CO)cc(Cl)c4F)[nH]c3nc2=O)cc1] | 598.5 |
| 134 | 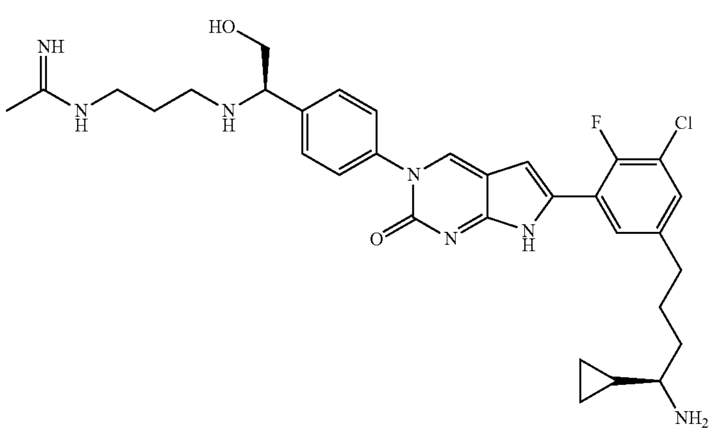 [SMILES: CC(=N)NCCCN[C@@H](CO)c1ccc(-n2cc3cc(-c4cc(CCC[C@@H](N)C5CC5)cc(Cl)c4F)[nH]c3nc2=O)cc1] | 608.5 |

TABLE 1-continued
| # | Structure | ESI, m/z [M + H]+ |
|---|---|---|
| 135 | 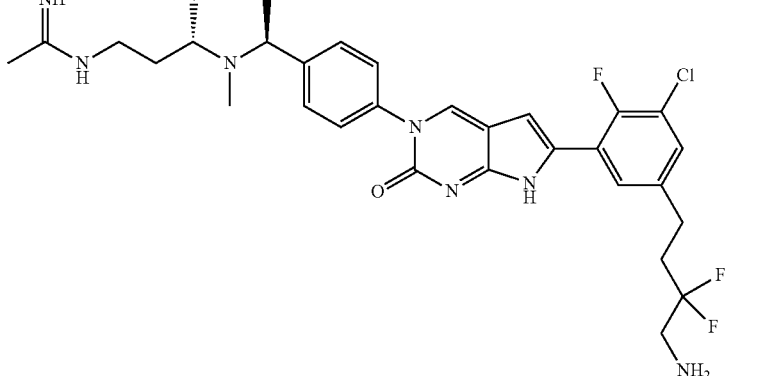 | 628.5 |
| 136 | 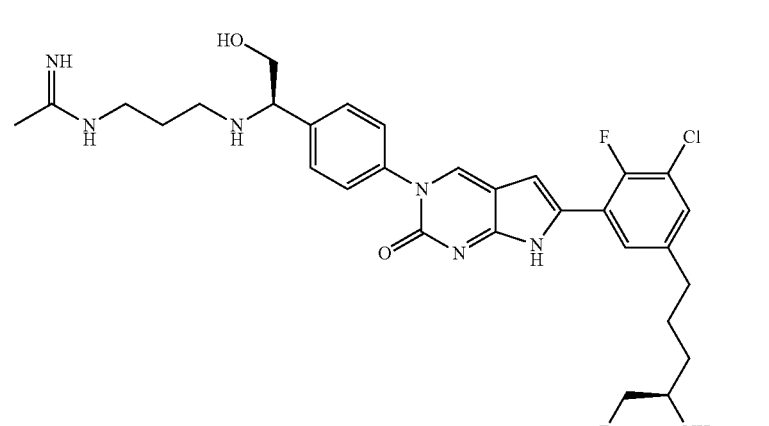 | 600.5 |
| 137 | 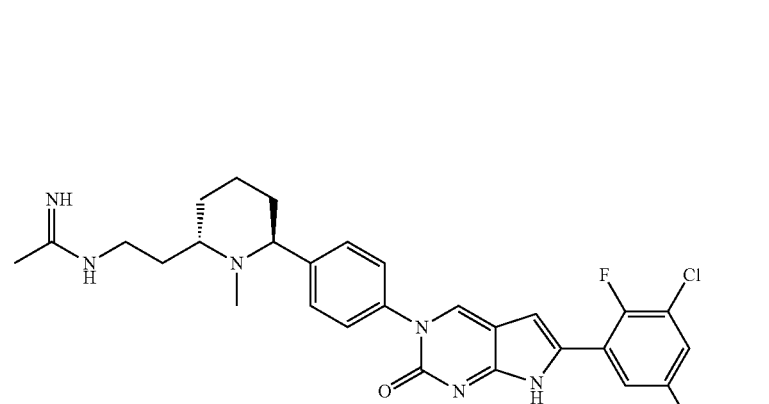 | 624.5 |

TABLE 1-continued
| # | Structure | ESI, m/z [M + H]+ |
|---|---|---|
| 138 | 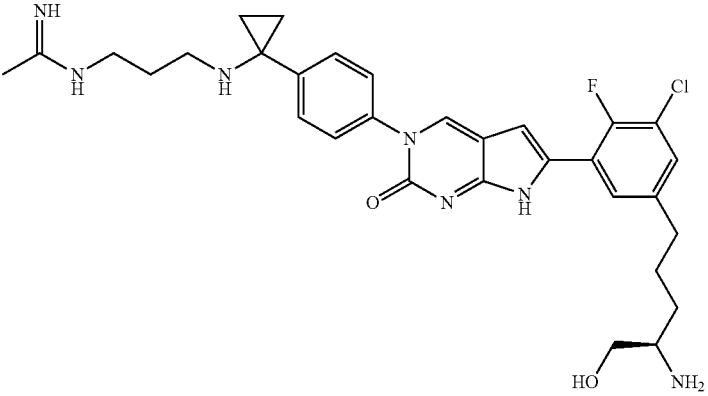 [SMILES: CC(=N)NCCCNC1(c2ccc(-n3cc4cc(-c5cc(CCC[C@@H](N)CO)cc(Cl)c5F)[nH]c4nc3=O)cc2)CC1] | 594.5 |
| 139 | 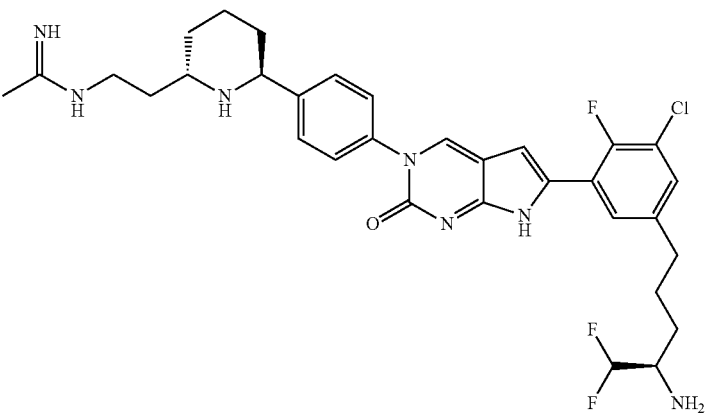 [SMILES: CC(=N)NCC[C@@H]1CCC[C@@H](c2ccc(-n3cc4cc(-c5cc(CCC[C@@H](N)C(F)F)cc(Cl)c5F)[nH]c4nc3=O)cc2)N1] | 628.5 |
| 140 | 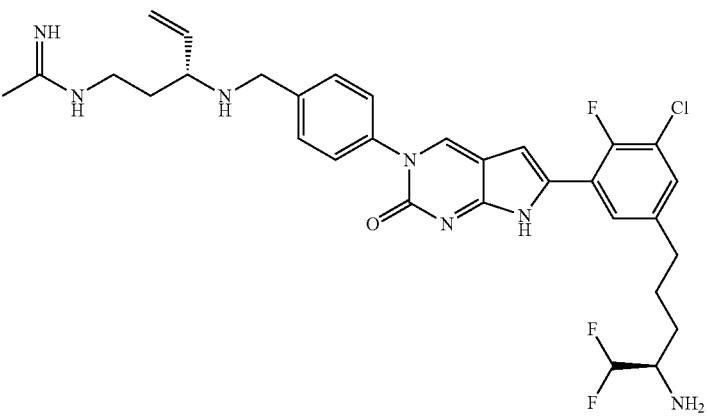 [SMILES: C=C[C@@H](CCNC(C)=N)NCc1ccc(-n2cc3cc(-c4cc(CCC[C@@H](N)C(F)F)cc(Cl)c4F)[nH]c3nc2=O)cc1] | 614.4 |

TABLE 1-continued

| # | Structure | ESI, m/z [M + H]+ |
|---|---|---|
| 141 | 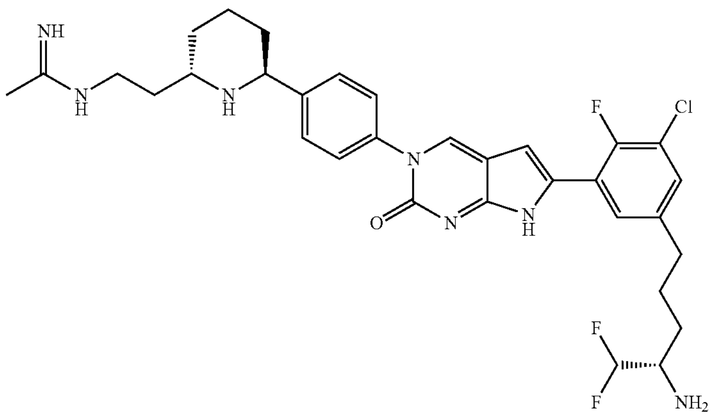 [SMILES: CC(=N)NCC[C@@H]1CCC[C@@H](c2ccc(-n3cc4cc(-c5cc(CCC[C@H](N)C(F)F)cc(Cl)c5F)[nH]c4nc3=O)cc2)N1] | 628.5 |
| 142 | 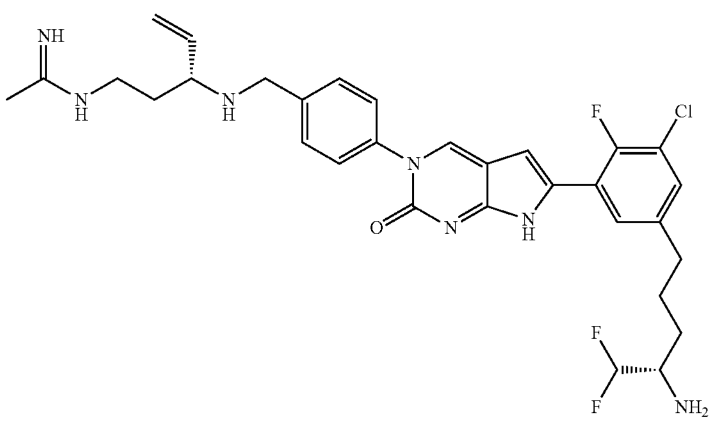 [SMILES: C=C[C@@H](CCNC(C)=N)NCc1ccc(-n2cc3cc(-c4cc(CCC[C@H](N)C(F)F)cc(Cl)c4F)[nH]c3nc2=O)cc1] | 614.5 |
| 143 | 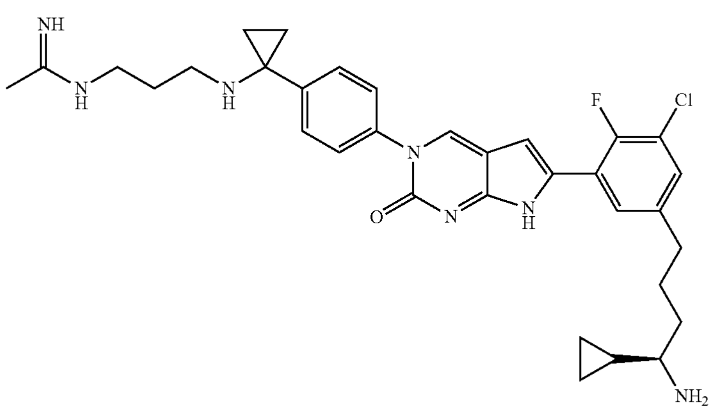 [SMILES: CC(=N)NCCCNC1(c2ccc(-n3cc4cc(-c5cc(CCC[C@@H](N)C6CC6)cc(Cl)c5F)[nH]c4nc3=O)cc2)CC1] | 604.4 |

TABLE 1-continued
| # | Structure | ESI, m/z [M + H]+ |
|---|---|---|
| 144 | 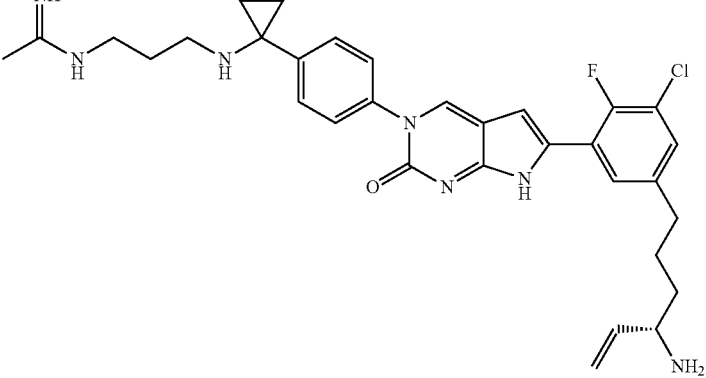 | 590.5 |
| 145 | 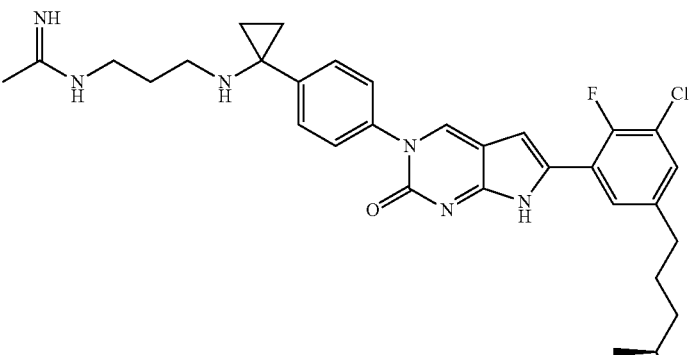 | 578.4 |
| 146 | 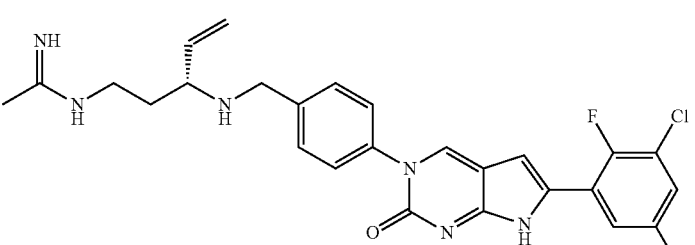 | 590.4 |

TABLE 1-continued

| # | Structure | ESI, m/z [M + H]+ |
|---|---|---|
| 147 | 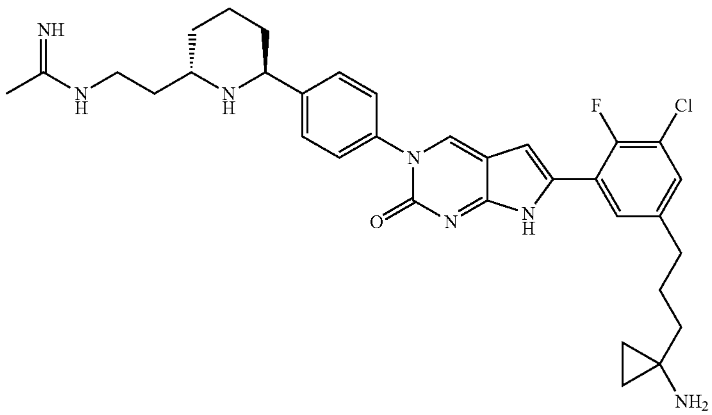 | 604.5 |
| 148 | 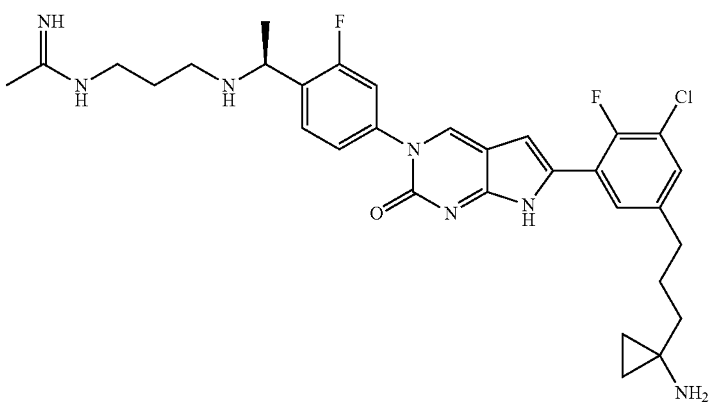 [SMILES: CC(=N)NCCCN[C@@H](C)c1ccc(-n2cc3cc(-c4cc(CCCC5(N)CC5)cc(Cl)c4F)[nH]c3nc2=O)cc1F] | 596.5 |
| 149 | 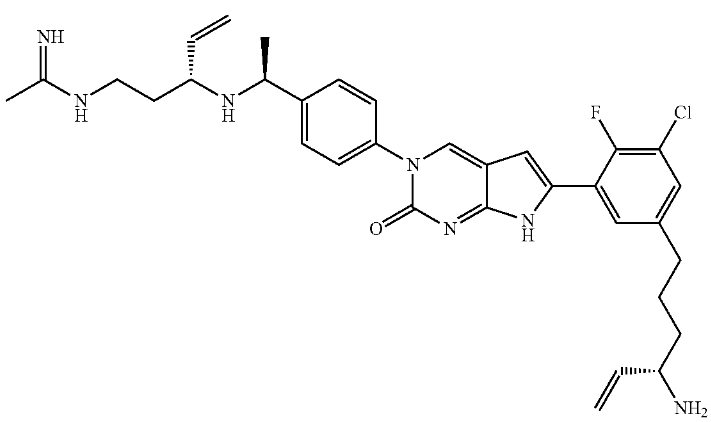 [SMILES: C=C[C@@H](N)CCCc1cc(Cl)c(F)c(-c2cc3cn(-c4ccc([C@H](C)N[C@@H](C=C)CCNC(C)=N)cc4)c(=O)nc3[nH]2)c1] | 604.5 |

TABLE 1-continued
| # | Structure | ESI, m/z [M + H]+ |
|---|---|---|
| 150 | 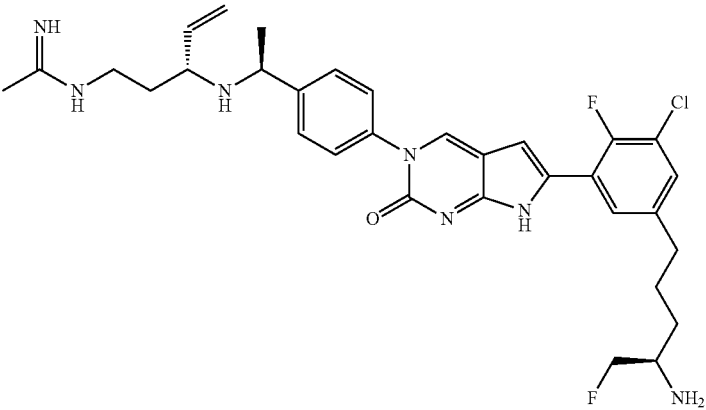 [SMILES: C=C[C@@H](CCNC(C)=N)N[C@@H](C)c1ccc(-n2cc3cc(-c4cc(CCC[C@@H](N)CO)cc(Cl)c4F)[nH]c3nc2=O)cc1] | 610.5 |
| 151 | 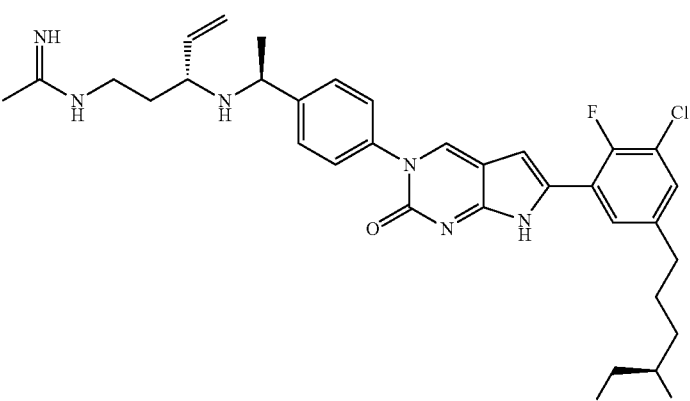 | 608.5 |
| 152 | 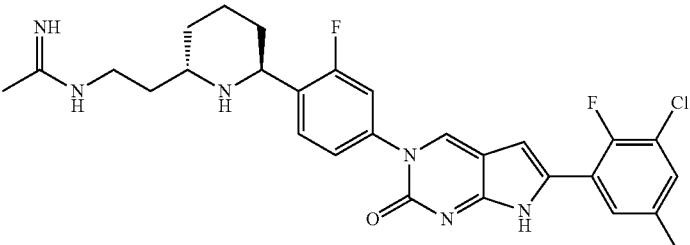 | 610 |

TABLE 1-continued
| # | Structure | ESI, m/z [M + H]+ |
|---|---|---|
| 153 | 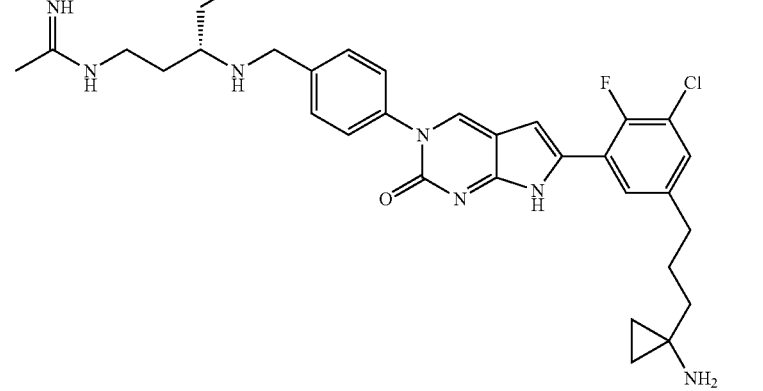 | 594.5 |
| 154 | 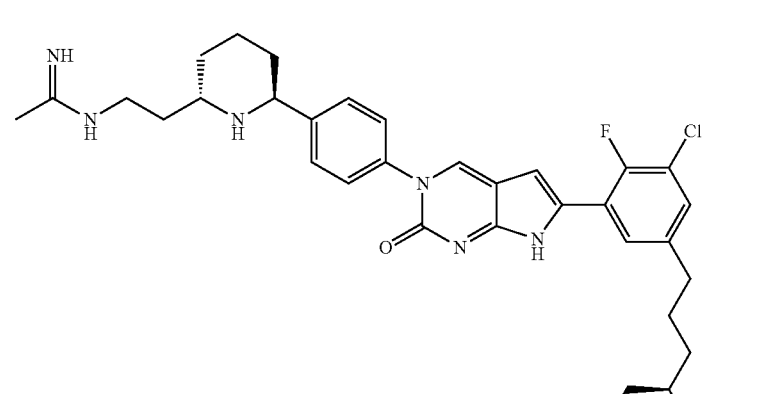 | 617.5 |
| 155 | 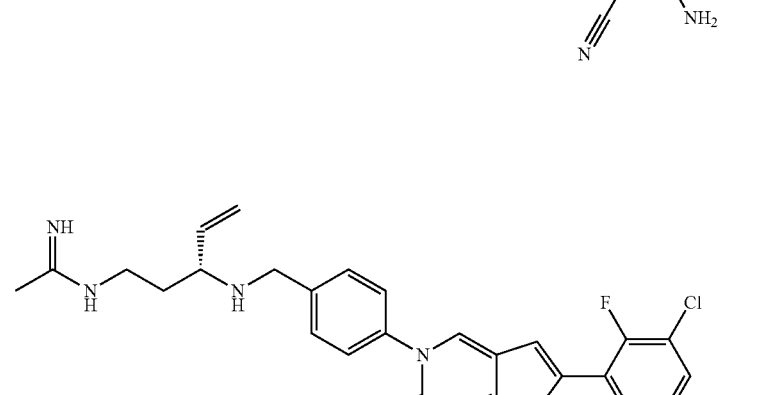 | 603.4 |

TABLE 1-continued

| # | Structure | ESI, m/z [M + H]+ |
|---|---|---|
| 156 | 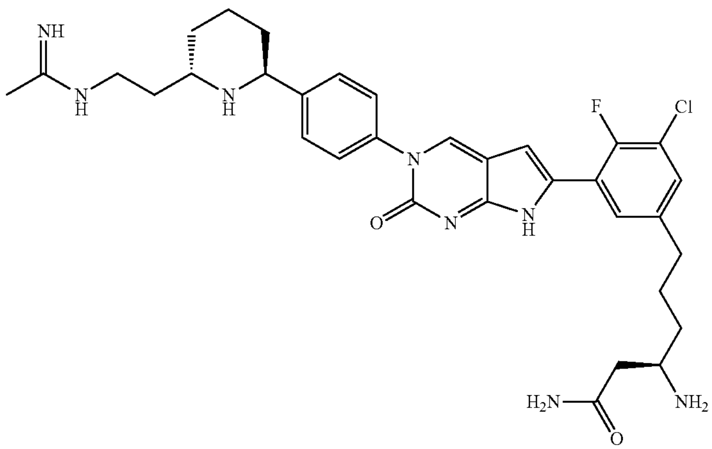 [SMILES: CC(=N)NCC[C@@H]1CCC[C@@H](c2ccc(-n3cc4cc(-c5cc(CCC[C@@H](N)CC(N)=O)cc(Cl)c5F)[nH]c4nc3=O)cc2)N1] | 635.5 |
| 157 | 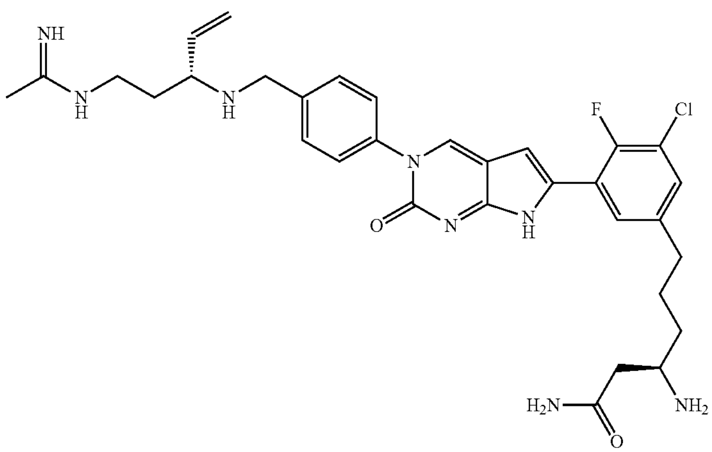 [SMILES: C=C[C@@H](CCNC(C)=N)NCc1ccc(-n2cc3cc(-c4cc(CCC[C@@H](N)CC(N)=O)cc(Cl)c4F)[nH]c3nc2=O)cc1] | 621.5 |
| 158 | 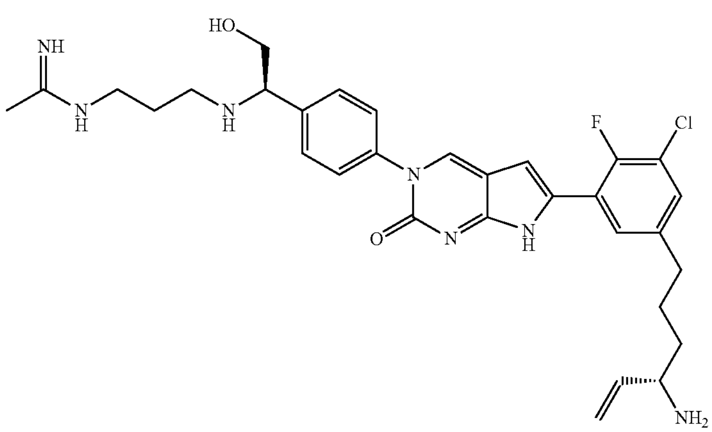 [SMILES: C=C[C@@H](N)CCCc1cc(Cl)c(F)c(-c2cc3cn(-c4ccc([C@H](CO)NCCCNC(C)=N)cc4)c(=O)nc3[nH]2)c1] | 594.5 |

TABLE 1-continued

| # | Structure | ESI, m/z [M + H]+ |
|---|---|---|
| 159 | 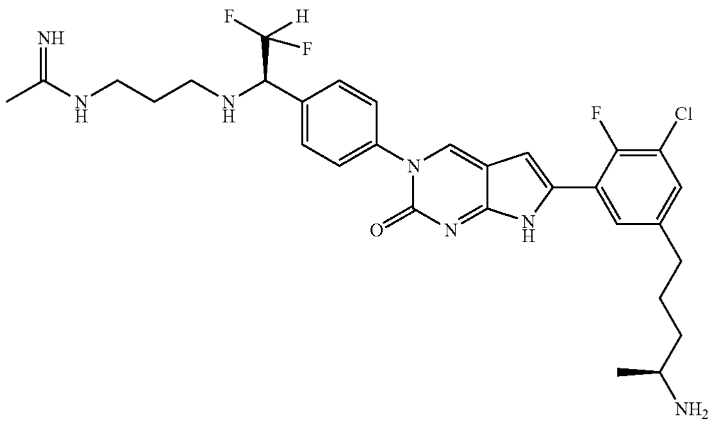 | 602.4 |
| 160 | 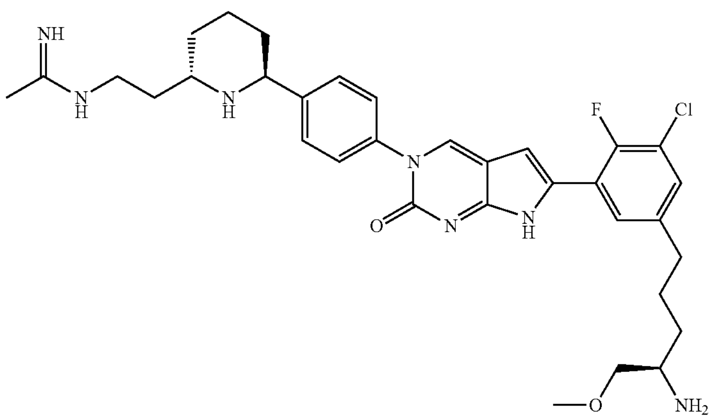 [SMILES: COC[C@H](N)CCCc1cc(Cl)c(F)c(-c2cc3cn(-c4ccc([C@@H]5CCC[C@@H](CCNC(C)=N)N5)cc4)c(=O)nc3[nH]2)c1] | 622.5 |
| 161 | 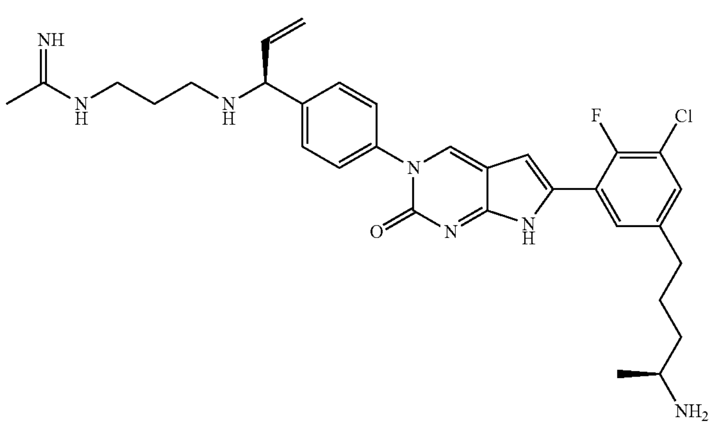 [SMILES: C=C[C@H](NCCCNC(C)=N)c1ccc(-n2cc3cc(-c4cc(CCC[C@H](C)N)cc(Cl)c4F)[nH]c3nc2=O)cc1] | 579 |

TABLE 1-continued

| # | Structure | ESI, m/z [M + H]+ |
|---|---|---|
| 162 | 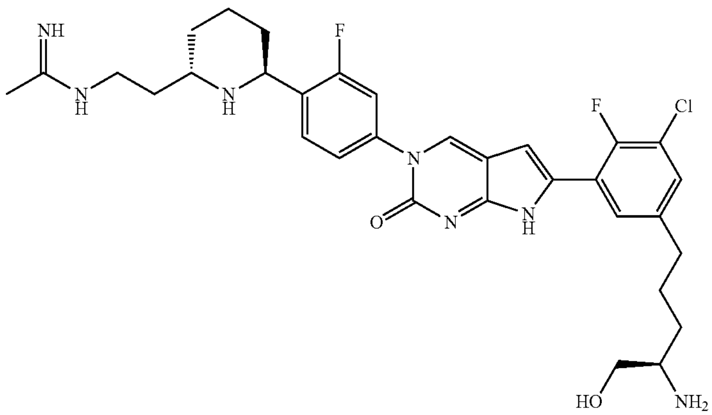 [SMILES: CC(=N)NCC[C@@H]1CCC[C@@H](c2ccc(-n3cc4cc(-c5cc(CCC[C@@H](N)CO)cc(Cl)c5F)[nH]c4nc3=O)cc2F)N1] | 626 |
| 163 | 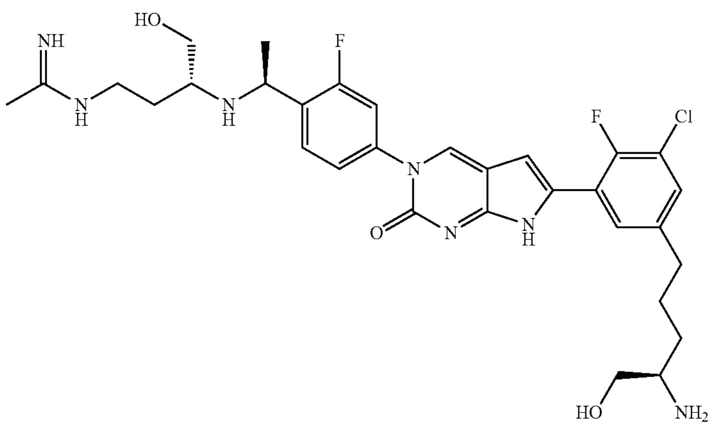 [SMILES: CC(=N)NCC[C@H](CO)N[C@@H](C)c1ccc(-n2cc3cc(-c4cc(CCC[C@@H](N)CO)cc(Cl)c4F)[nH]c3nc2=O)cc1F] | 630 |
| 164 | 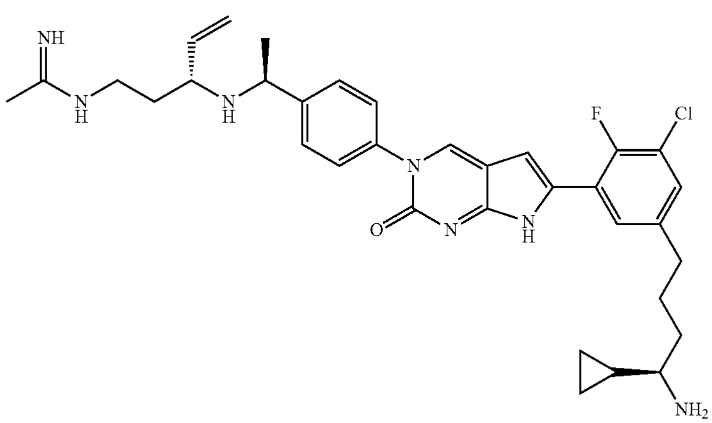 | 618.5 |

TABLE 1-continued
| # | Structure | ESI, m/z [M + H]+ |
|---|---|---|
| 165 | 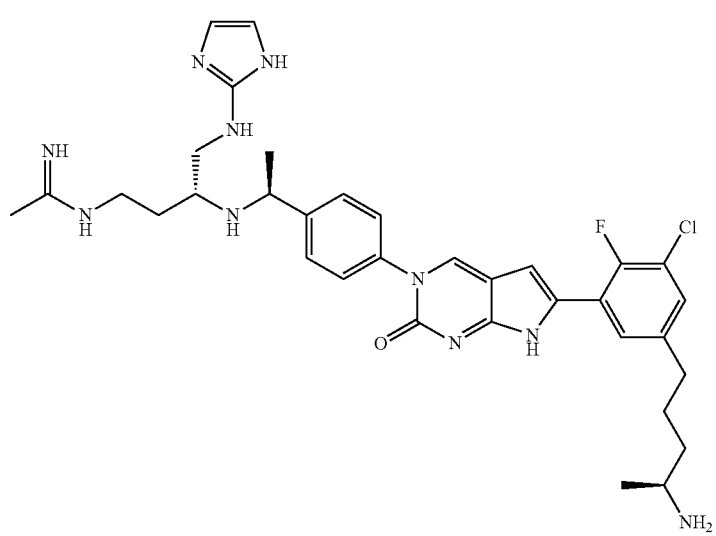 [SMILES: CC(=N)NCC[C@H](CNc1ncc[nH]1)N[C@@H](C)c1ccc(-n2cc3cc(-c4cc(CCC[C@H](C)N)cc(Cl)c4F)[nH]c3nc2=O)cc1] | 661.7 |
| 166 | 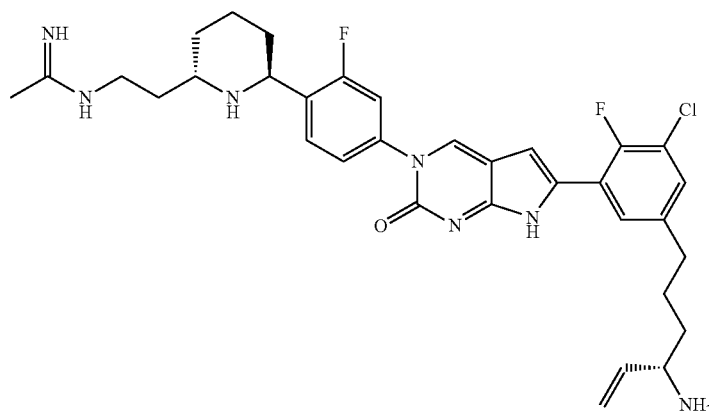 | 622.6 |
| 167 | 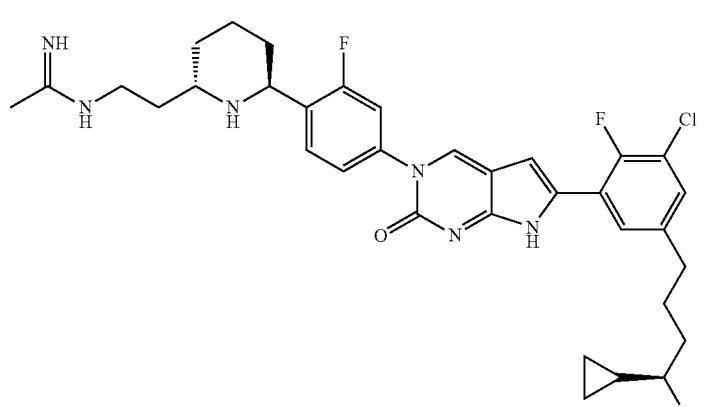 | 637.2 |

TABLE 1-continued

| # | Structure | ESI, m/z [M + H]+ |
|---|---|---|
| 168 | 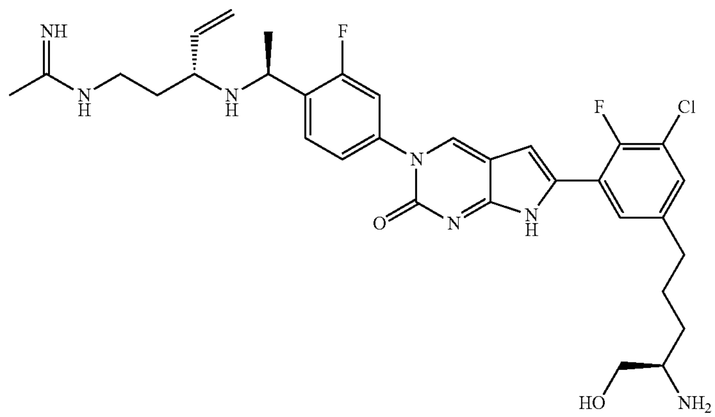 | 626 |
| 169 | 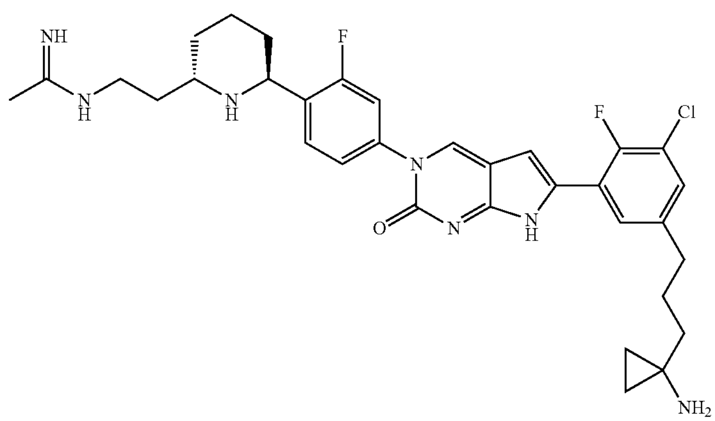 [SMILES: CC(=N)NCC[C@@H]1CCC[C@@H](c2ccc(-n3cc4cc(-c5cc(CCCC6(N)CC6)cc(Cl)c5F)[nH]c4nc3=O)cc2F)N1] | 622.5 |
| 170 | 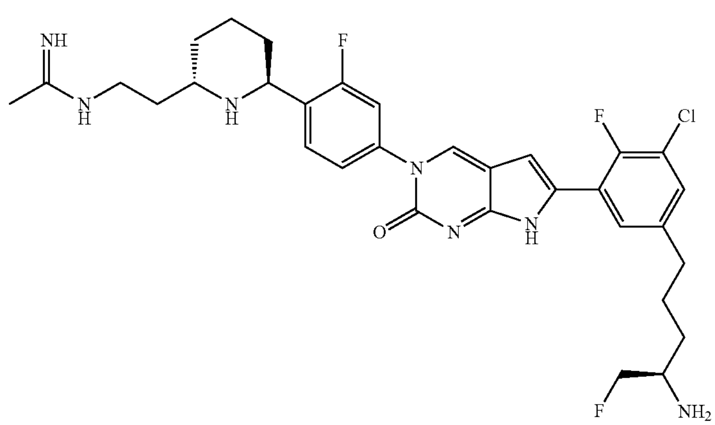 | 628.3 |

TABLE 1-continued
| # | Structure | ESI, m/z [M + H]+ |
|---|---|---|
| 171 | 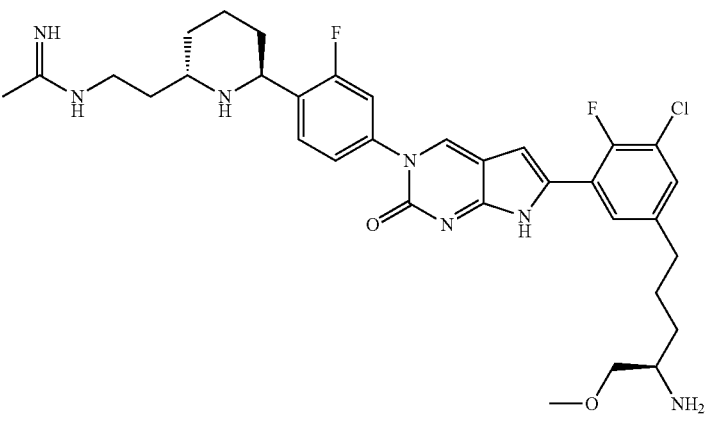 | 640.6 |
| 172 | 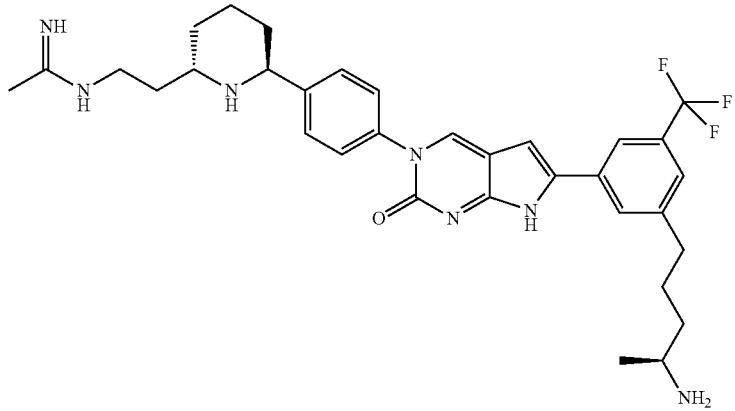 [SMILES: CC(=N)NCC[C@@H]1CCC[C@@H](c2ccc(-n3cc4cc(-c5cc(CCC[C@H](C)N)cc(C(F)(F)F)c5)[nH]c4nc3=O)cc2)N1] | 608.4 |
| 173 | 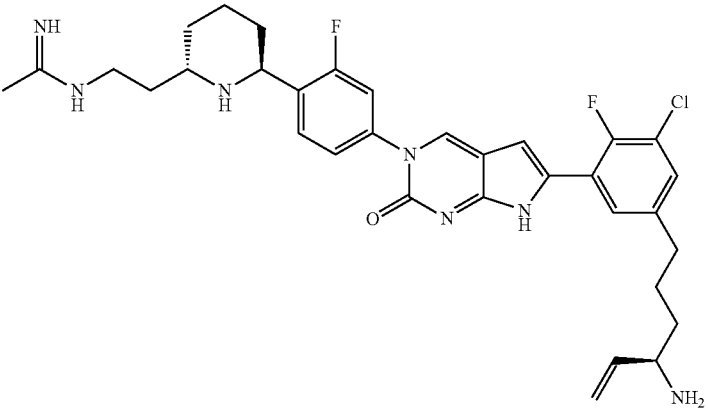 [SMILES: C=C[C@H](N)CCCc1cc(Cl)c(F)c(-c2cc3cn(-c4ccc([C@@H]5CCC[C@@H](CCNC(C)=N)N5)c(F)c4)c(=O)nc3[nH]2)c1] | 622.5 |

TABLE 1-continued

| # | Structure | ESI, m/z [M + H]+ |
|---|---|---|
| 174 | 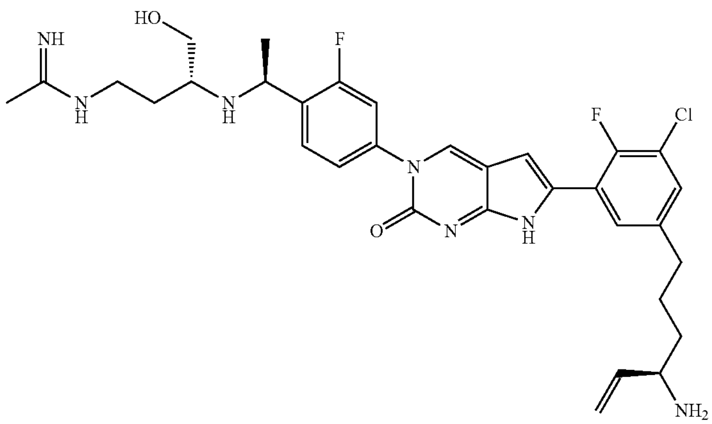 [SMILES: C=C[C@H](N)CCCc1cc(Cl)c(F)c(-c2cc3cn(-c4ccc([C@H](C)N[C@@H](CO)CCNC(C)=N)c(F)c4)c(=O)nc3[nH]2)c1] | 626.4 |
| 175 | 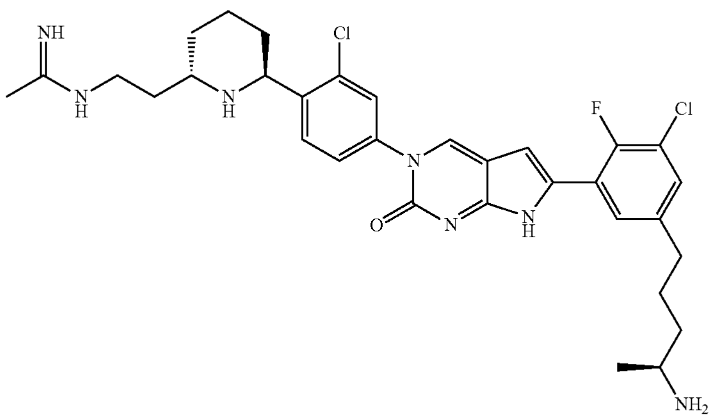 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2Cl)N1] | 626.6 |
| 176 | 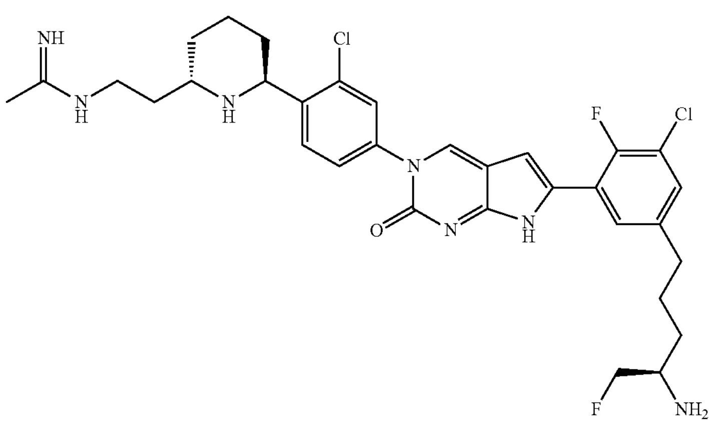 [SMILES: CC(=N)NCC[C@@H]1CCC[C@@H](c2ccc(-n3cc4cc(-c5cc(CCC[C@@H](N)CF)cc(Cl)c5F)[nH]c4nc3=O)cc2Cl)N1] | 646.0 |

TABLE 1-continued

| # | Structure | ESI, m/z [M + H]+ |
|---|---|---|
| 177 | 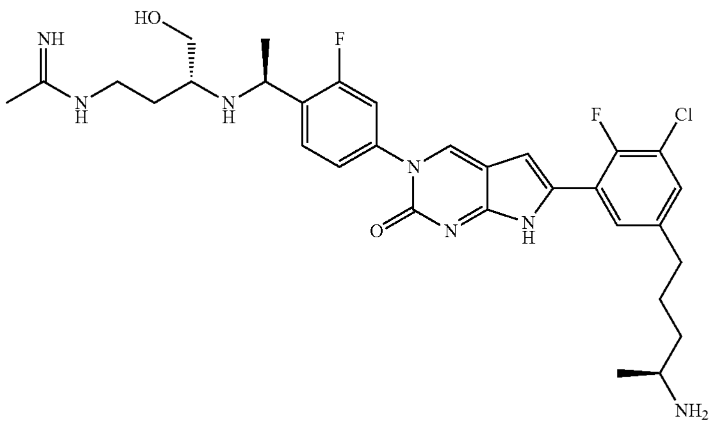 [SMILES: CC(=N)NCC[C@H](CO)N[C@@H](C)c1ccc(-n2cc3cc(-c4cc(CCC[C@H](C)N)cc(Cl)c4F)[nH]c3nc2=O)cc1F] | 614.4 |
| 178 | 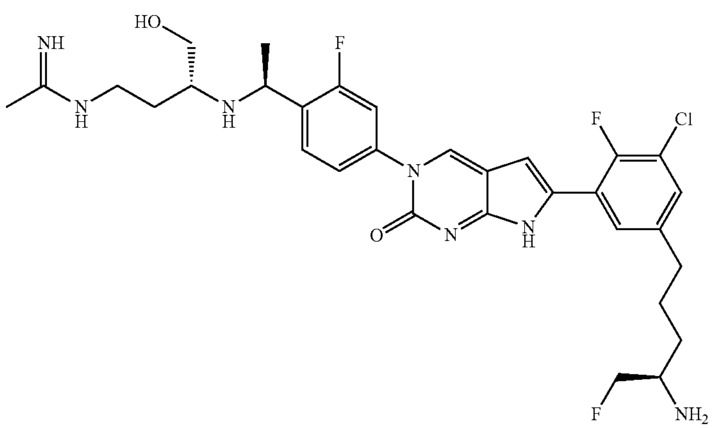 | 632.3 |
| 179 | 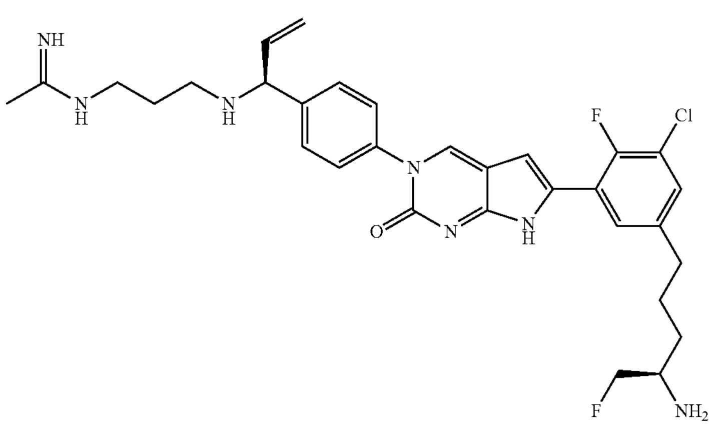 | 597 |

TABLE 1-continued
| # | Structure | ESI, m/z [M + H]+ |
|---|---|---|
| 180 | 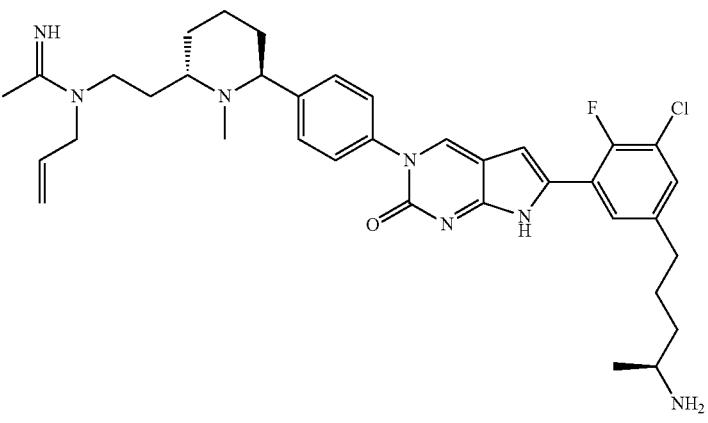 [SMILES: C=CCN(CC[C@@H]1CCC[C@@H](c2ccc(-n3cc4cc(-c5cc(CCC[C@H](C)N)cc(Cl)c5F)[nH]c4nc3=O)cc2)N1C)C(C)=N] | 646.5 |
| 181 | 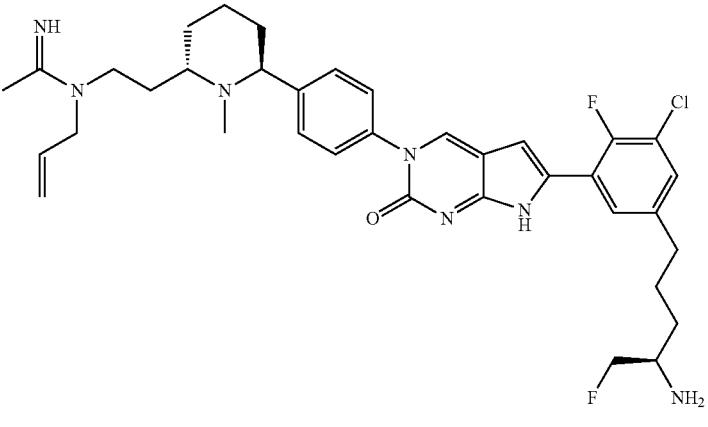 [SMILES: C=CCN(CC[C@@H]1CCC[C@@H](c2ccc(-n3cc4cc(-c5cc(CCC[C@@H](N)CF)cc(Cl)c5F)[nH]c4nc3=O)cc2)N1C)C(C)=N] | 664.5 |
| 182 | 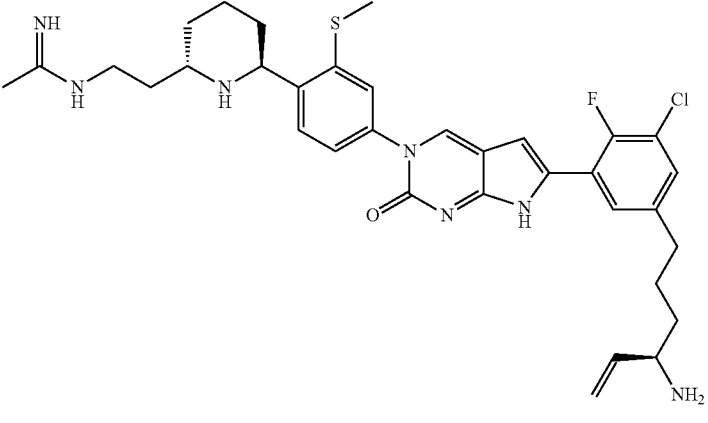 [SMILES: C=C[C@H](N)CCCc1cc(Cl)c(F)c(-c2cc3cn(-c4ccc([C@@H]5CCC[C@@H](CCNC(C)=N)N5)c(SC)c4)c(=O)nc3[nH]2)c1] | 650.4 |

TABLE 1-continued

| # | Structure | ESI, m/z [M + H]+ |
|---|---|---|
| 183 | 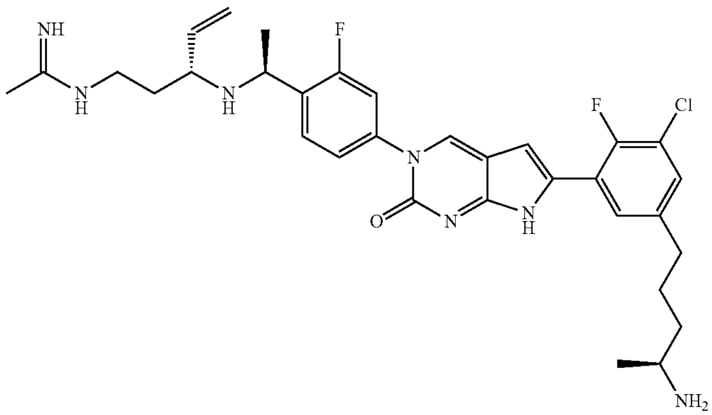 [SMILES: C=C[C@@H](CCNC(C)=N)N[C@@H](C)c1ccc(-n2cc3cc(-c4cc(CCC[C@H](C)N)cc(Cl)c4F)[nH]c3nc2=O)cc1F] | 610.4 |
| 184 | 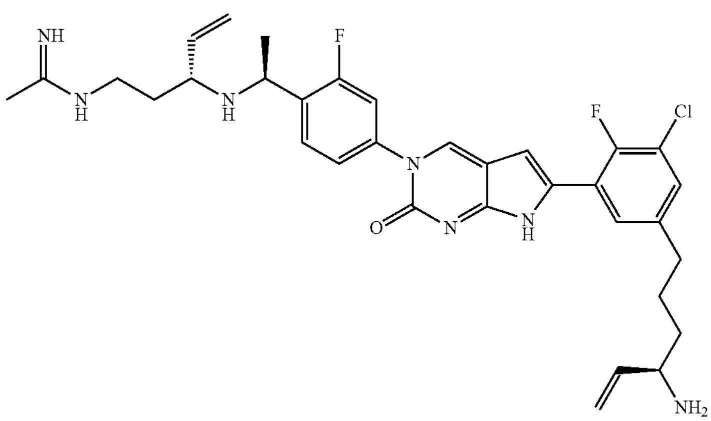 [SMILES: C=C[C@H](N)CCCc1cc(Cl)c(F)c(-c2cc3cn(-c4ccc([C@H](C)N[C@@H](C=C)CCNC(C)=N)c(F)c4)c(=O)nc3[nH]2)c1] | 622.5 |
| 185 | 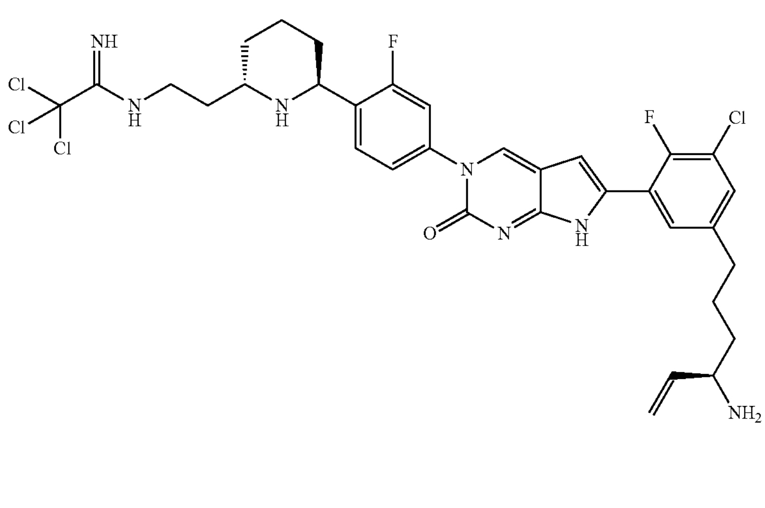 [SMILES: C=C[C@H](N)CCCc1cc(Cl)c(F)c(-c2cc3cn(-c4ccc([C@@H]5CCC[C@@H](CCNC(=N)C(Cl)(Cl)Cl)N5)c(F)c4)c(=O)nc3[nH]2)c1] | 727.4 |

TABLE 1-continued

| # | Structure | ESI, m/z [M + H]+ |
|---|---|---|
| 186 | 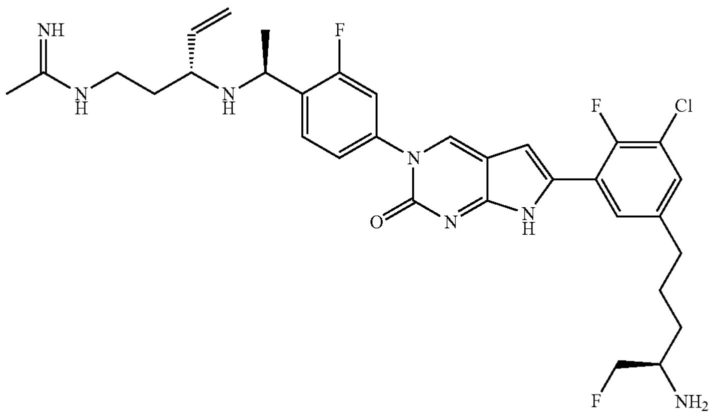 | 628.4 |
| 187 | 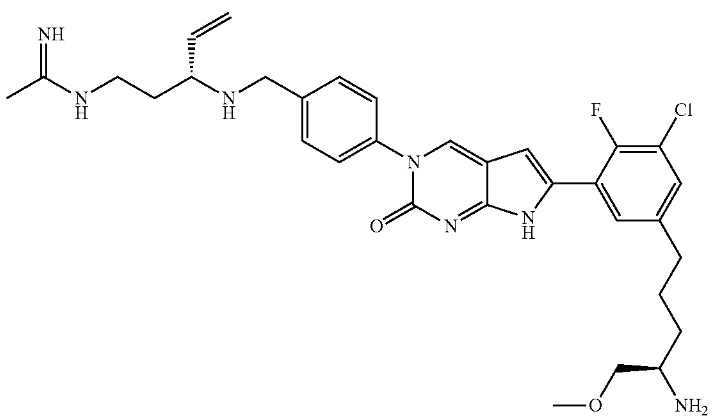 [SMILES: C=C[C@@H](CCNC(C)=N)NCc1ccc(-n2cc3cc(-c4cc(CCC[C@@H](N)COC)cc(Cl)c4F)[nH]c3nc2=O)cc1] | 608.4 |
| 188 | 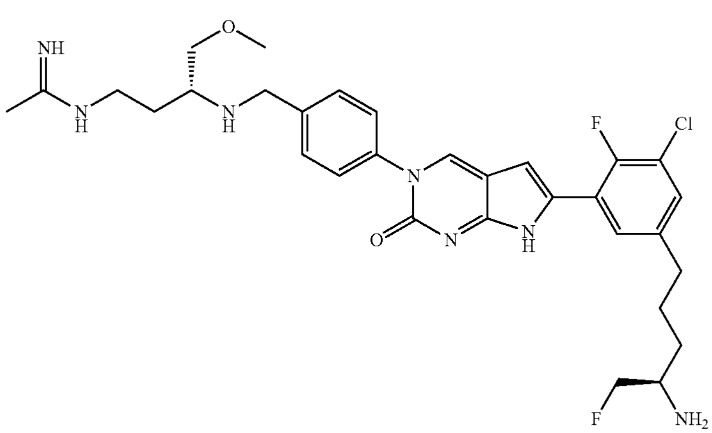 [SMILES: COC[C@@H](CCNC(C)=N)NCc1ccc(-n2cc3cc(-c4cc(CCC[C@@H](N)CF)cc(Cl)c4F)[nH]c3nc2=O)cc1] | 614.4 |

TABLE 1-continued
| # | Structure | ESI, m/z [M + H]+ |
|---|-----------|-------------------|
| 189 | 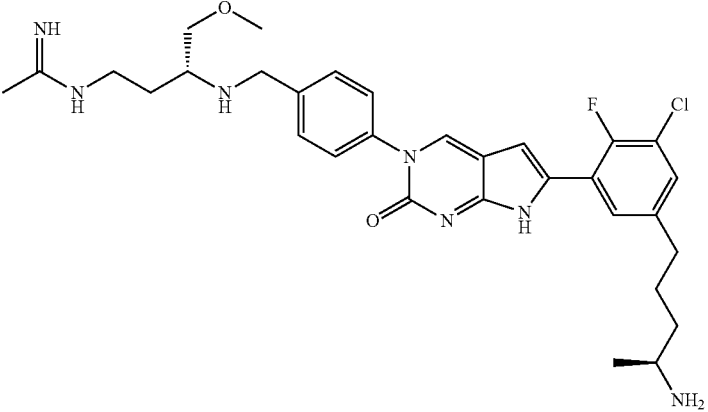 [SMILES: COC[C@@H](CCNC(C)=N)NCc1ccc(-n2cc3cc(-c4cc(CCC[C@H](C)N)cc(Cl)c4F)[nH]c3nc2=O)cc1] | 596.4 |
| 190 | 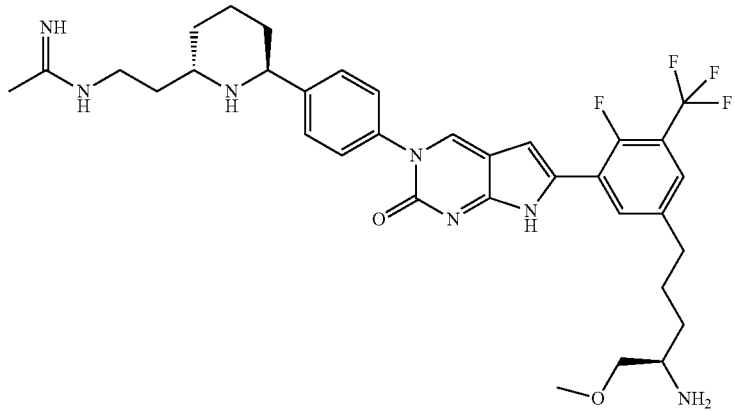 [SMILES: COC[C@H](N)CCCc1cc(-c2cc3cn(-c4ccc([C@@H]5CCC[C@@H](CCNC(C)=N)N5)cc4)c(=O)nc3[nH]2)c(F)c(C(F)(F)F)c1] | 656.6 |
| 191 | 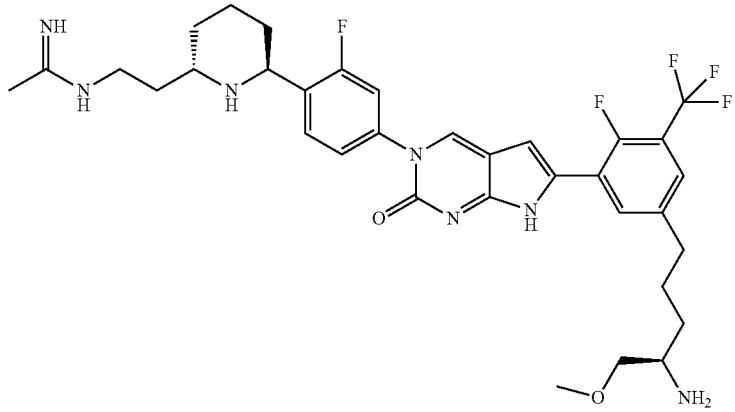 [SMILES: COC[C@H](N)CCCc1cc(-c2cc3cn(-c4ccc([C@@H]5CCC[C@@H](CCNC(C)=N)N5)c(F)c4)c(=O)nc3[nH]2)c(F)c(C(F)(F)F)c1] | 674.6 |

TABLE 1-continued

| # | Structure | ESI, m/z [M + H]+ |
|---|---|---|
| 192 | 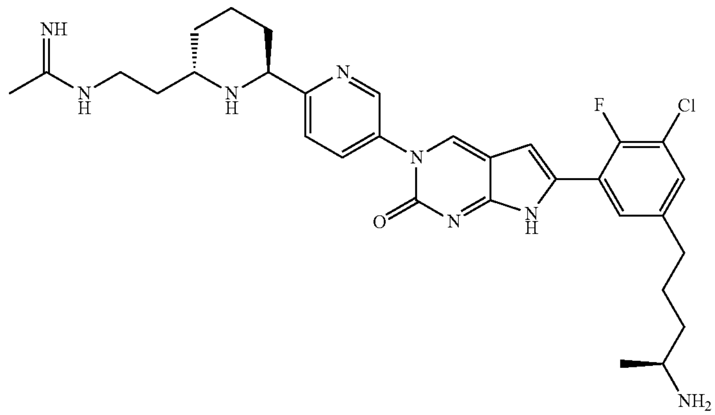 [SMILES: CC(=N)NCC[C@@H]1CCC[C@@H](c2ccc(-n3cc4cc(-c5cc(CCC[C@H](C)N)cc(Cl)c5F)[nH]c4nc3=O)cn2)N1] | 593.4 |
| 193 | 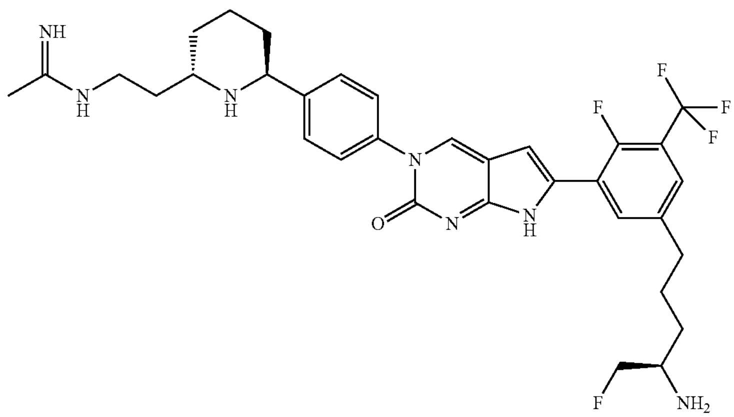 | 644.5 |
| 194 | 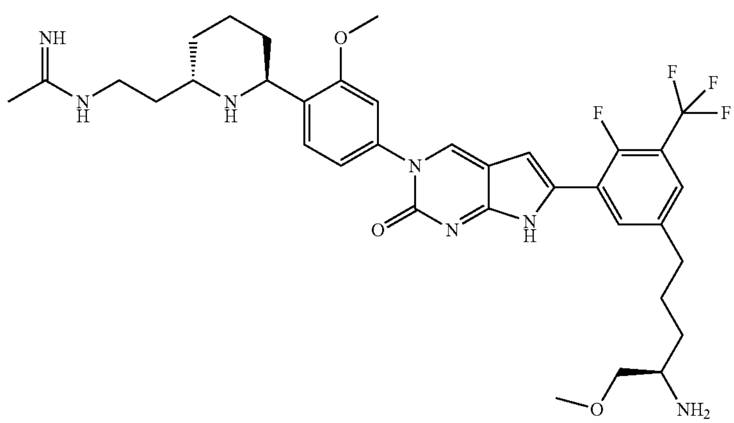 [SMILES: COC[C@H](N)CCCc1cc(-c2cc3cn(-c4ccc([C@@H]5CCC[C@@H](CCNC(C)=N)N5)c(OC)c4)c(=O)nc3[nH]2)c(F)c(C(F)(F)F)c1] | 686.5 |

TABLE 1-continued

| # | Structure | ESI, m/z [M + H]+ |
|---|---|---|
| 195 | 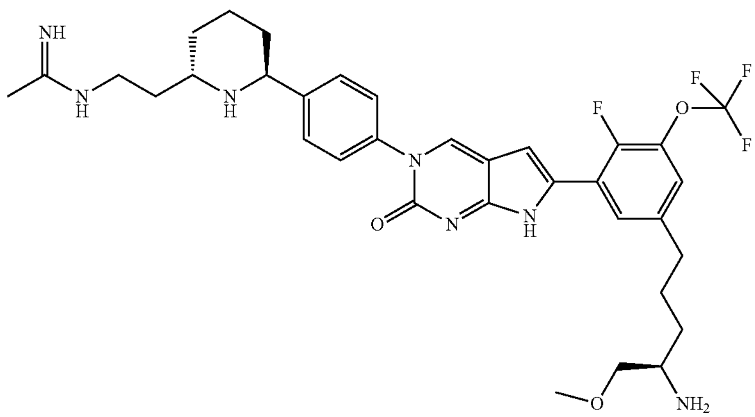 [SMILES: COC[C@H](N)CCCc1cc(OC(F)(F)F)c(F)c(-c2cc3cn(-c4ccc([C@@H]5CCC[C@@H](CCNC(C)=N)N5)cc4)c(=O)nc3[nH]2)c1] | 672 |
| 196 | 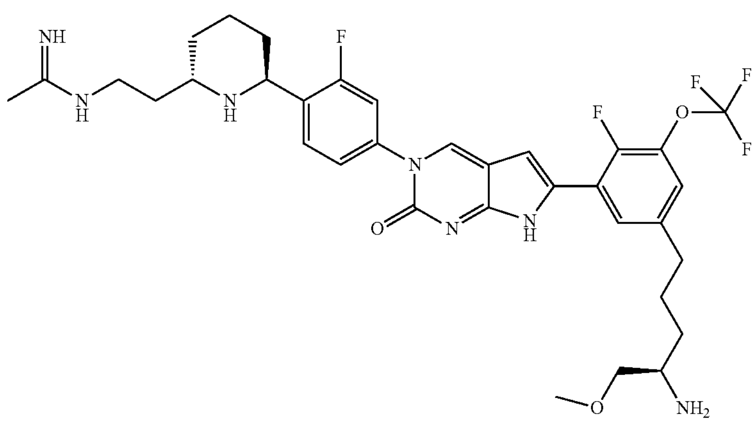 [SMILES: COC[C@H](N)CCCc1cc(OC(F)(F)F)c(F)c(-c2cc3cn(-c4ccc([C@@H]5CCC[C@@H](CCNC(C)=N)N5)c(F)c4)c(=O)nc3[nH]2)c1] | 690 |
| 197 | 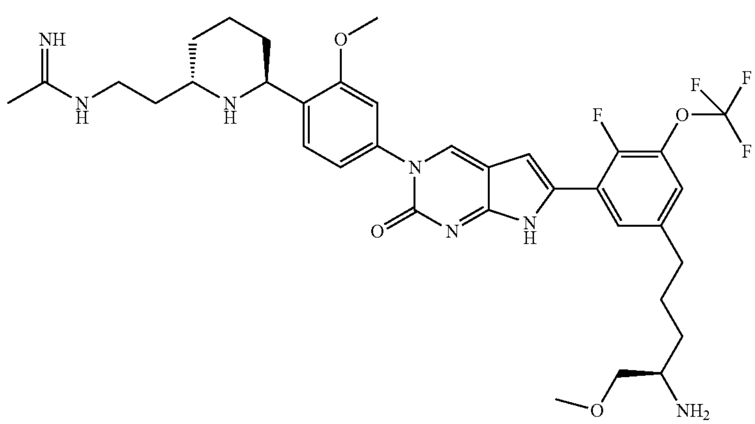 [SMILES: COC[C@H](N)CCCc1cc(OC(F)(F)F)c(F)c(-c2cc3cn(-c4ccc([C@@H]5CCC[C@@H](CCNC(C)=N)N5)c(SC)c4)c(=O)nc3[nH]2)c1] | 702 |

TABLE 1-continued

| # | Structure | ESI, m/z [M + H]+ |
|---|---|---|
| 198 | 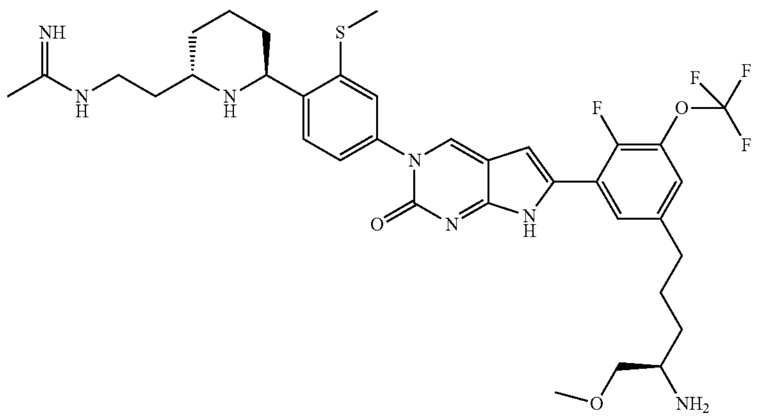 | 718.4 |
| 199 | 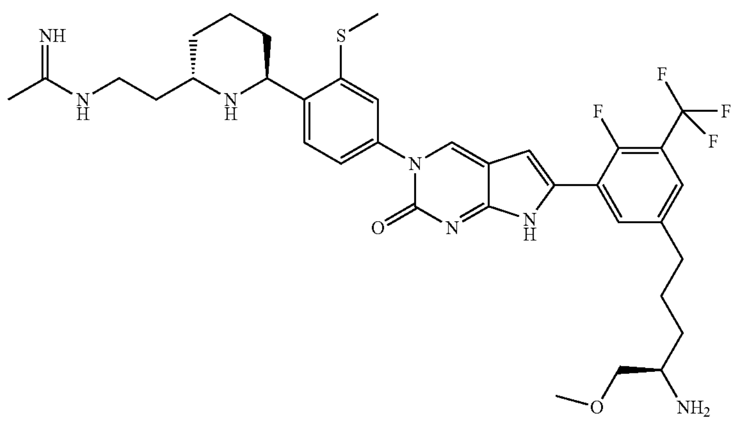 [SMILES: COC[C@H](N)CCCc1cc(-c2cc3cn(-c4ccc([C@@H]5CCC[C@@H](CCNC(C)=N)N5)c(SC)c4)c(=O)nc3[nH]2)c(F)c(C(F)(F)F)c1] | 702.5 |
| 200 | 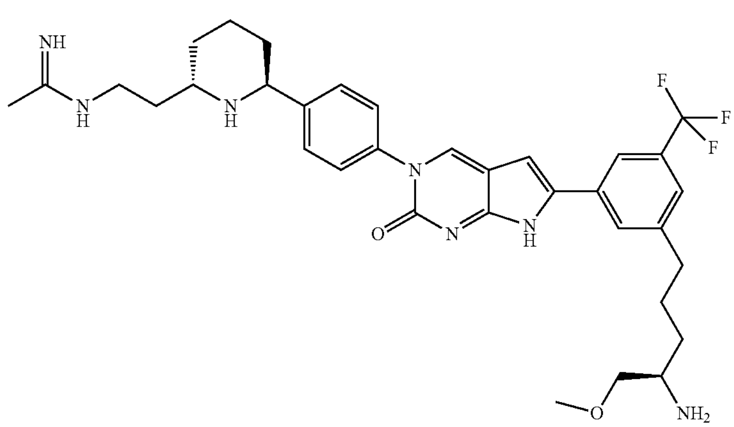 [SMILES: COC[C@H](N)CCCc1cc(-c2cc3cn(-c4ccc([C@@H]5CCC[C@@H](CCNC(C)=N)N5)cc4)c(=O)nc3[nH]2)cc(C(F)(F)F)c1] | 638.5 |

TABLE 1-continued

| # | Structure | ESI, m/z [M + H]+ |
|---|---|---|
| 201 | 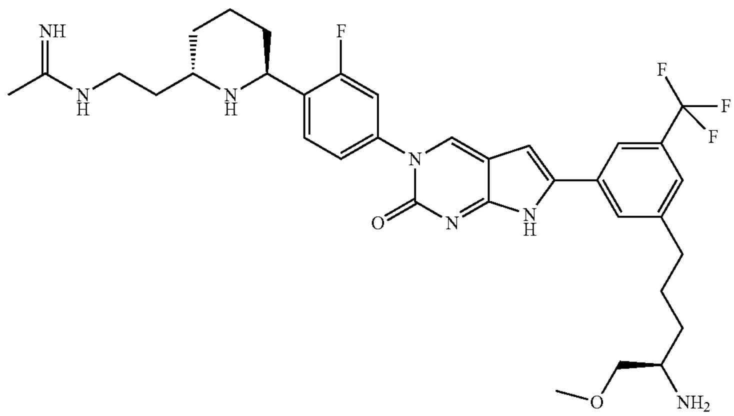 [SMILES: COC[C@H](N)CCCc1cc(-c2cc3cn(-c4ccc([C@@H]5CCC[C@@H](CCNC(C)=N)N5)c(F)c4)c(=O)nc3[nH]2)cc(C(F)(F)F)c1] | 656.5 |
| 202 | 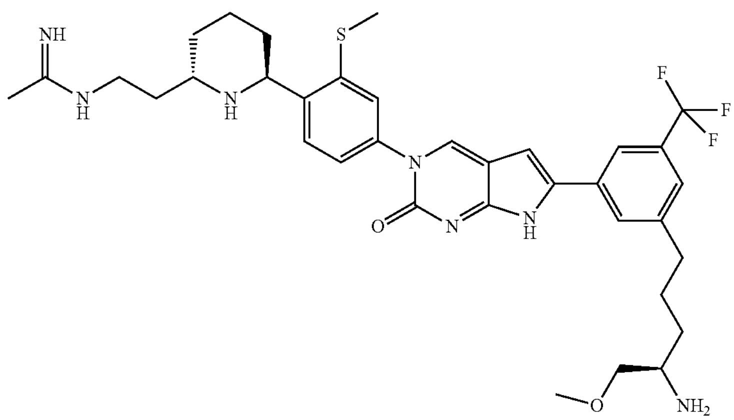 [SMILES: COC[C@H](N)CCCc1cc(-c2cc3cn(-c4ccc([C@@H]5CCC[C@@H](CCNC(C)=N)N5)c(SC)c4)c(=O)nc3[nH]2)cc(C(F)(F)F)c1] | 684.5 |
| 203 | 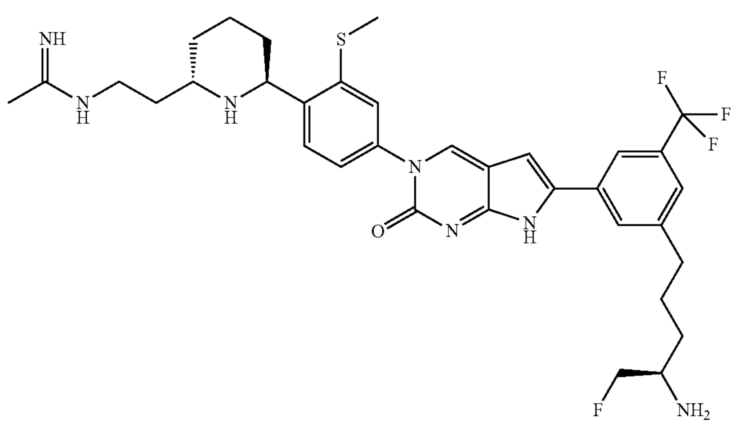 | 672.5 |

TABLE 1-continued
| # | Structure | ESI, m/z [M + H]+ |
|---|---|---|
| 204 | 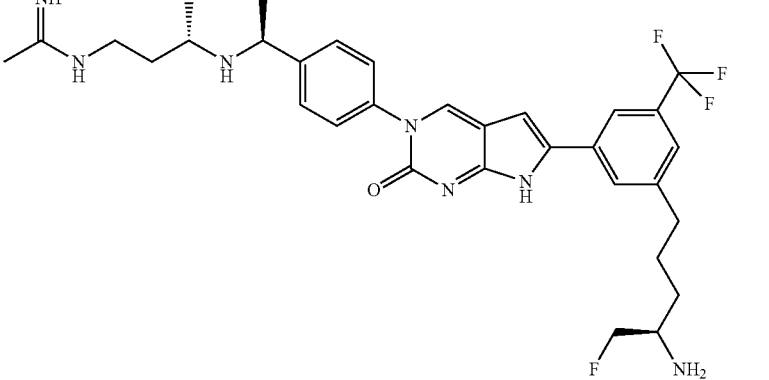 | 626.5 |
| 205 | 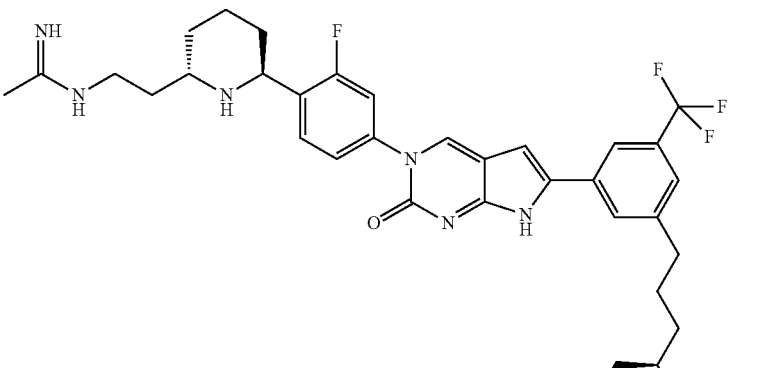 | 644.5 |
| 206 | 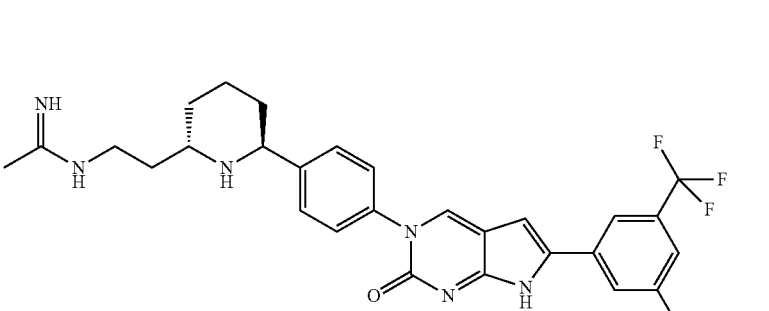 | 634 |

TABLE 1-continued
| # | Structure | ESI, m/z [M + H]+ |
|---|---|---|
| 207 | 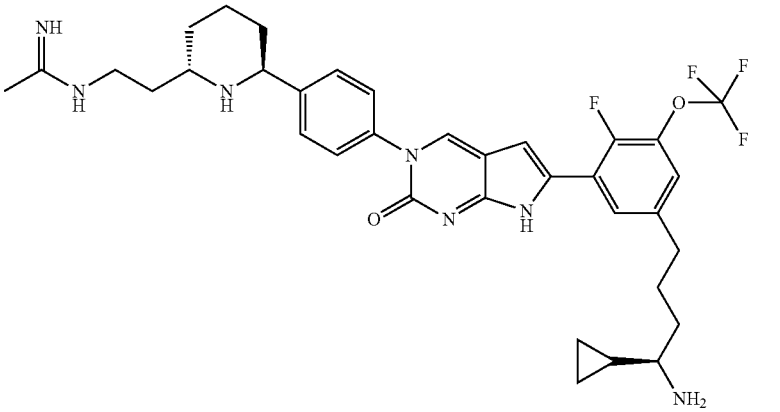 [SMILES: CC(=N)NCC[C@@H]1CCC[C@@H](c2ccc(-n3cc4cc(-c5cc(CCC[C@@H](N)C6CC6)cc(OC(F)(F)F)c5F)[nH]c4nc3=O)cc2)N1] | 668 |
| 208 | 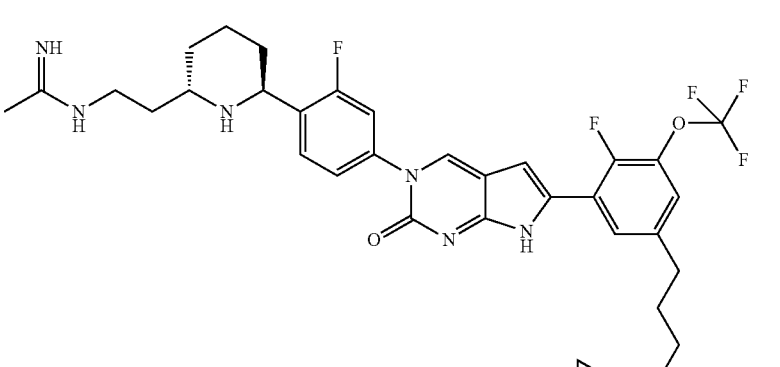 | 686 |
| 209 | 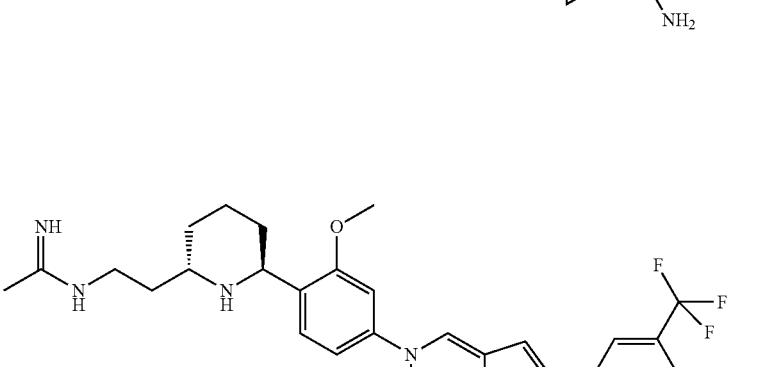 | 656.5 |

TABLE 1-continued

| # | Structure | ESI, m/z [M + H]+ |
|---|---|---|
| 210 | 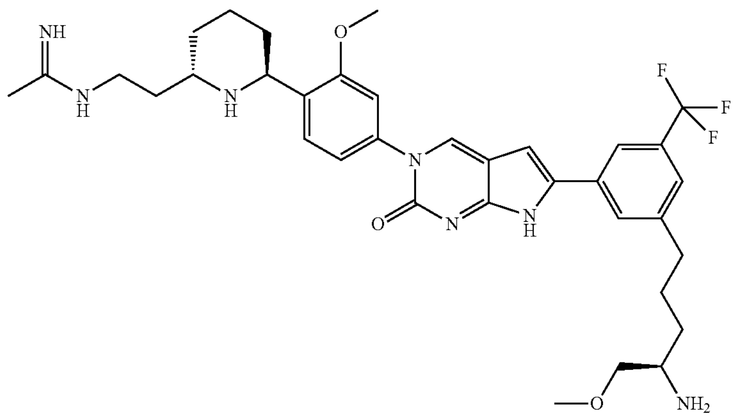 [SMILES: COC[C@H](N)CCCc1cc(-c2cc3cn(-c4ccc([C@@H]5CCC[C@@H](CCNC(C)=N)N5)c(OC)c4)c(=O)nc3[nH]2)cc(C(F)(F)F)c1] | 668.5 |
| 211 | 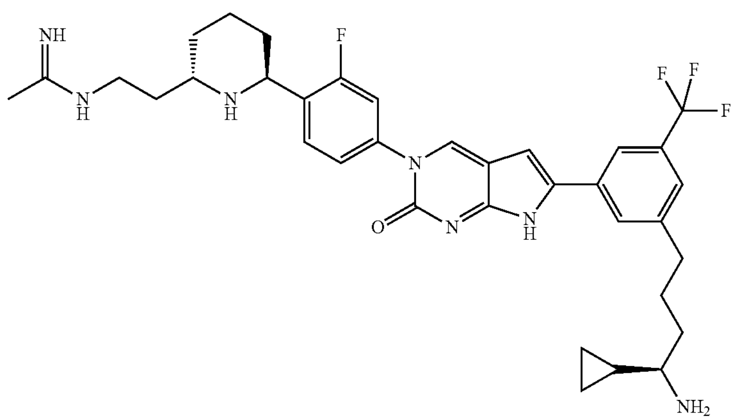 [SMILES: CC(=N)NCC[C@@H]1CCC[C@@H](c2ccc(-n3cc4cc(-c5cc(CCC[C@@H](N)C6CC6)cc(C(F)(F)F)c5)[nH]c4nc3=O)cc2F)N1] | 652 |
| 212 | 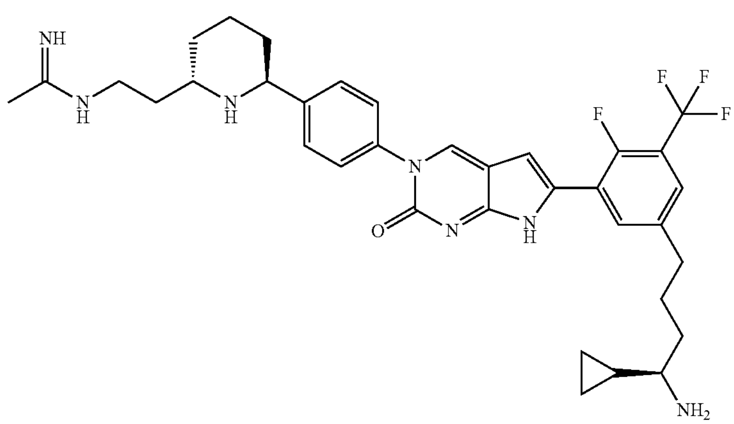 [SMILES: CC(=N)NCC[C@@H]1CCC[C@@H](c2ccc(-n3cc4cc(-c5cc(CCC[C@@H](N)C6CC6)cc(C(F)(F)F)c5F)[nH]c4nc3=O)cc2)N1] | 652 |

TABLE 1-continued
| # | Structure | ESI, m/z [M + H]+ |
|---|---|---|
| 213 | 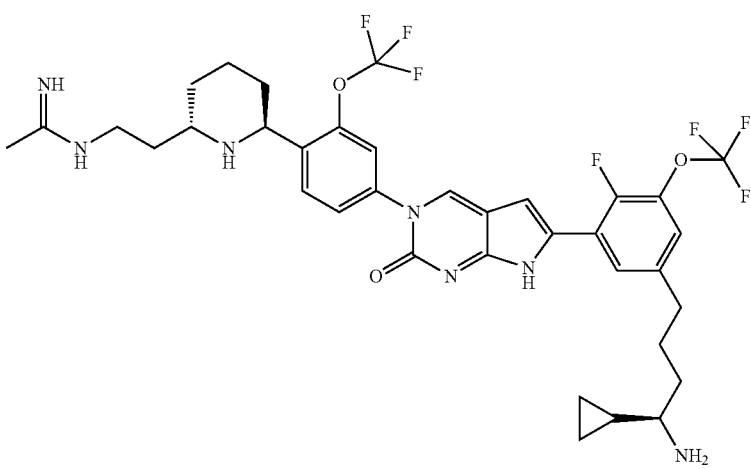 [SMILES: CC(=N)NCC[C@@H]1CCC[C@@H](c2ccc(-n3cc4cc(-c5cc(CCC[C@@H](N)C6CC6)cc(OC(F)(F)F)c5F)[nH]c4nc3=O)cc2OC(F)(F)F)N1] | 752 |
| 214 | 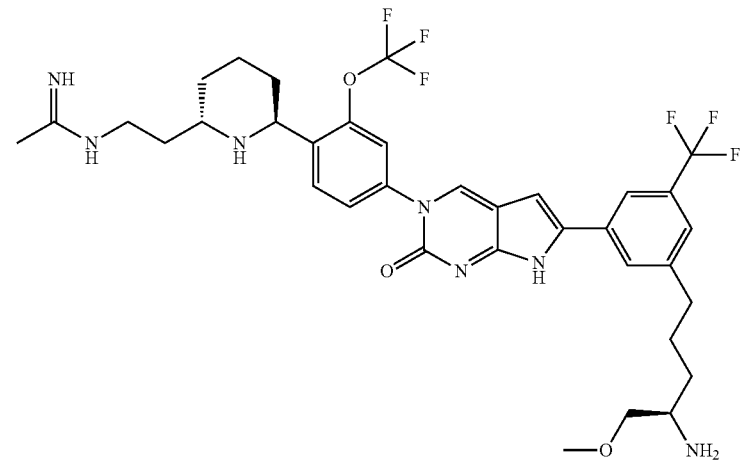 | 722.4 |
| 215 | 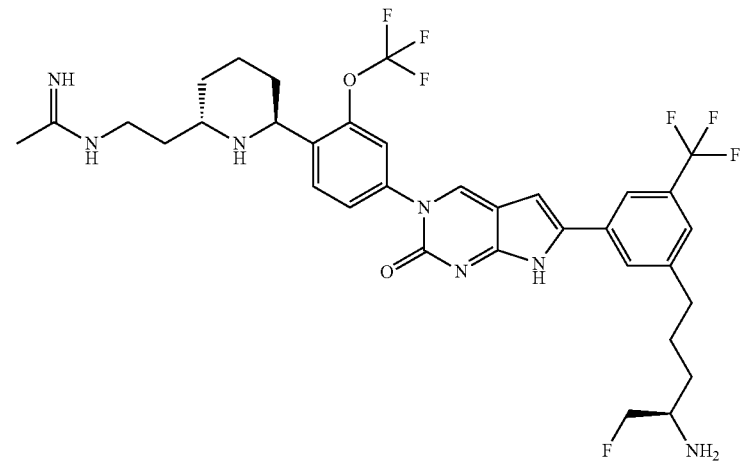 [SMILES: CC(=N)NCC[C@@H]1CCC[C@@H](c2ccc(-n3cc4cc(-c5cc(CCC[C@@H](N)CF)cc(C(F)(F)F)c5)[nH]c4nc3=O)cc2OC(F)(F)F)N1] | 710.4 |

TABLE 1-continued

| # | Structure | ESI, m/z [M + H]+ |
|---|---|---|
| 216 | 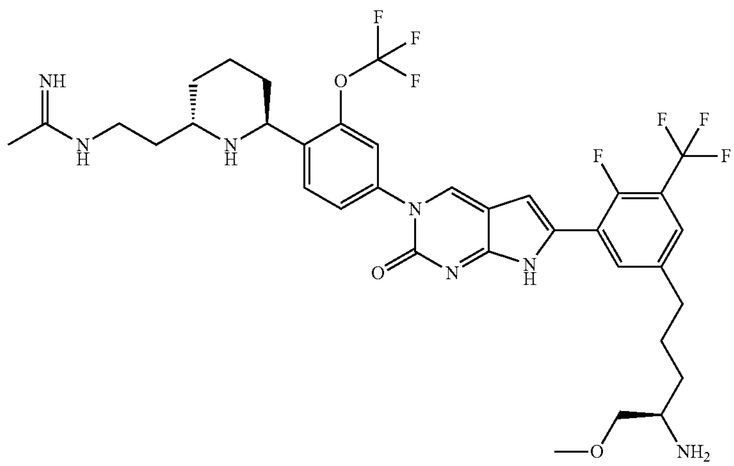 [SMILES: COC[C@H](N)CCCc1cc(-c2cc3cn(-c4ccc([C@@H]5CCC[C@@H](CCNC(C)=N)N5)c(OC(F)(F)F)c4)c(=O)nc3[nH]2)c(F)c(C(F)(F)F)c1] | 740.3 |
| 217 | 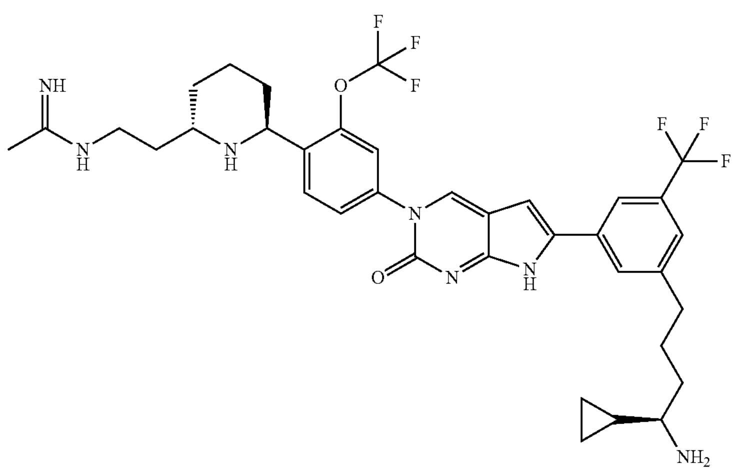 [SMILES: CC(=N)NCC[C@@H]1CCC[C@@H](c2ccc(-n3cc4cc(-c5cc(CCC[C@@H](N)C6CC6)cc(C(F)(F)F)c5)[nH]c4nc3=O)cc2OC(F)(F)F)N1] | 718 |
| 218 | 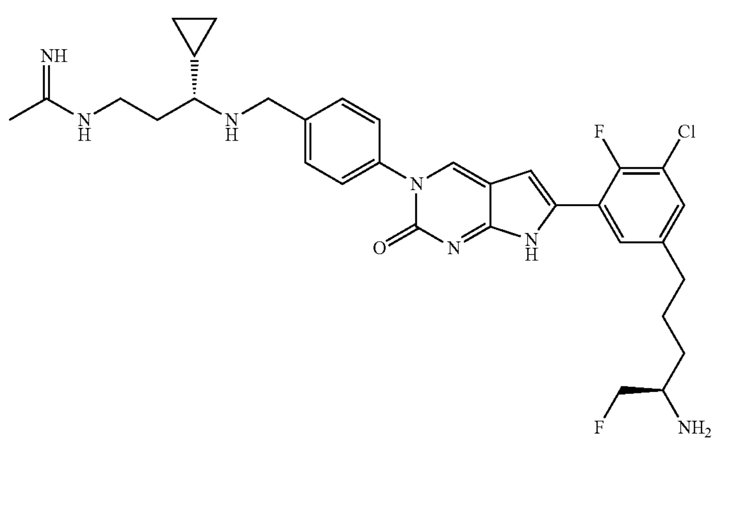 [SMILES: CC(=N)NCC[C@@H](NCc1ccc(-n2cc3cc(-c4cc(CCC[C@@H](N)CF)cc(Cl)c4F)[nH]c3nc2=O)cc1)C1CC1] | 611.3 |

TABLE 1-continued

| # | Structure | ESI, m/z [M + H]+ |
|---|---|---|
| 219 | 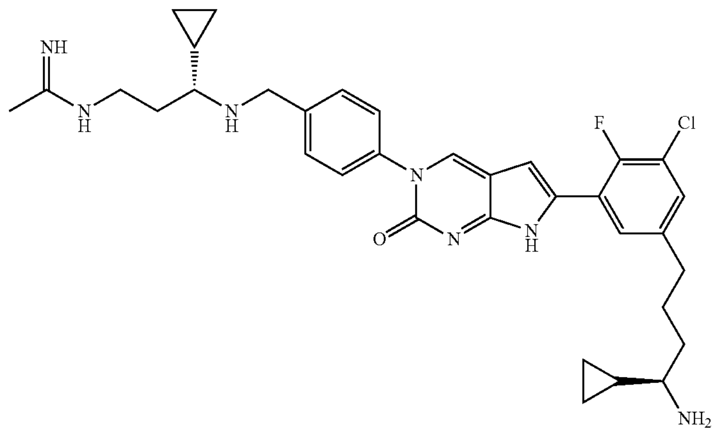 [SMILES: CC(=N)NCC[C@@H](NCc1ccc(-n2cc3cc(-c4cc(CCC[C@@H](N)C5CC5)cc(Cl)c4F)[nH]c3nc2=O)cc1)C1CC1] | 618.7 |
| 220 | 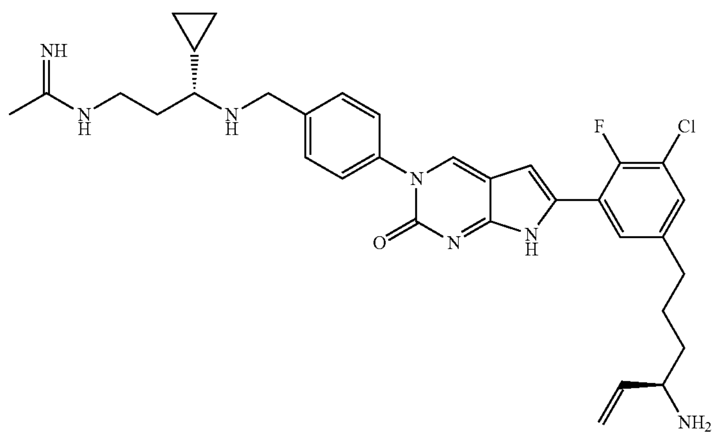 [SMILES: C=C[C@H](N)CCCc1cc(Cl)c(F)c(-c2cc3cn(-c4ccc(CN[C@H](CCNC(C)=N)C5CC5)cc4)c(=O)nc3[nH]2)c1] | 604.4 |
| 221 | 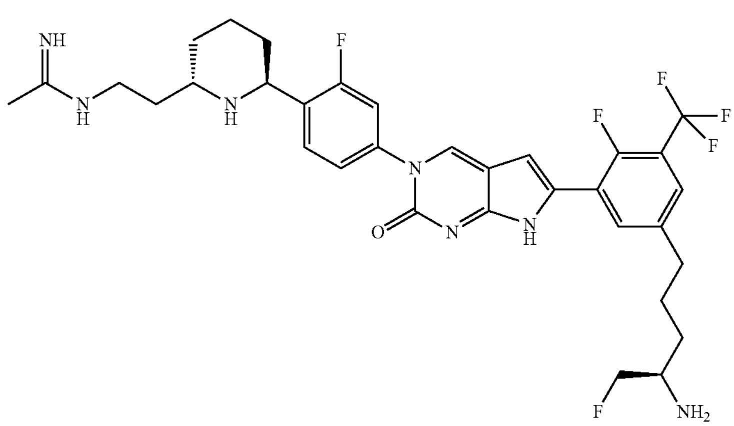 [SMILES: CC(=N)NCC[C@@H]1CCC[C@@H](c2ccc(-n3cc4cc(-c5cc(CCC[C@@H](N)CF)cc(C(F)(F)F)c5F)[nH]c4nc3=O)cc2F)N1] | 662.7 |

TABLE 1-continued
| # | Structure | ESI, m/z [M + H]+ |
|---|---|---|
| 222 | 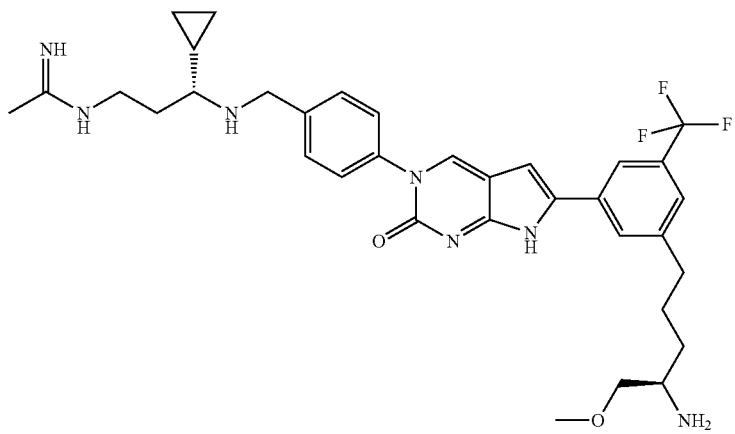 [SMILES: COC[C@H](N)CCCc1cc(-c2cc3cn(-c4ccc(CN[C@H](CCNC(C)=N)C5CC5)cc4)c(=O)nc3[nH]2)cc(C(F)(F)F)c1] | 638.8 |
| 223 | 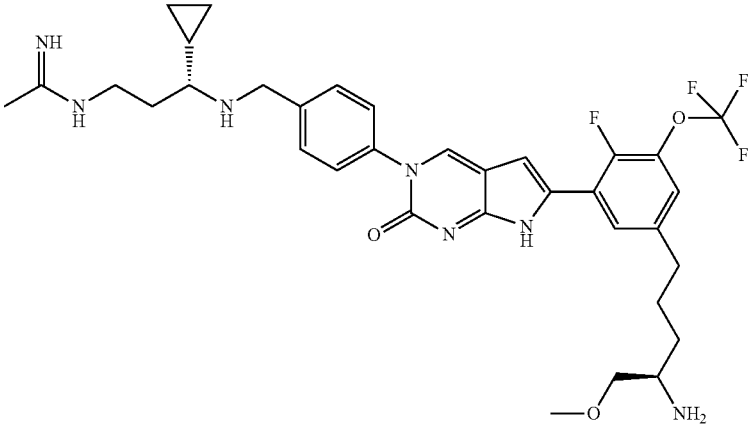 [SMILES: COC[C@H](N)CCCc1cc(OC(F)(F)F)c(F)c(-c2cc3cn(-c4ccc(CN[C@H](CCNC(C)=N)C5CC5)cc4)c(=O)nc3[nH]2)c1] | 672.8 |
| 224 | 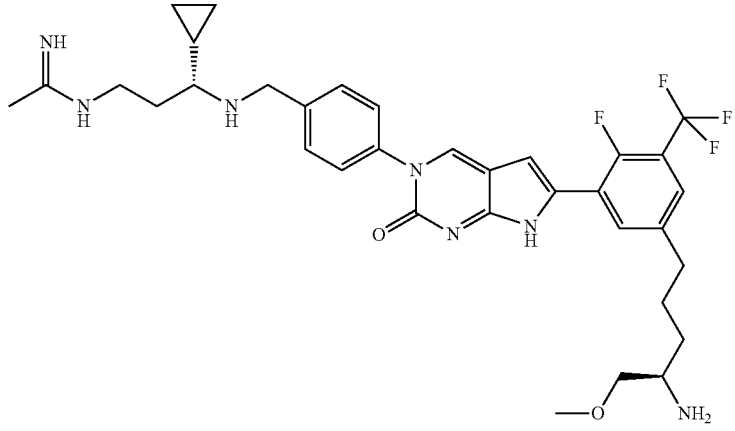 [SMILES: COC[C@H](N)CCCc1cc(-c2cc3cn(-c4ccc(CN[C@H](CCNC(C)=N)C5CC5)cc4)c(=O)nc3[nH]2)c(F)c(C(F)(F)F)c1] | 656.8 |

TABLE 1-continued

| # | Structure | ESI, m/z [M + H]+ |
|---|---|---|
| 225 | 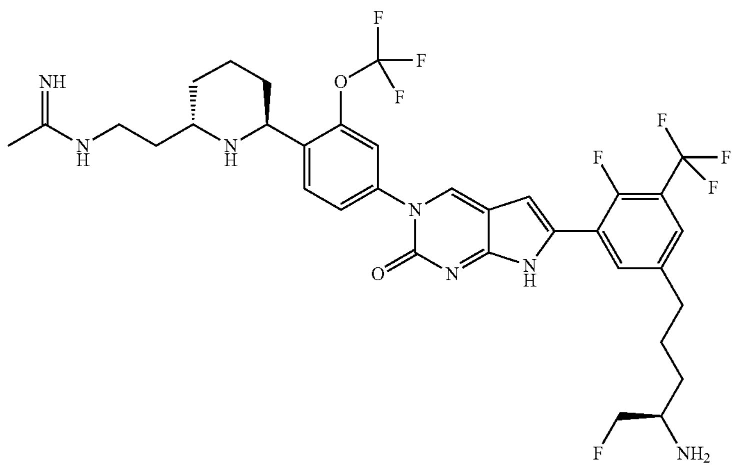 [SMILES: CC(=N)NCC[C@@H]1CCC[C@@H](c2ccc(-n3cc4cc(-c5cc(CCC[C@@H](N)CF)cc(C(F)(F)F)c5F)[nH]c4nc3=O)cc2OC(F)(F)F)N1] | 728.6 |
| 226 | 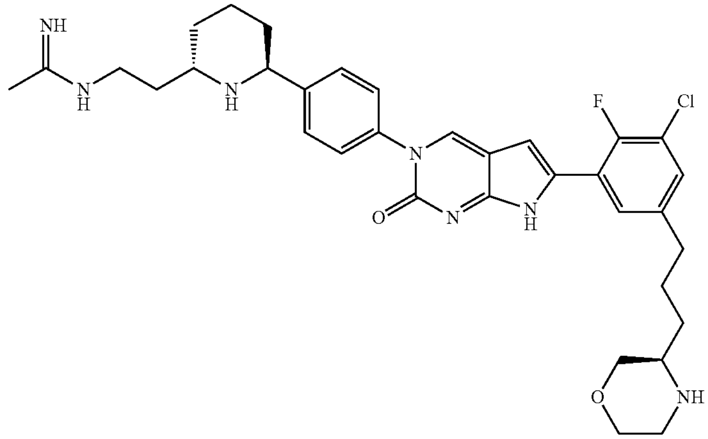 [SMILES: CC(=N)NCC[C@@H]1CCC[C@@H](c2ccc(-n3cc4cc(-c5cc(CCC[C@@H]6COCCN6)cc(Cl)c5F)[nH]c4nc3=O)cc2)N1] | 635.3 |
| 227 | 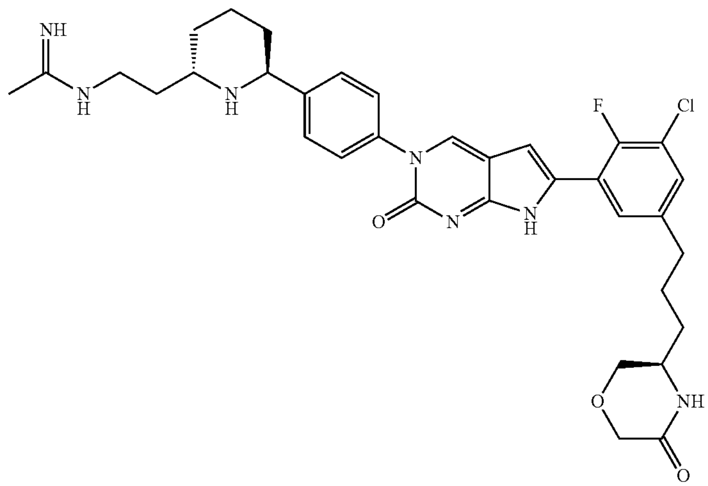 [SMILES: CC(=N)NCC[C@@H]1CCC[C@@H](c2ccc(-n3cc4cc(-c5cc(CCC[C@@H]6COCC(=O)N6)cc(Cl)c5F)[nH]c4nc3=O)cc2)N1] | 649.2 |

TABLE 1-continued

| # | Structure | ESI, m/z [M + H]+ |
|---|-----------|-------------------|
| 228 | 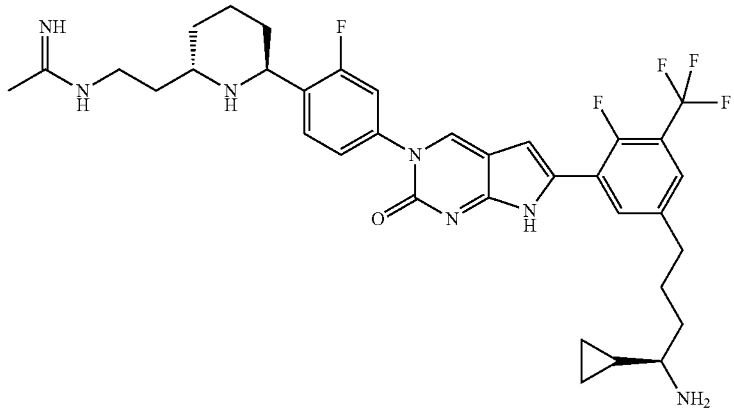 | n/a |
| 229 | 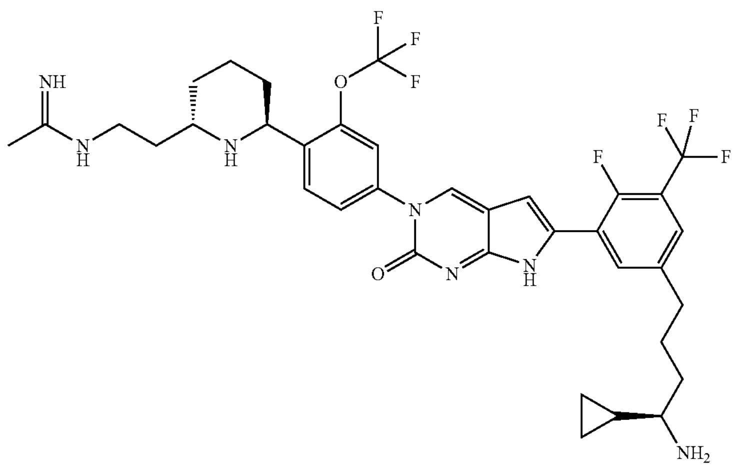 [SMILES: CC(=N)NCC[C@@H]1CCC[C@@H](c2ccc(-n3cc4cc(-c5cc(CCC[C@@H](N)C6CC6)cc(C(F)(F)F)c5F)[nH]c4nc3=O)cc2OC(F)(F)F)N1] | n/a |
| 230 | 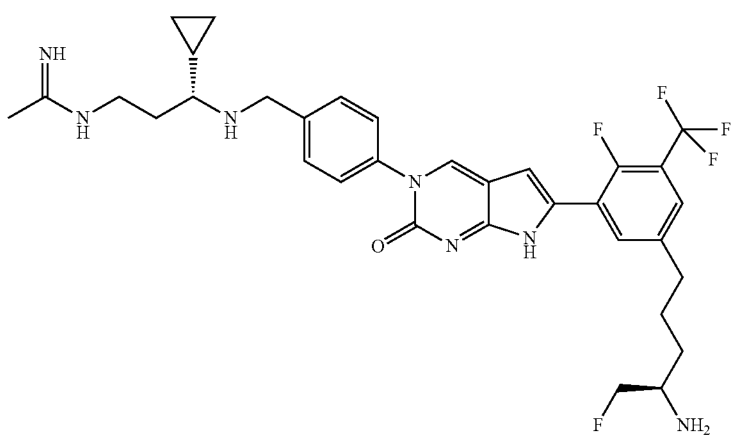 [SMILES: CC(=N)NCC[C@@H](NCc1ccc(-n2cc3cc(-c4cc(CCC[C@@H](N)CF)cc(C(F)(F)F)c4F)[nH]c3nc2=O)cc1)C1CC1] | 644.8 |

TABLE 1-continued

| # | Structure | ESI, m/z [M + H]+ |
|---|---|---|
| 231 | 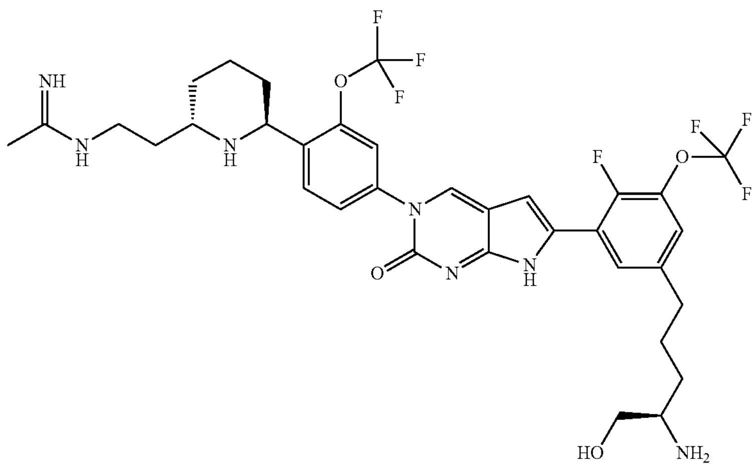 [SMILES: CC(=N)NCC[C@@H]1CCC[C@@H](c2ccc(-n3cc4cc(-c5cc(CCC[C@@H](N)CO)cc(OC(F)(F)F)c5F)[nH]c4nc3=O)cc2OC(F)(F)F)N1] | 742 |
| 232 | 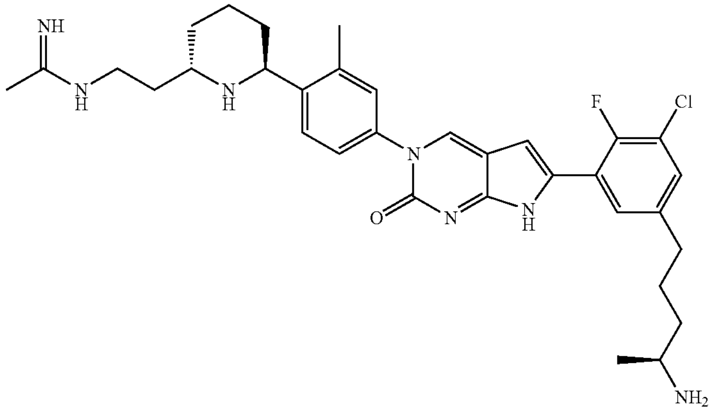 | 606.4 |
| 233 | 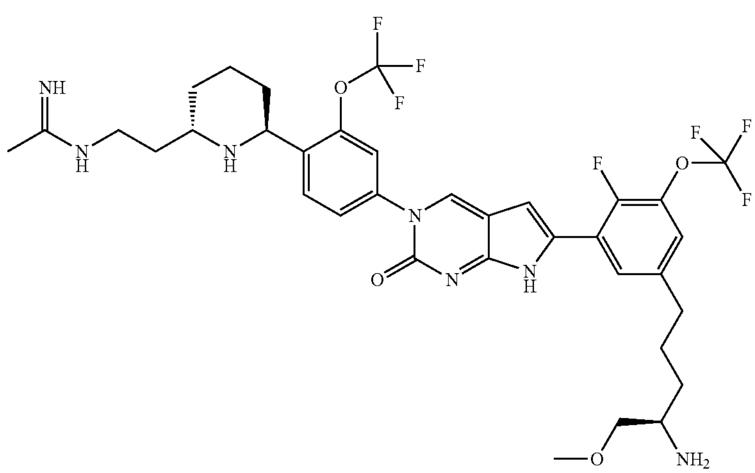 [SMILES: COC[C@H](N)CCCc1cc(OC(F)(F)F)c(F)c(-c2cc3cn(-c4ccc([C@@H]5CCC[C@@H](CCNC(C)=N)N5)c(OC(F)(F)F)c4)c(=O)nc3[nH]2)c1] | 756 |

TABLE 1-continued
| # | Structure | ESI, m/z [M + H]+ |
|---|---|---|
| 234 | 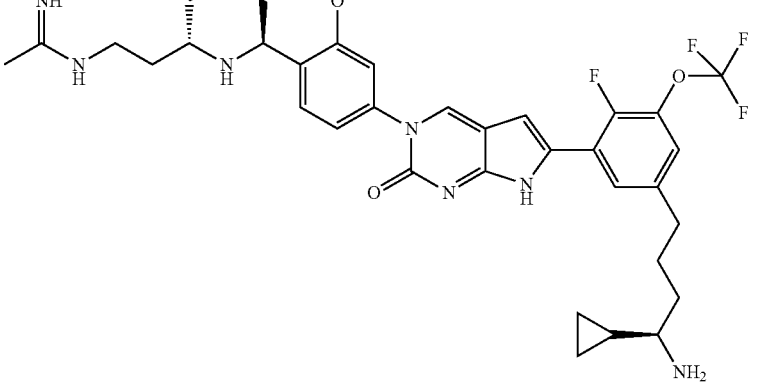 | 698.4 |
| 235 | 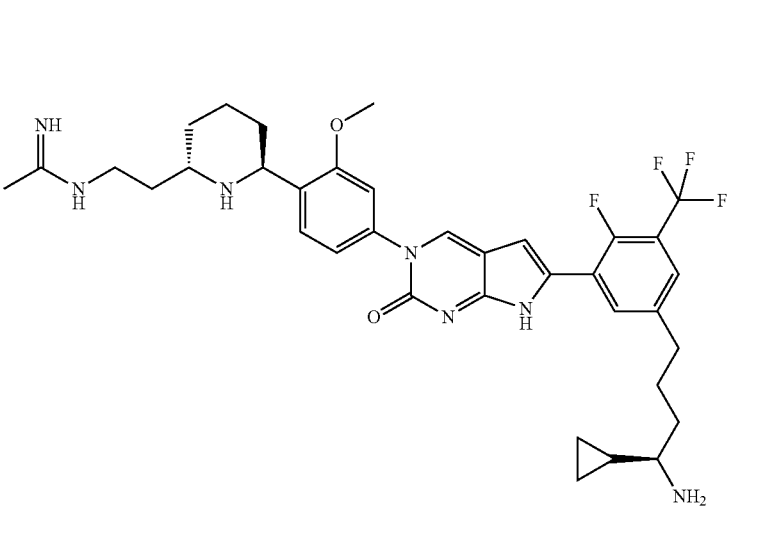 | 682.4 |
| 236 | 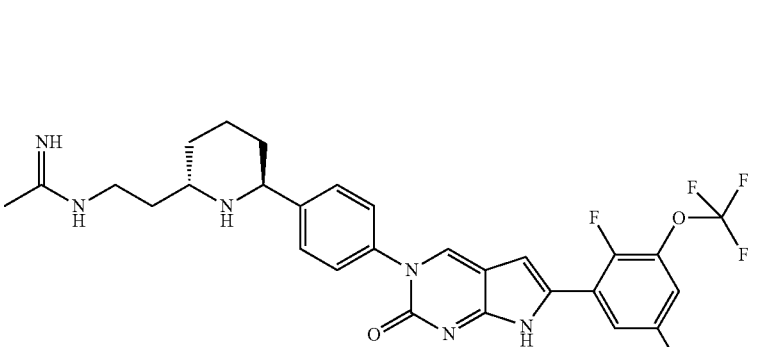 | 660.7 |

TABLE 1-continued

| # | Structure | ESI, m/z [M + H]+ |
|---|---|---|
| 237 | 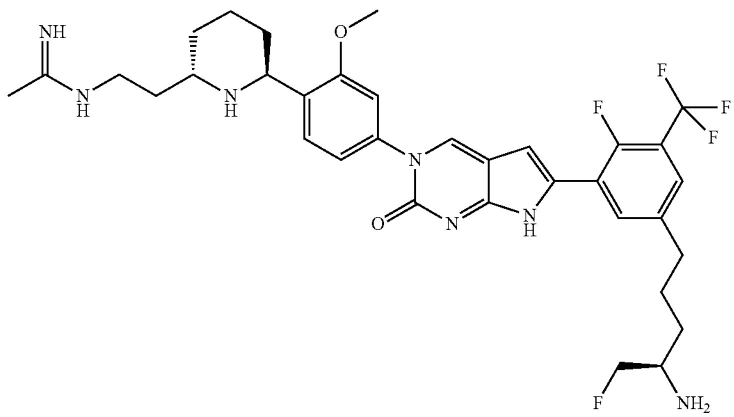 [SMILES: COc1cc(-n2cc3cc(-c4cc(CCC[C@@H](N)CF)cc(C(F)(F)F)c4F)[nH]c3nc2=O)ccc1[C@@H]1CCC[C@@H](CCNC(C)=N)N1] | 674.5 |
| 238 | 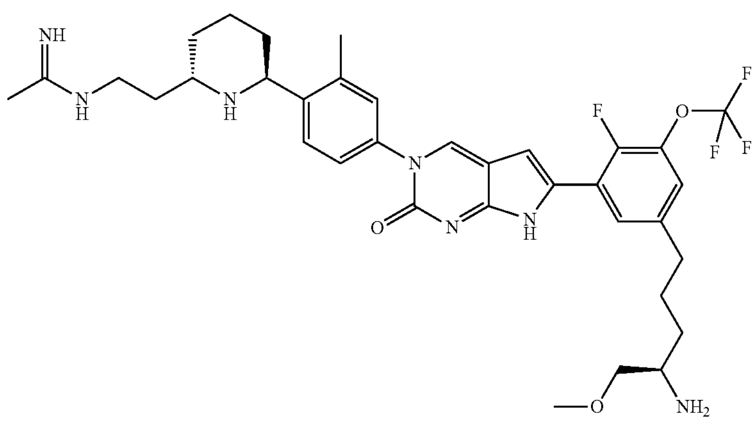 [SMILES: COC[C@H](N)CCCc1cc(OC(F)(F)F)c(F)c(-c2cc3cn(-c4ccc([C@@H]5CCC[C@@H](CCNC(C)=N)N5)c(C)c4)c(=O)nc3[nH]2)c1] | 686.8 |
| 239 | 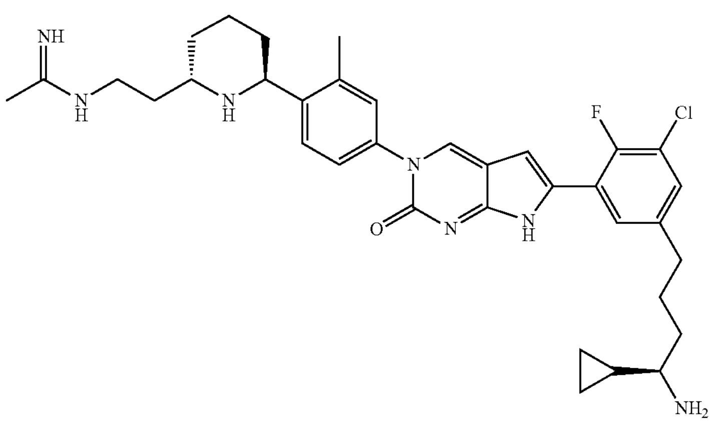 | 632.5 |

TABLE 1-continued
| # | Structure | ESI, m/z [M + H]+ |
|---|---|---|
| 240 | 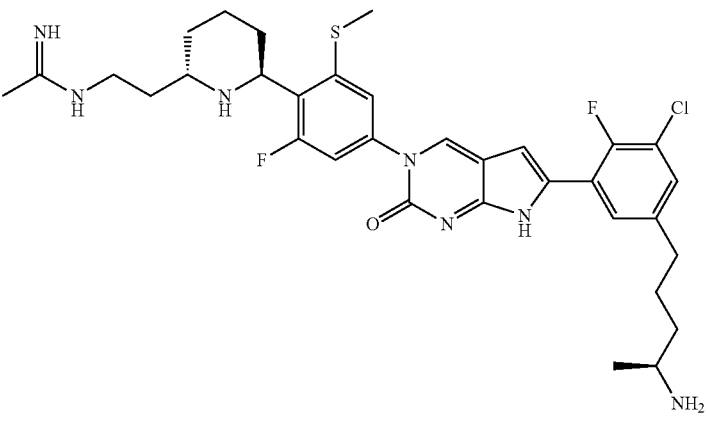 [SMILES: CSc1cc(-n2cc3cc(-c4cc(CCC[C@H](C)N)cc(Cl)c4F)[nH]c3nc2=O)cc(F)c1[C@@H]1CCC[C@@H](CCNC(C)=N)N1] | 656.4 |
| 241 | 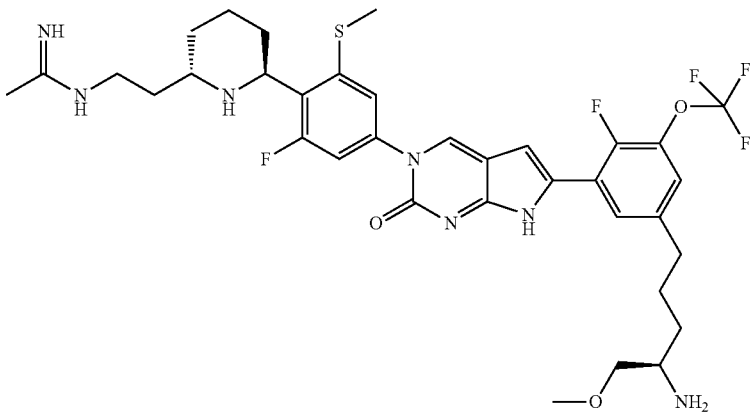 [SMILES: COC[C@H](N)CCCc1cc(OC(F)(F)F)c(F)c(-c2cc3cn(-c4cc(F)c([C@@H]5CCC[C@@H](CCNC(C)=N)N5)c(SC)c4)c(=O)nc3[nH]2)c1] | 736.4 |
| 242 | 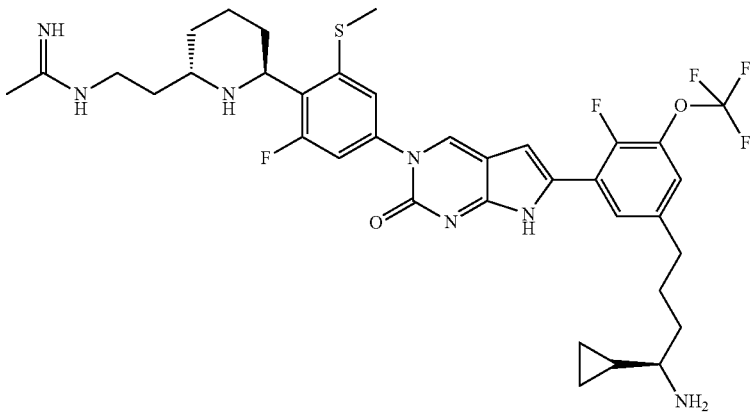 [SMILES: CSc1cc(-n2cc3cc(-c4cc(CCC[C@@H](N)C5CC5)cc(OC(F)(F)F)c4F)[nH]c3nc2=O)cc(F)c1[C@@H]1CCC[C@@H](CCNC(C)=N)N1] | 732.4 |

TABLE 1-continued

| # | Structure | ESI, m/z [M + H]+ |
|---|---|---|
| 243 | 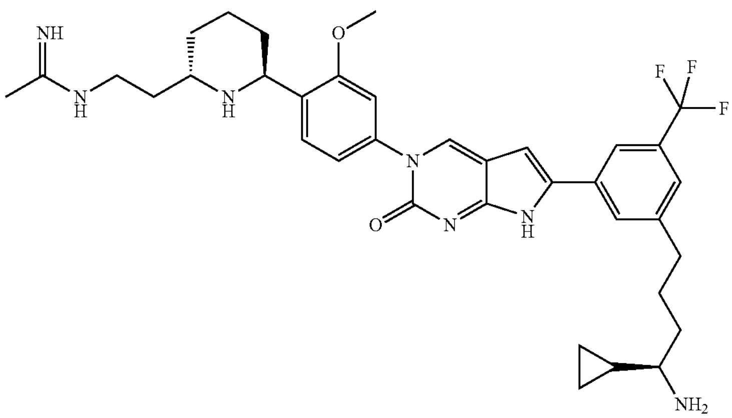 [SMILES: COc1cc(-n2cc3cc(-c4cc(CCC[C@@H](N)C5CC5)cc(C(F)(F)F)c4)[nH]c3nc2=O)ccc1[C@@H]1CCC[C@@H](CCNC(C)=N)N1] | 664.6 |
| 244 | 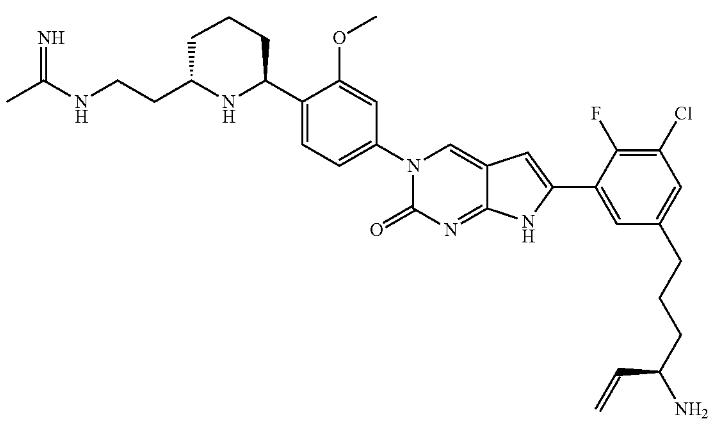 | 634.4 |
| 245 | 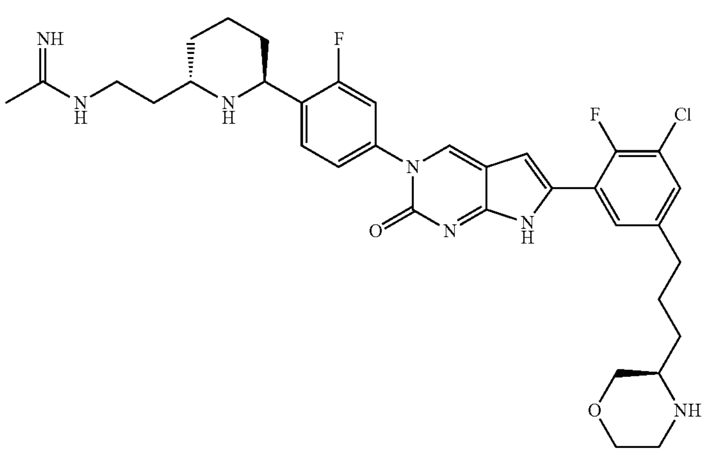 [SMILES: CC(=N)NCC[C@@H]1CCC[C@@H](c2ccc(-n3cc4cc(-c5cc(CCC[C@@H]6COCCN6)cc(Cl)c5F)[nH]c4nc3=O)cc2F)N1] | 652.4 |

TABLE 1-continued
| # | Structure | ESI, m/z [M + H]+ |
|---|---|---|
| 246 | 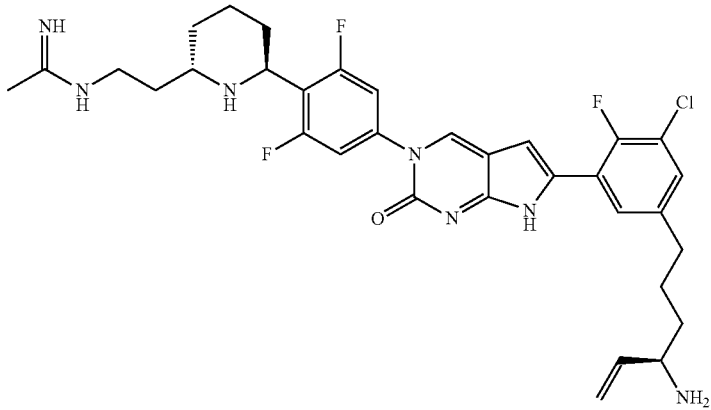 | 640.4 |
| 247 | 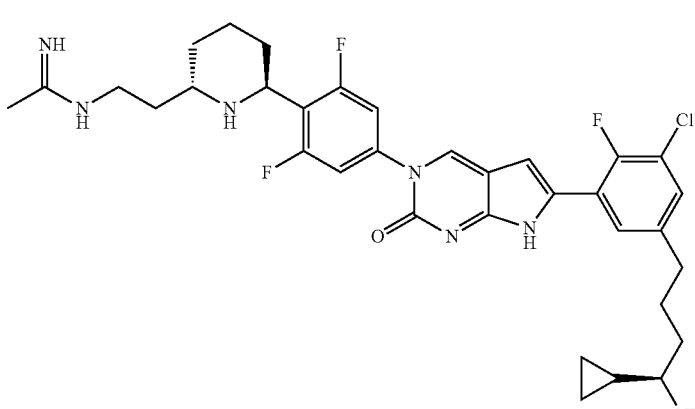 | 654.4 |
| 248 | 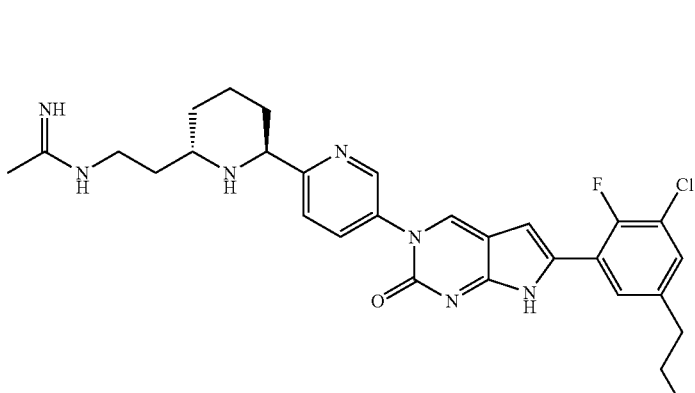 | 619.4 |

| # | Structure | ESI, m/z [M + H]+ |
|---|---|---|
| 249 | 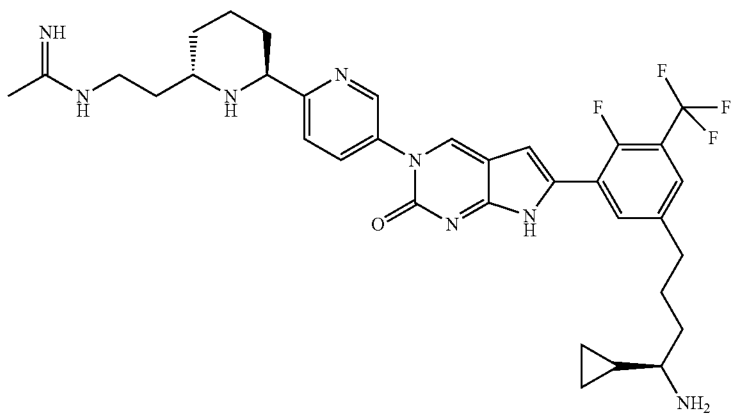 [SMILES: CC(=N)NCC[C@@H]1CCC[C@@H](c2ccc(-n3cc4cc(-c5cc(CCC[C@@H](N)C6CC6)cc(C(F)(F)F)c5F)[nH]c4nc3=O)cn2)N1] | 653.5 |
| 250 | 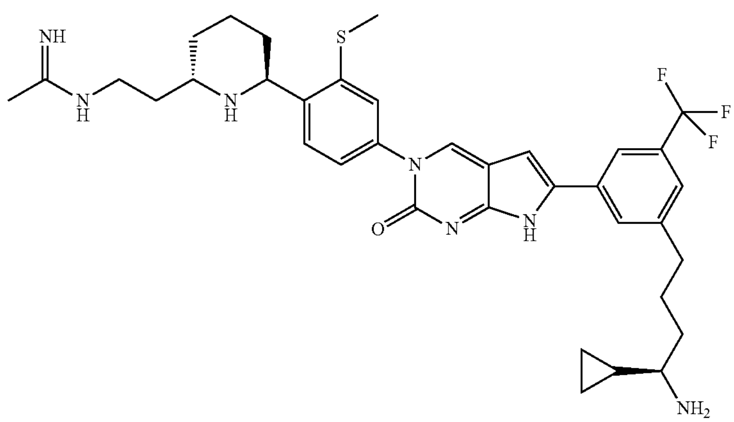 | 680.85 |
| 251 | 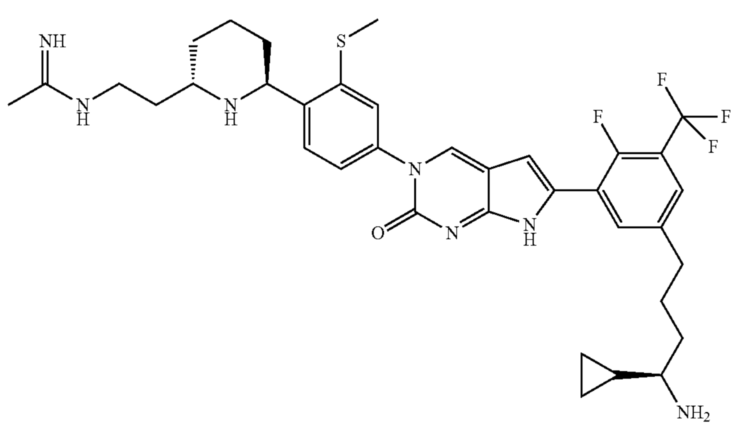 [SMILES: CSc1cc(-n2cc3cc(-c4cc(CCC[C@@H](N)C5CC5)cc(C(F)(F)F)c4F)[nH]c3nc2=O)ccc1[C@@H]1CCC[C@@H](CCNC(C)=N)N1] | 698.84 |

TABLE 1-continued
| # | Structure | ESI, m/z [M + H]+ |
|---|---|---|
| 252 | 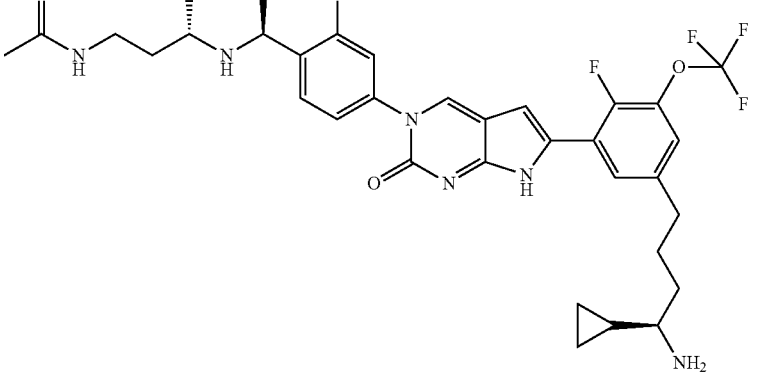 | 714.84 |
| 253 | 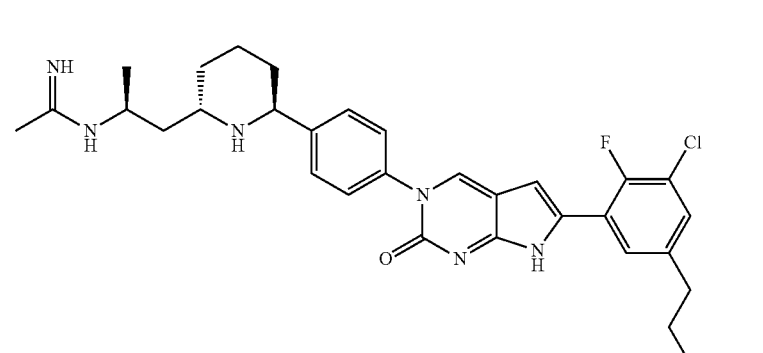 | 606.4 |
| 254 | 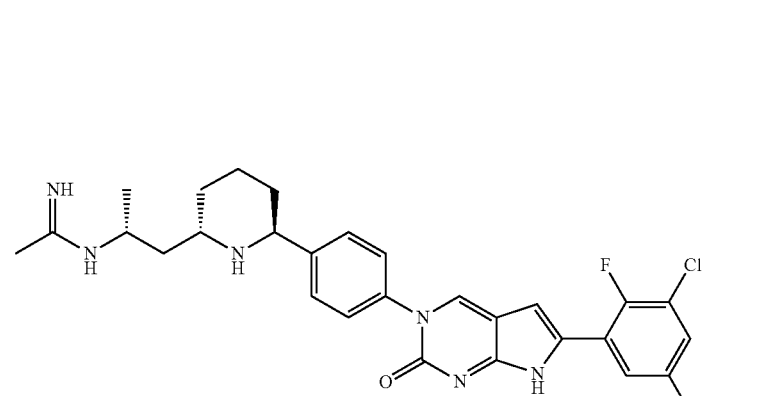 | 606.4 |

TABLE 1-continued
| # | Structure | ESI, m/z [M + H]+ |
|---|---|---|
| 255 | 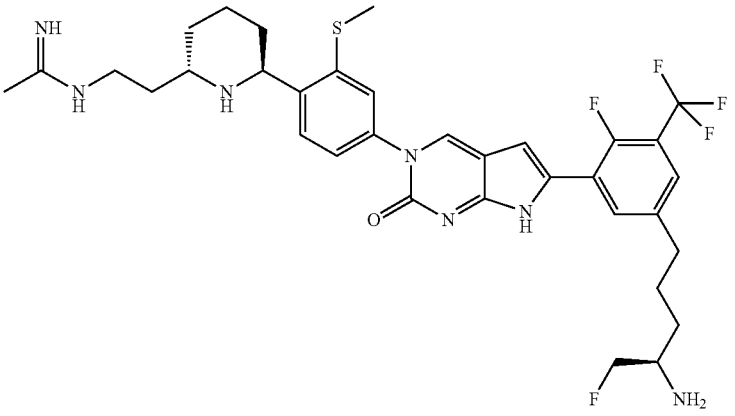 [SMILES: CSc1cc(-n2cc3cc(-c4cc(CCC[C@@H](N)CF)cc(C(F)(F)F)c4F)[nH]c3nc2=O)ccc1[C@@H]1CCC[C@@H](CCNC(C)=N)N1] | 690.4 |
| 256 | 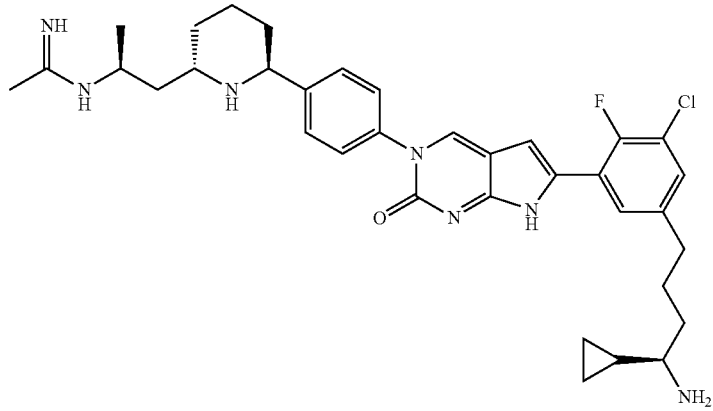 [SMILES: CC(=N)N[C@@H](C)C[C@@H]1CCC[C@@H](c2ccc(-n3cc4cc(-c5cc(CCC[C@@H](N)C6CC6)cc(Cl)c5F)[nH]c4nc3=O)cc2)N1] | 632.4 |
| 257 | 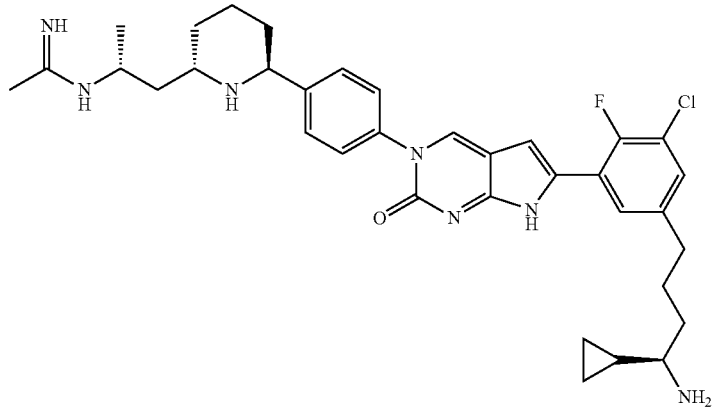 [SMILES: CC(=N)N[C@H](C)C[C@@H]1CCC[C@@H](c2ccc(-n3cc4cc(-c5cc(CCC[C@@H](N)C6CC6)cc(Cl)c5F)[nH]c4nc3=O)cc2)N1] | 632.4 |

TABLE 1-continued
| # | Structure | ESI, m/z [M + H]+ |
|---|---|---|
| 258 | 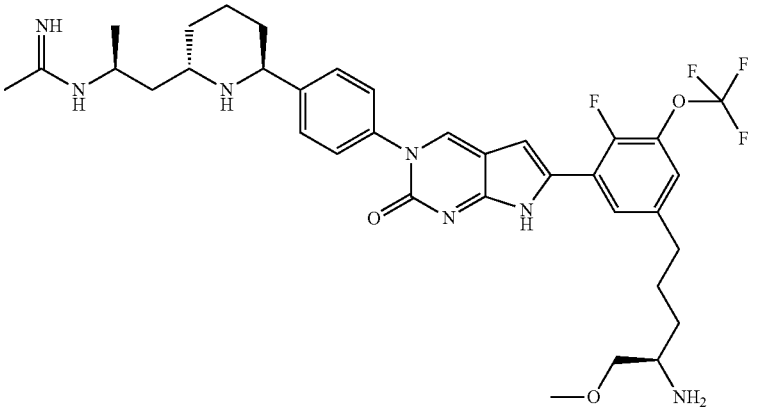 [SMILES: COC[C@H](N)CCCc1cc(OC(F)(F)F)c(F)c(-c2cc3cn(-c4ccc([C@@H]5CCC[C@@H](C[C@H](C)NC(C)=N)N5)cc4)c(=O)nc3[nH]2)c1] | 686.5 |
| 259 | 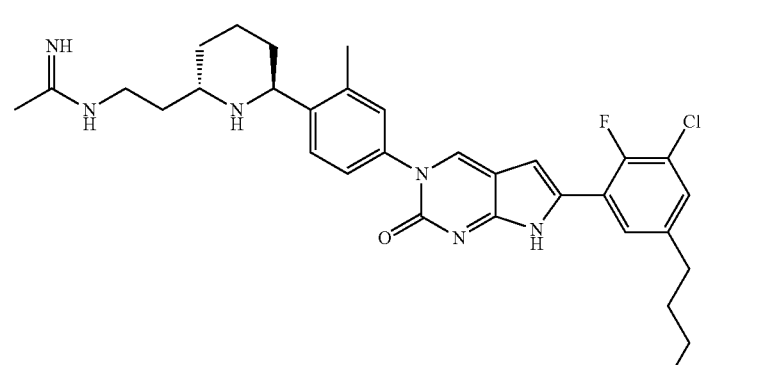 | 618.4 |
| 260 | 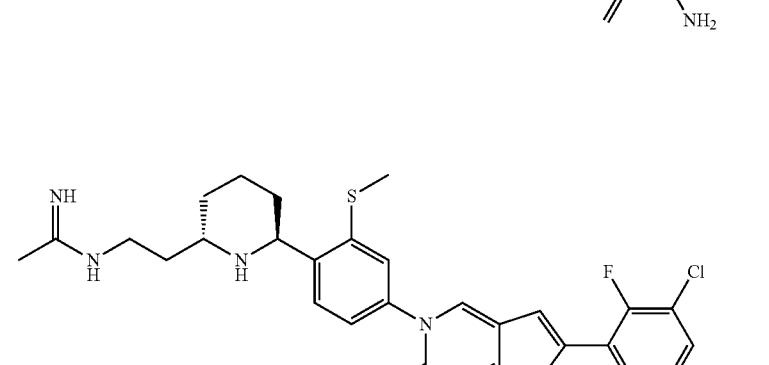 | 682.1 |

TABLE 1-continued
| # | Structure | ESI, m/z [M + H]+ |
|---|---|---|
| 261 | 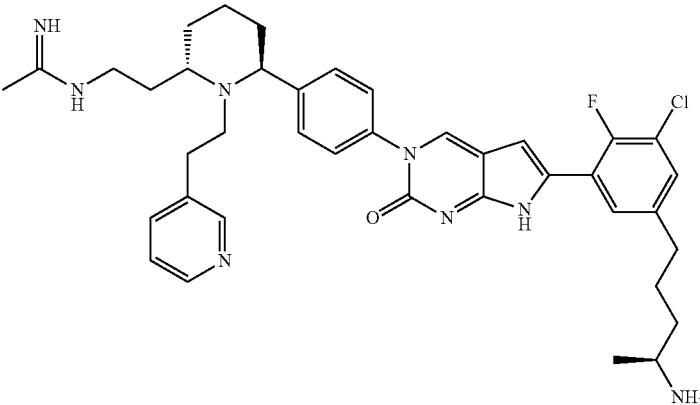 | 697 |
| 262 | 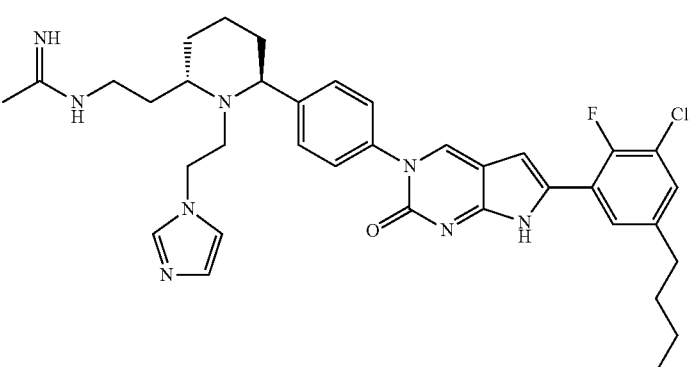 | 686 |
| 263 | 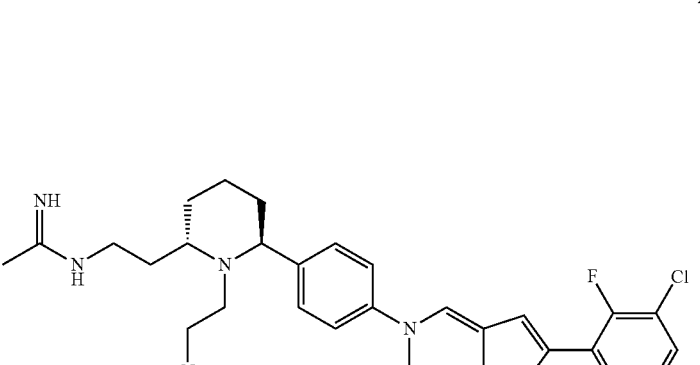 | 700 |

TABLE 1-continued
| # | Structure | ESI, m/z [M + H]+ |
|---|---|---|
| 264 | 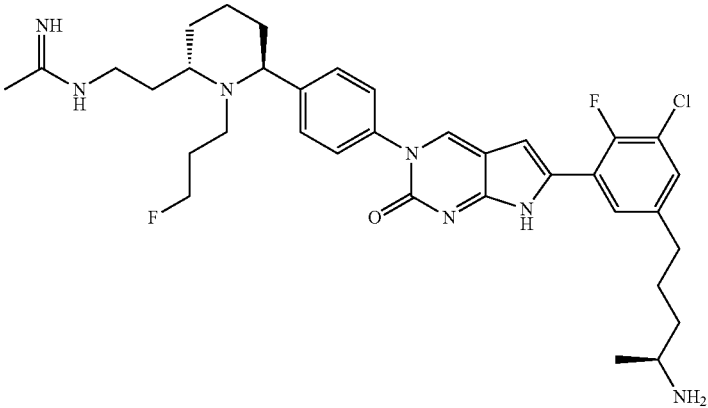 | 652 |
| 265 | 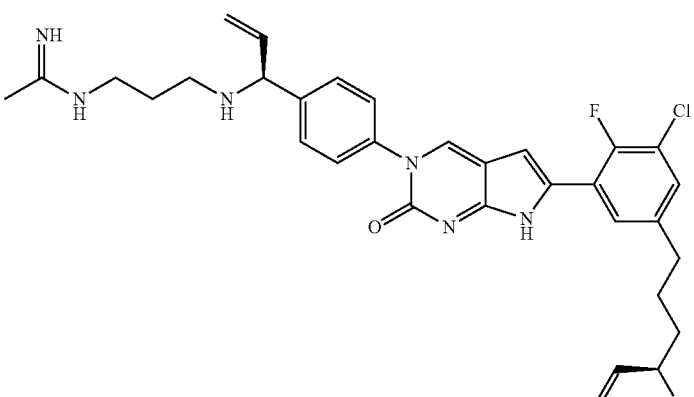 | 590.4 |
| 266 | 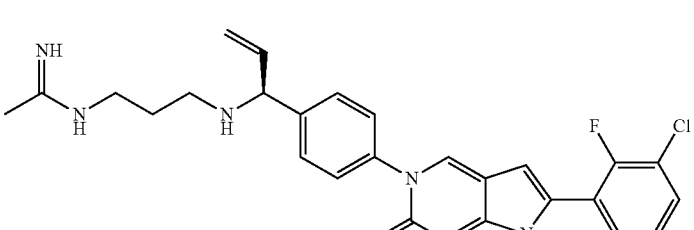 | 604.4 |

TABLE 1-continued
| # | Structure | ESI, m/z [M + H]+ |
|---|---|---|
| 267 | 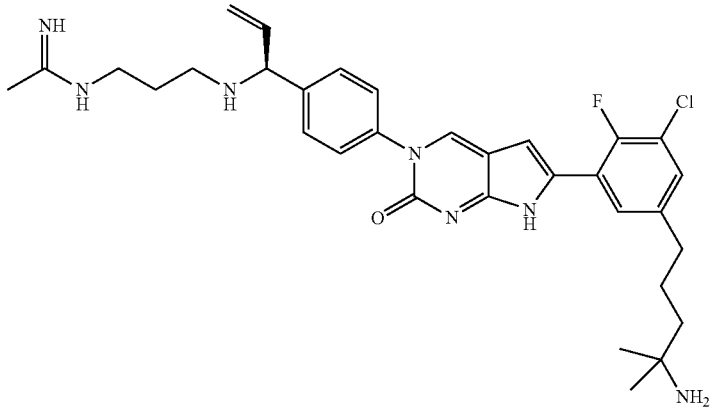 [SMILES: C=C[C@H](NCCCNC(C)=N)c1ccc(-n2cc3cc(-c4cc(CCCC(C)(C)N)cc(Cl)c4F)[nH]c3nc2=O)cc1] | 592.4 |
| 268 | 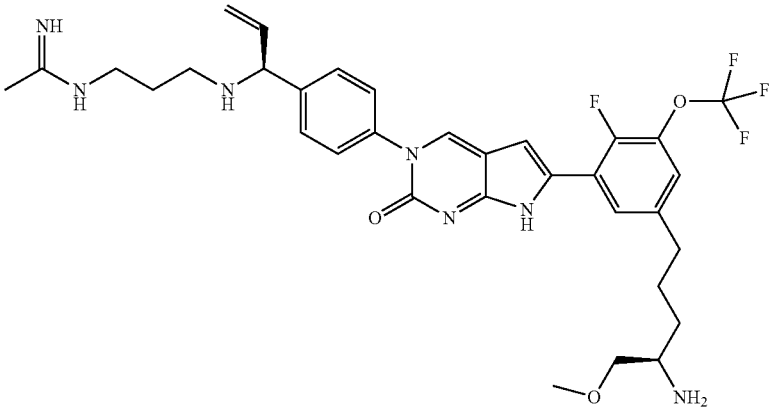 [SMILES: C=C[C@H](NCCCNC(C)=N)c1ccc(-n2cc3cc(-c4cc(CCC[C@@H](N)COC)cc(OC(F)(F)F)c4F)[nH]c3nc2=O)cc1] | 658.4 |
| 269 | 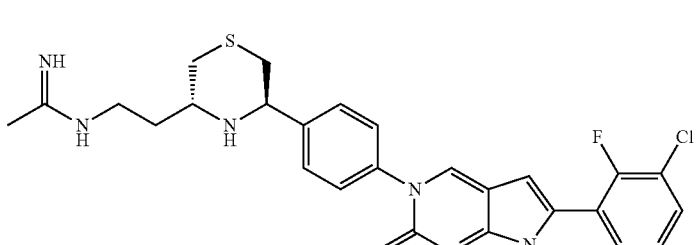 | 636.4 |

TABLE 1-continued
| # | Structure | ESI, m/z [M + H]+ |
|---|-----------|-------------------|
| 270 | 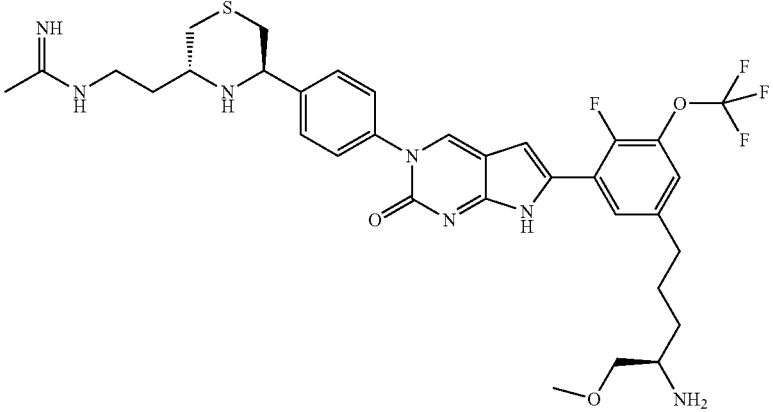 [SMILES: COC[C@H](N)CCCc1cc(OC(F)(F)F)c(F)c(-c2cc3cn(-c4ccc([C@@H]5CSC[C@@H](CCNC(C)=N)N5)cc4)c(=O)nc3[nH]2)c1] | 690.4 |
| 271 | 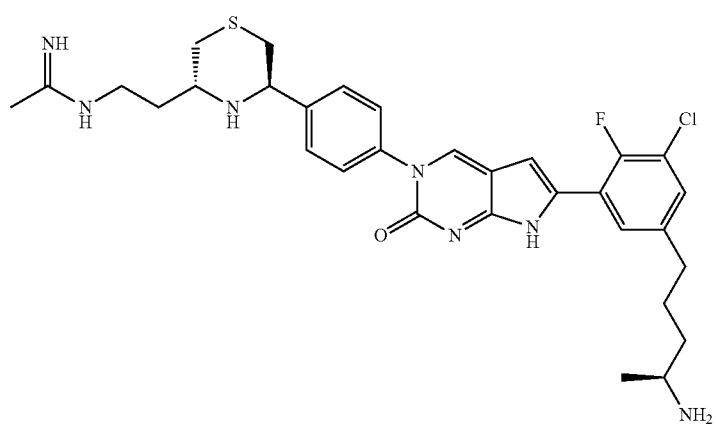 | 610.4 |
| 272 | 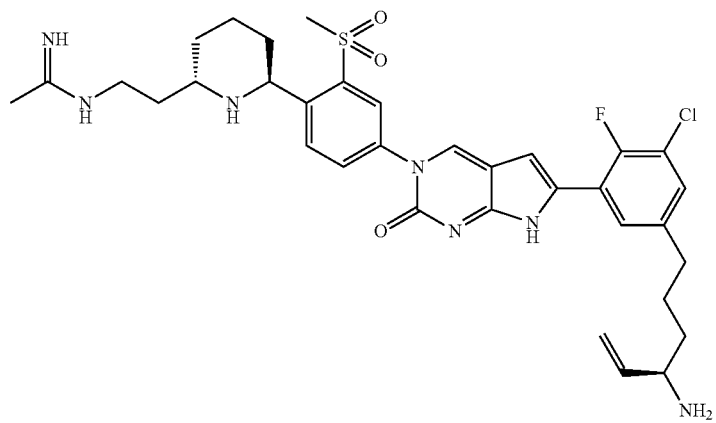 [SMILES: C=C[C@H](N)CCCc1cc(Cl)c(F)c(-c2cc3cn(-c4ccc([C@@H]5CCC[C@@H](CCNC(C)=N)N5)c(S(C)(=O)=O)c4)c(=O)nc3[nH]2)c1] | 682.3 |

TABLE 1-continued
| # | Structure | ESI, m/z [M + H]+ |
|---|---|---|
| 273 | 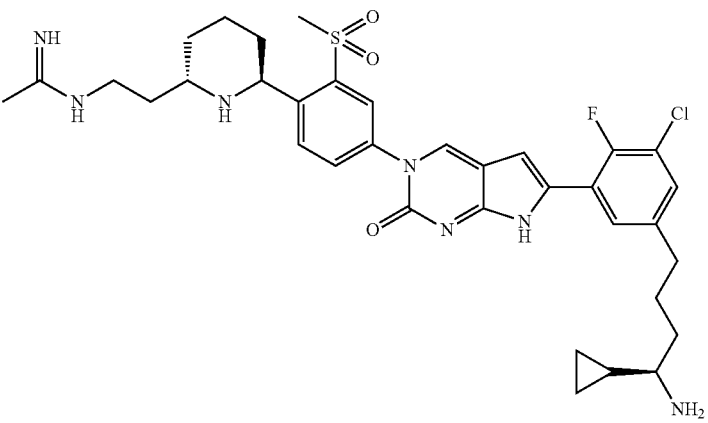 [SMILES: CC(=N)NCC[C@@H]1CCC[C@@H](c2ccc(-n3cc4cc(-c5cc(CCC[C@@H](N)C6CC6)cc(Cl)c5F)[nH]c4nc3=O)cc2S(C)(=O)=O)N1] | 696.3 |
| 274 | 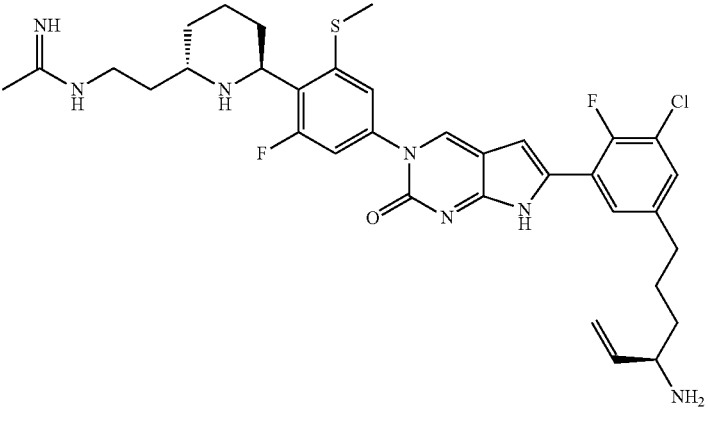 [SMILES: C=C[C@H](N)CCCc1cc(Cl)c(F)c(-c2cc3cn(-c4cc(F)c([C@@H]5CCC[C@@H](CCNC(C)=N)N5)c(SC)c4)c(=O)nc3[nH]2)c1] | 668.3 |
| 275 | 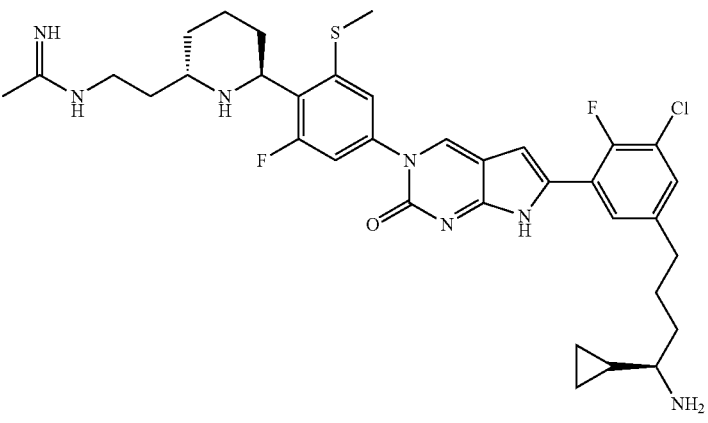 | 682.4 |

TABLE 1-continued

| # | Structure | ESI, m/z [M + H]+ |
|---|---|---|
| 276 | 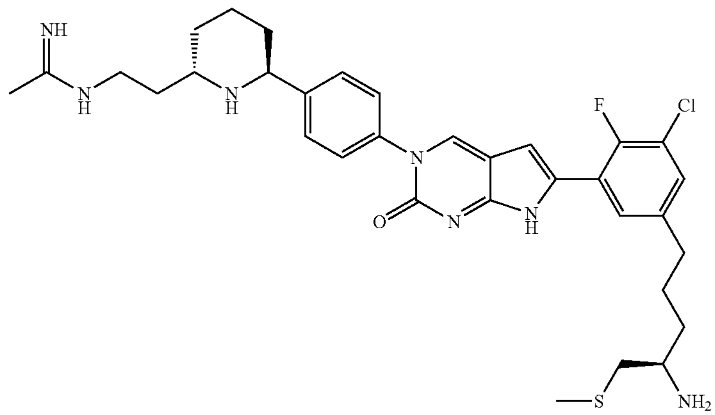 | 638.4 |
| 277 | 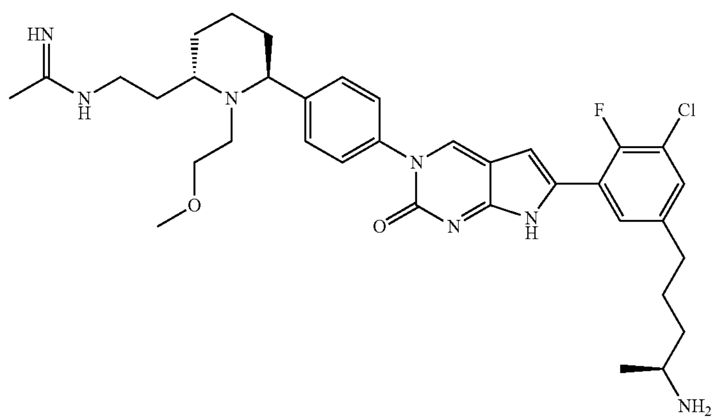 [SMILES: COCCN1[C@H](CCNC(C)=N)CCC[C@H]1c1ccc(-n2cc3cc(-c4cc(CCC[C@H](C)N)cc(Cl)c4F)[nH]c3nc2=O)cc1] | 650 |
| 278 | 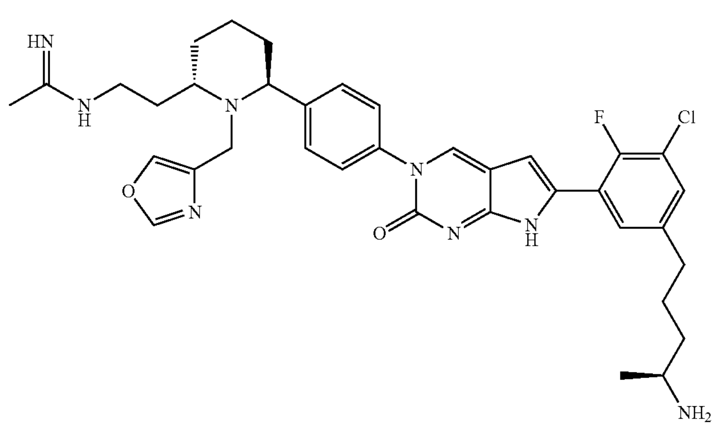 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1Cc1cocn1] | 673 |

TABLE 1-continued

| # | Structure | ESI, m/z [M + H]+ |
|---|---|---|
| 279 | 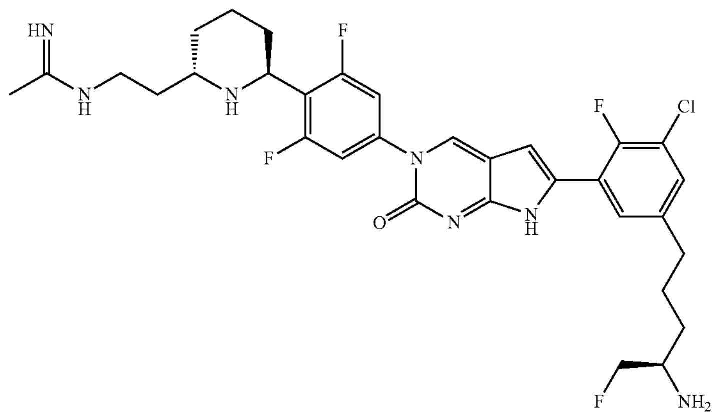 | 646.4 |
| 280 | 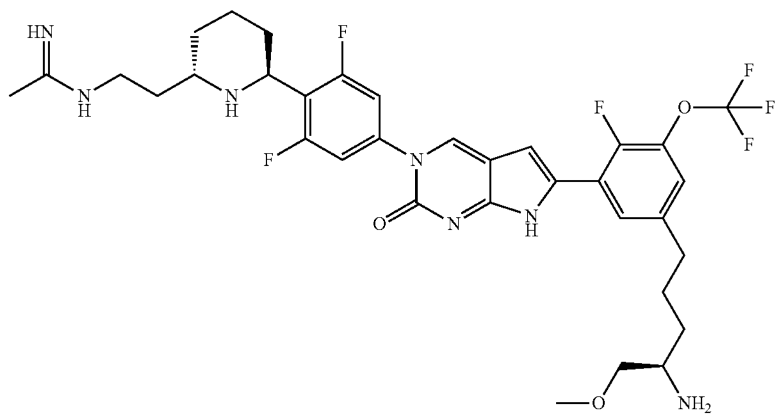 [SMILES: COC[C@H](N)CCCc1cc(OC(F)(F)F)c(F)c(-c2cc3cn(-c4cc(F)c([C@@H]5CCC[C@@H](CCNC(C)=N)N5)c(F)c4)c(=O)nc3[nH]2)c1] | 708.7 |
| 281 | 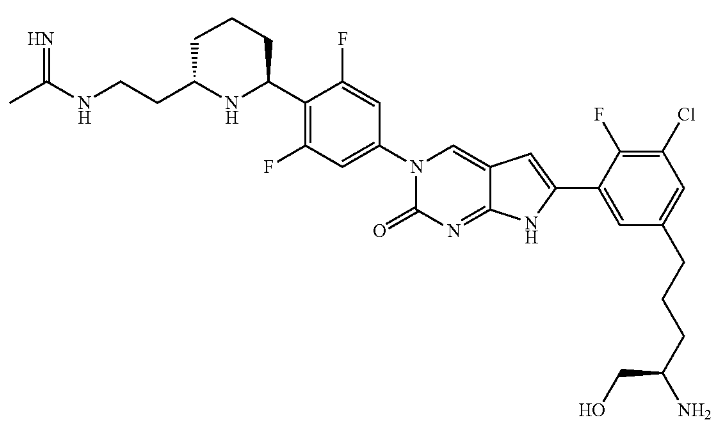 [SMILES: CC(=N)NCC[C@@H]1CCC[C@@H](c2c(F)cc(-n3cc4cc(-c5cc(CCC[C@@H](N)CO)cc(Cl)c5F)[nH]c4nc3=O)cc2F)N1] | 644.4 |

TABLE 1-continued

| # | Structure | ESI, m/z [M + H]+ |
|---|---|---|
| 282 | 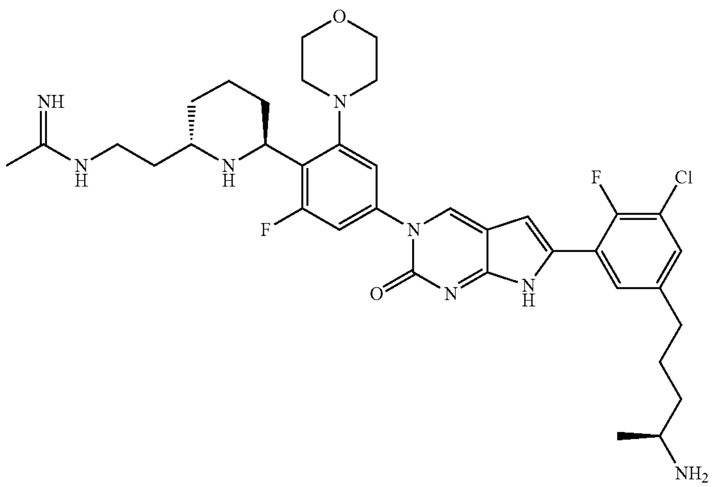 [SMILES: CC(=N)NCC[C@@H]1CCC[C@@H](c2c(F)cc(-n3cc4cc(-c5cc(CCC[C@H](C)N)cc(Cl)c5F)[nH]c4nc3=O)cc2N2CCOCC2)N1] | 695 |
| 283 | 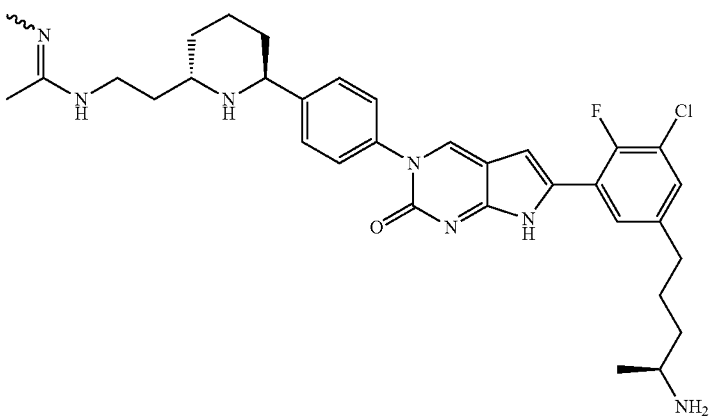 | 606.4 |
| 284 | 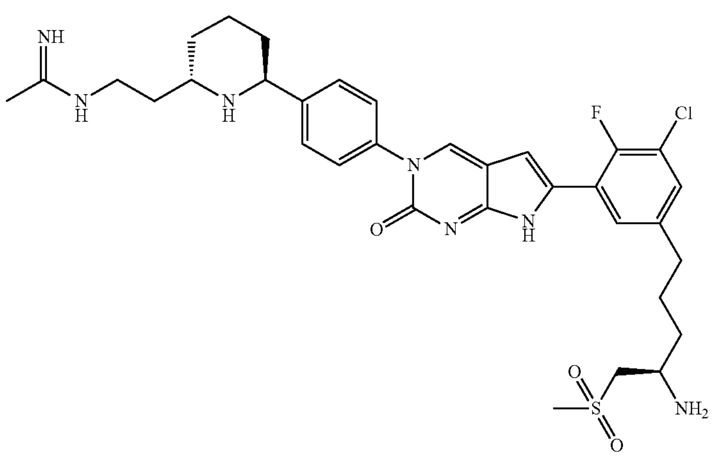 [SMILES: CC(=N)NCC[C@@H]1CCC[C@@H](c2ccc(-n3cc4cc(-c5cc(CCC[C@@H](N)CS(C)(=O)=O)cc(Cl)c5F)[nH]c4nc3=O)cc2)N1] | 670.3 |

TABLE 1-continued

| # | Structure | ESI, m/z [M + H]+ |
|---|---|---|
| 285 | 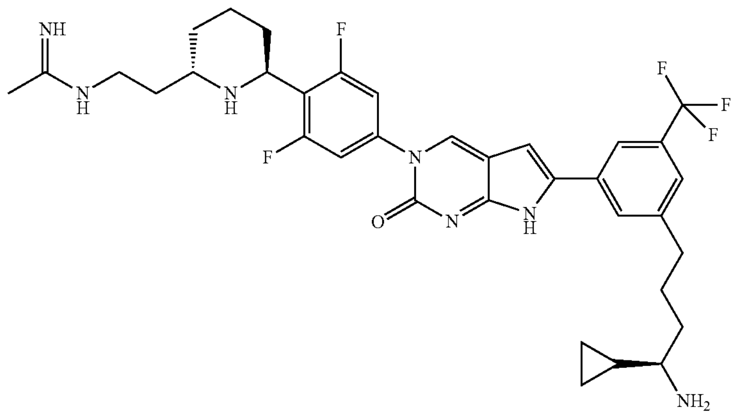 [SMILES: CC(=N)NCC[C@@H]1CCC[C@@H](c2c(F)cc(-n3cc4cc(-c5cc(CCC[C@@H](N)C6CC6)cc(C(F)(F)F)c5)[nH]c4nc3=O)cc2F)N1] | 670.7 |
| 286 | 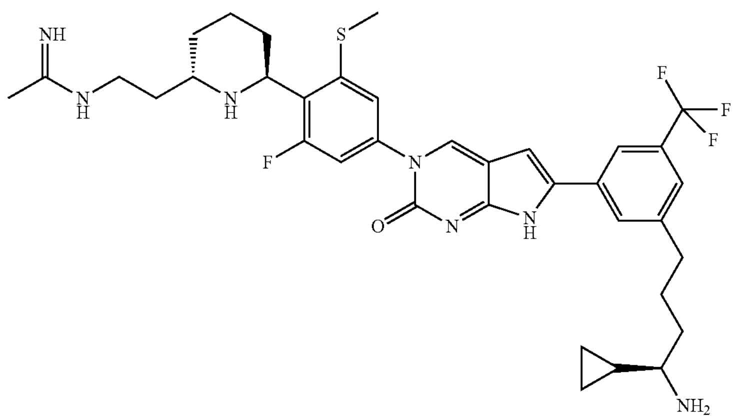 | 698.5 |
| 287 | 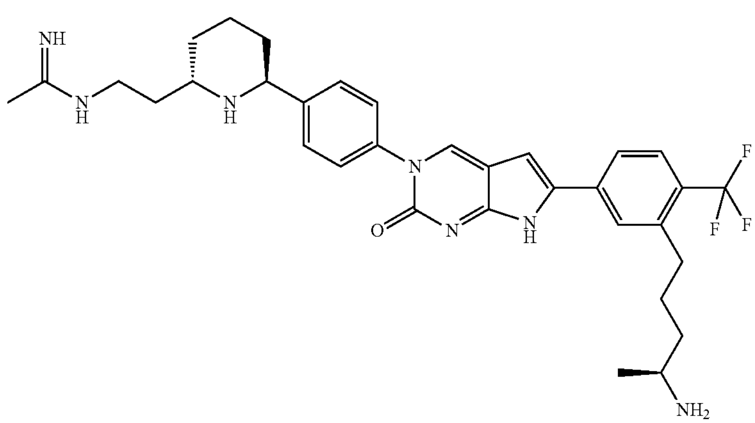 [SMILES: CC(=N)NCC[C@@H]1CCC[C@@H](c2ccc(-n3cc4cc(-c5ccc(C(F)(F)F)c(CCC[C@H](C)N)c5)[nH]c4nc3=O)cc2)N1] | 608.4 |

TABLE 1-continued

| # | Structure | ESI, m/z [M + H]+ |
|---|---|---|
| 288 | 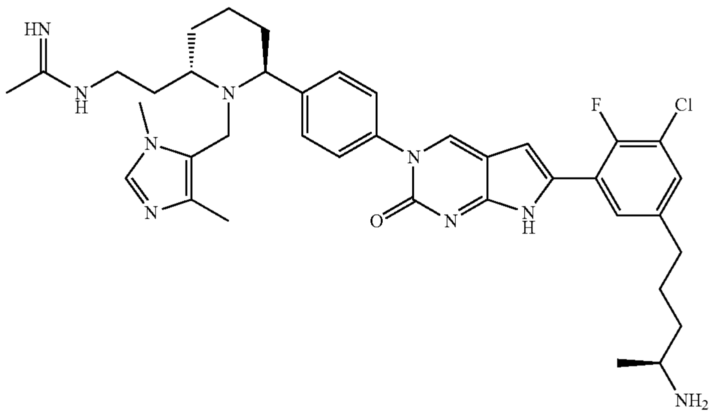 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1Cc1c(C)ncn1C] | 700 |
| 289 | 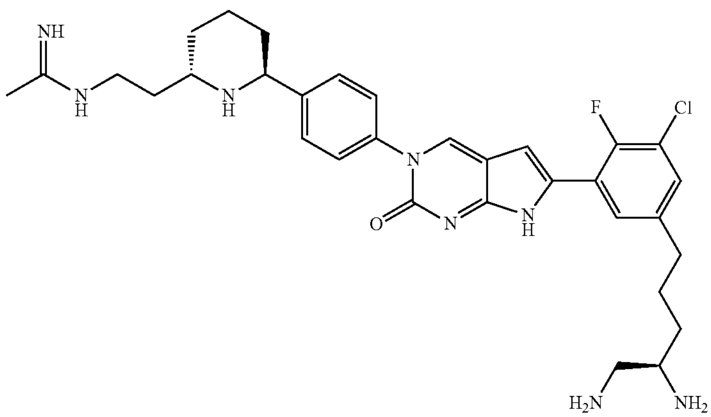 | 607.4 |
| 290 | 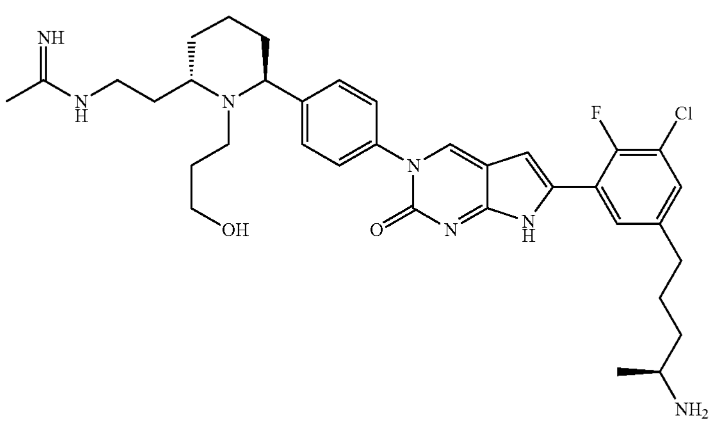 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1CCCO] | 650 |

TABLE 1-continued

| # | Structure | ESI, m/z [M + H]+ |
|---|---|---|
| 291 | 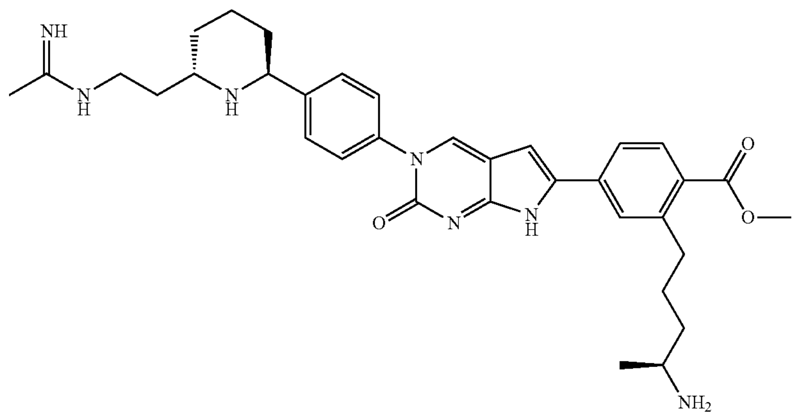 [SMILES: COC(=O)c1ccc(-c2cc3cn(-c4ccc([C@@H]5CCC[C@@H](CCNC(C)=N)N5)cc4)c(=O)nc3[nH]2)cc1CCC[C@H](C)N] | 598.4 |
| 292 | 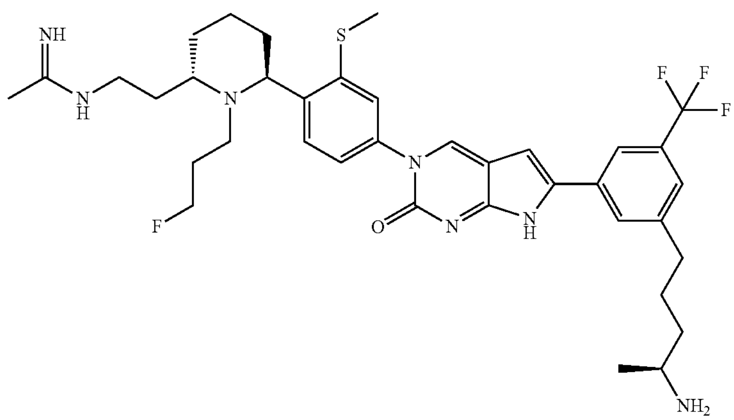 [SMILES: CSc1cc(-n2cc3cc(-c4cc(CCC[C@H](C)N)cc(C(F)(F)F)c4)[nH]c3nc2=O)ccc1[C@@H]1CCC[C@@H](CCNC(C)=N)N1CCCF] | 714 |
| 293 | 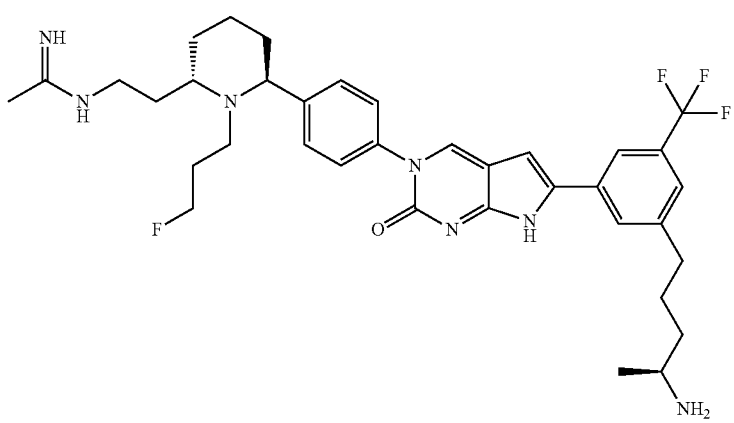 [SMILES: CC(=N)NCC[C@@H]1CCC[C@@H](c2ccc(-n3cc4cc(-c5cc(CCC[C@H](C)N)cc(C(F)(F)F)c5)[nH]c4nc3=O)cc2)N1CCCF] | 668 |

In some embodiments, the present disclosure provides any one of compounds listed in Table 1a, or a tautomer thereof or a pharmaceutically acceptable salt of the compound or tautomer.

TABLE 1a

| # | Structure |
|---|---|
| 294 | 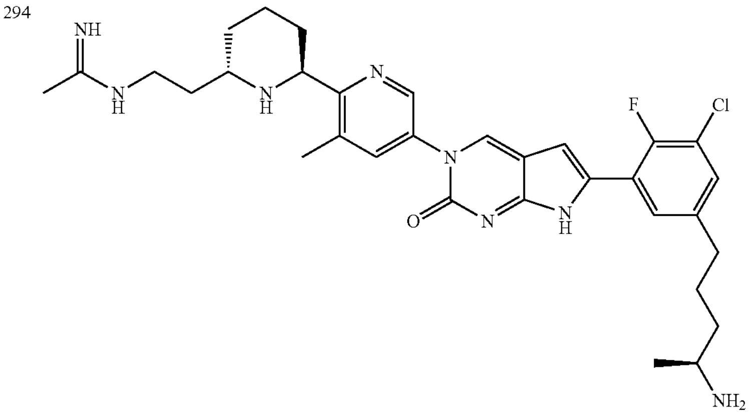 |
| 295 | 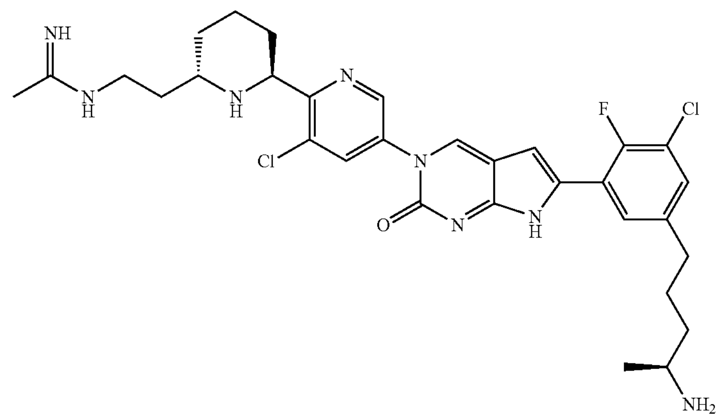 |
| 296 | 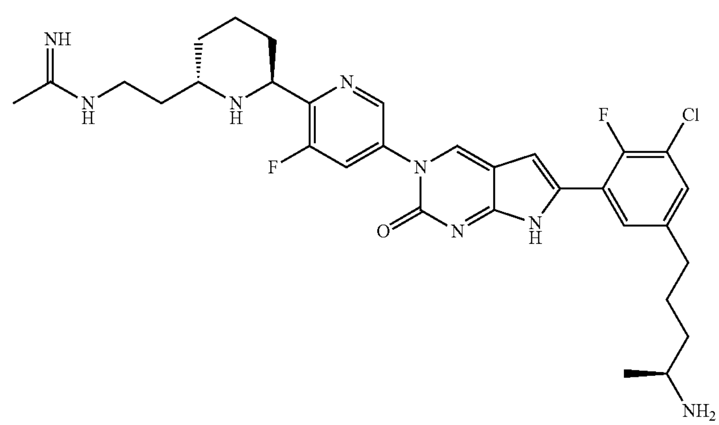 [SMILES: CC(=N)NCC[C@@H]1CCC[C@@H](c2ncc(-n3cc4cc(-c5cc(CCC[C@H](C)N)cc(Cl)c5F)[nH]c4nc3=O)cc2C)N1] |

TABLE 1a-continued

| # | Structure |
|---|---|
| 297 | 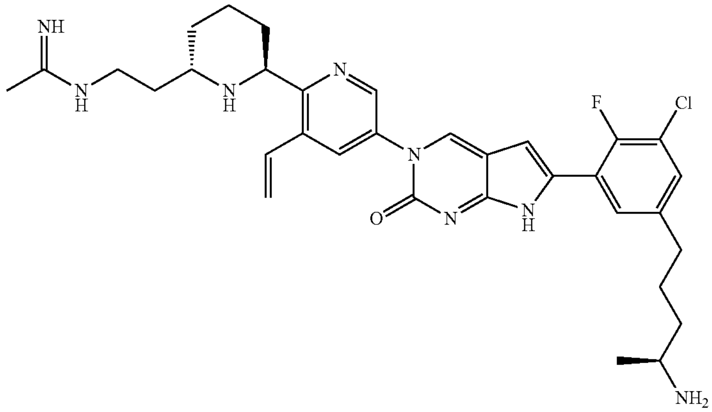 [SMILES: C=Cc1cc(-n2cc3cc(-c4cc(CCC[C@H](C)N)cc(Cl)c4F)[nH]c3nc2=O)cnc1[C@@H]1CCC[C@@H](CCNC(C)=N)N1] |
| 298 | 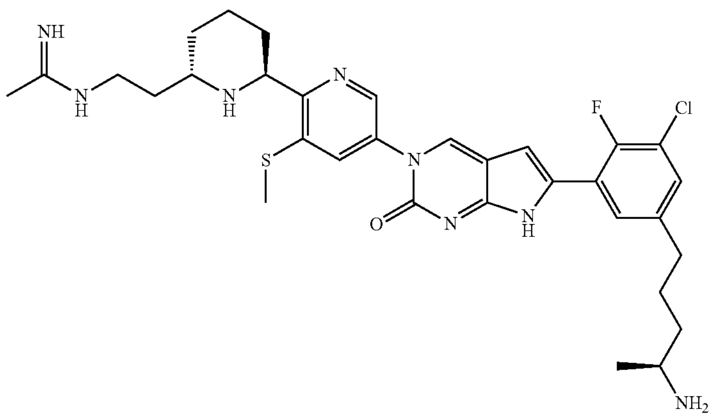 [SMILES: CSc1cc(-n2cc3cc(-c4cc(CCC[C@H](C)N)cc(Cl)c4F)[nH]c3nc2=O)cnc1[C@@H]1CCC[C@@H](CCNC(C)=N)N1] |
| 300 | 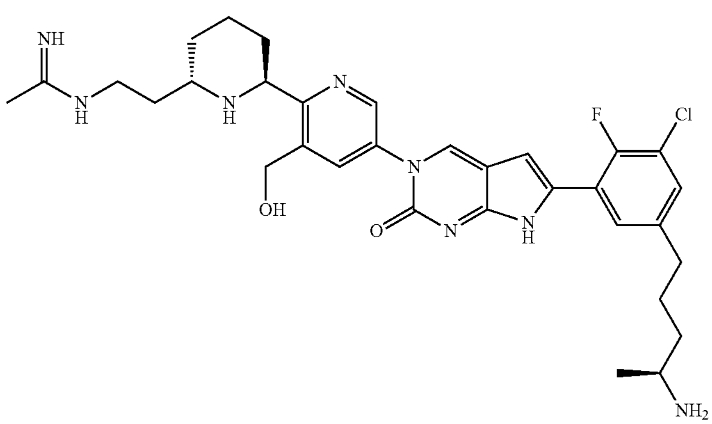 [SMILES: CC(=N)NCC[C@@H]1CCC[C@@H](c2ncc(-n3cc4cc(-c5cc(CCC[C@H](C)N)cc(Cl)c5F)[nH]c4nc3=O)cc2CO)N1] |

TABLE 1a-continued
| # | Structure |
|---|---|
| 305 | 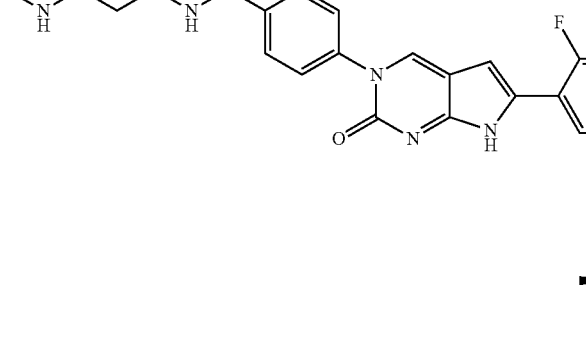 |
| 306 | 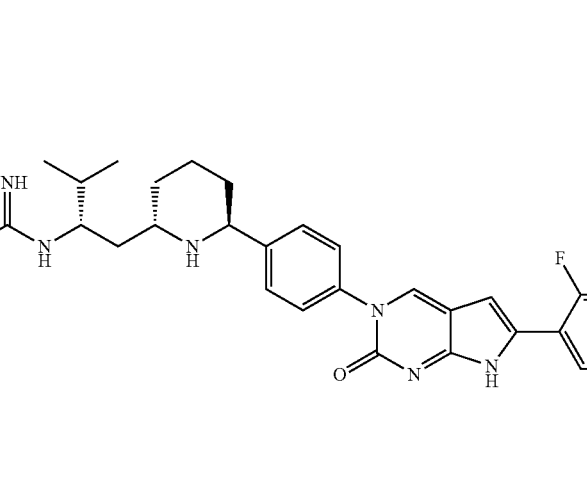 |
| 307 | 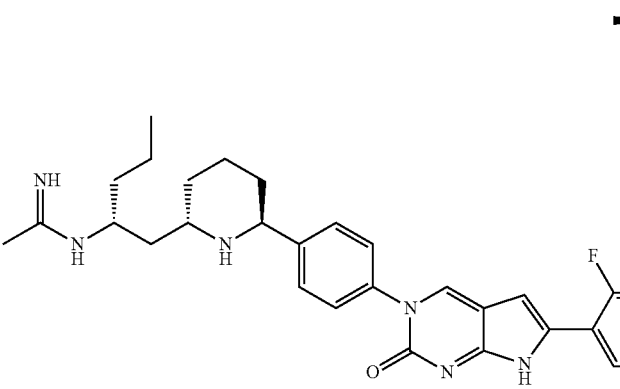 |

TABLE 1a-continued
| # | Structure |
|---|---|
| 308 | 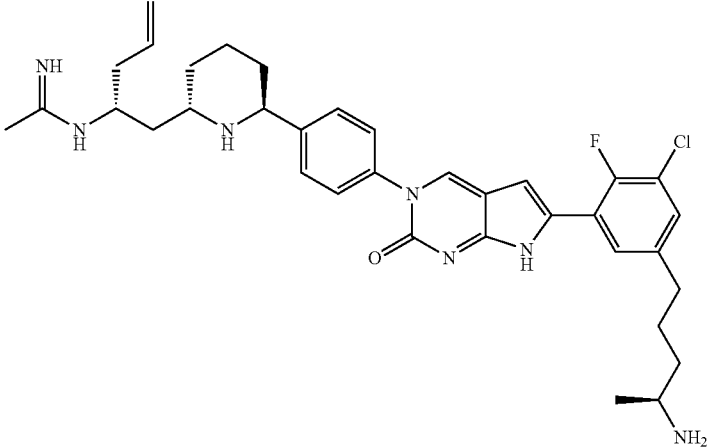 [SMILES: C=CC[C@H](C[C@@H]1CCC[C@@H](c2ccc(-n3cc4cc(-c5cc(CCC[C@H](C)N)cc(Cl)c5F)[nH]c4nc3=O)cc2)N1)NC(C)=N] |
| 309 | 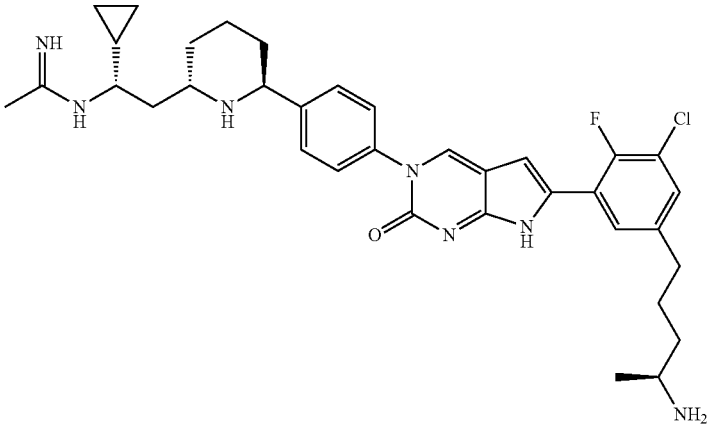 [SMILES: CC(=N)N[C@@H](C[C@@H]1CCC[C@@H](c2ccc(-n3cc4cc(-c5cc(CCC[C@H](C)N)cc(Cl)c5F)[nH]c4nc3=O)cc2)N1)C1CC1] |
| 310 | 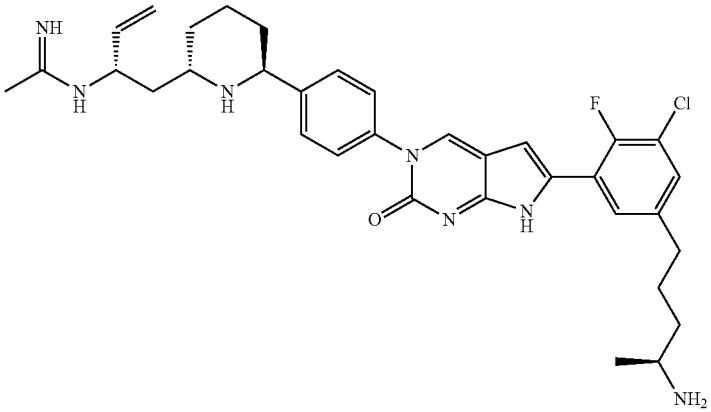 [SMILES: C=C[C@H](C[C@@H]1CCC[C@@H](c2ccc(-n3cc4cc(-c5cc(CCC[C@H](C)N)cc(Cl)c5F)[nH]c4nc3=O)cc2)N1)NC(C)=N] |

TABLE 1a-continued

| # | Structure |
|---|---|
| 311 | 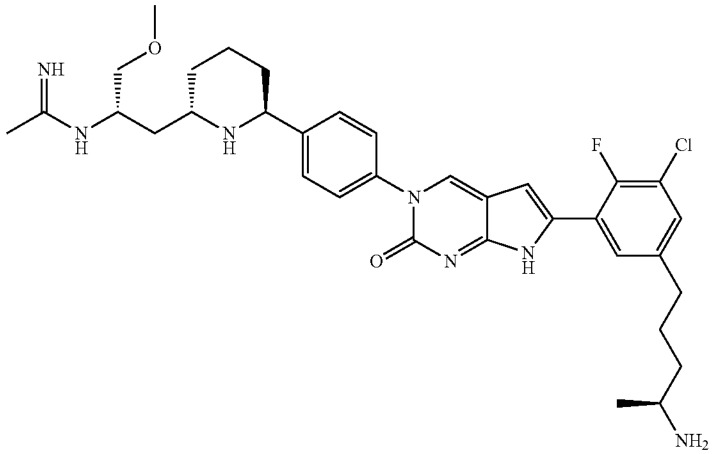 [SMILES: COC[C@H](C[C@@H]1CCC[C@@H](c2ccc(-n3cc4cc(-c5cc(CCC[C@H](C)N)cc(Cl)c5F)[nH]c4nc3=O)cc2)N1)NC(C)=N] |
| 312 | 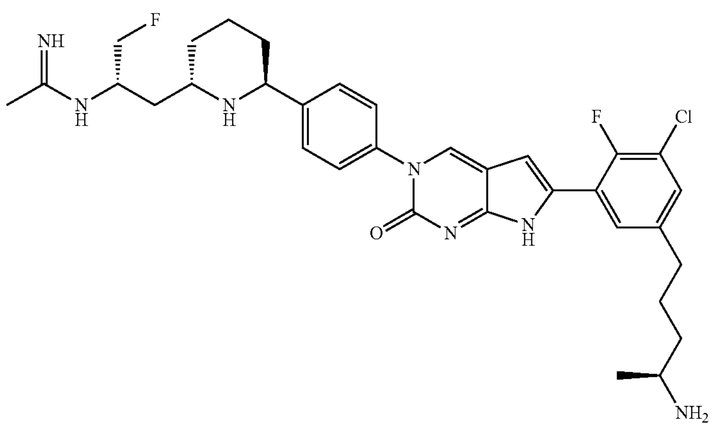 [SMILES: CC(=N)N[C@H](CF)C[C@@H]1CCC[C@@H](c2ccc(-n3cc4cc(-c5cc(CCC[C@H](C)N)cc(Cl)c5F)[nH]c4nc3=O)cc2)N1] |
| 313 | 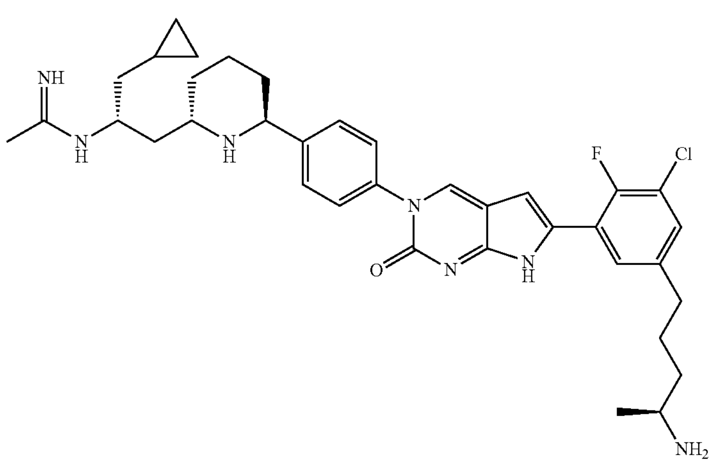 [SMILES: CC(=N)N[C@H](CC1CC1)C[C@@H]1CCC[C@@H](c2ccc(-n3cc4cc(-c5cc(CCC[C@H](C)N)cc(Cl)c5F)[nH]c4nc3=O)cc2)N1] |

TABLE 1a-continued
| # | Structure |
|---|---|
| 314 | 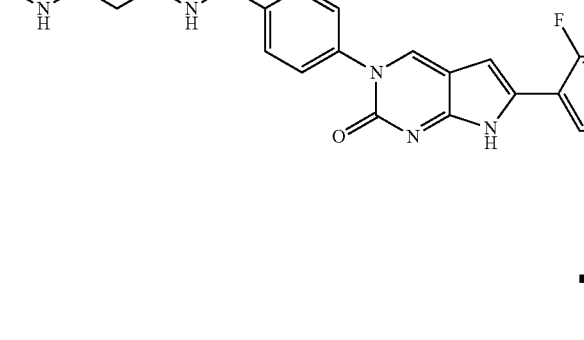 |
| 315 | 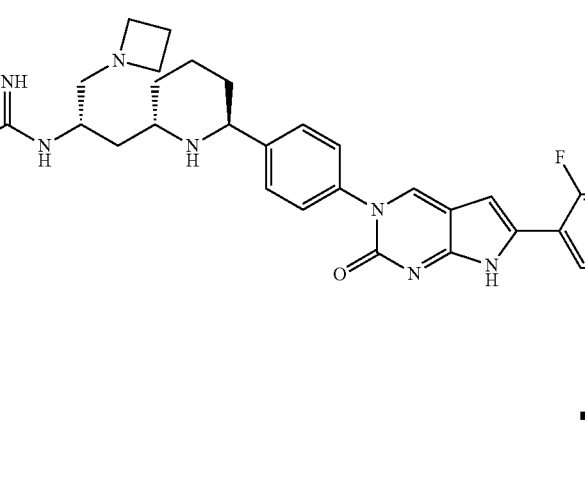 |
| 316 | 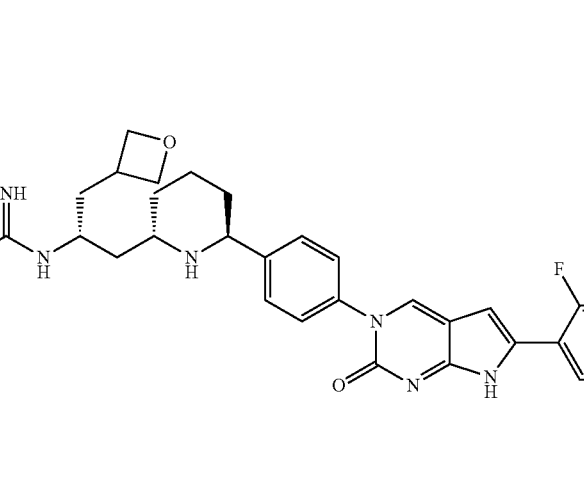 |

In some embodiments, the present disclosure provides any one of compounds listed in Table 1b, or a tautomer thereof or a pharmaceutically acceptable salt of the compound or tautomer.

TABLE 1b

| # | Structure | ESI, m/z [M + H]+ |
|---|---|---|
| 317 | 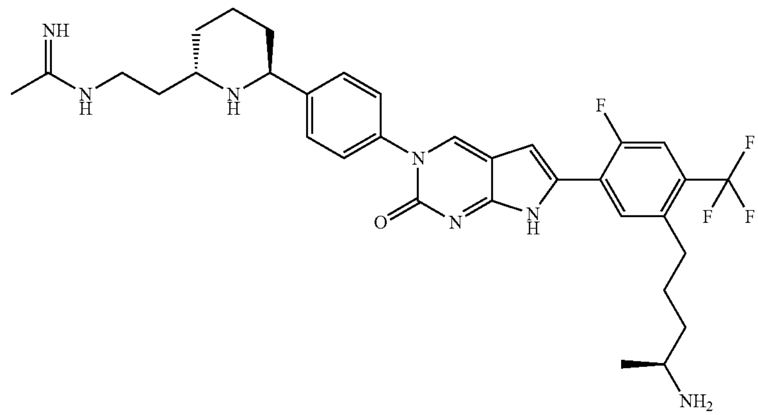 [SMILES: CC(=N)NCC[C@@H]1CCC[C@@H](c2ccc(-n3cc4cc(-c5cc(CCC[C@H](C)N)c(C(F)(F)F)cc5F)[nH]c4nc3=O)cc2)N1] | 626.8 |
| 318 | 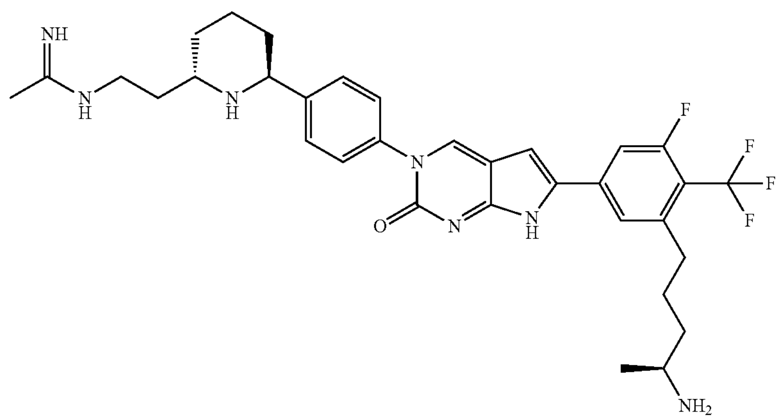 [SMILES: CC(=N)NCC[C@@H]1CCC[C@@H](c2ccc(-n3cc4cc(-c5cc(F)c(C(F)(F)F)c(CCC[C@H](C)N)c5)[nH]c4nc3=O)cc2)N1] | 626.8 |
| 319 | 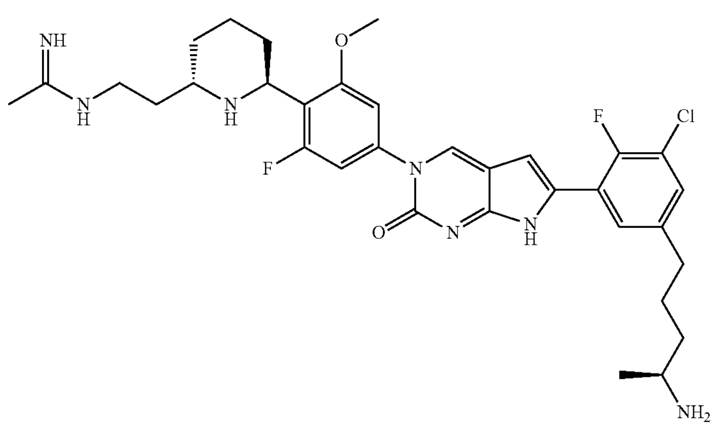 [SMILES: COc1cc(-n2cc3cc(-c4cc(CCC[C@H](C)N)cc(Cl)c4F)[nH]c3nc2=O)cc(F)c1[C@@H]1CCC[C@@H](CCNC(C)=N)N1] | 640.3 |

TABLE 1b-continued
| # | Structure | ESI, m/z [M + H]+ |
|---|---|---|
| 320 | 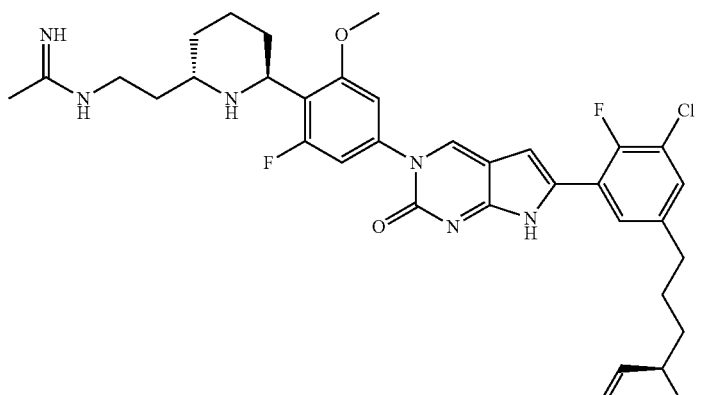 | 652.3 |
| 321 | 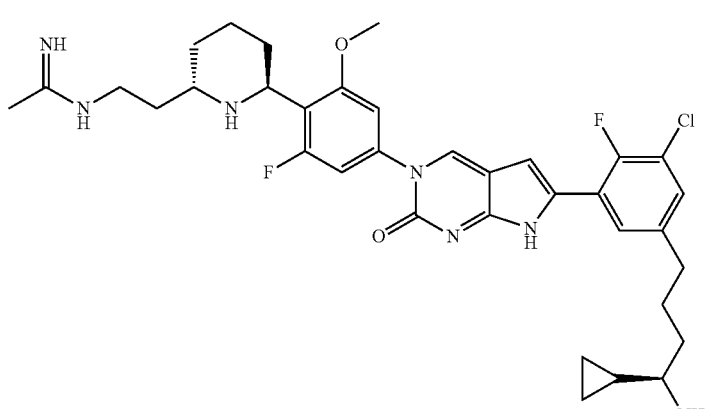 | 666.4 |
| 322 | 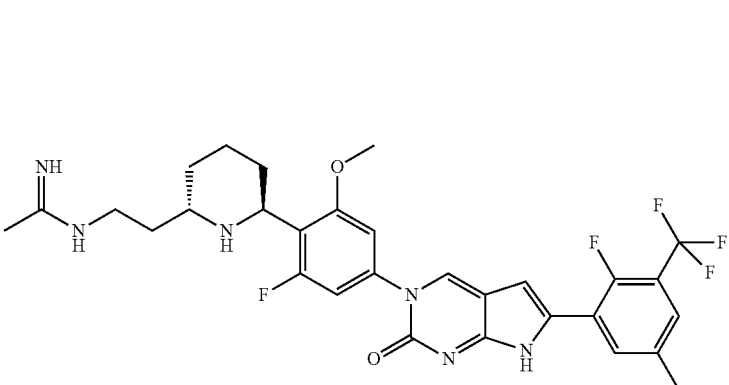 | 700.4 |

TABLE 1b-continued
| # | Structure | ESI, m/z [M + H]+ |
|---|---|---|
| 323 | 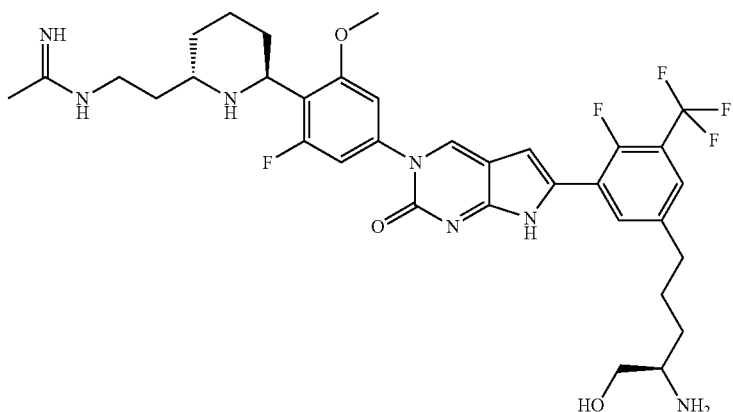 | 690.4 |
| 325 | 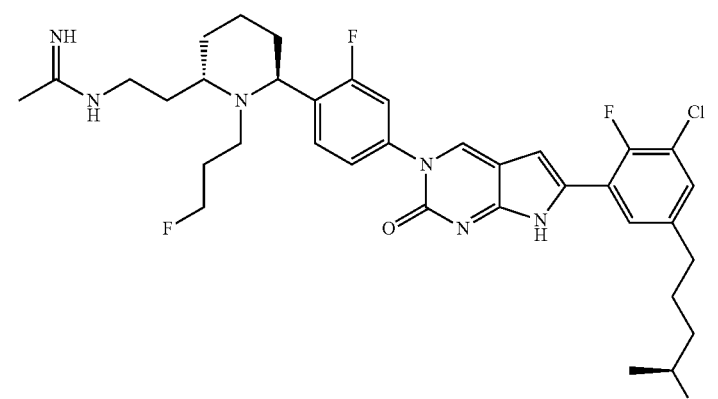 | 670 |
| 326 | 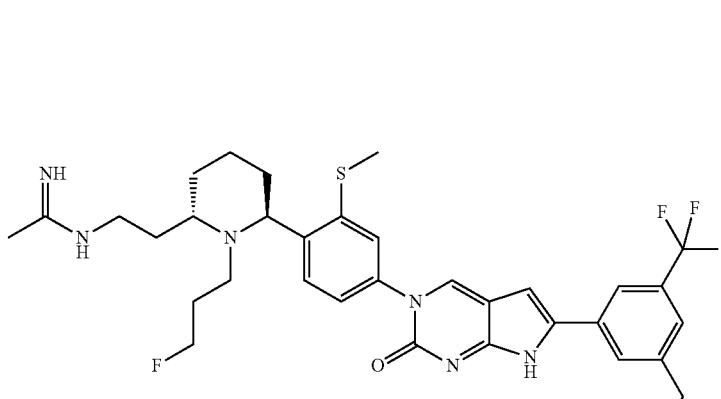 | 740 |

TABLE 1b-continued
| # | Structure | ESI, m/z [M + H]+ |
|---|---|---|
| 327 | 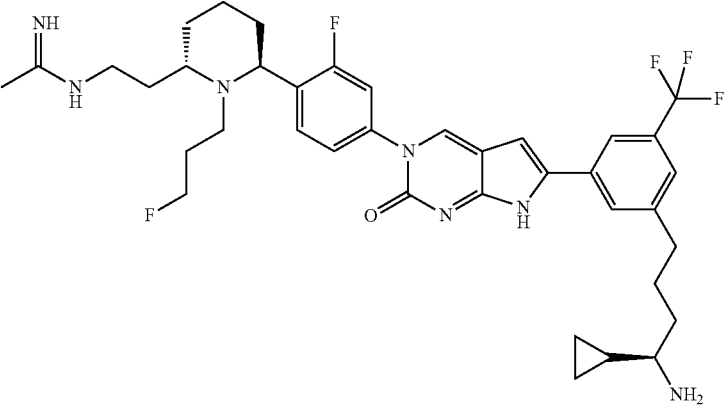 [SMILES: CC(=N)NCC[C@@H]1CCC[C@@H](c2ccc(-n3cc4cc(-c5cc(CCC[C@@H](N)C6CC6)cc(C(F)(F)F)c5)[nH]c4nc3=O)cc2F)N1CCCF] | 712 |
| 328 | 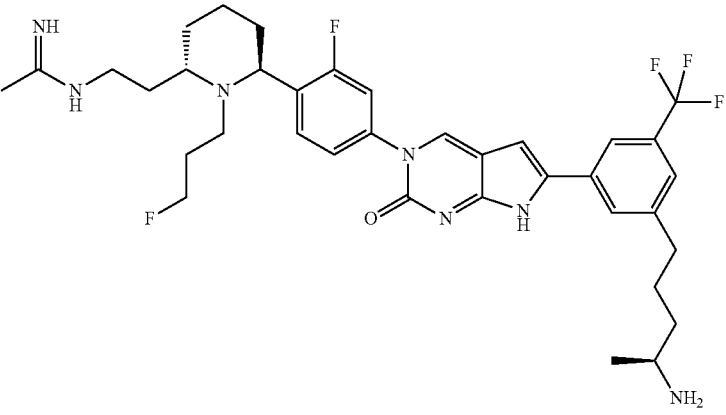 [SMILES: CC(=N)NCC[C@@H]1CCC[C@@H](c2ccc(-n3cc4cc(-c5cc(CCC[C@H](C)N)cc(C(F)(F)F)c5)[nH]c4nc3=O)cc2F)N1CCCF] | 686 |
| 329 | 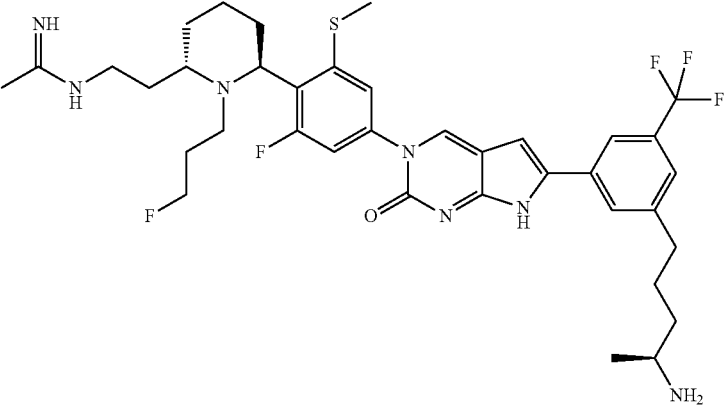 [SMILES: CSc1cc(-n2cc3cc(-c4cc(CCC[C@H](C)N)cc(C(F)(F)F)c4)[nH]c3nc2=O)cc(F)c1[C@@H]1CCC[C@@H](CCNC(C)=N)N1CCCF] | 732 |

TABLE 1b-continued
| # | Structure | ESI, m/z [M + H]+ |
|---|---|---|
| 330 | 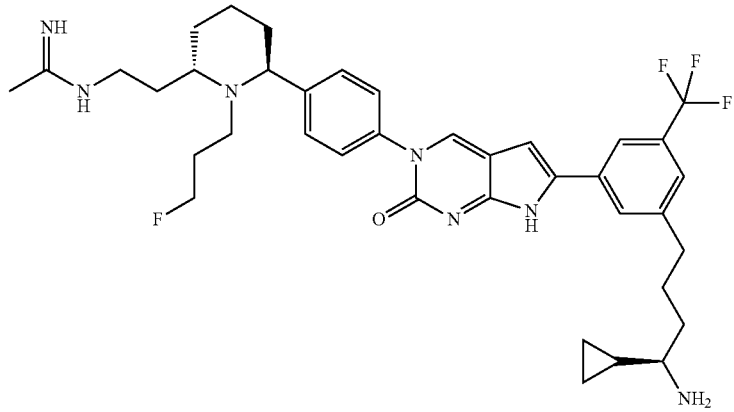 [SMILES: CC(=N)NCC[C@@H]1CCC[C@@H](c2ccc(-n3cc4cc(-c5cc(CCC[C@@H](N)C6CC6)cc(C(F)(F)F)c5)[nH]c4nc3=O)cc2)N1CCCF] | 694 |
| 331 | 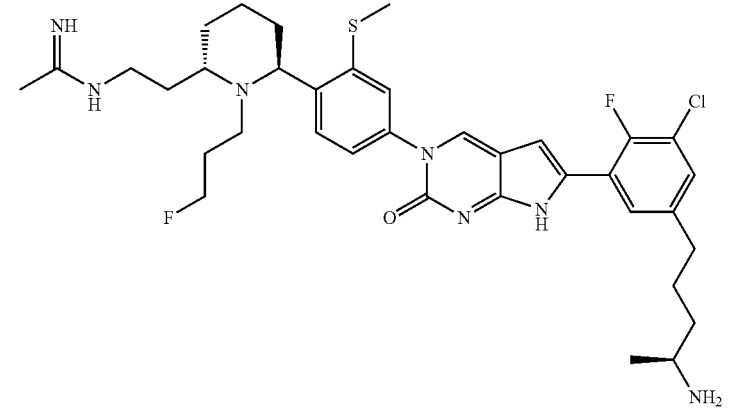 [SMILES: CSc1cc(-n2cc3cc(-c4cc(CCC[C@H](C)N)cc(Cl)c4F)[nH]c3nc2=O)ccc1[C@@H]1CCC[C@@H](CCNC(C)=N)N1CCCF] | 698 |
| 332 | 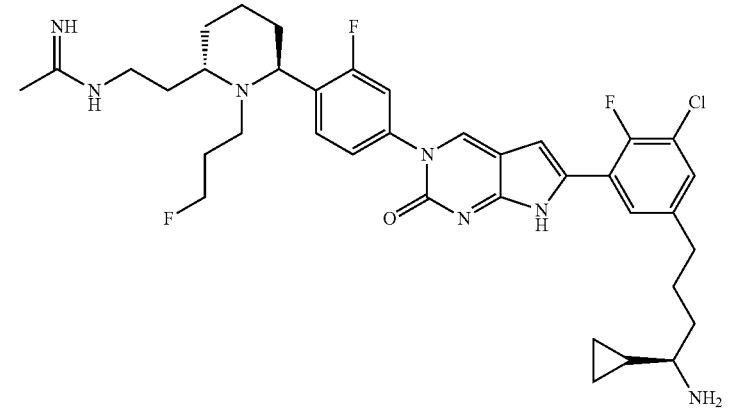 [SMILES: CC(=N)NCC[C@@H]1CCC[C@@H](c2ccc(-n3cc4cc(-c5cc(CCC[C@@H](N)C6CC6)cc(Cl)c5F)[nH]c4nc3=O)cc2F)N1CCCF] | 696 |

TABLE 1b-continued
| # | Structure | ESI, m/z [M + H]+ |
|---|---|---|
| 333 | 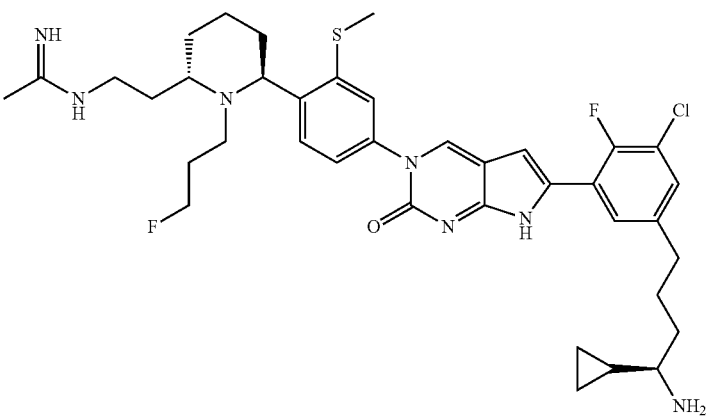 [SMILES: CSc1cc(-n2cc3cc(-c4cc(CCC[C@@H](N)C5CC5)cc(Cl)c4F)[nH]c3nc2=O)ccc1[C@@H]1CCC[C@@H](CCNC(C)=N)N1CCCF] | 724 |
| 334 | 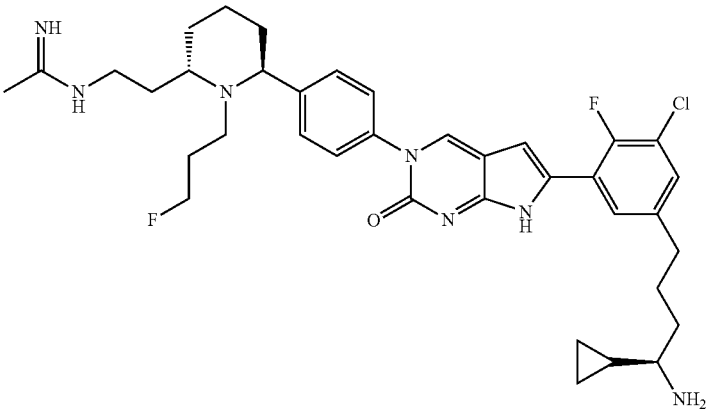 [SMILES: CC(=N)NCC[C@@H]1CCC[C@@H](c2ccc(-n3cc4cc(-c5cc(CCC[C@@H](N)C6CC6)cc(Cl)c5F)[nH]c4nc3=O)cc2)N1CCCF] | 678 |
| 335 | 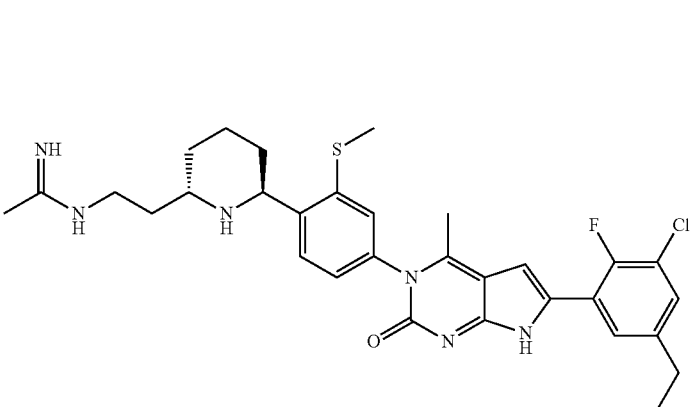 | 678.5 |

TABLE 1b-continued
| # | Structure | ESI, m/z [M + H]+ |
|---|-----------|-------------------|
| 336 | 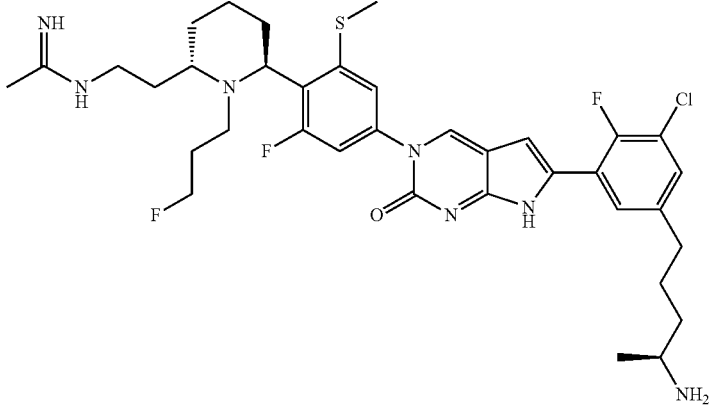 [SMILES: CSc1cc(-n2cc3cc(-c4cc(CCC[C@H](C)N)cc(Cl)c4F)[nH]c3nc2=O)cc(F)c1[C@@H]1CCC[C@@H](CCNC(C)=N)N1CCCF] | 716 |
| 337 | 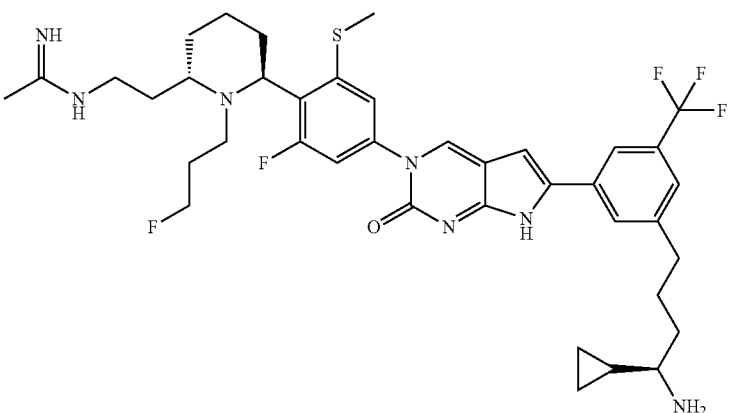 | 758 |
| 338 | 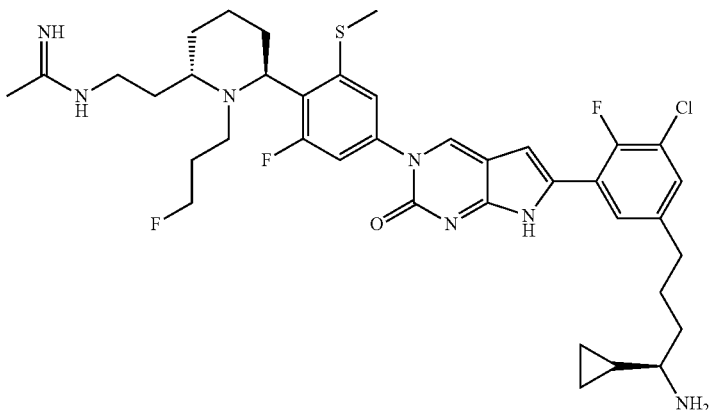 | 742 |

| # | Structure | ESI, m/z [M + H]+ |
|---|---|---|
| 339 | 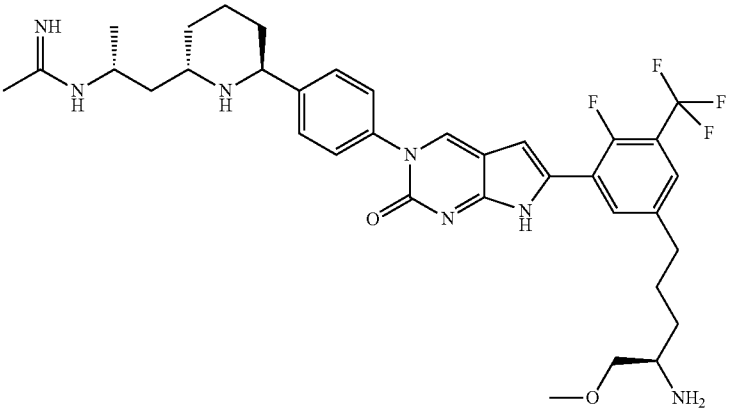 [SMILES: COC[C@H](N)CCCc1cc(-c2cc3cn(-c4ccc([C@@H]5CCC[C@@H](C[C@@H](C)NC(C)=N)N5)cc4)c(=O)nc3[nH]2)c(F)c(C(F)(F)F)c1] | 670.5 |
| 340 | 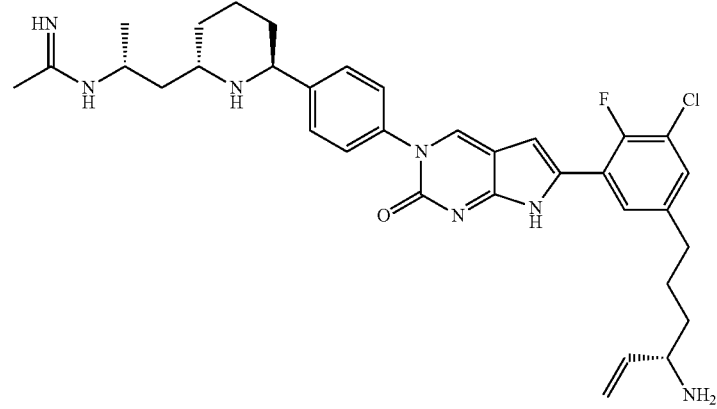 [SMILES: C=C[C@@H](N)CCCc1cc(Cl)c(F)c(-c2cc3cn(-c4ccc([C@@H]5CCC[C@@H](C[C@@H](C)NC(C)=N)N5)cc4)c(=O)nc3[nH]2)c1] | 618.4 |
| 341 | 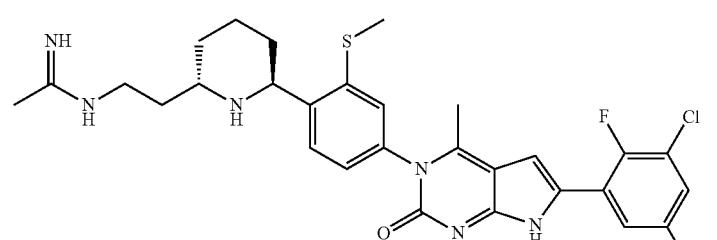 | 652.3 |

TABLE 1b-continued
| # | Structure | ESI, m/z [M + H]+ |
|---|---|---|
| 342 | 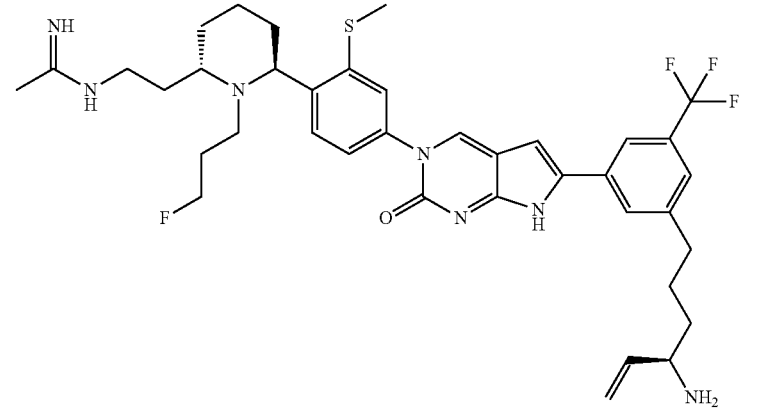 [SMILES: C=C[C@H](N)CCCc1cc(-c2cc3cn(-c4ccc([C@@H]5CCC[C@@H](CCNC(C)=N)N5CCCF)c(SC)c4)c(=O)nc3[nH]2)cc(C(F)(F)F)c1] | 726 |
| 343 | 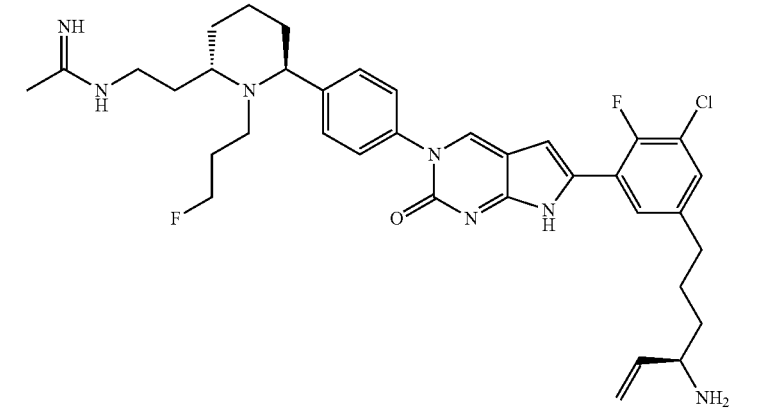 [SMILES: C=C[C@H](N)CCCc1cc(Cl)c(F)c(-c2cc3cn(-c4ccc([C@@H]5CCC[C@@H](CCNC(C)=N)N5CCCF)cc4)c(=O)nc3[nH]2)c1] | 664 |
| 344 | 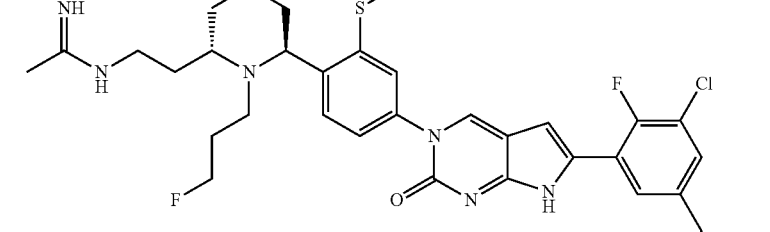 | 710 |

TABLE 1b-continued
| # | Structure | ESI, m/z [M + H]+ |
|---|---|---|
| 346 | 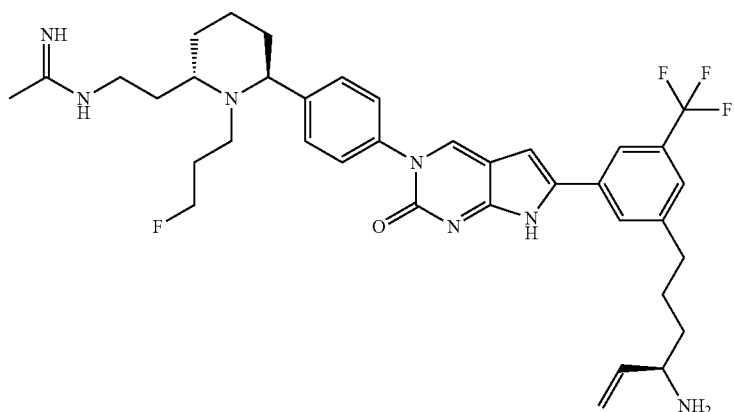 | 680 |
| 347 | 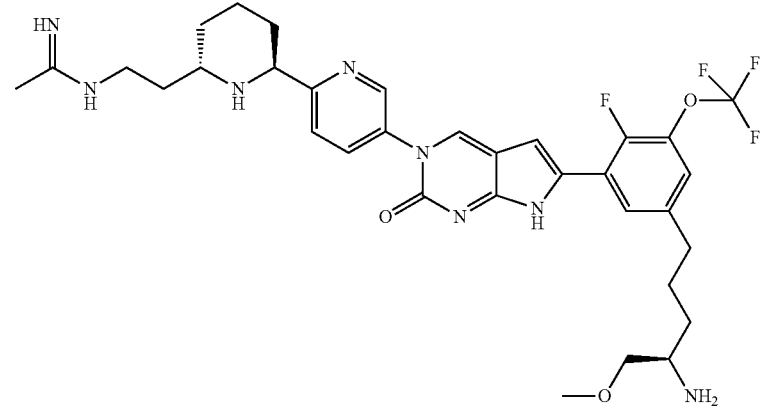 [SMILES: COC[C@H](N)CCCc1cc(OC(F)(F)F)c(F)c(-c2cc3cn(-c4ccc([C@@H]5CCC[C@@H](CCNC(C)=N)N5)nc4)c(=O)nc3[nH]2)c1] | 673.8 |
| 348 | 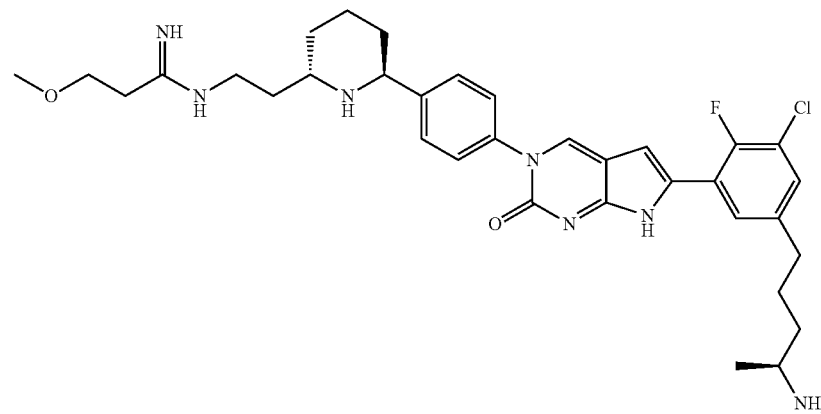 | 636 |

TABLE 1b-continued

| # | Structure | ESI, m/z [M + H]+ |
|---|-----------|---------------------|
| 349 | 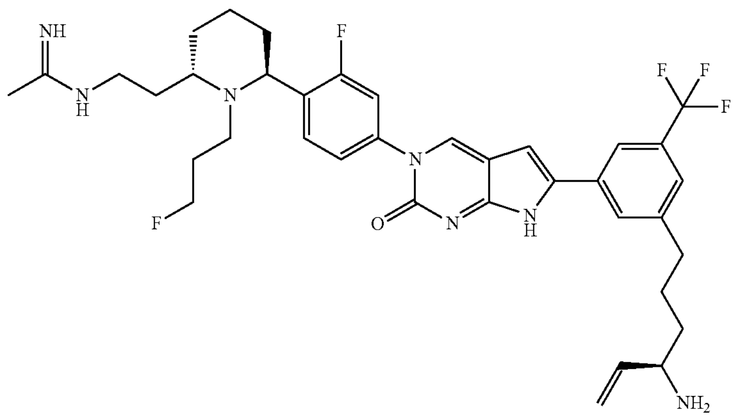 [SMILES: C=C[C@H](N)CCCc1cc(-c2cc3cn(-c4ccc([C@@H]5CCC[C@@H](CCNC(C)=N)N5CCCF)c(F)c4)c(=O)nc3[nH]2)cc(C(F)(F)F)c1] | 698 |
| 350 | 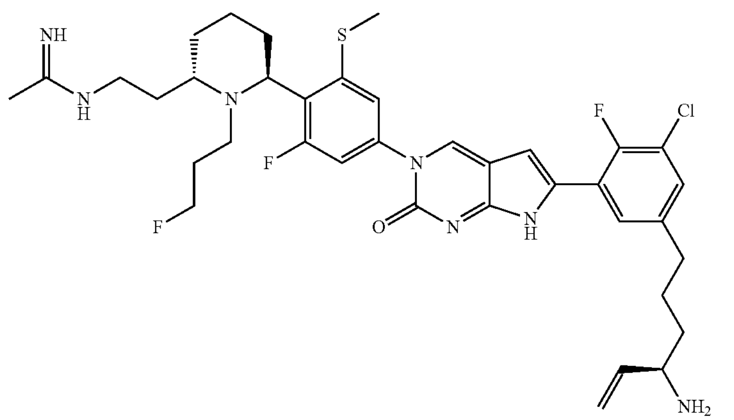 [SMILES: C=C[C@H](N)CCCc1cc(Cl)c(F)c(-c2cc3cn(-c4cc(F)c([C@@H]5CCC[C@@H](CCNC(C)=N)N5CCCF)c(SC)c4)c(=O)nc3[nH]2)c1] | 728 |
| 351 | 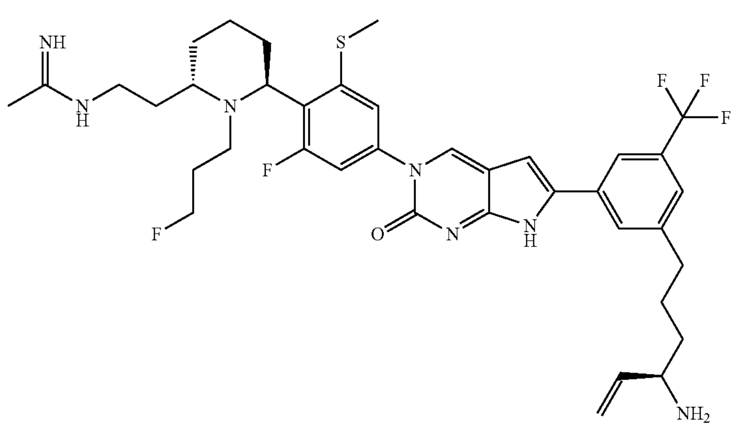 [SMILES: C=C[C@H](N)CCCc1cc(-c2cc3cn(-c4cc(F)c([C@@H]5CCC[C@@H](CCNC(C)=N)N5CCCF)c(SC)c4)c(=O)nc3[nH]2)cc(C(F)(F)F)c1] | 744 |

TABLE 1b-continued
| # | Structure | ESI, m/z [M + H]+ |
|---|---|---|
| 352 | 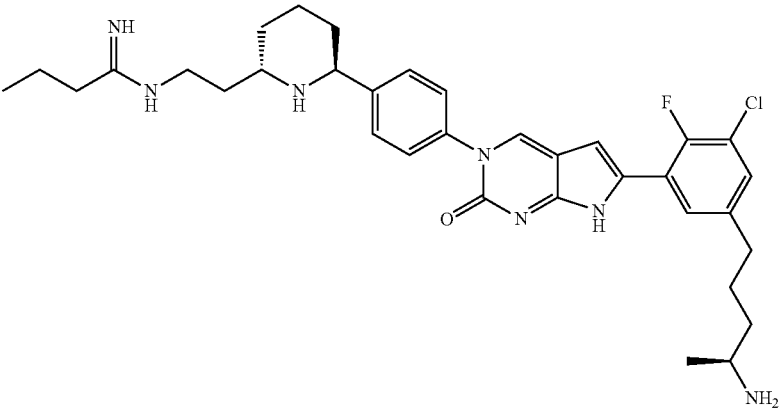 | 620.3 |
| 353 | 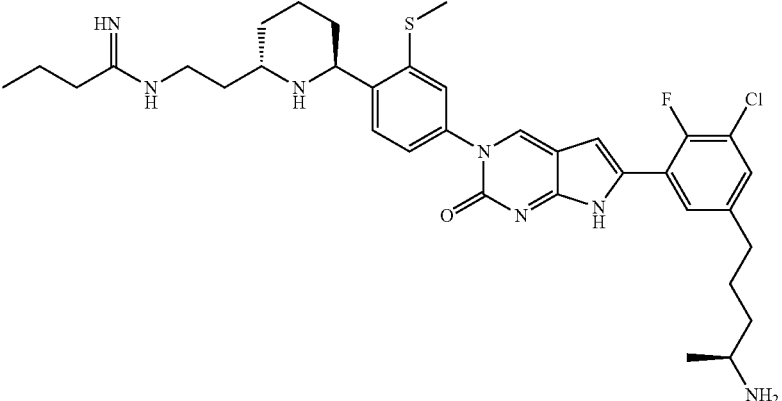 | 666.2 |
| 355 | 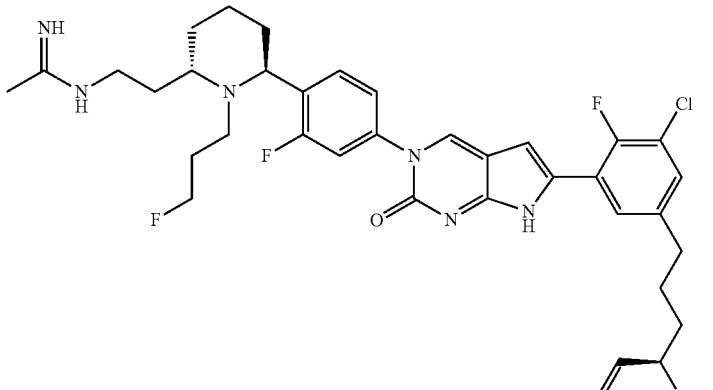 | 682 |

TABLE 1b-continued

| # | Structure | ESI, m/z [M + H]+ |
|---|-----------|-------------------|
| 356 | 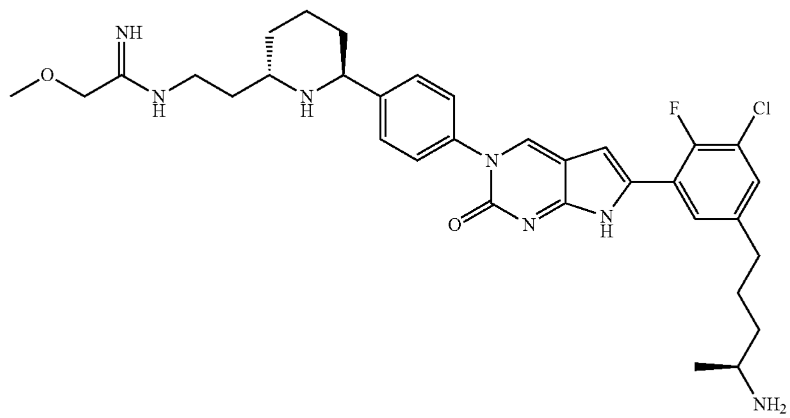 [SMILES: COCC(=N)NCC[C@@H]1CCC[C@@H](c2ccc(-n3cc4cc(-c5cc(CCC[C@H](C)N)cc(Cl)c5F)[nH]c4nc3=O)cc2)N1] | 622.3 |
| 357 | 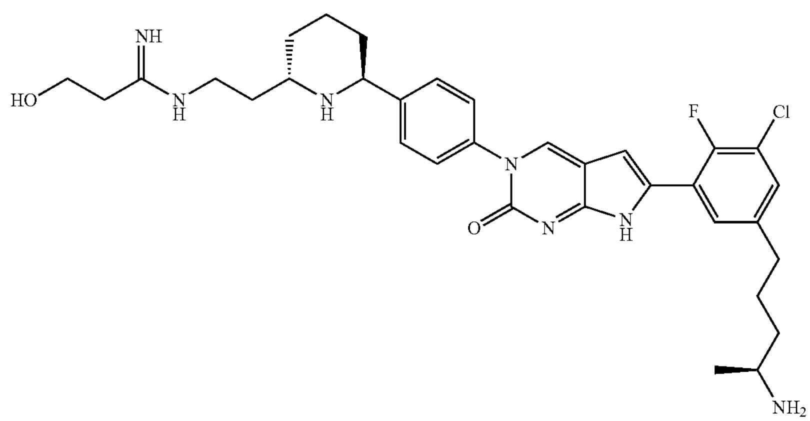 [SMILES: C[C@H](N)CCCc1cc(Cl)c(F)c(-c2cc3cn(-c4ccc([C@@H]5CCC[C@@H](CCNC(=N)CCO)N5)cc4)c(=O)nc3[nH]2)c1] | 622.1 |
| 358 | 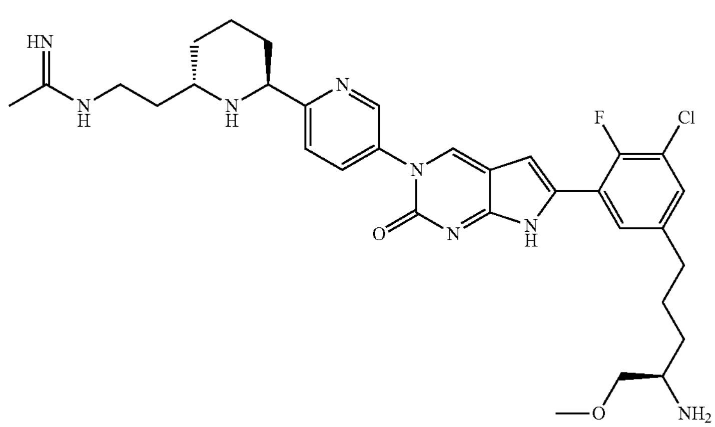 [SMILES: COC[C@H](N)CCCc1cc(Cl)c(F)c(-c2cc3cn(-c4ccc([C@@H]5CCC[C@@H](CCNC(C)=N)N5)nc4)c(=O)nc3[nH]2)c1] | 623.3 |

TABLE 1b-continued

| # | Structure | ESI, m/z [M + H]+ |
|---|---|---|
| 360 | 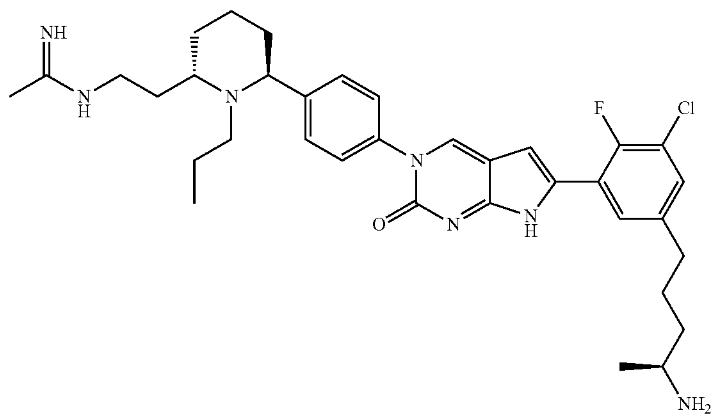 [SMILES: CCCN1[C@H](CCNC(C)=N)CCC[C@H]1c1ccc(-n2cc3cc(-c4cc(CCC[C@H](C)N)cc(Cl)c4F)[nH]c3nc2=O)cc1] | 634 |
| 362 | 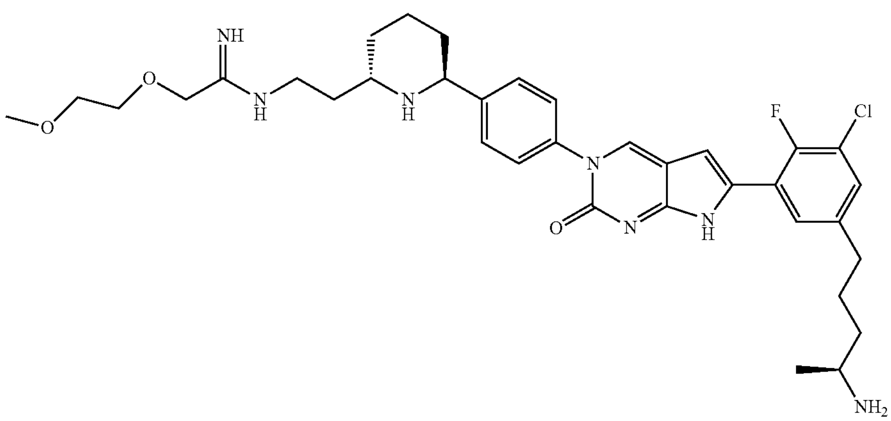 [SMILES: COCCOCC(=N)NCC[C@@H]1CCC[C@@H](c2ccc(-n3cc4cc(-c5cc(CCC[C@H](C)N)cc(Cl)c5F)[nH]c4nc3=O)cc2)N1] | 666 |
| 363 | 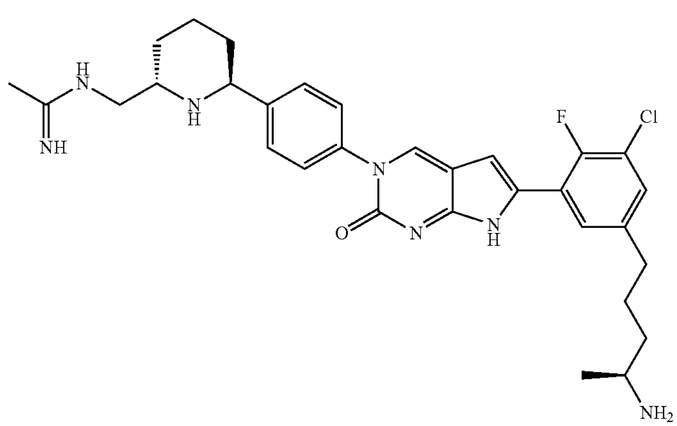 [SMILES: CC(=N)NC[C@@H]1CCC[C@@H](c2ccc(-n3cc4cc(-c5cc(CCC[C@H](C)N)cc(Cl)c5F)[nH]c4nc3=O)cc2)N1] | 578 |

TABLE 1b-continued

| # | Structure | ESI, m/z [M + H]+ |
|---|---|---|
| 364 | 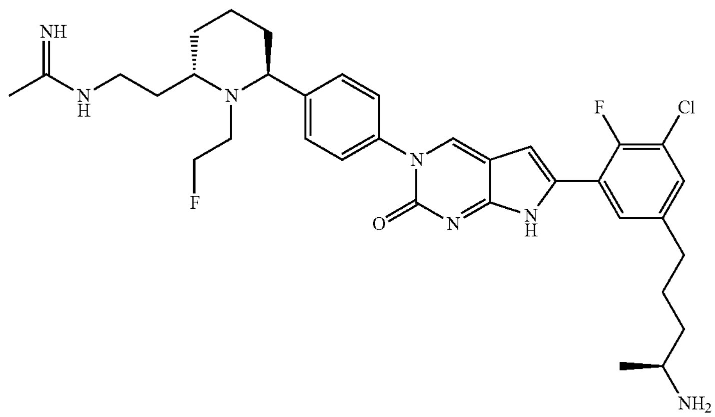 | 638 |
| 365 | 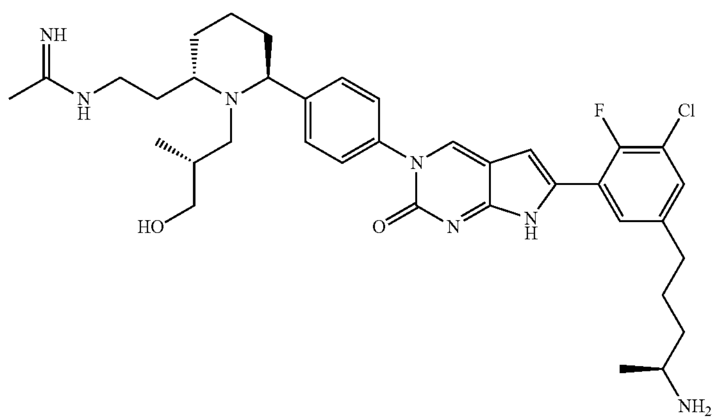 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1C[C@@H](C)CO] | 664 |
| 366 | 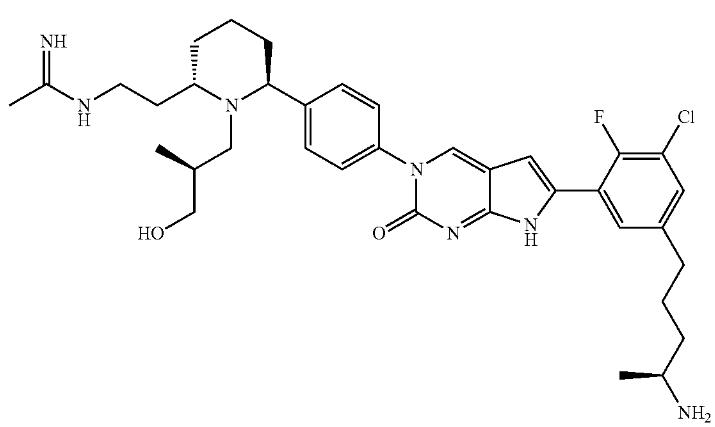 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1C[C@H](C)CO] | 664 |

TABLE 1b-continued

| # | Structure | ESI, m/z [M + H]+ |
|---|-----------|------------------|
| 369 | 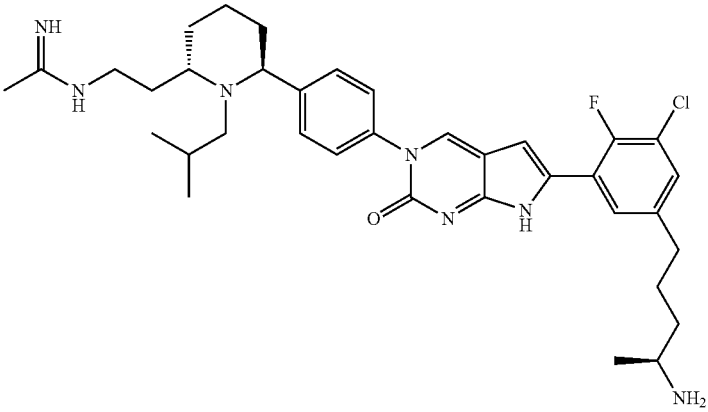 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1CC(C)C] | 648 |
| 370 | 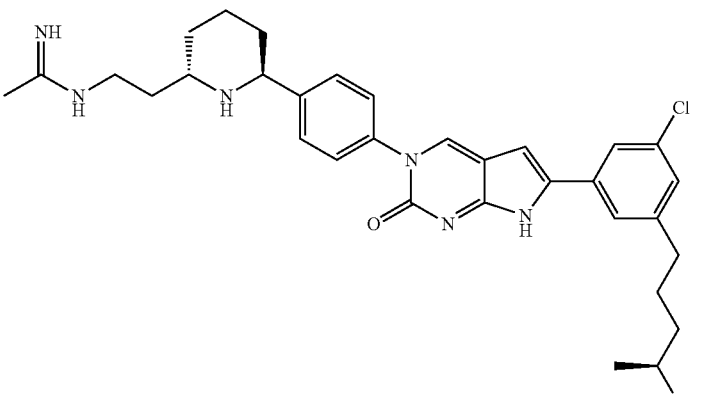 | 574.4 |
| 377 | 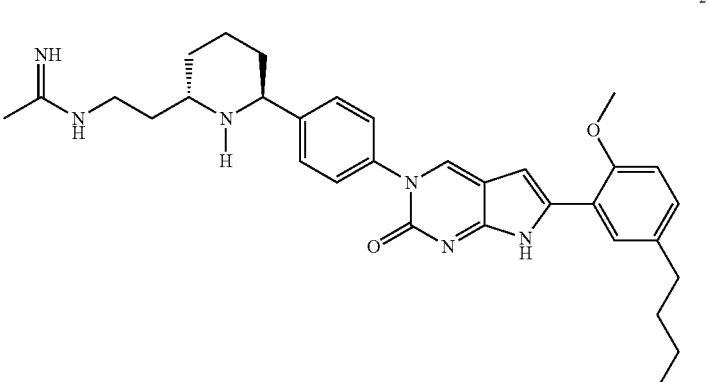 | 570.5 |

In some embodiments, the present disclosure relates to a compound or a tautomer thereof, or a pharmaceutically acceptable salt of said compound or tautomer that binds the ribosome. In some embodiments, the ribosome is a bacterial ribosome.

In some embodiments, the present disclosure relates to a pharmaceutical composition comprising a compound disclosed herein, or a tautomer thereof, or a pharmaceutically acceptable salt of said compound or tautomer, and a pharmaceutically acceptable carrier. In some embodiments, the present disclosure relates to a compound or a tautomer thereof, or a pharmaceutically acceptable salt of said compound or tautomer disclosed herein and a means for delivery.

In some embodiments, the present disclosure relates to a method of treating, preventing, reducing the risk of or delaying the onset of a disease state in a human or animal comprising administering to the human or animal in need thereof an effective amount of a compound disclosed herein, or a tautomer thereof, or a pharmaceutically acceptable salt of said compound or tautomer.

In some embodiments, the present disclosure relates to a method of treating, preventing, reducing the risk of, or delaying the onset of a microbial infection in a human or animal comprising administering to the human or animal an effective amount of a compound disclosed herein, or a tautomer thereof, or a pharmaceutically acceptable salt of said compound or tautomer.

In some embodiments, the present disclosure relates to use of a compound disclosed herein, or a tautomer thereof, or a pharmaceutically acceptable salt of said compound or tautomer, in the manufacture of a medicament for treating, preventing, reducing the risk of, or delaying the onset of, a microbial infection in a human or animal. In another aspect, the present disclosure relates to a compound for use in the manufacture of a medicament for treating a microbial infection in a subject, wherein the compound is selected from a compound of the present disclosure, or a tautomer thereof, or a pharmaceutically acceptable salt of said compound or tautomer.

In some embodiments, the present disclosure relates to a compound for use in the manufacture of a medicament for preventing a microbial infection in a subject, wherein the compound is selected from a compound of the present disclosure, or a tautomer thereof, or a pharmaceutically acceptable salt of said compound or tautomer.

In some embodiments, the present disclosure relates to a compound for use in the manufacture of a medicament for reducing the risk of a microbial infection in a subject, wherein the compound is selected from a compound of the present disclosure, or a tautomer thereof, or a pharmaceutically acceptable salt of said compound or tautomer.

In some embodiments, the present disclosure relates to a compound for use in the manufacture of a medicament for delaying the onset of a microbial infection in a subject, wherein the compound is selected from a compound of the present disclosure, or a tautomer thereof, or a pharmaceutically acceptable salt of said compound or tautomer.

In some embodiments, the present disclosure relates to a compound disclosed herein, or a tautomer thereof, or a pharmaceutically acceptable salt of said compound or tautomer, for use in treating, preventing, reducing the risk of, or delaying the onset of a microbial infection in a human or animal.

In some embodiments, the present disclosure relates to a compound disclosed herein, or a tautomer thereof, or a pharmaceutically acceptable salt of said compound or tautomer, for use in treating a microbial infection in a human or animal.

In some embodiments, the present disclosure relates to a compound disclosed herein, or a tautomer thereof, or a pharmaceutically acceptable salt of said compound or tautomer, for use in preventing a microbial infection in a human or animal.

In some embodiments, the present disclosure relates to a compound disclosed herein, or a tautomer thereof, or a pharmaceutically acceptable salt of said compound or tautomer, for use in reducing the risk of a microbial infection in a human or animal.

In some embodiments, the present disclosure relates to a compound disclosed herein, or a tautomer thereof, or a pharmaceutically acceptable salt of said compound or tautomer, for use in delaying the onset of a microbial infection in a human or animal.

In some embodiments, a microbial infection as described herein is caused by one or more microoganisms selected from the group consisting of: *Enterococcus faecium*, *Staphylococcus aureus*, *Klebsiella pneumoniae*, *Acinetobacter baumannii*, *Pseudomonas aeruginosa*, *Enterobacter species*, and *Escherichia coli*. This group of microoganisms can be referred to generally as the ESKAPE pathogens. In some embodiments, the microbial infection is caused by a microorganism which is resistant to at least one antibacterial. For example, the microorganism can be classified as multi-drug resistant or extremely-drug resistant.

In some embodiments, the present disclosure relates to a method of treating, preventing, reducing the risk of, or delaying the onset of a microbial infection in a human or animal comprising administering to the human or animal an effective amount of a compound or a tautomer thereof, or a pharmaceutically acceptable salt of said compound or tautomer, wherein said microbial infection is caused by one or more of the following microorganisms: *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *Citrobacter freundii*, *Citrobacter koser*, *Chlamydia trachomatis*, *Chlamydia psittaci*, *Chlamydia pneumoniae*, *Chlamydia pecorum*, *Hlamydia suis*, *Chlaymdia muridarum*, *Chlamydophila psittaci*, *Chlamydophila pneumoniae*, *Chlamydophila pecorum*, *Clostridium clostridioforme*, *Clostridium perfringens*, *Enterobacter aerogenes*, *Enterobacter cloacae*, *Enterococcus faecalis*, *Enterococcus* spp. (vancomycin susceptible and resistant isolates), *Escherichia coli* (including ESBL and KPC producing isolates), *Eubacterium lentum*, *Fusobacterium* spp., *Haemophilus influenzae* (including beta-lactamase positive isolates), *Haemophilus parainfluenzae*, *Klebsiella pneumoniae* (including ESBL and KPC producing isolates), *Klebsiella oxytoca* (including ESBL and KPC producing isolates), *Legionella pneumophilia* *Moraxella catarrhalis*, *Morganella morganii*, *Mycoplasma* spp., *Neisseria gonorrhoeae* (including *Neisseria gonorrhoeae* ATCC49266, *Neisseria gonorrhoeae* 255123, *Neisseria gonorrhoeae* 255124, *Neisseria gonorrhoeae* 255125, *Neisseria gonorrhoeae* 255126, *Neisseria gonorrhoeae* 255127, *Neisseria gonorrhoeae* J9104300210, *Neisseria gonorrhoeae* J9107400107, *Neisseria gonorrhoeae* J9109510210, *Neisseria gonorrhoeae* J9108110210), *Peptostreptococcus* spp., *Porphyromonas asaccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus* (methicillin susceptible and resistant isolates), *Staphylococcus epidermidis* (methicillin susceptible and resistant isolates), *Stenotrophomonas maltophilia*, *Streptococcus agalactiae*, *Streptococcus constellatus*, *Streptococcus pneumoniae* (penicillin susceptible and resistant isolates), *Streptococcus pyogenes*, or *Streptococcus pyogenes*.

In some embodiments, the present disclosure relates to a method of treating, preventing, reducing the risk of, or delaying the onset of a microbial infection in a human or animal comprising administering to the human or animal an effective amount of a compound or a tautomer thereof, or a pharmaceutically acceptable salt of said compound or tautomer, wherein said infection is caused by or involves one or more microorganisms selected from: *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *Citrobacter freundii*, *Citrobacter koser*, *Chlamydia trachomatis*, *Chlamydia psittaci*, *Chlamydia pneumoniae*, *Chlamydia pecorum*, *Hlamydia suis*, *Chlaymdia muridarum*, *Chlamydophila psittaci*, *Chlamydophila pneumoniae*, *Chlamydophila pecorum*, *Clostridium clostridioforme*, *Clostridium perfringens*, *Enterobacter aerogenes*, *Enterobacter cloacae*, *Enterococcus faecalis*, *Enterococcus* spp., *Escherichia coli*,

*Eubacterium lentum, Fusobacterium* spp., *Haemophilus influenzae, Haemophilus parainfluenzae, Klebsiella pneumoniae, Klebsiella oxytoca, Legionella pneumophilia, Moraxella catarrhalis, Morganella morganii, Mycoplasma* spp., *Neisseria gonorrhoeae, Peptostreptococcus* spp., *Porphyromonas asaccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus, Staphylococcus epidermidis, Stenotrophomonas maltophilia, Streptococcus agalactiae, Streptococcus constellatus, Streptococcus pneumoniae, Streptococcus pyogenes,* and *Streptococcus pyogenes.*

In some embodiments, the present disclosure relates to a method wherein said infection is caused by or involves one or more of aerobic and facultative gram-positive microorganisms selected from: *Staphylococcus aureus, Streptococcus pneumoniae, Enterococcus* spp., *Streptococcus agalactiae, Streptococcus pyogenes,* and *Staphylococcus epidermidis.*

In some embodiments, the present disclosure relates to a method wherein said infection is caused by or involves one or more of aerobic and facultative gram-negative microorganisms selected from: *Escherichia coli, Haemophilus influenzae, Klebsiella pneumoniae, Citrobacter freundii, Chlamydia trachomatis, Chlamydia psittaci, Chlamydia pneumoniae, Chlamydia pecorum, Hlamydia suis, Chlaymdia muridarum, Chlamydophila psittaci, Chlamydophila pneumoniae, Chlamydophila pecorum, Enterobacter aerogenes, Enterobacter cloacae, Morganella morganii, Neisseria gonorrhoeae, Serratia marcescens, Pseudomonas aeruginosa, Acinetobacter baumanni, Moraxella catarrhalis, Proteus mirabilis, Citrobacter koseri, Haemophilus parainfluenzae, Klebsiella oxytoca, Proteus vulgaris, Providencia rettgeri,* and *Providencia stuartii.*

In some embodiments, the present disclosure relates to a method wherein the infection is caused by or involves one or more anaerobic microorganisms: *Bacteroides fragilis, Bacteroides distasonis, Bacteroides ovatus, Bacteroides thetaiotaomicron, Bacteroides uniformis, Clostridium clostridioforme, Eubacterium lentum, Peptostreptococcus* spp., *Porphyromonas asaccharolytica, Prevotella bivia, Bacteroides vulgatus, Clostridium perfringens,* and *Fusobacterium* spp.

In some embodiments, the present disclosure relates to a method, wherein the microorganism *Enterococcus* spp. is selected from vancomycin susceptible isolate and vancomycin resistant isolate.

In some embodiments, the present disclosure relates to a method wherein the microorganism *Escherichia coli* is selected from extended spectrum beta-lactamase (ESBL) producing isolate and *Klebsiella pneumoniae* carbapenemase (KPC) producing isolate.

In some embodiments, the present disclosure relates to a method wherein the microorganism *Haemophilus influenzae* is a beta-lactamase positive isolate.

In some embodiments, the present disclosure relates to a method wherein the microorganism *Klebsiella pneumoniae* is selected from extended spectrum beta-lactamase (ESBL) producing isolate and *Klebsiella pneumoniae* carbapenemase (KPC) producing isolate.

In some embodiments, the present disclosure relates to a method wherein the microorganism *Klebsiella oxytoca* selected from extended spectrum beta-lactamase (ESBL) producing isolate and *Klebsiella pneumoniae* carbapenemase (KPC) producing isolate.

In some embodiments, the present disclosure relates to a method wherein the microorganism *Staphylococcus aureus* is selected from methicillin susceptible isolate and methicillin resistant isolate.

In some embodiments, the present disclosure relates to a method wherein the microorganism *Staphylococcus epidermidis* is selected from methicillin susceptible isolate and methicillin resistant isolate.

In some embodiments, the present disclosure relates to a method wherein the microorganism *Streptococcus pneumoniae* is selected from penicillin susceptible isolate and penicillin resistant isolate.

In some embodiments, the present disclosure relates to a method wherein the microorganism *Neisseria gonorrhoeae* is selected from susceptible and resistant isolates, including, for example, ceftriaxone-resistant, ciprofloxacin-resistant and azithromycin-resistant isolates.

In some embodiments, the present disclosure relates to a method of treating, preventing, reducing the risk of, or delaying the onset of a microbial infection in a human or animal comprising administering to the human or animal an effective amount of a compound or a tautomer thereof, or a pharmaceutically acceptable salt of said compound or tautomer, wherein said microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei,* and *Burkholderia pseudomallei.*

In some embodiments, the present disclosure pertains, at least in part, to a compound disclosed herein, or a tautomer thereof, or a pharmaceutically acceptable salt of said compound or tautomer, or a pharmaceutical composition thereof, for use in a method of preventing a microbial, e.g., bacterial, infection in a subject, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei,* and *Burkholderia pseudomallei.*

In some embodiments, the present disclosure pertains, at least in part, to a compound disclosed herein, or a tautomer thereof, or a pharmaceutically acceptable salt of said compound or tautomer, or a pharmaceutical composition thereof, for use in a method of reducing the risk of a microbial, e.g., bacterial, infection in a subject, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei,* and *Burkholderia pseudomallei.*

In some embodiments, the present disclosure pertains, at least in part, to a compound disclosed herein, or a tautomer thereof, or a pharmaceutically acceptable salt of said compound or tautomer, or a pharmaceutical composition thereof, for use in a method of delaying the onset of a microbial, e.g., bacterial, infection in a subject, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei,* and *Burkholderia pseudomallei.*

In some embodiments, the present disclosure relates to a method of treating, preventing, reducing the risk of, or delaying the onset of a microbial infection in a human or animal comprising administering to the human or animal an effective amount of a compound disclosed herein, or a tautomer thereof, or a pharmaceutically acceptable salt of said compound or tautomer, or use of a compound disclosed herein, or a tautomer thereof, or a pharmaceutically acceptable salt of said compound or tautomer, in the manufacture of a medicament for treating, preventing, reducing the risk of, or delaying the onset of a microbial infection in a human or animal, wherein the microbial infection is selected from the group consisting of: a skin infection, a Gram positive infection, a Gram negative infection, nosocomial pneumonia, community acquired pneumonia, post-viral pneumonia, hospital acquired pneumonia/ventilator associated pneumonia, a respiratory tract infection such as chronic respiratory tract infection (CRTI), acute pelvic infection, a complicated skin and skin structure infection, a skin and soft tissue infection (SSTI) including uncomplicated skin and soft tissue infections (uSSTI)s and complicated skin and soft tissue infections, an abdominal infection, a complicated intra-abdominal infection, a urinary tract infection, bacteremia, septicemia, endocarditis, an atrio-ventricular shunt infection, a vascular access infection, meningitis, surgical prophylaxis, a peritoneal infection, a bone infection, a joint infection, a methicillin-resistant *Staphylococcus aureus* infection, a vancomycin-resistant Enterococci infection, a linezolid-resistant organism infection, gonorrhea, *chlamydia*, and tuberculosis.

The compounds of the present disclosure can be used, for example for the treatment of patients with moderate to severe infections, which may be caused by susceptible isolates of the indicated microorganisms.

In some embodiments, the present disclosure relates to a method of treating, preventing, reducing the risk of, or delaying the onset of a complicated intra-abdominal infection in a human or animal comprising administering to the human or animal an effective amount of a compound disclosed herein, or a tautomer thereof, or a pharmaceutically acceptable salt of said compound or tautomer, or to the use of a compound disclosed herein, or a tautomer thereof, or a pharmaceutically acceptable salt of said compound or tautomer, in the manufacture of a medicament for treating, preventing, reducing the risk of, or delaying the onset of a complicated intra-abdominal infection in a human or animal.

In some embodiments, the complicated intra-abdominal infection is selected from polymicrobial infections such as abscess due to *Escherichia coli, Clostridium clostridioforme, Eubacterium lentum, Peptostreptococcus* spp., *Bacteroides fragilis, Bacteroides distasonis, Bacteroides ovatus, Bacteroides thetaiotaomicron, Bacteroides uniformis, Streptococcus anginosus, Streptococcus constellatus, Enterococcus faecalis, Proteus mirabilis*, or *Clostridium perfringens*.

In some embodiments, the present disclosure relates to a method of treating, preventing, reducing the risk of, or delaying the onset of a complicated skin and skin structure infection (cSSSI, also known as acute bacterial skin and skin structure infections or ABSSSI) in a human or animal comprising administering to the human or animal an effective amount of a compound disclosed herein, or a tautomer thereof, or a pharmaceutically acceptable salt of said compound or tautomer, or to the use of a compound disclosed herein, or a tautomer thereof, or a pharmaceutically acceptable salt of said compound or tautomer, in the manufacture of a medicament for treating, preventing, reducing the risk of, or delaying the onset of a complicated skin and skin structure infection.

In some embodiments, the complicated skin and skin structure infection is selected from diabetic foot infections without osteomyelitis due to *Staphylococcus aureus* (methicillin susceptible and resistant isolates), *Streptococcus agalactiae, Streptococcus pyogenes, Escherichia coli, Klebsiella pneumoniae, Proteus mirabilis, Bacteroides fragilis, Peptostreptococcus species, Porphyromonas asaccharolytica*, or *Prevotella bivia*.

In some embodiments, the present disclosure relates to a method of treating, preventing, reducing the risk of, or delaying the onset of a community acquired pneumonia (CAP) in a human or animal comprising administering to the human or animal an effective amount of a compound disclosed herein, or a tautomer thereof, or a pharmaceutically acceptable salt of said compound or tautomer, or to the use of a compound disclosed herein, or a tautomer thereof, or a pharmaceutically acceptable salt of said compound or tautomer, in the manufacture of a medicament for treating, preventing, reducing the risk of, or delaying the onset of community acquired pneumonia.

In some embodiment, the community acquired pneumonia is due to *Streptococcus pneumoniae* (penicillin susceptible and resistant isolates) including cases with concurrent bacteremia, *Haemophilus influenzae* (including beta-lactamase positive isolates), *Moraxella catarrhalis*, or atypical bacteria like *Mycoplasma* spp.

In some embodiments, the present disclosure relates to a method of treating, preventing, reducing the risk of, or delaying the onset of a complicated urinary tract infection (cUTI) in a human or animal comprising administering to the human or animal an effective amount of a compound disclosed herein, or a tautomer thereof, or a pharmaceutically acceptable salt of said compound or tautomer, or to the use of a compound disclosed herein, or a tautomer thereof, or a pharmaceutically acceptable salt of said compound or tautomer, in the manufacture of a medicament for treating, preventing, reducing the risk of, or delaying the onset of a complicated urinary tract infection.

In some embodiment, the complicated urinary tract infection is selected from pyelonephritis due to *Escherichia coli*, concurrent bacteremia, or *Klebsiella pneumoniae*.

In some embodiments, the present disclosure relates to a method of treating, preventing, reducing the risk of, or delaying the onset of an acute pelvic infection in a human or animal comprising administering to the human or animal an effective amount of a compound disclosed herein, or a tautomer thereof, or a pharmaceutically acceptable salt of said compound or tautomer, or to the use of a compound disclosed herein, or a tautomer thereof, or a pharmaceutically acceptable salt of said compound or tautomer, in the manufacture of a medicament for treating, preventing, reducing the risk of, or delaying the onset of a acute pelvic infection.

In some embodiments, the acute pelvic infection is selected from postpartum endomyometritis, septic abortion and post-surgical gynecologic infections and the infection is due to a microorganism selected from *Streptococcus agalactiae, Escherichia coli, Bacteroides fragilis, Porphyromonas asaccharolytica, Peptostreptococcus* spp., and *Prevotella bivia*.

In some embodiments, the present disclosure relates to a method of treating, preventing, reducing the risk of, or delaying the onset of a hospital acquired pneumonia (HAP)/ventilator associated pneumonia (VAP) in a human or animal comprising administering to the human or animal an effective amount of a compound disclosed herein, or a tautomer thereof, or a pharmaceutically acceptable salt of said compound or tautomer, or to the use of a compound disclosed herein, or a tautomer thereof, or a pharmaceutically acceptable salt of said compound or tautomer, in the manufacture of a medicament for treating, preventing, reducing the risk of, or delaying the onset of hospital acquired pneumonia/ventilator associated pneumonia.

In some embodiments, the hospital acquired pneumonia/ventilator associated pneumonia is due to a microorganism selected from *Streptococcus pneumoniae* (penicillin susceptible and resistant isolates), *Staphylococcus aureus* (methicillin susceptible and resistant isolates), *Klebsiella pneumoniae, Pseudomonas aeruginosa, Acinetobacter* spp., *Stenotrophomonas maltophilia, Haemophilus influenzae* (including beta-lactamase positive isolates), and *Legionella pneumophilia*.

The compounds or tautomers or pharmaceutically acceptable salts of said compounds or tautomers of the present disclosure may also be useful for the prevention, prophylaxis, or reduction of surgical site infections. In some embodiments, the compounds or tautomers or pharmaceutically acceptable salts of said compounds or tautomers of the present disclosure are useful following elective colorectal surgery.

Appropriate specimens for bacteriological examination should be obtained in order to isolate and identify the causative organisms and to determine their susceptibility to the compounds of the present disclosure. Therapy with the compounds or tautomers or pharmaceutically acceptable salts of said compounds or tautomers of the present disclosure may be initiated empirically before results of these tests are known; once results become available, antimicrobial therapy should be adjusted accordingly.

To reduce the development of drug-resistant bacteria and maintain the effectiveness of the compounds or tautomers or pharmaceutically acceptable salts of said compounds or tautomers of the present disclosure and other antibacterial drugs, the compounds or tautomers or pharmaceutically acceptable salts of said compounds or tautomers should be used only to treat or prevent infections that are proven or strongly suspected to be caused by susceptible bacteria. When culture and susceptibility information are available, they should be considered in selecting or modifying antibacterial therapy. In the absence of such data, local epidemiology and susceptibility patterns may contribute to the empiric selection of therapy.

In some embodiments, the present disclosure relates to a method of treating, preventing, reducing the risk of, or delaying the onset of a microbial infection due to an aerobic or facultative gram-positive microorganism in a human or animal comprising administering to the human or animal an effective amount of a compound disclosed herein, or a tautomer thereof, or a pharmaceutically acceptable salt of said compound or tautomer, or to the use of a compound disclosed herein, or a tautomer thereof, or a pharmaceutically acceptable salt of said compound or tautomer, in the manufacture of a medicament for treating, preventing, reducing the risk of, or delaying the onset of a microbial infection due to an aerobic or facultative gram-positive microorganism.

In some embodiments, the aerobic or facultative gram-positive microorganism is selected from: *Staphylococcus aureus* (methicillin susceptible and resistant isolates), *Streptococcus pneumoniae* (penicillin susceptible and resistant isolates), *Enterococcus* spp. (vancomycin susceptible and resistant isolates), *Streptococcus agalactiae, Streptococcus pyogenes*, and *Staphylococcus epidermidis* (methicillin susceptible and resistant isolates).

In some embodiments, the present disclosure relates to a method of treating, preventing, reducing the risk of, or delaying the onset of a microbial infection due to an aerobic and facultative gram-negative microorganism in a human or animal comprising administering to the human or animal an effective amount of a compound disclosed herein, or a tautomer thereof, or a pharmaceutically acceptable salt of said compound or tautomer, or to the use of a compound disclosed herein, or a tautomer thereof, or a pharmaceutically acceptable salt of said compound or tautomer, in the manufacture of a medicament for treating, preventing, reducing the risk of, or delaying the onset of a microbial infection due to an aerobic or facultative gram-positive microorganism.

In some embodiments, the aerobic and facultative gram-negative microorganism is selected from: *Escherichia coli* [including extended spectrum beta-lactamase (ESBL) and *Klebsiella pneumoniae* (KPC) producing isolates), *Haemophilus influenzae* (including Beta-lactamase positive isolates), *Klebsiella pneumoniae* (including ESBL and KPC producing isolates), *Citrobacter freundii, Enterobacter aerogenes, Enterobacter cloacae, Morganella morganii, Serratia marcescens, Pseudomonas aeruginosa, Acinetobacter baumanni, Moraxella catarrhalis, Proteus mirabilis, Citrobacter koseri, Haemophilus parainfluenzae, Klebsiella oxytoca* (including ESBL and KPC producing isolates), *Proteus vulgaris, Providencia rettgeri*, and *Providencia stuartii*.

In some embodiments, the present disclosure relates to a method of treating, preventing, reducing the risk of, or delaying the onset of a microbial infection due to an anaerobic microorganism in a human or animal comprising administering to the human or animal an effective amount of a compound disclosed herein, or a tautomer thereof, or a pharmaceutically acceptable salt of said compound or tautomer, or to the use of a compound disclosed herein, or a tautomer thereof, or a pharmaceutically acceptable salt of said compound or tautomer, in the manufacture of a medicament for treating, preventing, reducing the risk of, or delaying the onset of a microbial infection due to an anaerobic microorganism.

In some embodiments, the anaerobic microorganism is selected from: *Bacteroides fragilis, Bacteroides distasonis, Bacteroides ovatus, Bacteroides thetaiotaomicron, Bacteroides uniformis, Clostridium clostridioforme, Eubacterium lentum, Peptostreptococcus species, Porphyromonas asaccharolytica, Prevotella bivia, Bacteroides vulgates, Clostridium perfringens*, and *Fusobacterium* spp.

In some embodiments, the present disclosure relates to a method of treating or reducing the risk of a microbial infection in a human or animal comprising administering to the human or animal an effective amount of a compound disclosed herein, or a tautomer thereof, or a pharmaceutically acceptable salt of said compound or tautomer, or to the use of a compound disclosed herein, or a tautomer thereof, or a pharmaceutically acceptable salt of said compound or tautomer, in the manufacture of a medicament for treating, preventing, reducing the risk of, or delaying the onset of a microbial infection.

In some embodiments, the microorganism is *Legionella pneumophilia*.

In some embodiments, the microorganism *Enterococcus* spp. is selected from vancomycin susceptible isolate and vancomycin resistant isolate. In some embodiments, the microorganism *Escherichia coli* is selected from extended spectrum beta-lactamase (ESBL) producing isolate and *Klebsiella pneumoniae* carbapenemase (KPC) producing isolate. In some embodiments, the microorganism *Haemophilus influenzae* is a beta-lactamase positive isolate. In some embodiments, the microorganism *Klebsiella pneumoniae* is selected from extended spectrum beta-lactamase (ESBL) producing isolate and *Klebsiella pneumoniae* carbapenemase (KPC) producing isolate. In some embodiments, the microorganism *Klebsiella oxytoca* selected from extended spectrum beta-lactamase (ESBL) producing isolate and *Klebsiella pneumoniae* carbapenemase (KPC) producing isolate. In some embodiments, the microorganism *Staphylococcus aureus* is selected from methicillin susceptible isolate and methicillin resistant isolate. In some embodiments, the microorganism *Staphylococcus epidermidis* is selected from methicillin susceptible isolate and methicillin resistant isolate. In some embodiments, the microorganism *Streptococcus pneumoniae* is selected from penicillin susceptible isolate and penicillin resistant isolate.

In some embodiments, a method or use disclosed herein is a method or use to treat a subject that would be subjected to a surgical or invasive medical procedure. Such a subject can be considered to be in need of the methods of treating, reducing the risk of or preventing the infection due to a surgical procedure or an invasive medical procedure. Such a subject can also be considered to be in need of peri-operative prophylaxis.

In some embodiments, the present disclosure relates to a method, use, or compound disclosed herein, wherein the amount of compound or a tautomer thereof, or a pharmaceutically acceptable salt of said compound or tautomer comprises from 0.1 mg to 1500 mg.

In some embodiments, the present disclosure relates to a method, use, or compound disclosed herein wherein the compound, or a tautomer thereof, or a pharmaceutically acceptable salt of said compound or tautomer, is administered optically, ophthalmically, nasally, orally, parenterally, topically, or intravenously.

In some embodiments, the present disclosure relates to a method of synthesizing a compound disclosed herein, or a tautomer thereof, or a pharmaceutically acceptable salt of said compound or tautomer.

In some embodiments, the present disclosure relates to a medical device containing a compound disclosed herein or a tautomer thereof, or a pharmaceutically acceptable salt of said compound or tautomer. In some embodiments, the device is a stent.

3. Synthesis of the Compounds of the Disclosure

The compounds of the present disclosure can be synthesized by using art recognized techniques, such as those described in US 2012-0220566, WO 2012/173689, or PCT/US2014/054869, the contents of each of which are incorporated herein by reference in their entireties. The compounds thus obtained can be further purified, for example, by flash column chromatography, high performance liquid chromatography, crystallization, or any known purification method.

In one embodiment, compounds of the present disclosure can be synthesized according to the synthetic Schemes 1-3 below:

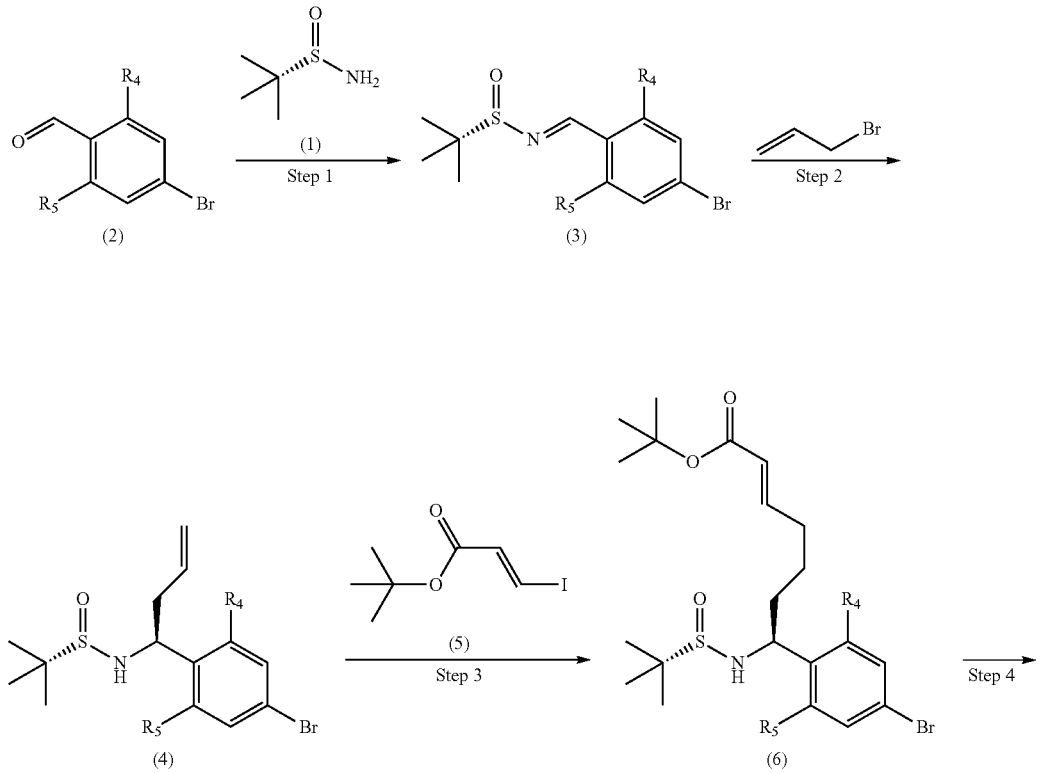

-continued
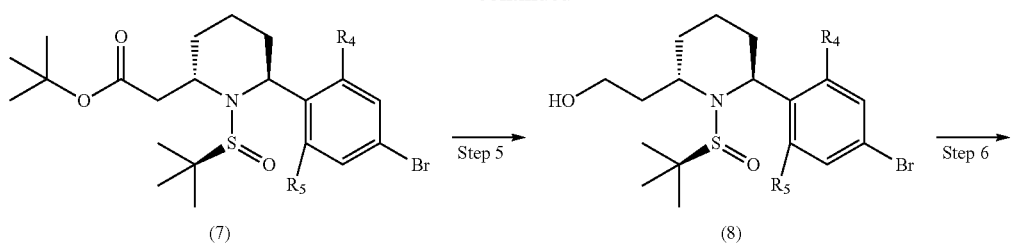
(7) → Step 5 → (8) → Step 6 →
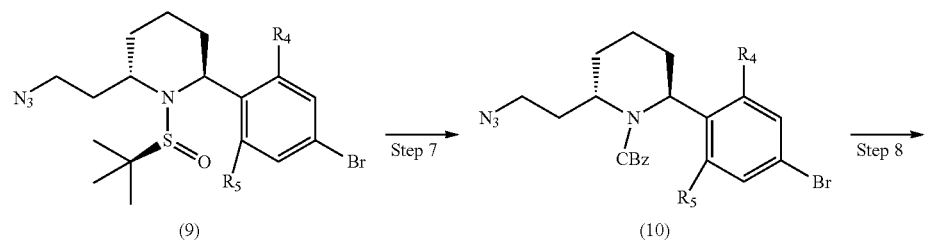
(9) → Step 7 → (10) → Step 8 →
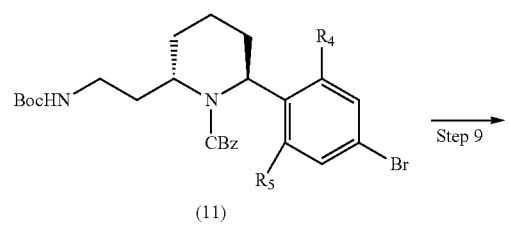
(11) → Step 9 →
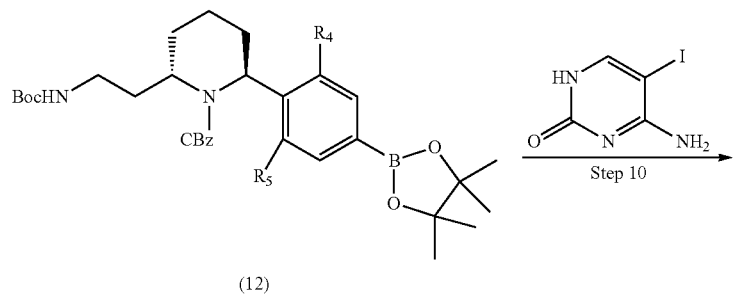
(12) + Step 10 →
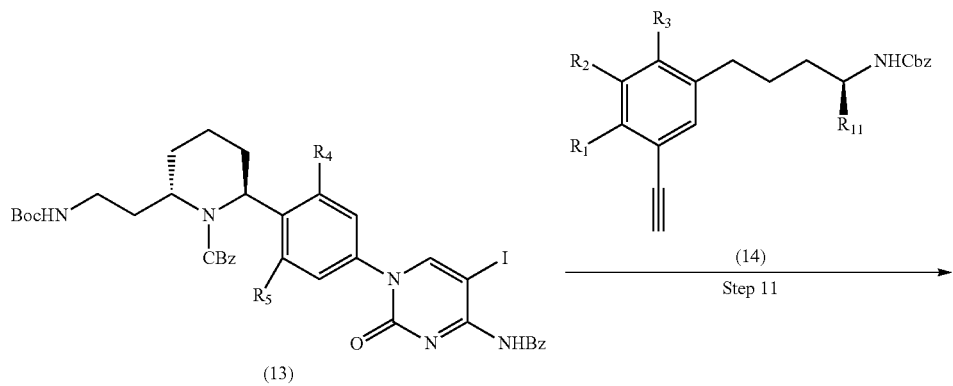
(13) + (14) → Step 11 →

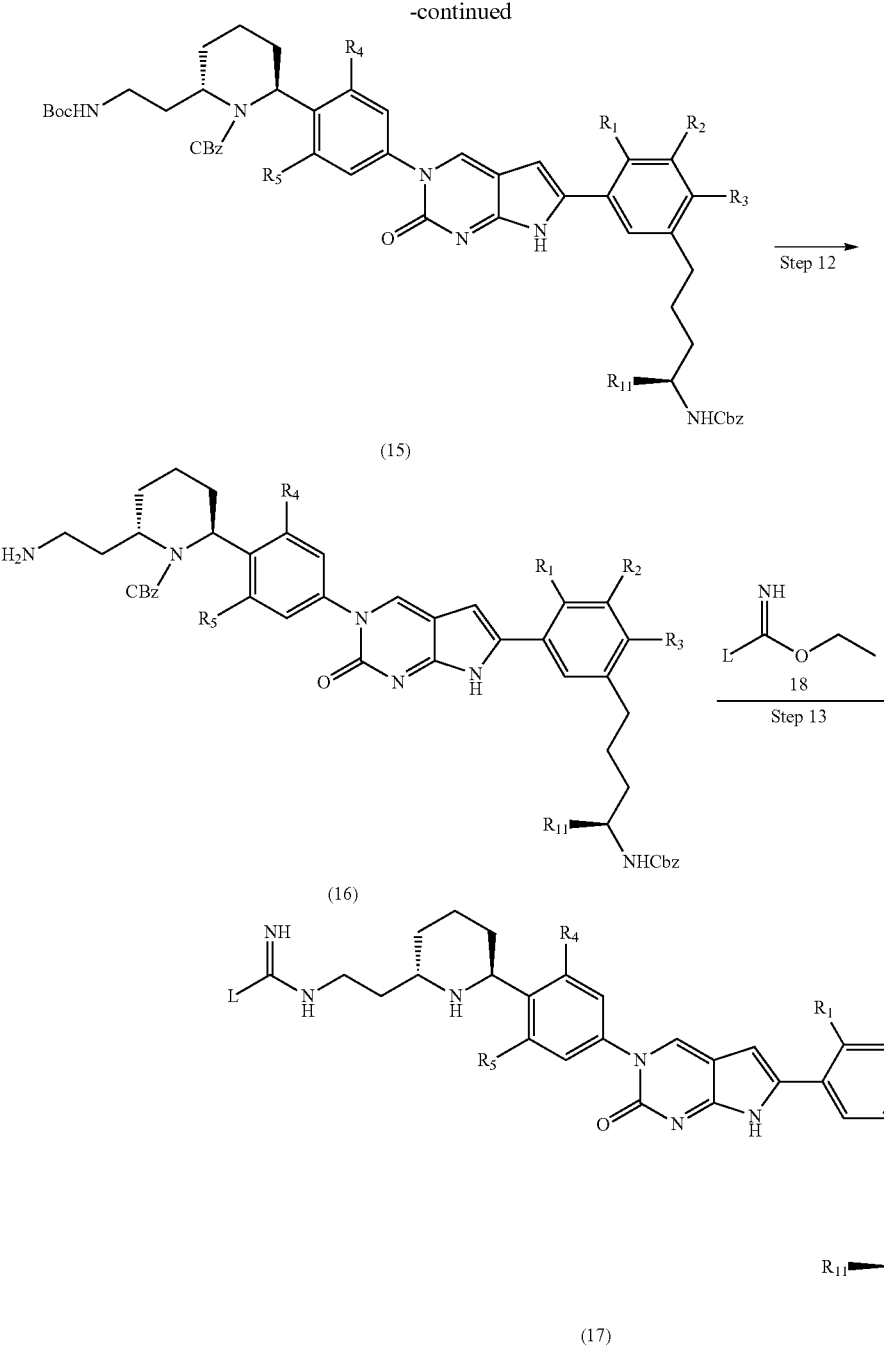

Referring to Scheme 1:

Step 1: (S)-(−)-2-methyl-2-propanesulfinamide (1) and aldehyde (2) are reacted to yield (3). In some embodiments, the reaction is carried out is a solvent (e.g., dichloromethane). In some embodiments, the reaction is carried out at a temperature from about 30° C. to about 50° C. (e.g., at 40° C.). In some embodiments, the reaction is carried out in the presence of a base (e.g., cesium carbonate).

Step 2: Intermediate (3) is reacted with allyl bromide to obtain (4). In some embodiments, the reaction is carried out in a solvent (e.g., N—N'-dimethylformamide). In some embodiments, the reaction is carried out in the presence of activated zinc.

Step 3: Intermediate (4) is reacted with iodoacrylate (5) to yield (6). In some embodiments, the reaction is carried out in the presence of a catalyst. In some embodiments, the catalyst is Pd(PPh$_3$)$_4$.

Step 4: Intermediate (6) is reacted with a base to afford (7). In some embodiments, the base is cesium carbonate. n some embodiments, the reaction is carried out in a solvent (e.g., N—N'-dimethylformamide).

Step 5: Intermediate (7) is reacted with a reducing agent to obtain (8). In some embodiments, the reducing agent is DIBAL.

Step 6: Intermediate (8) is reacted with azide-containing reagent to obtain (9). In some embodiments, the azide-containing reagent is diphenylphosphoryl azide (DPPA). In some embodiments, the reaction is carried out in the presence of a base (e.g., DBU). In some embodiments, the reaction is carried out at a temperature from about 40° C. to about 120° C. (e.g., at about 80° C.).

Step 7: Intermediate (9) is treated with an acid (e.g., HCl)) to remove tert-butylsulfinyl auxiliary group. The resultant NH-containing intermediate is reacted with a protecting group (e.g., Cbz-$C_1$) to yield intermediate (10).

Step 8: Intermediate (10) is reacted with triphenylphosphine to reduce the azide group. In some embodiments, the reaction is carried out at a temperature from about 35° C. to about 75° C. (e.g., at about 55° C.). The resultant $NH_2$-containing intermediate is reacted with a protecting group (e.g., Boc anhydride) to yield (11).

Step 9: Intermediate (11) is reacted with bispinacolatodiborane to obtain (12). In some embodiments, the reaction is carried out in the presence of a catalyst (e.g., $PdCl_2$(dppf).$CH_2Cl_2$). In some embodiments, the reaction is carried out in a solvent (e.g., dimethyl sulfoxide (DMSO)). In some embodiments, the reaction is carried out in the presence of a base (e.g., potassium acetate).

Step 10: Intermediate (12) is reacted with 5-iodocytosine to yield the free amine intermediate. In some embodiments, the reaction is carried out in presence of a catalyst and a ligand (e.g., copper acetate monohydrate and tetramethylehtylenediamine). The free amine intermediate is reacted with a protecting group (e.g., benzoic anhydride) to yield (13).

Step 11: Intermediate (13) is reacted with (14) to yield a protected intermediate. In some embodiments, the reaction is carried out under Sonogashira coupling conditions. In some embodiments, the reaction is carried in the presence of catalyst (e.g., Pd($PPh_3$)$_4$ and CuI) and a ligand (e.g., N—N-diisopropylethylamine). The protected intermediate is hydrolyzed in the presence of an alcohol (e.g., methanol) to yield (15).

Step 12: Intermediate (15) is reacted with an acid (e.g., HCl) to yield (16). In some embodiments, the reaction is carried out in the presence of Charcoal-siliathiol.

Step 13: Intermediate (16) is reacted with ethoxyimine (18) to a protected intermediate. In some embodiments, the reaction is carried out in the presence of diisopropylethyl amine (DIPEA). The resultant Cbz-protected intermediate was reacted with an acid (e.g., HBr or HBr solution in acetic acid) to yield (17).

An analogous scheme may be used starting with 2', shown below, instead of 2, to obtain a compound of Formula (I) or Formula (II) wherein W is N.

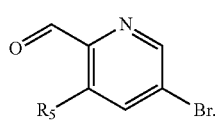

(2')

Scheme 2

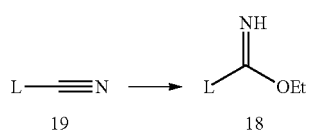

Referring to Scheme 2:

Substituted acetonitrile (19) is reacted with ethanol in the presence of an acid (e.g., HCl) to obtain (18). In some embodiments, the reaction is carried out 0° C. In some embodiments, the reaction is carried out in 4N HCl solution in organic solvent (e.g., 1,4-dioxane).

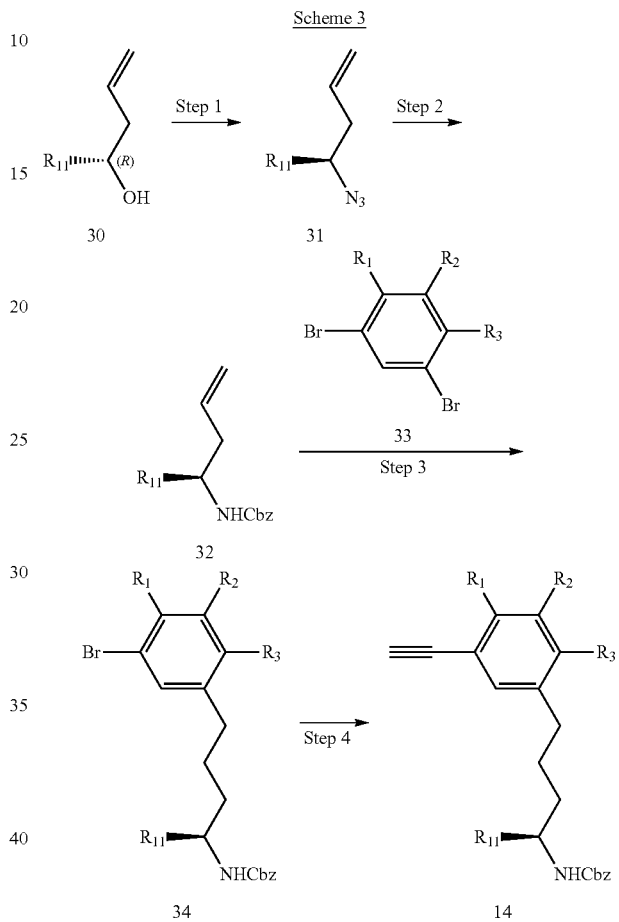

Scheme 3

Referring to Scheme 3:

Step 1: Alcohol (30) is reacted with an azide-containing reagent to obtain an azide (31). In some embodiments, the azide-containing reagent is $NaN_3$. In some embodiments, the alcohol (30) is reacted with methanesulfonyl chloride prior to reaction with $NaN_3$.

Step 2: The azide (31) is reacted with triphenylphosphine to reduce the azide group and obtain the free amine-containing intermediate. The free-amine containing intermediate is reacted with a protecting group (e.g., Cbz-C1) to yield (32).

Step 3: Alkene (32) is reacted with a boron reagent (e.g., 9-BBN) to obtain a boron intermediate which is further reacted with bromobenzene (33) to yield (34). In some embodiments, the reaction in carried out in the presence of a catalyst (e.g., Pd($PPh_3$)$_4$). In some embodiments, the reaction is carried out at a temperature from about 40° C. to about 80° C. (e.g., about 60° C.).

Step 4: bromobenzene (34) is reacted with an acetylene reagent (e.g., TMS-acetylene) to yield (14). In some embodiments, the reaction is carried out in the presence of a base (e.g., $K_2CO_3$).

In some embodiments, intermediate 14 can be prepared using methods and procedures analogous to those described in PCT/US2014/054869 and U.S. provisional application 61/875,643, the disclosures of which are incorporated herein by reference in their entireties.

The specific approaches and compounds shown in the schemes above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R_1$, $R_2$, $R_3$, etc.) or not. The suitability of a chemical group in a compound structure for use in the synthesis of another compound is within the knowledge of one of ordinary skill in the art.

Additional methods of synthesizing compounds of the formulae herein and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, Comprehensive Organic Transformations, VCH Publishers (1989); Fieser L et al., Fieser and Fieser's Reagents for Organic Synthesis, John Wiley and Sons (1994); and Paquette L, ed., Encyclopedia of Reagents for Organic Synthesis, John Wiley and Sons (1995) and subsequent editions thereof.

4. Characterization of Compounds of the Disclosure

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules disclosed herein for activity, for example, as anti-cancer, anti-bacterial, anti-fungal, anti-parasitic or anti-viral agents. Also, it can be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

(1) Surface Binding Studies. A variety of binding assays can be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor® from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization. Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis. It is contemplated that, in addition to characterization by the foregoing biochemical assays, the compound of interest can also be characterized as a modulator (for example, an inhibitor of protein synthesis) of the functional activity of the ribosome or ribosomal subunit.

Furthermore, more specific protein synthesis inhibition assays can be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3$H leucine or $^{35}$S methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is an inhibitor of protein synthesis.

(4) Antimicrobial assays and other evaluation. Furthermore, the compounds can be assayed for anti-proliferative or anti-infective properties on a cellular level. For example, where the target organism is a microorganism, the activity of compounds of interest can be assayed by growing the microorganisms of interest in media either containing or lacking the compound. Growth inhibition can be indicative that the molecule can be acting as a protein synthesis inhibitor. More specifically, the activity of the compounds of interest against bacterial pathogens can be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms.

(5) The translation-only assay for ribosomal protein production uses purified 70S ribosomes, corresponding S100 extracts containing the biological molecules necessary to support protein translation, and mRNA encoding firefly luciferase or another protein reporter. The resulting luminescence signal is proportional to protein translation and is determined by a luminescence assay plate reader (i.e. Victor2V Multilabel Reader). This assay is performed with varying concentrations of potential translation inhibitors in the assay. The resulting data are used to calculate IC50 values of inhibition for the compounds using appropriate software (i.e. MDL Assay Explorer with a one-site competition model of binding).

The in vitro activity of the compounds of the present disclosure can be determined. Antimicrobial testing is typically performed to determine the minimum inhibitory concentration (MIC). Minimum inhibitory concentrations (MICs) are determined by the microdilution method in a final volume of 100 µl according to protocols outlined by The Clinical and Laboratory Standards Institute (CLSI). Performance standards for reference strains are assessed within the same experimental design to maintain quality control. See, for example, Clinical Laboratory Standards Institute: Methods for dilution antimicrobial susceptibility tests for bacteria that grow aerobically M7-A8. Approved Standard-Eighth Edition. Wayne, Pa.: CLSI; December 2008; and Clinical Laboratory Standards Institute: Performance Standards for Antimicrobial Susceptibility Testing M100-S20; Approved Standard-Twentieth Edition. Wayne, Pa.: CLSI; June 2010.

For example, an agar-dilution MIC assay could be run using the following protocol. Pure cultures of isolates to be tested are grown on Chocolate Agar at 35° C. to 36.5° C. in a $CO_2$ enriched (5%) atmosphere for 16-18 hours. Using a cotton applicator or a bacteriologic loop, isolated colonies (or cells from less dense areas of growth on the plate) are suspended in 5 mL saline. The density of the suspension is then adjusted to contain $10^8$ colony forming units (CFU)/ml by comparison with a 0.5 McFarland $BaSO_4$ turbidity standard. This suspension is then diluted in 1:10 in MH broth to give $10^7$ CFU/ml. Using a multichannel pipettor, 0.002 mL spots of the bacterial suspension is dispensed onto the surface of the medium, i.e., $10^4$ CFU. Each plate of the set of antibiotic containing media plus a plate of Chocolate Agar or GCS medium (as a control to determine that all isolates grew) is inoculated. The inoculated plates are air-dried at room temperature for approximately 15 minutes. The plates are then inverted and incubated at 35° C. to 36.5° C. in a $CO_2$-enriched (5%) atmosphere for 24 hours. The plates are then examined for growth.

Another in vitro assay that can be performed is a time-kill kinetic assay. Using this assay, bactericidal activity can be determined by time-kill methodology as described by Clinical Laboratory Standards Institute. For example, the compounds to be tested are added to test flasks at concentrations of 2X-32X the MIC (determined, for example, using the assays described herein). Once dissolved, compounds are diluted in Giolitti Cantoni (GC) broth to a volume of 1 mL at the 25× desired final concentration; a flask containing 1 mL of GC broth without compound is prepared as a growth control. A 0.5 McFarland equivalent is prepared for the test organism, diluted 1:200 in pre-warmed GC broth, and incubated in 5% $CO_2$-enriched atmosphere at 35° C. for 30 minutes prior to exposure to the test compound. After the 30-minute pre-incubation, 24 mL is removed and added to each test flask for a final volume of 25 mL. A sample is removed from the growth control flask, diluted in Phosphate Buffered Saline (PBS) and plated on Chocolate Agar (CA) to confirm an inoculum of approximately $5 \times 10^5$ CFU/mL. Samples are then removed from all flasks at 1, 2, 4, 6, 8, and 24 hours, diluted in PBS and plated on CA to determine the number of viable cells in each flask. Plate counts are incubated at 35° C. in 5% $CO_2$-enriched atmosphere for 48 hours and colonies are counted. Plate counts are then graphed.

The antimicrobial and other drug properties of the compounds can further be evaluated in various in vivo mammalian assays, such as a mouse or rat peritonitis infectious models, skin and soft tissue models (often referred to as the thigh model), or a mouse pneumonia model. There are septicemia or organ infection models known to those skilled in the art. These efficacy models can be used as part of the evaluation process and can be used as a guide of potential efficacy in humans. Endpoints can vary from reduction in bacterial burden to lethality. For the latter endpoint, results are often expressed as a $PD_{50}$ value, or the dose of drug that protects 50% of the animals from mortality.

To further assess a compound's drug-like properties, measurements of inhibition of cytochrome P450 enzymes and phase II metabolizing enzyme activity can also be measured either using recombinant human enzyme systems or more complex systems like human liver microsomes. Further, compounds can be assessed as substrates of these metabolic enzyme activities as well. These activities are useful in determining the potential of a compound to cause drug-drug interactions or generate metabolites that retain or have no useful antimicrobial activity.

To get an estimate of the potential of the compound to be orally bioavailable, one can also perform solubility and Caco-2 assays. The latter is a cell line from human epithelium that allows measurement of drug uptake and passage through a Caco-2 cell monolayer often growing within wells of a 24-well microtiter plate equipped with a 1 micron membrane. Free drug concentrations can be measured on the basolateral side of the monolayer, assessing the amount of drug that can pass through the intestinal monolayer. Appropriate controls to ensure monolayer integrity and tightness of gap junctions are needed. Using this same system one can get an estimate of P-glycoprotein mediated efflux. P-glycoprotein is a pump that localizes to the apical membrane of cells, forming polarized monolayers. This pump can abrogate the active or passive uptake across the Caco-2 cell membrane, resulting in less drug passing through the intestinal epithelial layer. These results are often done in conjunction with solubility measurements and both of these factors are known to contribute to oral bioavailability in mammals. Measurements of oral bioavailability in animals and ultimately in man using traditional pharmacokinetic experiments will determine the absolute oral bioavailability.

Experimental results can also be used to build models that help predict physical-chemical parameters that contribute to drug-like properties. When such a model is verified, experimental methodology can be reduced, with increased reliance on the model predictability.

(5) Animal Pharmacology and Toxicology. The compounds of the present disclosure can be evaluated for efficacy in well-known animal models. The following table provides representative animal models for various infection indications.

| Target Infection Indication | Animal Model of Efficacy |
| --- | --- |
| HAP/VAP | Efficacy in mouse and/or rat pneumoniae model vs. respiratory tract infection pathogens of interest (*Streptococcus pneumoniae*, including multi-drug resistant *Streptococcus pneumoniae*, *H. influenzae*, methicillin resistant *Staphylococcus aureus* (MRSA), and *Pseudomonas. aeruginosa*) |
| cSSSI | Efficacy in mouse model against pathogens of interest (MRSA, *K. pneumoniae*) |
| Sepsis | Efficacy in mouse peritonitis model vs. pathogens of interest (*E. coli*, *K. pneumoniae*, *E. faecalis*, MRSA) |
| cUTI | Efficacy in mouse model against *E. coli*, *K. pneumoniae* and/or MRSA) |
| Febrile neutropenia | Efficacy in mouse peritonitis model against *S. aureus*, *S. epidermidis*, *S. pneumoniae*, *S. pyogenes*, *P. aeruginosa* |

Animal Model for Complicated Skin and Skin Structure Infections (cSSSI): Murine Skin and Soft Tissue Infection Model of *Klebsiella pneumoniae* 1705966 in Thighs of Neutropenic Female CD-1 Mice This model is useful to assess the efficacy of compounds of the present disclosure in a *Klebsiella pneumoniae* 1705966 neutropenic mouse thigh infection model using female ICR (CD-1) mice.

Study Design:

Species: Female ICR (CD-1) Mice, 8 to 9 weeks old, weighting 25-29 g.

Inoculum: *Klebsiella pneumoniae* 17059663 was streaked from frozen stock onto Blood agar (Tryptic Soy Agar+5% Sheep Blood), BD, #221261) and incubated overnight at 35° C. After overnight incubation, enough bacteria (approx. 1 full loop) to measure $OD_{625}$=0.990 was transferred to plate and diluted into 10 ml pre-warmed Mueller-Hinton broth. This culture was further diluted 1:1000 into pre-warmed MH broth and grown for approximately 2 hours at 35° C. with shaking. Each mouse was given 0.1 mL of 1:1000 dilution culture injected into both caudal thigh muscles under isoflurane inhalation anesthesia.

| Dilution | Initial O.D. | Final O.D. (after ~2 hr. incubation) |
| --- | --- | --- |
| 1:10 | 0.135 | 0.424 |
| 1:100 | 0.014 | 0.215 |
| 1:1000 | 0.001 | 0.035 |

Neutropenia is induced by intraperitoneal (I. P.) administration of Cyclophosphamide monohydrate on Day −4 (150 mg/kg) and Day −1 (100 mg/kg).

Vehicle: 0.9% sodium chloride

Dosing: Each mouse in the treated groups was given the appropriate dose of the compound to be tested in a volume of 0.2 ml, 2 and 8 hrs. post bacterial inoculation.

Time points:
Controls: 0, 2, 6, and 24 hrs.
Treated: 24 hrs.

Sampling: 2 or 3 mice/time point were euthanized via $CO_2$, and their caudal thigh muscles excised and homogenized. The thigh muscles were placed in 5 ml sterile PBS in Stomacher Filter bag and homogenized with MicroBiomaster80 (Brinkmann) for 60 seconds, normal setting and 1:10 dilutions were made per standard protocol in a 96-well plate. Aliquots of 25 ul for each dilution, as well as the homogenate, were plated on blood agar plates and incubated at 35° C. to determine the CFU/mL over the time course. After overnight incubation, colonies were counted.

Animal Model for Sepsis:

Murine Peritonitis Model (*E. coli, K. Pneumoniae, E. Faecalis*, MRSA) This model is used to evaluate the effect of subcutaneous (SC) treatment with compounds of the present disclosure on growth of *Escherichia coli A* TCC 25922 in a mouse peritonitis model using female Swiss Webster mice.

Controls:
Negative: Inoculum only
Inoculum Vehicle Intraperitoneal
Positive: Ciprofloxacin Study Design:
Species: Female Swiss Webster Mice
Inoculation: *Escherichia coli* ATCC 25922 is made by adding 1 ml (4/6/07) stock to 9 ml 0.25% Brewer's Yeast to make (1:10), then 1 ml of the (1:10) will be added to 9 ml 0.25% Brewer's Yeast to make (1:100), then 1 ml of the (1:100) will be added to 9 ml 0.25% Brewer's Yeast to make (1:1000), then 2.5 ml of the (1:1000) will be added to 122.5 ml 0.25% Brewer's Yeast to make (1:50,000), 1 ml/mouse will be inoculated intraperitoneally (IP).

Route of Administration: SC

Dosing: Vehicle for compounds of the present disclosure: Saline or 50 mM Sodium phosphate buffer in 10% Captisol in water, pH=7.2.

Dose Administration: Q3H×3 beginning at 30 min post bacterial inoculation Study Duration: 24 hrs. 0.25% Brewer's Yeast Extract (BYE): Dilute 2% prepared on 11/12/09 (Lot. 2158K, MP Biomedicals) 25 ml 2%+175 ml 1×PBS.

Outcome Measures: Colony Forming Unit's from peritoneal wash and spleen homogenate and drug levels from wash, spleen homogenate, and plasma.

Blood is collected via cardiac puncture while mouse is under $CO_2$ narcosis. The whole blood sample is placed in heparinized eppendorf tubes and kept on wet ice until centrifuged (4 min @ 14,000 rpm). Plasma is transferred to 96 deep-well block on dry ice and stored at −20° C. Immediately following blood collection, 2 ml of sterile PBS (phosphate buffered saline) was injected into the peritoneal cavity with a 25G needle. The abdomen was gently massaged, and a small incision was made to allow access to the peritoneal cavity. The peritoneal wash fluid was collected using sterile technique, serially diluted 1:10, plated on blood agar plates, and incubated overnight at 35° C.

Spleens were harvested and placed in 1 ml sterile PBS in Stomacher bag and homogenized with MicroBiomaster80 (Brinkmann) for 60 seconds, normal setting and 1:10 dilutions were made. 25 µl of each dilution, as well as the homogenate, was plated on blood agar plates and incubated at 35° C. to determine the CFU/mL over the time course. After overnight incubation, colonies were counted.

Other Animal Models

Similarly, other animal infection models can be used for hospital acquired pneumonia (HAP)/ventilator acquired pneumonia (VAP), complicated urinary tract infections (cUTI), and febrile neutropenia.

5. Formulation and Administration

The compositions and methods of the present disclosure can be practiced by delivering the compounds of the present disclosure using a means for delivery e.g., any suitable carrier. The dose of active compound, mode of administration and use of suitable carrier will depend upon the intended patient or subject and the targeted microorganism, e.g., the target bacterial organism. The formulations, both for human medical use and veterinary use, of compounds according to the present disclosure typically include such compounds in association with a pharmaceutically acceptable carrier.

The carrier(s) should be "acceptable" in the sense of being compatible with compounds of the present disclosure and not deleterious to the recipient. Pharmaceutically acceptable carriers, in this regard, are intended to include any and all solvents, dispersion media, coatings, absorption delaying agents, and the like, compatible with pharmaceutical administration. Supplementary active compounds (identified or designed according to the disclosure and/or known in the art) also can be incorporated into the compositions. In some embodiments, some formulations are prepared by bringing the compound into association with a liquid carrier or a finely divided solid carrier or both, and then, if necessary, shaping the product into the desired formulation.

A pharmaceutical composition of the disclosure should be formulated to be compatible with its intended route of administration. Solutions or suspensions can include the following components: a sterile diluent such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present disclosure suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants include, for example, for transmucosal administration, detergents and bile salts. Transmucosal administration can be accomplished through the use of nasal sprays or suppositories. For transdermal administration, the active compounds typically are formulated into ointments, salves, gels, or creams.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Liposomal suspensions can also be used as pharmaceutically acceptable carriers.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations disclosed herein. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

Generally, an effective amount of dosage of active compound will be in the range of from about 0.1 to about 100 mg/kg of body weight/day, more preferably from about 1.0 to about 50 mg/kg of body weight/day. The amount administered will also likely depend on such variables as the type of surgery or invasive medical procedure, the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

Nonlimiting doses of active compound comprise from about 0.1 to about 1500 mg per dose.

As is understood by one of ordinary skill in the art, generally, when dosages are described for a pharmaceutical active, the dosage is given on the basis of the parent or active moiety. Therefore, if a salt, hydrate, or another form of the parent or active moiety is used, a corresponding adjustment in the weight of the compound is made, although the dose is still referred to on the basis of the parent or active moiety delivered. As a nonlimiting example, if the parent or active moiety of interest is a monocarboxylic acid having a molecular weight of 250, and if the monosodium salt of the acid is desired to be delivered to be delivered at the same dosage, then an adjustment is made recognizing that the monosodium salt would have a molecular weight of approximately 272 (i.e., minus 1H or 1.008 atomic mass units and plus 1 Na or 22.99 atomic mass units). Therefore, a 250 mg dosage of the parent or active compound would correspond to about 272 mg of the monosodium salt, which would also deliver 250 mg of the parent or active compound. Said another way, about 272 mg of the monosodium salt would be equivalent to a 250 mg dosage of the parent or active compound.

Formulation Examples

IA. Formulation for Intravenous Administration

| Ingredients | Amount |
|---|---|
| Antimicrobial Compound of the present disclosure | 0.1-1500 total mg |
| Dextrose, USP | 50 mg/ml |
| Sodium citrate, USP | 1.60-1.75 mg/ml |
| Citric Acid, USP | 0.80-0.90 mg/ml |
| Water, USP | q.s |

This formulation for intravenous administration is formulated by heating water for injection to about 60° C. Next the sodium citrate, citric acid and dextrose are added and stirred until dissolved. A solution or aqueous slurry of the antimicrobial compound is added to the previous mixture and stirred until dissolved. The mixture is cooled to 25° C. with stirring. The pH is measured and adjusted if necessary. Lastly the mixture is brought to the desired volume, if necessary, with water for injection. The mixture is filtered, filled into the desired container (vial, syringe, infusion container, etc.), over wrapped and terminally moist heat sterilized.

This formulation is useful for intravenous administration, either bolus or infusion, to a patient for treating, preventing, reducing the risk of, or delaying the onset of infection.

IB. Formulation for Intravenous Administration

This formulation for intravenous administration utilizes 6.5 nM tartaric acid buffer in 5% Dextrose, and has a pH of 4.4. This formulation is useful for intravenous administration, either bolus or infusion, to a patient for treating, preventing, reducing the risk of, or delaying the onset of infection.

II. Lyophilisate for Reconstitution

Alternatively, the antimicrobial compound can be provided as a lyophilisate which can be reconstituted before intravenous or intramuscular administration.

| Ingredient | mg per injection vial |
|---|---|
| Antimicrobial Compound of the present disclosure | 0.1-1500 |
| Cyclodextrin | 1500 |

Reconstitution solution for a volume to be administered of 50 ml (infusion): 5% aqueous glucose solution.
Reconstitution solution for a volume to be administered of 15 ml (bolus): 3.3% aqueous glucose solution.
The foregoing lyophilisate is useful for reconstitution and intravenous administration, either bolus or infusion, to a patient for treating, preventing, reducing the risk of, or delaying the onset of infection.

III. Lyophilisate for Reconstitution

| Ingredient | mg per injection vial |
|---|---|
| Antimicrobial Compound of the present disclosure | 0.1-1500 |
| soya lecithin | 2250 |
| Sodium cholate | 1500 |

Reconstitution solution for a volume to be administered of 50 ml (infusion): 4% aqueous glucose solution.
Reconstitution solution for a volume to be administered of 15 ml (bolus): 2% aqueous glucose solution
The foregoing lyophilisate is useful for reconstitution and intravenous administration, either bolus or infusion, to a patient for treating, preventing, reducing the risk of, or delaying the onset of infection.

IV. Lyophilisate for Reconstitution

| Ingredient | mg per injection vial |
|---|---|
| Antimicrobial Compound of the present disclosure | 0.1-1500 |
| soya lecithin | 900 |
| Sodium glycocholate | 540 |

Reconstitution solution for a volume to be administered of 15 ml (bolus): 3.3% aqueous glucose solution.
The foregoing lyophilisate is useful for reconstitution and intravenous administration, either bolus or infusion, to a patient for treating, preventing, reducing the risk of, or delaying the onset of infection.

V. Tablet for Oral Administration

| Ingredients | Per Tablet | Per 4000 Tablets |
|---|---|---|
| Antimicrobial Compound of the present disclosure | 0.1-1500 mg | 0.4-6000 g |
| Anhydrous Lactose, NF | 110.45 mg | 441.8 g |
| Microcrystalline Cellulose NF | 80.0 mg | 320.0 g |
| Magnesium Stearate Impalpable Powder NF | 1.00 mg | 4.0 g |
| Croscarmellose Sodium NF Type A | 2.00 mg | 8.0 g |

The antimicrobial compound (any of the compounds equivalent to the desired delivery strength, e.g., 50 to 1500 mg per tablet) is premixed with ⅓ of the microcrystalline cellulose NF and ½ of the anhydrous lactose NF in a ribbon blender for 5 minutes at 20 RPM. To the premix is added the remaining ⅔ of the microcrystalline cellulose NF and the remaining ½ of the anhydrous lactose NF. This is blended for 10 minutes at 20 RPM. Croscarmellose sodium is added to the blended powders and mixed for 5 minutes at 20 RPM. Finally the magnesium stearate is added to the mixture by passing through a 90 mesh screen and blended for an additional 5 minutes at 20 RPM. The lubricated mixture is compressed to provide tablets of 500 mg active ingredient.

These tablets are useful for oral administration to a patient for treating, prevention, reducing the risk of, or delaying the onset of infection.

6. Examples

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

The compounds or tautomers thereof, or pharmaceutically acceptable salts of said compounds or tautomers of the present disclosure can be prepared using known chemical transformations adapted to the particular situation at hand.

Some of the abbreviations used in the following experimental details of the synthesis of the examples are defined below: h or hr=hour(s); min=minute(s); mol=mole(s); mmol=millimole(s); M=molar; μM=micromolar; g=gram(s); μg=microgram(s); rt=room temperature; L=liter(s); mL=milliliter(s); Et$_2$O=diethyl ether; THF=tetrahydrofuran; DMSO=dimethyl sulfoxide; EtOAc=ethyl acetate; Et$_3$N=triethylamine; i-Pr$_2$NEt or DIPEA=diisopropylethylamine; CH$_2$Cl$_2$=methylene chloride; CHCl$_3$=chloroform; CDCl$_3$=deuterated chloroform; CCl$_4$=carbon tetrachloride; MeOH=methanol; CD$_3$OD=deuterated methanol; EtOH=ethanol; DMF=dimethylformamide; BOC=t-butoxycarbonyl; CBZ=benzyloxycarbonyl; TBS=t-butyldimethylsilyl; TBSCl=t-butyldimethylsilyl chloride; TFA=trifluoroacetic acid; DBU=diazabicycloundecene; TBDPSCl=t-butyldiphenylchlorosilane; Hunig's Base=N,N-diisopropylethylamine; DMAP=4-dimethylaminopyridine; CuI=copper (I) iodide; MsCl=methanesulfonyl chloride; NaN$_3$=sodium azide; Na$_2$SO$_4$=sodium sulfate; NaHCO$_3$=sodium bicarbonate; NaOH=sodium hydroxide; MgSO$_4$=magnesium sulfate; K$_2$CO$_3$=potassium carbonate; KOH=potassium hydroxide; NH$_4$OH=ammonium hydroxide; NH$_4$Cl=ammonium chloride; SiO$_2$=silica; Pd—C=palladium on carbon; Pd(dppf)C$_{12}$=dichloro[1,1'-bis(diphenylphosphino)ferrocene] palladium (II).

Exemplary compounds synthesized in accordance with the disclosure are listed in Table 1, Table 1a, or Table 1b. A bolded or dashed bond is shown to indicate a particular stereochemistry at a chiral center, whereas a wavy bond indicates that the substituent can be in either orientation or that the compound is a mixture thereof.

The compounds of the present disclosure can be prepared, formulated, and delivered as salts. For convenience, the compounds are generally shown without indicating a particular salt form.

The compounds of the present disclosure can be made using synthetic chemical techniques well known to those of skill in the art.

Example 1: Syntheses of Compounds 1-293

Compounds 1-293 may be prepared according to the methods described in Schemes 1-3 and according to the methods and procedures similar to those described for the synthesis of compound 120. Compound 120 was synthesized according to the methods described below:

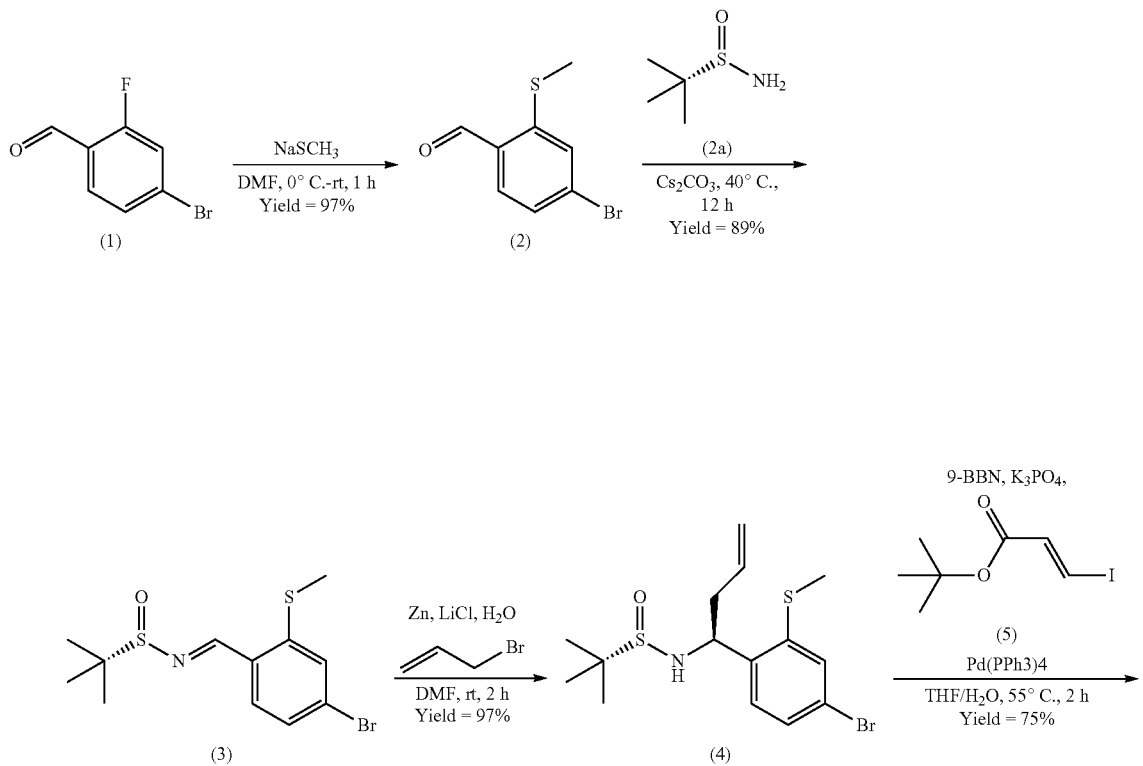

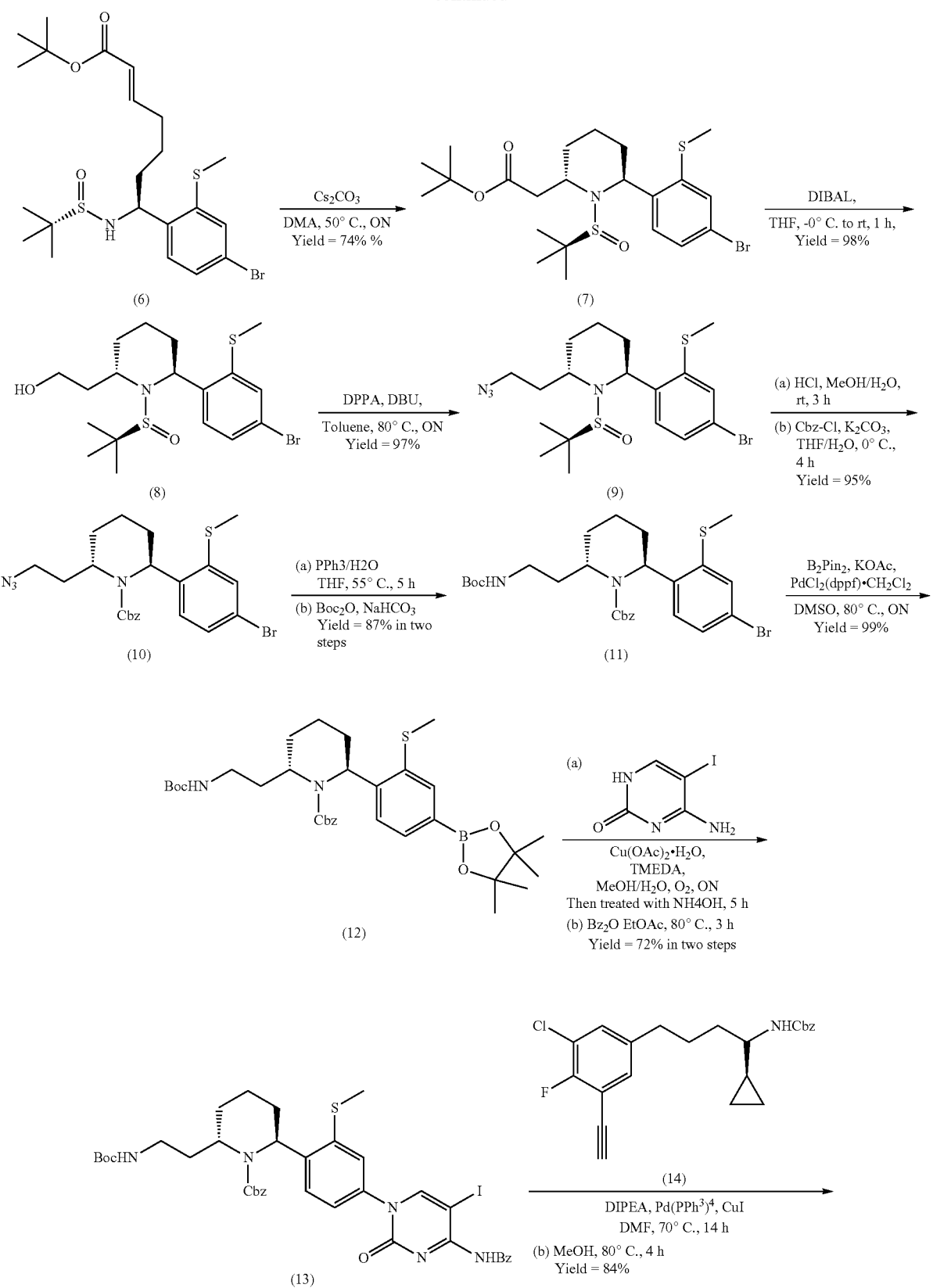

-continued

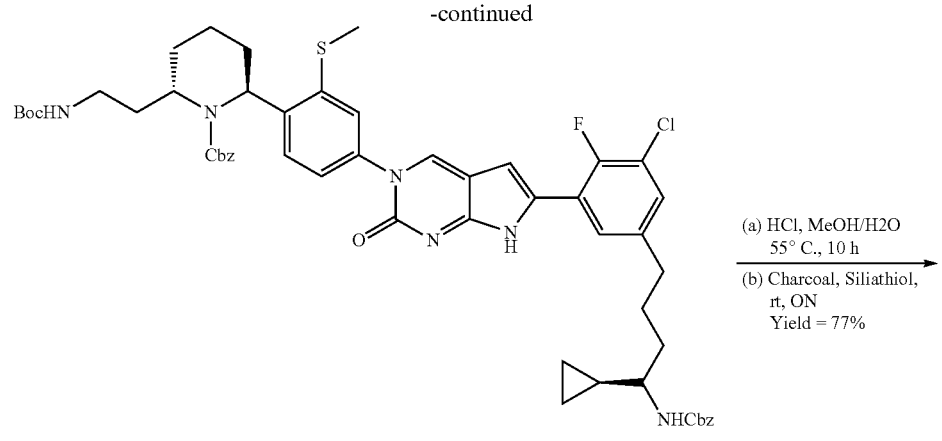

(a) HCl, MeOH/H2O
 55° C., 10 h
(b) Charcoal, Siliathiol,
 rt, ON
 Yield = 77%

(15)

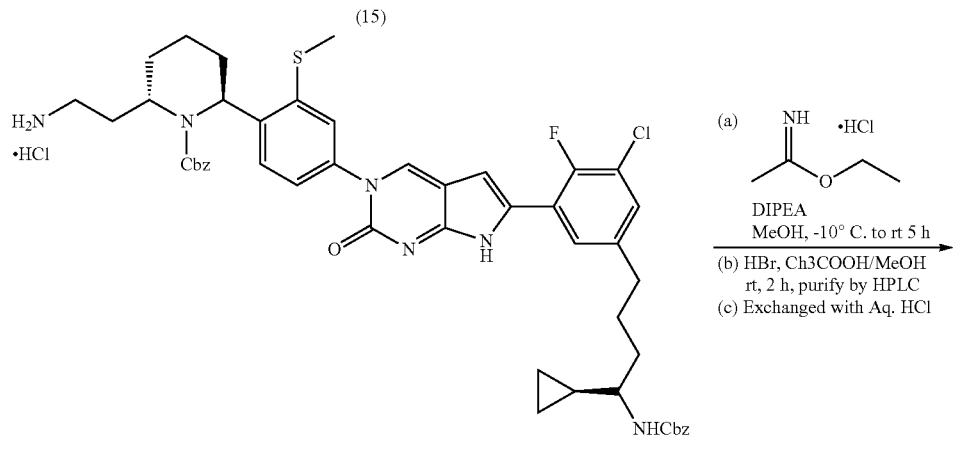

(a) ![structure: ethyl acetimidate HCl] DIPEA
MeOH, -10° C. to rt 5 h
(b) HBr, Ch3COOH/MeOH
rt, 2 h, purify by HPLC
(c) Exchanged with Aq. HCl (16)

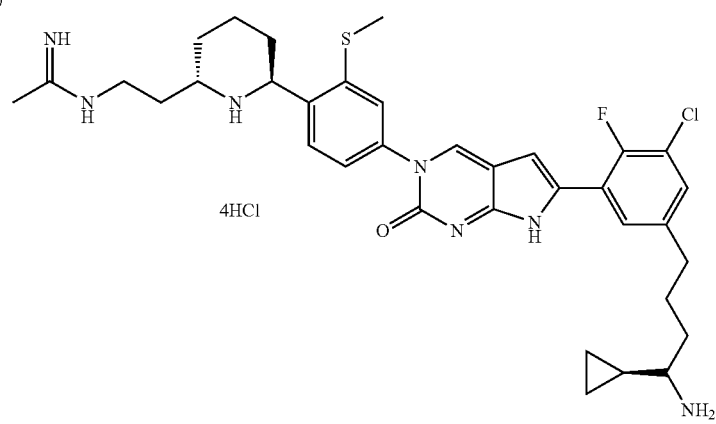

(compounds 120)

Experimental (Referring to Synthetic Scheme for Compound 120)

The solution of 4-Bromo-2-fluoro-benzaldehyde (1) (30.45 g, 150 mmol) in anhydrous dimethylformamide (214 ml) was cooled down to 0° C. To this cold solution 11.05 g (157.5 mmol) of sodium thioacetate was added in 10 portions in 3 min interval. After addition was complete the reaction mixture was stirred at the same temperature for 20 min then the cooling bath was removed and the reaction mixture was stirred for additional 30 min. Water (250 ml) was added and the product was extracted with Ethyl acetate (100 ml×2). Combined organic phase was washed with water (100 ml) and brine (100 ml), dried over sodium sulfate, concentrated and purified by flash chromatography (SiO$_2$ column, Heptane/Ethyl acetate gradient) to obtain 34 g of (yield, 98%) of 2 as yellowish solid. MS (ESI) m/z [M+H]+; calcd for C$_8$H$_8$BrOS; 230.9, found 230.8.

To the solution of tert-Butane sulfonamide 2a (18.36 g, 150 mmol) and 2 (34.66 g, 150 mmol) in anhydrous dichloromethane (150 ml) at room temperature under argon atmosphere was added cesium carbonate (50.35 g, 150 mmol). The mixture was stirred at 40° C. for about 14 h. LCMS showed the completion of the reaction. The reaction mixture was filtered through a pad of celite, concentrated and purified by flash chromatography (SiO$_2$ column, heptane/Ethyl acetate gradient) to obtain 44 g (yield, 88%) of 3 as a yellowish solid. MS (ESI) m/z [M+H]+; calcd for $C_{12}H_{17}BrNOS_2$; 333.9, found 333.9.

To the solution of 3 (30.08 g, 90 mmol) in 128 ml of anhydrous N—N'-dimethylformamide under argon atmosphere, activated zinc (10.29 g, 157.5 mmol), LiCl (6.67 g, 157.5 mmol) and water (0.127 g, 7.11 mmol) were added, placed in water bath and stirred for 5 min. To this mixture was added allyl bromide (19.05 g, 157.5 mmol) continued to stir vigorously for 1 h. LCMS showed complete consumption of 2. The reaction mixture was cooled down to 0° C., mixture of ethyl acetate (250 ml) and 1 N aqueous hydrochloric acid (250 ml) were slowly was slowly added and vigorously stirred until the entire solid disappeared which took approximately 2 h. Organic phase was separated, aqueous phase was extracted once more with ethyl acetate (100 ml). Combined organic phases were washed with water (150 ml) and brine (150 ml), dried over sodium sulfate, concentrated and purified by flash chromatography (SiO$_2$ column, Heptane/Ethyl acetate gradient) to obtain 30.77 g (yield, 91%) of 4 as a brownish solid. MS (ESI) m/z [M+H]+; calcd for $C_{15}H_{23}BrNOS_2$; 376.0, found 376.0.

To the stirring solution of 4 (28 g, 74.4 mmol) in 31 ml of anhydrous THF under argon atmosphere, the solution of 9-BBN (297.6 ml of 0.5 M in THF, 148.8 mmol) was added dropwise over a period of time of 1 h and 30 min. After completion of addition, the mixture was stirred for another 2 h. LCMS showed complete consumption of 4. To this mixture iodoacrylate 5 (prepared as described herein) was added and the mixture was then degassed and purged with argon three times followed by addition of Pd(PPh$_3$)$_4$ (2.68 g, 2.35 mmol). The mixture was stirred under argon at 55° C. for 2 h. LCMS showed compete consumption of the intermediate and formation of product. 50% of THF was evaporated, 250 ml of ethyl acetate was added, and organic phase was separated. Aqueous phase was extracted with another 250 ml of ethyl acetate. Combined organic phases was washed with water (150 ml) and brine (150 ml), dried over sodium sulfate, concentrated and purified by flash chromatography (SiO$_2$ column, Heptane/Ethyl acetate gradient) to obtain 35 g (yield, 93%) of 6 as a brownish sticky solid. MS (ESI) m/z [M+H]+; calcd for $C_{22}H_{35}BrNO_3S_2$; 504.1, found 504.2.

To the stirring solution of 6 (37.84 g, 75 mmol) in anhydrous dimethyl acetamide (187 ml), anhydrous cesium carbonate (122.18 g, 375 mmol) was added and the mixture was vigorously stirred at 50° C. for about 17 h. LCMS showed the presence of traces of 6, the reaction mixture was stirred for another 3 h at the same temperature. LCMS did not show any change. Reaction mixture was cooled down, filtered through a plug of celite, the filter cake was washed with 100 ml of ethyl acetate. To this solution 300 ml of water was added and product was extracted with ethyl acetate (250 ml×2). Combined organic phases were washed with water (150 ml) and brine (150 ml), dried over sodium sulfate, concentrated and purified by flash chromatography (SiO$_2$ column, Heptane/Ethyl acetate gradient) to obtain 28.3 g (yield 75%) of 7 as a yellowish solid. MS (ESI) m/z [M+H]+; calcd for $C_{22}H_{35}BrNO_3S_2$; 504.1, found 504.2.

To the stirring solution of 7 (29.76 g, 59 mmol) in anhydrous THF (147 ml) under argon atmosphere, the solution of DIBAL (177 ml of 1 M soln in THF, 177 mmol) was added dropwise (1 h 30 min). After completion of addition the reaction mixture was stirred for another 1 h. LCMS showed the complete consumption of 7 and formation of 8. The mixture was cooled down to 0° C., Rochelle's salt (100 ml 2N aqueous) was added dropwise (30 min, initial 10 ml was very slow) and left stirring at room temperature overnight. 300 ml of water was added organic phase was separated. Aqueous phase was extracted with 200 ml of ethyl acetate. Combined organic phases was washed with water (150 ml) and brine (150 ml), dried over sodium sulfate, concentrated and purified by flash chromatography (SiO$_2$ column, Heptane/Ethyl acetate gradient) to obtain 25.5 g (yield 97%) of 8 as a white solid. MS (ESI) m/z [M+H]$^+$; calcd for $C_{18}H_{29}BrNO_2S_2$; 434.1, found 434.1.

To the stirring solution of 8 (20.33 g, 49 mmol) in anhydrous toluene (140 ml), at 0° C. temperature under argon atmosphere diphenyl phosphoryl azide (18.8 g, 68.6 mmol) was added followed by dropwise addition of DBU (10.44 g, 68.6 mmol). Cooling bath was removed, stirred for 30 min and then it was placed in 80° C. temperature oil bath and stirred for about 12 h. LCMS shows the completion of the reaction. Reaction mixture was cooled down to room temperature, 20 ml of water was added and the product was extracted by EtOAc (100 ml×2). Combined organic phases were washed with water (100 ml×2) and brine (100 ml), dried over sodium sulfate and concentrated to dryness to obtain 22.5 g (crude yield, 99.93%) of 9 as yellowish sticky solid. The crude was approximately 90% pure and was directly used for the next step without further purification. MS (ESI) m/z [M+H]$^+$; calcd for $C_{18}H_{28}BrN_4OS_2$; 459.1, found 459.1.

To the stirring solution of 8 (22.49 g, ~49 mmol) in methanol (98 ml) aqueous HCl (12.25 ml 12 N, 147 mmol) was added dropwise and the mixture was stirred at room temperature for 1 h LCMS showed complete removal of tert-butyl sulfonyl group. Evaporated to dryness, dissolved in THF (98 ml), cooled down to 0° C., Cbz-Cl (10.03 g, 58.8 mmol) was added followed by dropwise addition of K$_2$CO$_3$ solution (98 ml, 2N) and reaction mixture was stirred for 2 h. LCMS showed completion of Cbz protection. Organic phase was separated; aqueous phase was extracted with 100 ml of ethyl acetate. Combined organic phases was washed with water (100 ml) and brine (100 ml), dried over sodium sulfate, concentrated and purified by flash chromatography (SiO$_2$ column, Heptane/Ethyl acetate gradient) to obtain 22 g (yield 92%) of 10 as a white solid. MS (ESI) m/z [M+H]$^+$; calcd for $C_{22}H_{26}BrN_4O_2S$; 489.1, found 489.1.

To the stirring solution of 10 (22 g, 45 mmol) in THF (277 ml), triphenylphosphine (17.7 g, 67.5 mmol) and water (23 ml) were added. The mixture was stirred at 55° C. for 4 h. LCMS showed complete reduction of azide to amine. The reaction mixture was cooled down to 0° C., Boc anhydride (11.79 g, 54 mmol) was added, followed by addition of 85.7 ml of saturated sodium bicarbonate solution and stirred for 2 h. LCMS showed complete consumption of intermediate amine and formation of 11. Organic phase was separated; aqueous phase was extracted with 100 ml of ethyl acetate. Combined organic phases was washed with brine (100 ml), dried over sodium sulfate, concentrated and purified by flash chromatography (SiO$_2$ column, Heptane/Ethyl acetate gradient) to obtain 19.74 g (yield 78%) of 11 as a white solid. MS (ESI) m/z [M+H]$^+$; calcd for $C_{27}H_{36}BrN_2O_4S$; 563.2, found 563.3.

To the solution of 11 (19.72 g, 35 mmol) in anhydrous DMSO (175 ml), bispinacolatodiborane (17.95 g, 70 mmol), potassium acetate (12.14 g, 122.5 mmol) and PdCl$_2$(dppf).CH$_2$Cl$_2$ (1.44 g, 1.75 mmol) were added. The mixture was degassed, purged with argon twice and stirred at 80° C. for 13 h. LCMS showed complete consumption of 11 and formation of 12. Cooled down to room temperature, 200 ml of water was added. Product was extracted with ethyl acetate (150 ml×2). Combined organic phases were washed with water (150 ml), 14% ammonium hydroxide (150 ml), water (150 ml) and brine (150 ml). It was dried over sodium sulfate, concentrated and purified by flash silica gel chromatography (Heptane/Ethyl acetate gradient) to obtain 19.70 g (yield, 93%) of 12 as a white solid. MS (ESI) m/z [M+H]$^+$; calcd for $C_{33}H_{48}BN_2O_6S$; 611.3, found 611.4.

To the solution of 12 (19.7 g, 32.3 mmol) in methanol (470 ml), 117 ml of water was added. To this mixture were added 5-iodocytosine (10.82 g, 45.22 mmol), and copper acetate monohydrate (6.44 g, 32.3 mmol) followed by tetramethylehtylenediamine (15 g, 129.2 mmol). The mixture was stirred at room temperature under open air for 14 h. Formation of green precipitate was observed. LCMS showed presence of around 5% of 12. It was stirred for another 3 h. LCMS showed no change. Methanol was evaporated. 400 ml of 28% NH$_4$OH and 400 ml of THF were added and stirred vigorously for 4 h until green precipitate was dissolved. Organic phase was separated, aqueous phase was extracted with 100 ml of ethyl acetate. Combined organic phases was washed with water (100 ml), and brine (1000 ml), dried over sodium sulfate and concentrated to dryness. The crude residue was dissolved in 235 ml of ethyl acetate, benzoic anhydride (10.33 g, 45.22 mmol) was added and the mixture was stirred at 80° C. for 2 h 30 min. LCMS showed completion of benzoylation of the intermediate amine. The reaction mixture was cooled down, washed with saturated sodium bicarbonate solution (100 ml×2) and brine (100 ml), dried over sodium sulfate, concentrated and purified by flash chromatography (silica gel column, Heptane/Ethyl acetate gradient) to obtain 19.14 g (yield, 72%) of 13 as a white solid. MS (ESI) m/z [M+H]$^+$; calcd for $C_{38}H_{43}IN_5O_6S$; 824.2, found 824.2. The solution of 13 (19.14 g, 23.25 mmol) and alkyne (10.22 g, 25.6 mmol) in anhydrous DMF (155 ml) was degassed and purged with argon three times. To this solution were added N—N-diisopropylethylamine (12.14 g, 93 mmol) followed by Pd(PPh$_3$)$_4$ (1.35 g, 1.16 mmol) and CuI (0.44 g, 2.32 mmol). The mixture was stirred at 70° C. for 12 h. LCMS showed completion of Sonogashira cyclization. The reaction mixture was cooled down to room temperature, 100 ml of methanol was added and stirred at 80° C. for 2 h 30 min. LCMS showed completion of debenzoylation and formation of 15. The reaction mixture was cooled down to room temperature, methanol was evaporated, 200 ml of water was added. Product was extracted by ethyl acetate (100 ml×3). Combined organic phases was washed with water (100 ml), 14% ammonium hydroxide (100 ml×2), water (100 ml) and brine (100 ml). The residue was dried over sodium sulfate, concentrated and purified by flash column chromatography (silica gel column, CH$_2$Cl$_2$/(90% CH$_2$Cl$_2$+9.8% methanol+ 0.2% NH$_4$OH)) to obtain 17.91 g (yield, 84%) of 15 as an orange solid. MS (ESI) m/z [M+H]$^+$; calcd for $C_{54}H_{61}C_1FN_6O_7S$; 991.4, found 991.5.

To the solution of 15 (20.82 g, 21 mmol) in 300 ml of methanol, HCl (73 ml of 2N in water, 147 mmol) was added and stirred at 70° C. for 4 h. LCMS showed complete removal of Boc group. The reaction mixture was cooled down, 5 g of siliathiol and 5 g of activated charcoal were added and the mixture was stirred overnight. Filtered through 10 g celite and evaporated to dryness in vacuo. The residue was dissolved in 50 ml of methanol and the product was precipitated by adding 500 ml of diethyl ether which was filtered and dried to obtain 15.77 g (yield, 81%) of 16 as yellow solid. MS (ESI) m/z [M+H]$^+$; calcd for $C_{49}H_{53}C_1FN_6O_5S$; 891.4, found 891.5.

To the solution of 16 (16.2 g, 17.5 mmol) in anhydrous methanol under argon atmosphere, ehtylacetimidate hydrochloride (4.35 g, 35 mmol) was added. The mixture was cooled down to about −10° C. and N—N-diisopropylethylamine (9.10 g, 70 mmol) was added dropwise and left stirring overnight without adding any more coolant. LCMS showed completion of amidination. Solvent was removed, residue was redissolved in 62 ml of methanol, cooled down to 0° C., 125 ml of HBr solution (33% in acetic acid) was added and stirred for 10 min. Cooling bath was removed and stirred for another 2 h and 30 min at room temperature. LCMS showed complete removal of Cbz groups. The solution was concentrated in vacuo and purified by HPLC using C$_{18}$ stationary phase (Column; Varian 300 g Microsorb 60-8 C$_{18}$, Irregular, Solvent A, water with 0.15% TFA, Solvent B, Methanol with 0.15% TFA, gradient 20-80% in 45 min, flow rate 60 ml/min, diluent; 1:1 mixture of methanol and water with 0.15% TFA, injection volume: 10 ml, product elution starts at 28 min). Desired fractions were concentrated to dryness after each run (which contains around 420 mg of product), TFA was exchanged partially with HCl (6N aq., 10 ml) dissolved in ethanol. For combined batches, TFA was fully exchanged with HCl (6N aq., 100 ml×2 with 100 ml of ethanol each time) and lyophilized to obtain 6.5 g (yield, 48%) of compound 120 as yellow solid. $^1$H NMR (300 MHz, D$_2$O): δ 8.42 (s, 1H), 7.71 (d, J=9 Hz, 2H), 7.50 (s, 2H), 7.45 (d, J=12 Hz, 3H), 7.34 (d, J=9 Hz, 1H), 6.81 (s, 1H), 4.92 (s, br, 1H), 3.81 (s, br, 1H), 3.53-3.37 (m, 2H), 2.70 (s, br, 2H), 2.57-2.45 (m, 5H), 2.33-2.21 (m, 4H), 2.17-2.01 (s, br, 2H), 2.01-1.90 (s, br, 4H), 1.83-1.70 (m, 4H), 0.97-0.84 (m, 1H), 0.71-0.53 (m, 2H). 0.37-0.27 (m, 2H), MS (ESI) m/z [M+H]$^+$; calcd for $C_{35}H_{44}C_1FN_7OS$; 664.3, found 664.3.

Synthetic scheme for Intermediate 5

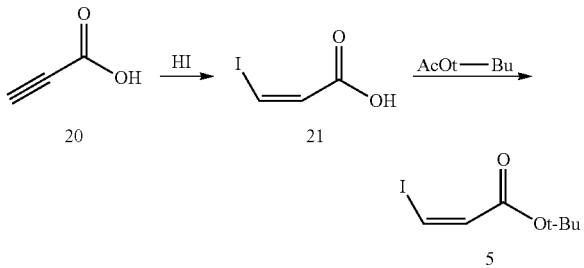

Experimental (Referring to Synthetic Scheme for Intermediate 5)

To a solution of 57% hydrogen iodide (60 mL) in water (90 mL) was added propynoic acid (propiolic acid) 20 (20 g). The resulting mixture was heated at 50° C. for 24 h. The mixture was cooled to room temperature and MTBE (100 mL) was added. The two layers were separated. The aqueous layer was extracted with MTBE (100 mL). The combined organic phase was washed with 2 M NaS$_2$O$_3$ (2×50 mL), 5% NaCl and dried over MgSO$_4$. The solution was filtered and concentrated to dryness to afford a beige solid product 21 (49 g, 87%). To a solution of (Z)-3-iodo-acrylic acid 21 (48 g) and t-BuOAc (140 g) in CH$_2$Cl$_2$ (144 mL, 3 vol.) was added TfOH (1.8 g). The solution was stirred at room temperature for 1 h. The reaction was deemed complete (acid: HPLC area % 20.27%). The solution was neutralized with 2 M K$_2$CO$_3$ (242 mL). Heptane (144 mL) was added. The two layers were separated. The aqueous layer was extracted with heptane (144 mL). The combined organic phase was washed with water (144 mL) and dried over MgSO$_4$. The solution was filtered and concentrated to dryness to afford an oil product 5 (49 g, 80%, HPLC area %: 98.22%).

Example 2—Antimicrobial Activity

The compounds of the present disclosure were tested for antimicrobial activity. These data are presented in Table 2. The Compounds 1-293 were run against *Eschericia coli* (*E. coli*) strain ATCC25922 and against *Staphylococcus aureus* (*S. aureus*) 11540 strain using a standard microdilution assay to determine minimum inhibitory concentrations (MICs). The data is presented whereby a "+" indicates that the compound has an MIC value of 16 micrograms/mL or less and a "−" indicates that the compound has an MIC value greater than 16 micrograms/mL. It will be recognized by one skilled in the art that the compounds can be assessed against other bacterial organisms and that the presentation of data for activity against *Eschericia coli* and *Staphylococcus aureus* are illustrative and in no way is intended to limit the scope of the present disclosure. The compounds of the present disclosure can be assayed against a range of other microorganisms depending upon the performance activity desired to be gathered. Furthermore, the "+" and "−" representation and the selection of a cutoff value of 16 micrograms/mL is also illustrative and in no way is intended to limit the scope of the present disclosure. For example, a "−" is not meant to indicate that the compound necessarily lacks activity or utility, but rather that its MIC value against the indicated microorganism is greater than 16 micrograms/mL.

TABLE 2

| # | MIC S. aureus | MIC E. coli |
|---|---|---|
| 2 | + | + |
| 3 | + | + |
| 4 | + | + |
| 6 | + | + |
| 7 | + | + |
| 8 | + | + |
| 9 | + | + |
| 10 | + | + |
| 11 | + | − |
| 12 | + | + |
| 13 | − | − |
| 14 | + | + |
| 15 | + | + |
| 16 | + | + |
| 17 | + | + |
| 18 | + | + |
| 19 | + | + |
| 20 | + | + |
| 21 | + | + |
| 22 | + | + |
| 23 | + | + |
| 24 | + | + |
| 25 | + | + |
| 26 | + | + |
| 27 | + | + |
| 28 | + | + |
| 29 | + | + |
| 30 | + | + |
| 31 | + | + |
| 32 | + | + |
| 33 | + | + |
| 34 | + | + |
| 35 | + | + |
| 36 | + | + |
| 37 | + | + |
| 38 | + | + |
| 39 | + | + |
| 40 | + | + |
| 41 | + | + |
| 42 | + | + |
| 43 | + | + |
| 44 | + | − |
| 45 | + | + |
| 46 | + | + |
| 47 | + | + |
| 48 | + | + |
| 49 | + | + |
| 50 | + | + |
| 51 | + | + |
| 52 | + | + |
| 53 | + | + |
| 54 | + | + |
| 55 | + | + |
| 56 | + | + |
| 57 | + | + |
| 58 | + | + |
| 59 | + | + |
| 60 | + | + |
| 61 | + | + |
| 62 | + | + |
| 63 | + | + |
| 64 | + | + |
| 65 | + | + |
| 66 | − | − |
| 67 | − | − |
| 68 | + | + |
| 69 | + | + |
| 70 | + | + |
| 71 | + | + |
| 72 | + | + |
| 73 | + | + |
| 74 | + | + |
| 75 | + | + |
| 76 | + | + |
| 77 | + | + |
| 78 | + | + |
| 79 | + | + |
| 80 | + | + |
| 81 | + | + |
| 82 | + | + |
| 83 | + | + |
| 84 | + | + |
| 85 | + | + |
| 86 | + | + |
| 87 | + | + |
| 88 | + | + |
| 89 | + | + |
| 90 | + | + |
| 91 | + | + |
| 92 | + | + |
| 93 | + | + |
| 94 | + | + |
| 95 | + | + |
| 96 | + | + |
| 97 | + | + |
| 98 | + | + |
| 99 | + | + |
| 100 | + | + |
| 101 | + | + |
| 102 | + | + |
| 103 | + | + |
| 104 | + | + |
| 105 | + | + |
| 106 | + | + |
| 107 | + | + |
| 108 | + | + |
| 109 | + | + |
| 110 | + | + |
| 111 | + | + |
| 112 | + | + |
| 113 | + | + |
| 114 | + | + |
| 115 | + | + |
| 116 | + | + |

TABLE 2-continued

| # | MIC S. aureus | MIC E. coli |
|---|---|---|
| 117 | + | + |
| 118 | + | + |
| 119 | + | + |
| 120 | + | + |
| 121 | + | + |
| 122 | + | + |
| 123 | + | + |
| 124 | + | + |
| 125 | + | + |
| 126 | + | + |
| 127 | + | + |
| 128 | + | + |
| 129 | + | + |
| 130 | + | + |
| 131 | + | + |
| 132 | + | + |
| 133 | + | + |
| 134 | + | + |
| 135 | + | + |
| 136 | + | + |
| 137 | + | + |
| 138 | + | + |
| 139 | + | + |
| 140 | + | + |
| 141 | + | + |
| 142 | + | + |
| 143 | + | + |
| 144 | + | + |
| 145 | + | + |
| 146 | + | + |
| 147 | + | + |
| 148 | + | + |
| 149 | + | + |
| 150 | + | + |
| 151 | + | + |
| 152 | + | + |
| 153 | + | + |
| 154 | + | + |
| 155 | + | + |
| 156 | + | + |
| 157 | + | + |
| 158 | + | + |
| 159 | + | + |
| 160 | + | + |
| 161 | + | + |
| 162 | + | + |
| 163 | + | + |
| 164 | + | + |
| 165 | + | + |
| 166 | + | + |
| 167 | + | + |
| 168 | + | + |
| 169 | + | + |
| 170 | + | + |
| 171 | + | + |
| 172 | + | + |
| 173 | + | + |
| 174 | + | + |
| 175 | + | + |
| 176 | + | + |
| 177 | + | + |
| 178 | + | + |
| 179 | + | + |
| 180 | + | + |
| 181 | + | + |
| 182 | + | + |
| 183 | + | + |
| 184 | + | + |
| 185 | + | + |
| 186 | + | + |
| 187 | + | + |
| 188 | + | + |
| 189 | + | + |
| 190 | + | + |
| 191 | + | + |
| 192 | + | + |
| 193 | + | + |
| 194 | + | + |
| 195 | + | + |
| 196 | + | + |
| 197 | + | + |
| 198 | + | + |
| 199 | + | + |
| 200 | + | + |
| 201 | + | + |
| 202 | + | + |
| 203 | + | + |
| 204 | + | + |
| 205 | + | + |
| 206 | + | + |
| 207 | + | + |
| 208 | + | + |
| 209 | + | + |
| 210 | + | + |
| 211 | + | + |
| 212 | + | + |
| 213 | + | + |
| 214 | + | + |
| 215 | + | + |
| 216 | + | + |
| 217 | + | + |
| 218 | + | + |
| 219 | + | + |
| 220 | + | + |
| 221 | + | + |
| 222 | + | + |
| 223 | + | + |
| 224 | + | + |
| 225 | + | + |
| 226 | + | + |
| 227 | + | + |
| 228 | + | + |
| 229 | + | + |
| 230 | + | + |
| 231 | + | + |
| 232 | + | + |
| 233 | + | + |
| 234 | + | + |
| 235 | + | + |
| 236 | + | + |
| 237 | + | + |
| 238 | + | + |
| 239 | + | + |
| 240 | + | + |
| 241 | + | + |
| 242 | + | + |
| 243 | + | + |
| 244 | + | + |
| 245 | + | + |
| 246 | + | + |
| 247 | + | + |
| 248 | + | + |
| 249 | + | + |
| 250 | + | + |
| 251 | + | + |
| 252 | + | + |
| 253 | + | + |
| 254 | + | + |
| 255 | + | + |
| 256 | + | + |
| 257 | + | + |
| 258 | + | + |
| 259 | + | + |
| 260 | + | + |
| 261 | + | + |
| 262 | + | + |
| 263 | + | + |
| 264 | + | + |
| 265 | + | + |
| 266 | + | + |
| 267 | + | + |
| 268 | + | + |
| 269 | + | + |
| 270 | + | + |

TABLE 2-continued

| # | MIC S. aureus | MIC E. coli |
|---|---|---|
| 271 | + | + |
| 272 | + | + |
| 273 | + | + |
| 274 | + | + |
| 275 | + | + |
| 276 | + | + |
| 277 | + | + |
| 278 | + | + |
| 279 | + | + |
| 280 | + | + |
| 281 | + | + |
| 282 | + | + |
| 283 | + | + |
| 284 | + | + |
| 285 | + | + |
| 286 | + | + |
| 287 | + | + |
| 288 | + | + |
| 289 | + | + |
| 290 | + | + |
| 291 | + | + |
| 292 | + | + |
| 293 | + | + |
| 317 | + | + |
| 318 | + | + |
| 319 | + | + |
| 320 | + | + |
| 321 | + | + |
| 322 | + | + |
| 323 | + | + |
| 325 | + | + |
| 326 | + | + |
| 327 | + | + |
| 328 | + | + |
| 329 | + | + |
| 330 | + | + |
| 331 | + | + |
| 332 | + | + |
| 333 | + | + |
| 334 | + | + |
| 335 | + | + |
| 336 | + | + |
| 337 | + | + |
| 338 | + | + |
| 339 | + | + |
| 340 | + | + |
| 341 | + | + |
| 342 | + | + |
| 343 | + | + |
| 344 | + | + |
| 346 | + | + |
| 347 | + | + |
| 348 | + | + |
| 349 | + | + |
| 350 | + | + |
| 351 | + | + |
| 352 | + | + |
| 353 | + | + |
| 355 | + | + |
| 356 | + | + |
| 357 | + | + |
| 358 | + | + |
| 360 | + | + |
| 362 | + | + |
| 363 | + | + |
| 364 | + | + |
| 365 | + | + |
| 366 | + | + |
| 369 | + | + |
| 370 | + | + |
| 377 | + | + |

Example 3—Rat Five Day Safety Study

The compounds of the present disclosure were tested for safety in a multi-day dosing study in rat. Key parameters that were monitored are bodyweight gain and hematological changes, particularly changes in reticulocyte counts. Male Sprague-Dawley (CD) juvenile rats were received from Charles River with double jugular vein catheters. For each compound, n=5. Doses for each compound were variable and were chosen to be at or near the maximum-tolerated dose in rat and were administered once daily via slow intravenous infusion at 10 mg/kg for 10 minutes, for 5 days. Bodyweights were recorded daily for the first 5 days (during the dosing period), then 2 to 3 times per week thereafter. Blood was collected via a jugular vein catheter into EDTA anti-coagulated tubes for complete blood counts (CBC) on Days 0 (baseline), 3 and 7. On Day 22, blood was drawn via a cardiac puncture into EDTA coated tubes for final CBC, and serum separator tubes for the complete clinical chemistry profile. The blood that was collected into serum separator tubes was allowed to clot at room temperature for approximately 30 minutes, spun in a centrifuge at 2000 rpm, and the resulting serum was aliquoted. All samples were sent on wet ice to Charles River Labs for analysis. The data is presented in Table 3 whereby a "+" in "BW result" indicates that the rat exhibited a weight gain of 20% or more and a "−" indicates that the rat exhibited a weight gain of less than 20%. Furthermore, a "+" in "Hematology result" indicates that the rat exhibited a reticulocyte count change of 65% or less and a "−" indicates that the rat exhibited a reticulocyte count change of greater than 65%.

TABLE 3

| Compound No. | BW Result | Hematology Result |
|---|---|---|
| 23 | + | + |
| 36 | − | − |
| 36 | + | − |
| 50 | + | + |
| 110 | − | − |
| 117 | − | + |
| 119 | − | − |
| 120 | + | + |
| 123 | + | + |
| 127 | + | + |
| 152 | + | + |
| 162 | − | − |
| 182 | − | − |
| 190 | − | − |
| 191 | + | + |
| 196 | + | + |
| 199 | + | − |
| 200 | + | − |
| 249 | + | + |
| 254 | + | + |
| 264 | + | + |
| 290 | + | + |
| 317 | − | − |
| 341 | + | + |
| 360 | + | + |

Example 4—Activity of Pyrrolocytosine Protein Synthesis Inhibitors Against Multiresistant Gram-Negative Bacteria Four compounds, including Compound Nos. 120 and 162 of the present application (RX-04B and RX-04C, respectively) were tested against (i) multiresistant Enterobacteriaceae and Acinetobacter with carbapenemases; (ii) Enterobacteriaceae with MCR-1; and (iii) P. aeruginosa with altered efflux (see Tables 4 and 5). In this case, MCR-1 is relevant because its activity reduces the negative charge of lipopolysaccharides, potentially affecting binding of polybasic molecules such as the compounds tested herein, as well as polymyxins.

TABLE 4
Compounds Tested
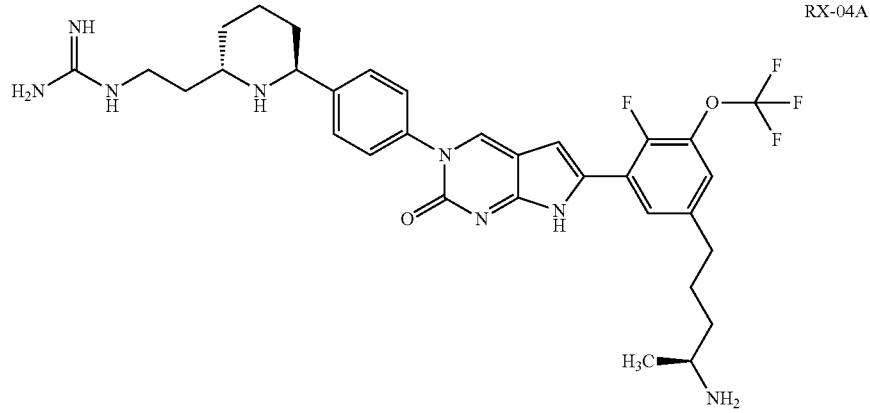
RX-04A
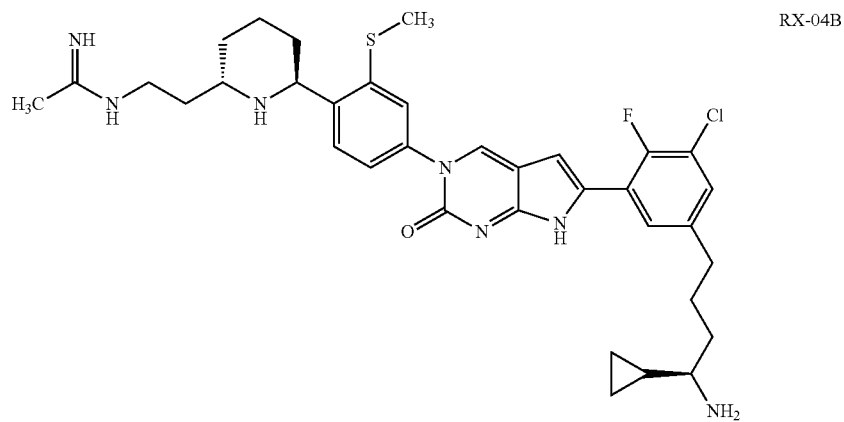
RX-04B
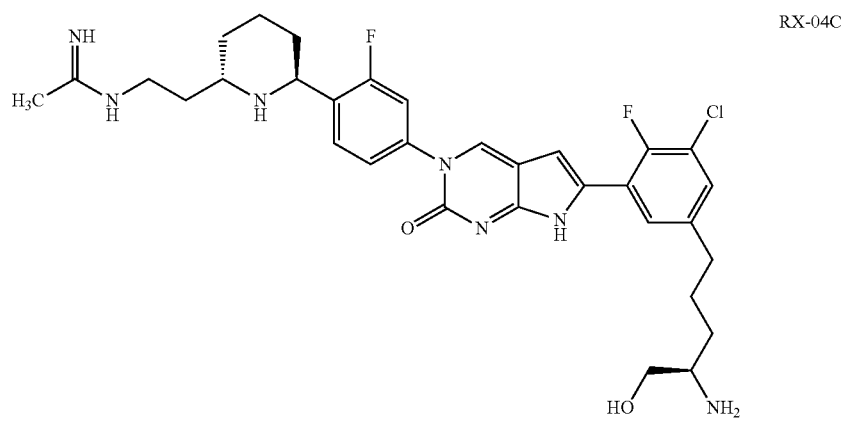
RX-04C TABLE 4-continued Compounds Tested

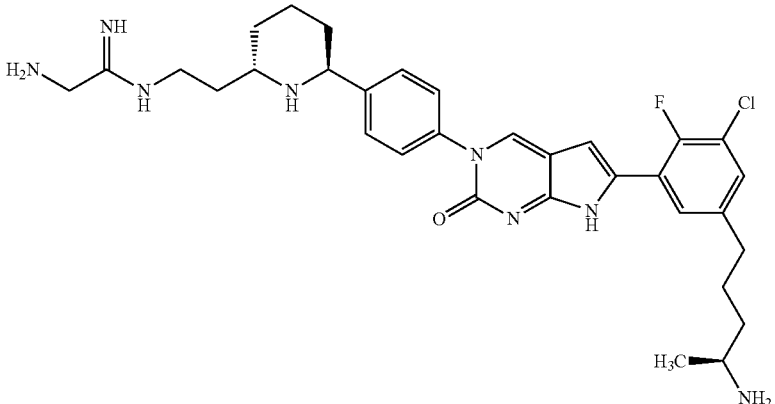 [SMILES: C[C@H](N)CCCc1cc(Cl)c(F)c(-c2cc3cn(-c4ccc([C@@H]5CCC[C@@H](CCNC(=N)CN)N5)cc4)c(=O)nc3[nH]2)c1]

RX-04D

TABLE 5

Test Panel

| | | Resistance mechanism/phenotype* | | | | | | | | | |
|---|---|---|---|---|---|---|---|---|---|---|---|
| Species | Carbapenem + cephalosporin susceptible controls | KPC | SME | MBL | OXA-48 | OXA-23 | Low efflux | Normal efflux | Raised efflux | MCR-1 | E. coli DH10B recipient | DH10B mcr-1 transformant |
| E. coli | 5 | 5 | — | 5 | 5 | — | — | — | — | 3 | 1 | 1 |
| S. enterica | — | — | — | — | — | — | — | — | — | 11 | — | — |
| K. pneumoniae | 5 | 5 | — | 5 | 5 | — | — | — | — | — | — | — |
| Enterobacter spp. | 4 | 2 | — | 1 | 1 | — | — | — | — | — | — | — |
| S. marcescens | 2 | — | 1 | — | 1 | — | — | — | — | — | — | — |
| P. aeruginosa | — | — | — | 5 | — | — | 5 | 5 | 5 | — | — | — |
| A. baumannii | 5 | — | — | — | — | 5 | — | — | — | — | — | — |

*E. coli* ATCC 25922 and *P. aeruginosa* ATCC 27853 were controls throughout
*numbers in the table refer to the number of each species that exhibit the particular resistance/genotype.

MICs of the four tested compounds and comparators (amikacin, cefepime, colistin, meropenem and tigecyline) were determined by CLSI broth microdilution using pre-prepared plates (Trek Diagnostic Systems) (CLSI Approved Standard M7-A10). Carbapenemase and mcr-1 genes were detected by PCR or sequencing. Efflux levels in *P. aeruginosa* isolates were inferred by interpretive reading of antibiogram data.

MICs for the 68 Enterobacteriaceae were unimodal, with peaks at 1 mg/L for analogues RX-04A and RX-04B and 2 mg/L for RX-04C and RX-04D (FIG. 1). For RX-04A, the most active of the tested analogues, 67/68 (>98%) MICs were 0.25-2 mg/L. For all of the tested compounds, MICs were lowest for *E. Coli* and highest for *S. marcescens* (MICs from 8 to greater than 16 mg/L were seen for one *Serratia*).

Figure 2:
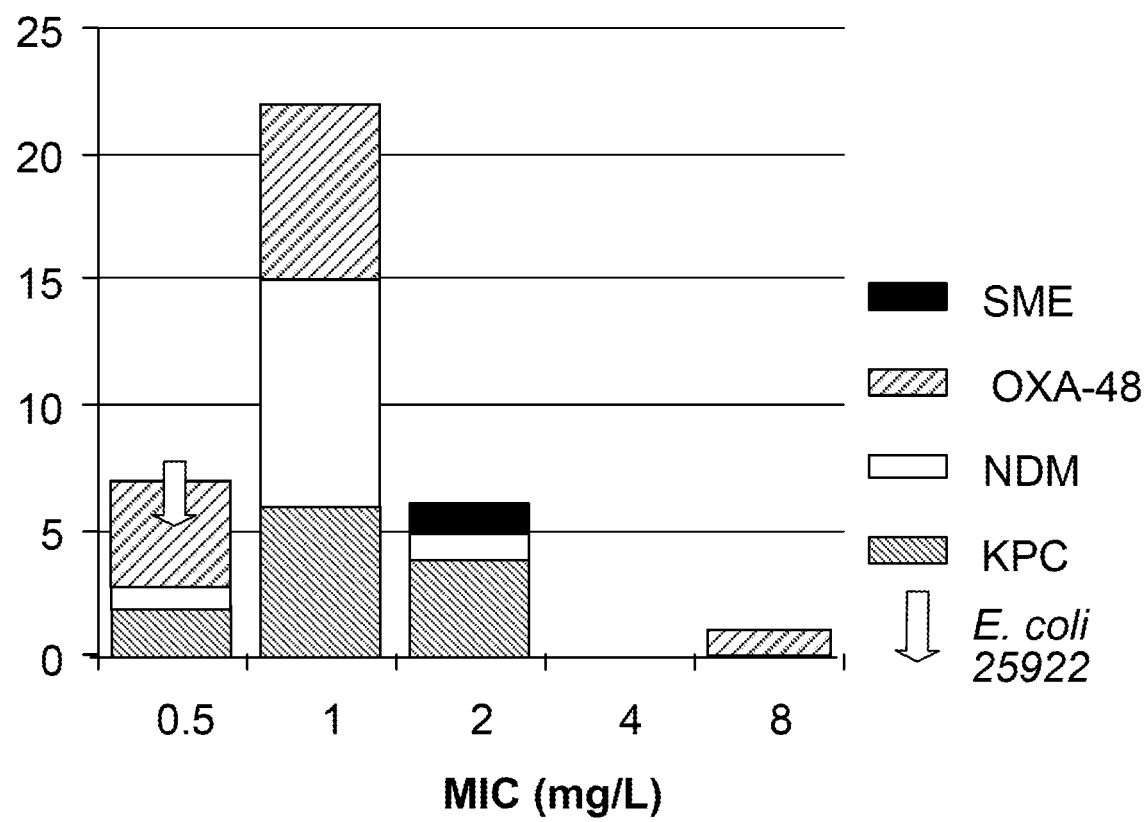
FIG. 2 provides a bar graph illustrating the MIC distributions of RX-04A for CPE (n=36).
Figure 3:
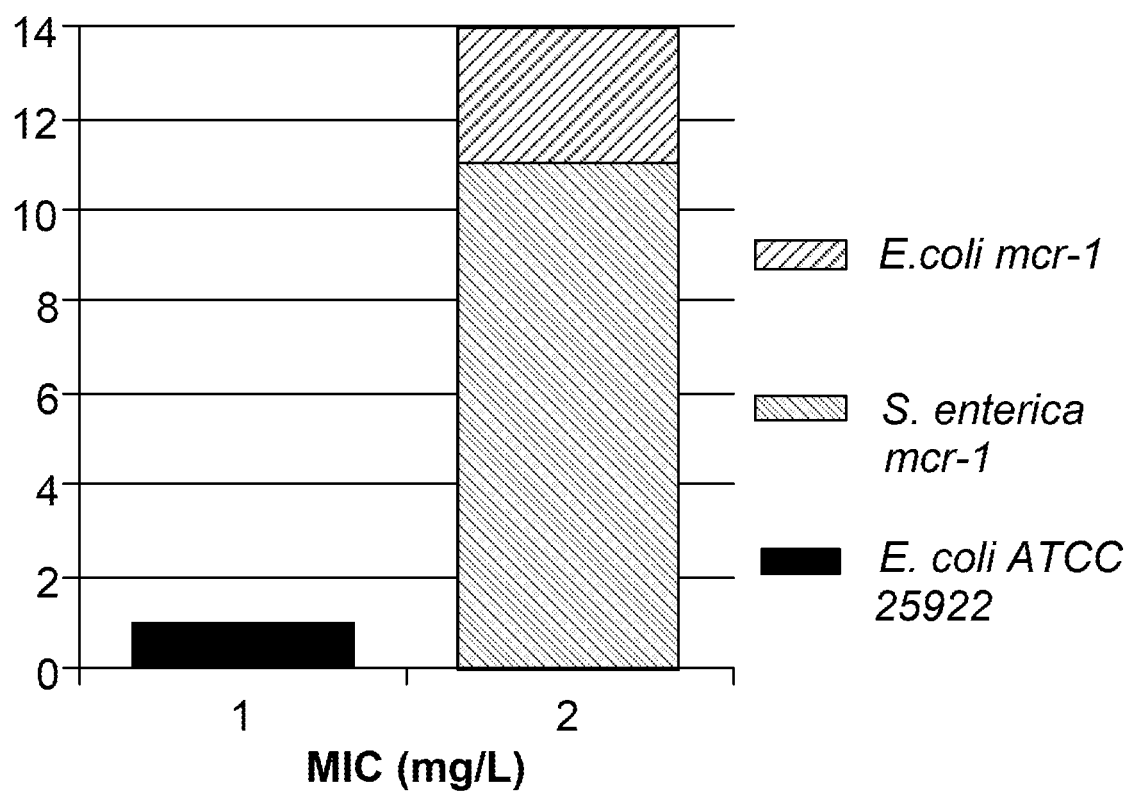
FIG. 3 provides a bar graph illustrating the MIC distributions of RX-04A for MCR-1 isolates (N=14).

MICs of RX-04A for 35/36 (97%) of CPE were within 4-fold of the MIC for *E. coli* ATCC 25922 (FIG. 2). MIC differentials for analogues RX-04B-D were similarly small. MICs of RX-04A for all MCR-1 isolates (n=14) were within 2-fold of that for *E. coli* ATCC 25922 (FIG. 3). MIC differentials for analogues RX-04B-D were similarly small. Acquisition of mcr-1 did not raise RX-04 MICs for *E. coli* DH10B (Table 6).

TABLE 6

MICs of RX04-A-D and colistin for *E. coli* DH10B and its mcr-1 transformant

| | MIC (mg/L) | | | | |
|---|---|---|---|---|---|
| Strain | RX-04A | RX-04B | RX-04C | RX-04D | COL |
| DH10B Recipient | 0.25 | 0.5 | 0.5 | 1 | 0.25 |
| MCR-1 Transformant | 0.25 | 0.5 | 0.5 | 1 | 4 |

Figure 4:
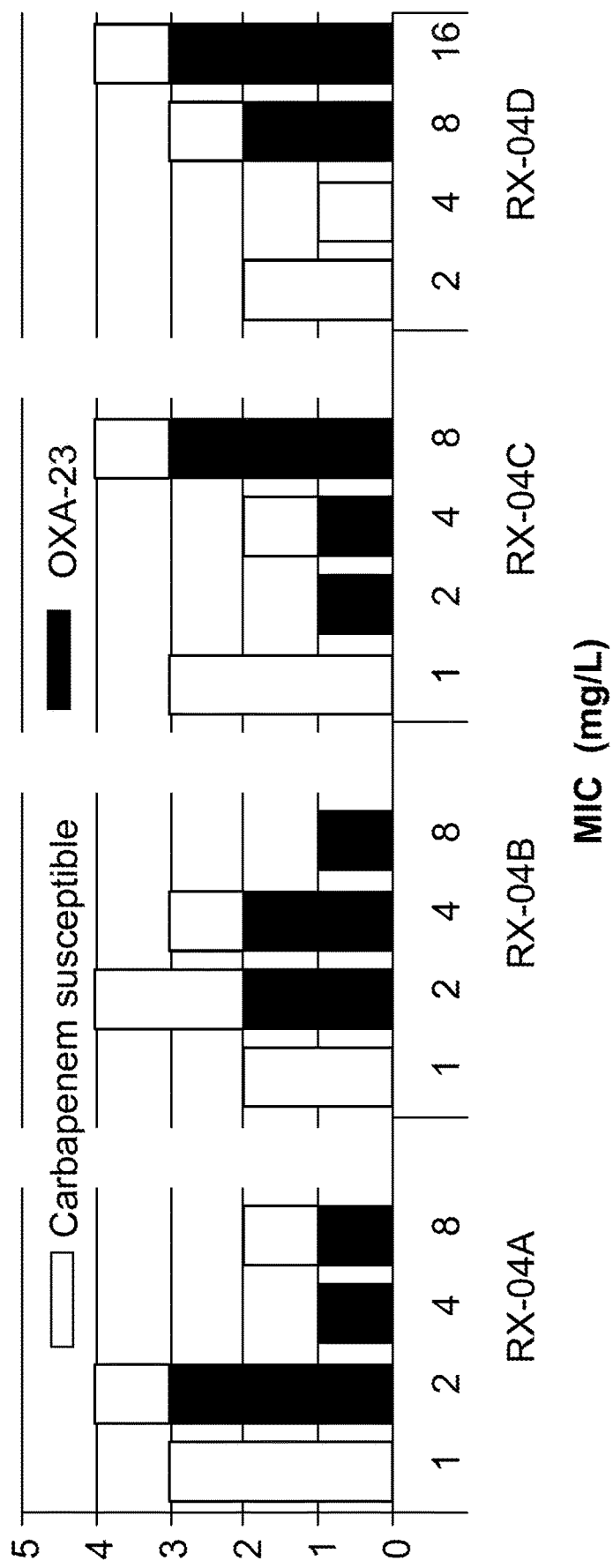
FIG. 4 provides a bar graph illustrating the MIC distributions of RX-04A-D for *A. baumannii* isolates (n=10).
Figure 5:
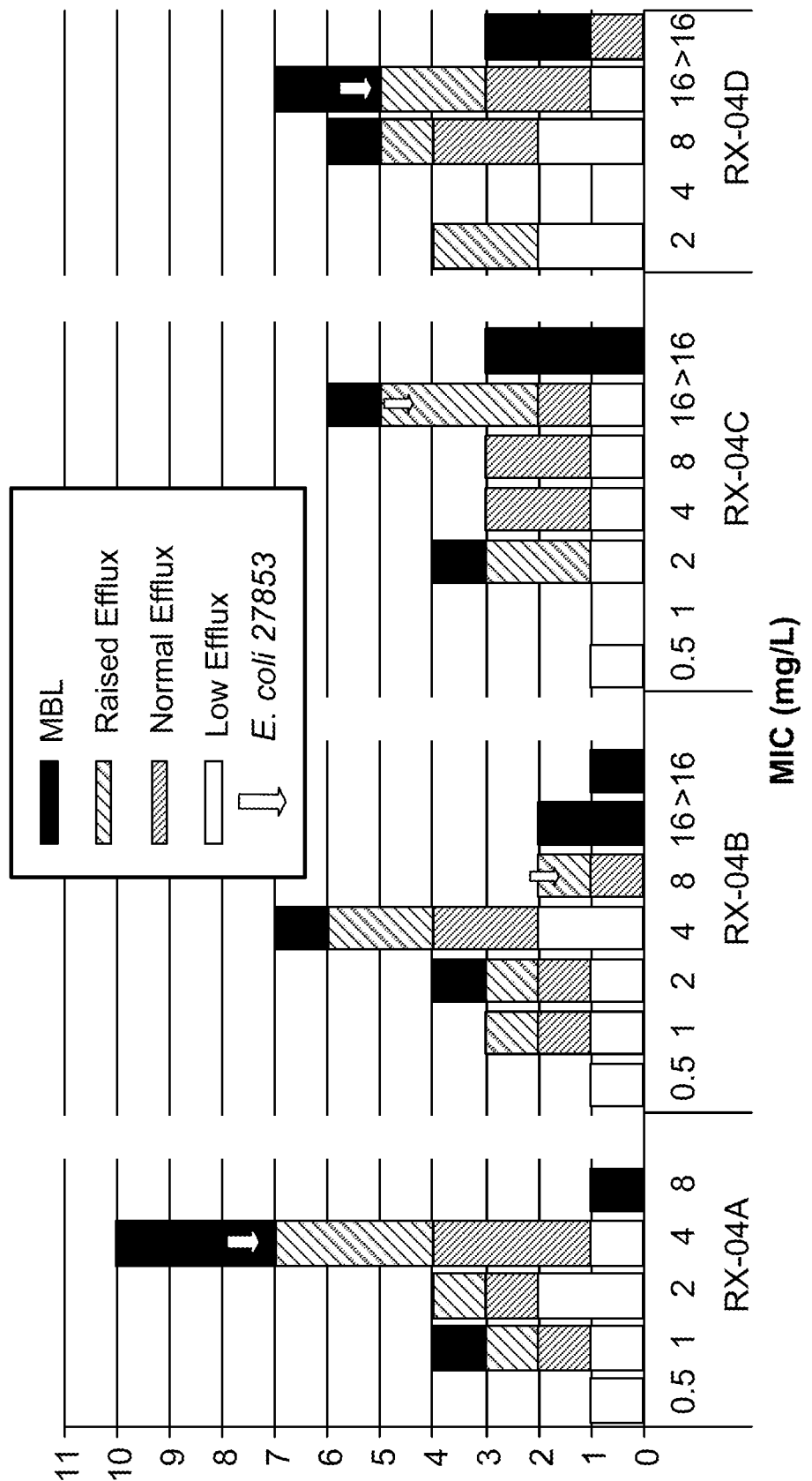
FIG. 5 provides bar graphs illustrating MIC distributions of RX-04A-D for *P. aeruginosa* (n=20).

MIC distributions of RX-04 analogues A-C straddled 1-8 mg/L for the 10 *A. baumannii*. RX-04A had the lowest MICs, with 7/10 values from 1-2 mg/L, D was the least active analogue (FIG. 4). MICs for *A. baumannii* with OXA-23 carbapenemases were mostly higher than carbapenem-susceptible isolates, but numbers were small and 3/5 OXA-23 isolates belonged to the same lineage (International Clone II; the other 2 were unique pulsotypes). RX-04A again was the most active analogue against *P. aeruginosa* isolates, with MICs from 1-4 mg/L for 19/20 (95%) isolates. Almost half (48%) of the MICs were ≥16 mg/L for analogues C and D (FIG. 5). MICs of all analogues tended to be higher for *P. aeruginosa* with 'normal' vs. low efflux, but not further raised for those with elevated efflux.

The four analogues had broad activity against Enterobacteriaceae and non-fermenters. RX-04A was the most active analogue with MICs mostly 1-2 mg/L for Enterobacteriaceae and A. baumannii and 1-4 mg/L for P. aeruginosa. Among Enterobacteriaceae, E. coli was the most susceptible species and S. marcescens the least susceptible. MICs for carbapenemase producers and MCR-1 isolates were only 2-4-fold above a highly susceptible control. Acquisition of MCR-1 did not affect susceptibility to these basic molecules, despite affective surface charge. RX-04A MICs were not raised in P. aeruginosa isolates with elevated efflux. MICs were slightly raised against multiresistant A. baumannii. Pyrrolocytosines showed promising activity against this challenging collection of multiresistant Gram-negative bacteria.

INCORPORATION BY REFERENCE

The entire disclosure of each of the patent documents and scientific articles referred to herein is incorporated by reference for all purposes.

EQUIVALENTS

The disclosure can be embodied in other specific forms without departing from the spirit or essential characteristics thereof. The foregoing embodiments are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

What is claimed is:
1. A compound of Formula (I):

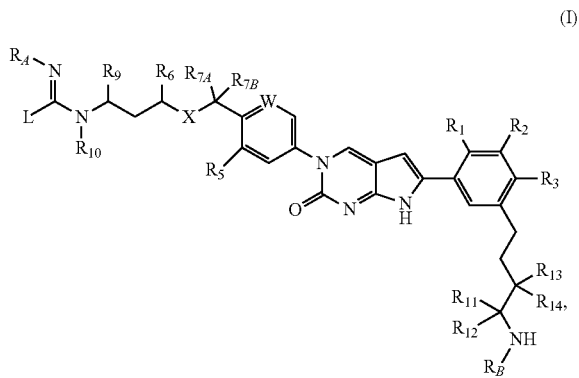

or a tautomer thereof or a pharmaceutically acceptable salt of the compound or tautomer, wherein:
$R_1$ is selected from the group consisting of H, halo, and $C_{1-4}$ alkoxy;
$R_2$ is selected from the group consisting of H, halo, $C_{1-6}$ alkyl, $C_{1-4}$ haloalkyl, and $OR^{a1}$;
$R_3$ is selected from the group consisting of H, $C_{1-6}$ alkyl, $C_{1-4}$ haloalkyl, and $C(O)OR^{a1}$;
W is selected from the group consisting of N and $CR_4$;
$R_4$ is selected from the group consisting of H, halo, $OR^{a2}$, $SR^{a2}$, 5-6 membered heterocycloalkyl, $S(O)_2R^{b2}$, $C_{1-6}$ alkyl, and $C_{2-6}$ alkenyl, wherein the $C_{1-6}$ alkyl is optionally substituted with a substituent selected from the group consisting of $ORa^2$;

$R_5$ is selected from the group consisting of H, halo, $C_{1-6}$ alkyl, and $C_{2-6}$ alkenyl, wherein the $C_{1-6}$ alkyl is optionally substituted with a substituent selected from the group consisting of $ORa^{a2}$;
$R_{7B}$ is H;
$R_6$ and $R_{7A}$ together with the carbon atoms to which they are attached and the X atom connecting the two carbon atoms form a 5- to 6-membered heterocycloalkyl containing 1-3 heteroatoms selected from the group consisting of N, O and S;
X is selected from the group consisting of O and $NR_8$;
$R_8$ is selected from the group consisting of H, $C_{1-6}$ alkyl, and $C_{1-4}$ haloalkyl, wherein the $C_{1-6}$ alkyl is optionally substituted with $R_{8A}$;
$R_{8A}$ is selected from the group consisting of $OR^{a3}$ and 5- to 6-membered heteroaryl, wherein the 5- to 6-membered heteroaryl is optionally substituted with one or two $C_{1-6}$ alkyl;
$R_9$ is selected from the group consisting of H, $C_{2-4}$ alkenyl, $C_{1-4}$ haloalkyl and $C_{1-4}$ alkyl optionally substituted with a substituent selected from the group consisting of amino, $C_{1-4}$ alkoxy, $C_{3-5}$ cycloalkyl, and 3- to 6-membered heterocycloalkyl;
$R_{10}$ is selected from the group consisting of H and $C_{2-6}$ alkenyl;
$R_A$ is selected from the group consisting of H and $C_{1-6}$ alkyl;
L is selected from the group consisting of $C_{1-6}$ alkyl and $C_{2-6}$ alkenyl, wherein the $C_{1-6}$ alkyl is optionally substituted with 1, 2, or 3 substituents independently selected from the group consisting of halo, $OR^{a4}$, and $SR^{a4}$;
$R_{11}$ is selected from the group consisting of H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with 1, 2, or 3 substituents independently selected from the group consisting of CN, $OR^{a5}$, $SR^{a5}$, $C(O)NR^{c5}R^{d5}$, $NR^{c5}R^{d5}$, and $S(O)_2R^{b5}$;
$R_{12}$ is selected from the group consisting of H and $C_{1-6}$ alkyl; or
$R_{11}$ and $R_{12}$ together with the carbon atom to which they are attached form a $C_{3-5}$ cycloalkyl;
$R_{13}$ is selected from the group consisting of H, halo, and $C_{1-6}$ alkyl;
$R_{14}$ is selected from the group consisting of H, halo, and $C_{1-6}$ alkyl; and
$R_B$ is selected from the group consisting of H and $C(=NR^{e5})R^{b5}$; or
$R_{11}$ and $R_B$ together with the carbon atom to which $R_{11}$ is attached and the nitrogen atom to which $R_B$ is attached form a 5- to 6-membered heterocycloalkyl containing 1-3 heteroatoms selected from the group consisting of N, O and S, wherein the 5- to 6-membered heterocycloalkyl is optionally substituted with oxo;
each $R^{a1}$, $R^{a2}$, $R^{a3}$, $R^{a4}$, $R^{a5}$, $R^{b2}$, $R^{b5}$, $R^{c5}$, and $R^{d5}$ is independently selected from the group consisting of H, $C_{1-6}$ alkyl, $C_{1-4}$ haloalkyl, and 5-membered heteroaryl; and
$R^{e5}$ is selected from the group consisting of H and $C_{1-4}$ alkyl;
provided that the compound is not one of the following compounds:

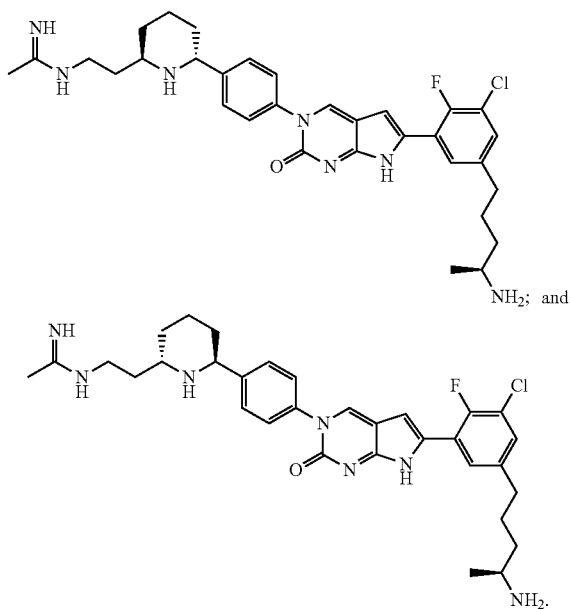

2. The compound of claim 1, wherein
R$_1$ is selected from the group consisting of H and halo;
L is selected from the group consisting of C$_{1-6}$ alkyl and C$_{2-6}$ alkenyl, wherein the C$_{1-6}$ alkyl is optionally substituted with 1, 2, or 3 substituents independently selected from the group consisting of halo, OR$^{a4}$, and SR$^{a4}$; and
R$^{e5}$ is selected from the group consisting of H and C$_{1-4}$ alkyl.

3. The compound of claim 1, wherein
R$_1$ is halo; or
R$_1$ is selected from the group consisting of H and fluoro; or
R$_1$ is fluoro; or
R$_1$ is C$_{1-4}$ alkoxy; or
R$_1$ is methoxy.

4. The compound of claim 1, wherein
R$_2$ is selected from the group consisting of H, halo, C$_{1-4}$ haloalkyl, and C$_{1-4}$ haloalkoxy; or
R$_2$ is selected from the group consisting of halo, C$_{1-4}$ haloalkyl, and C$_{1-4}$ haloalkoxy; or
R$_2$ is selected from the group consisting of H, trifluoromethoxy, trifluoromethyl and chloro; or
R$_2$ is selected from the group consisting of trifluoromethoxy, trifluoromethyl and chloro.

5. The compound of claim 1, wherein
R$_1$ is halo and R$_2$ is halo; or
R$_1$ is fluoro and R$_2$ is chloro.

6. The compound of claim 1, wherein
R$_3$ is selected from the group consisting of H, C$_{1-4}$ haloalkyl, and C(O)OR$^{a1}$; or
R$_3$ is selected from the group consisting of H, C$_{1-4}$ haloalkyl, and C(O)C$_{1-4}$ alkoxy; or
R$_3$ is selected from the group consisting of H, trifluoromethyl, and C(=O)(methoxy); or
R$_3$ is H.

7. The compound of claim 1, wherein
W is CR$_4$.

8. The compound of claim 1, wherein
R$_4$ is selected from the group consisting of H, halo, C$_{1-6}$ alkyl, C$_{1-4}$ alkoxy, C$_{1-4}$ haloalkoxy, S(C$_{1-4}$ alkyl), 6-membered heterocycloalkyl, and S(O)$_2$C$_{1-4}$ alkyl; or R$_4$ is selected from the group consisting of halo, C$_{1-6}$ alkyl, C$_{1-4}$ alkoxy, C$_{1-4}$ haloalkoxy, S(C$_{1-4}$ alkyl), 6-membered heterocycloalkyl, and S(O)$_2$C$_{1-4}$ alkyl; or
R$_4$ is selected from the group consisting of H, fluoro, chloro, methylthio, methoxy, methyl, S(=O)$_2$(methyl), trifluoromethoxy, and N-morpholino; or
R$_4$ is selected from the group consisting of fluoro, chloro, methylthio, methoxy, methyl, S(=O)$_2$(methyl), trifluoromethoxy, and N-morpholino; or
R$_4$ is H.

9. The compound of claim 1, wherein
R$_5$ is halo; or
R$_5$ is selected from the group consisting of H and F; or
R$_5$ is F; or
R$_5$ is H.

10. The compound of claim 1, wherein
R$_5$ is halo and R$_4$ is selected from the group consisting of halo, S(C$_{1-4}$ alkyl), and 6-membered heterocycloalkyl; or
R$_5$ is halo, and R$_4$ is S(C$_{1-4}$ alkyl); or
R$_5$ is fluoro and R$_4$ is selected from the group consisting of fluoro, methylthio, and N-morpholino; or
R$_5$ is fluoro and R$_4$ is methylthio.

11. The compound of claim 1, wherein
R$_6$ and R$_{7A}$ together with the carbon atoms to which they are attached and the X atom connecting the two carbon atoms form a 6-membered heterocycloalkyl containing 1-3 heteroatoms selected from the group consisting of N, O and S; or
R$_6$ and R$_{7A}$ together with the carbon atoms to which they are attached and the X atom connecting the two carbon atoms form a ring of any one of the following formulae:

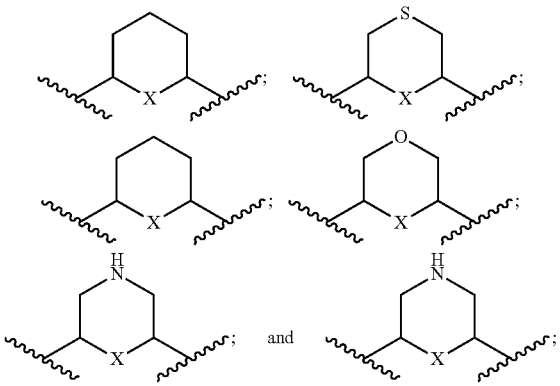

or
R$_6$ and R$_{7A}$ together with the carbon atoms to which they are attached and the X atom connecting the two carbon atoms form a ring of the following formulae:

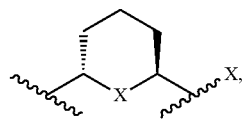

wherein x indicates a point of attachment to the ring containing the W atom and substituted with R$_5$; or
R$_6$ and R$_{7A}$ together with the carbon atoms to which they are attached and the X atom connecting the two carbon atoms form a ring of any one of the following formulae:

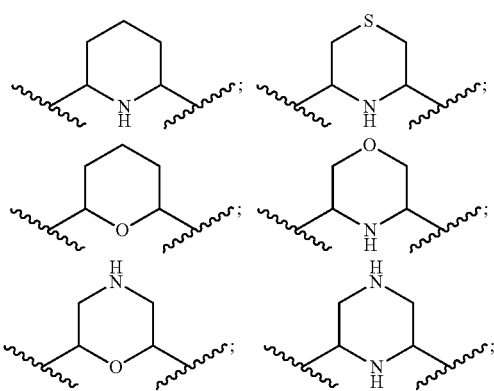

or

R$_6$ and R$_{7A}$ together with the carbon atoms to which they are attached and the X atom connecting the two carbon atoms form a ring of formula:

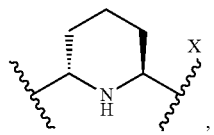

wherein x indicates a point of attachment to the ring containing the W atom and substituted with R$_5$; or R$_6$ and R$_{7A}$ together with the carbon atoms to which they are attached and the X atom connecting the two carbon atoms form a ring of any one of the following formulae:

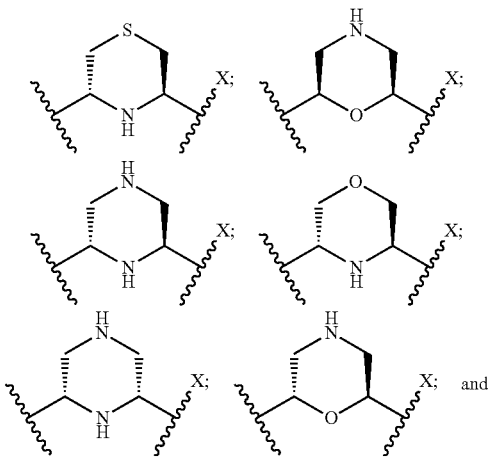

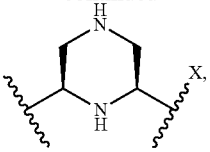

wherein x indicates a point of attachment to the ring containing the W atom and substituted with R$_5$.

12. The compound of claim 1, wherein
   X is NR$_8$.
13. The compound of claim 1, wherein
   R$_8$ is selected from the group consisting of H, C$_{1-6}$ alkyl, C$_{1-4}$ haloalkyl, C$_{1-4}$ hydroxyalkyl, C$_{1-6}$ alkyl substituted with C$_{1-6}$ alkoxy, and C$_{1-6}$ alkyl substituted with 5- to 6-membered heteroaryl, wherein the 5- to 6-membered heteroaryl is optionally substituted with 1, or 2 C$_{1-6}$ alkyl; or
   R$_8$ is selected from the group consisting of H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl; or
   R$_8$ is selected from the group consisting of the following formulae:

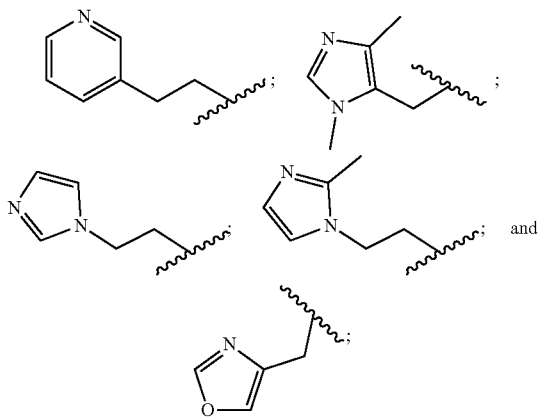

or
   R$_8$ is selected from the group consisting of methyl, 3-fluoropropyl, 2-methoxyethyl, and 3-hydroxypropyl; or
   R$_8$ is H.
14. The compound of claim 1, wherein
   R$_9$ is H; or
   R$_9$ is C$_{1-6}$ alkyl; or
   R$_9$ is methyl.

* * * * *